US009816117B2

(12) United States Patent
Conradie et al.

(10) Patent No.: US 9,816,117 B2
(45) Date of Patent: *Nov. 14, 2017

(54) METHODS, REAGENTS AND CELLS FOR BIOSYNTHESIZING COMPOUNDS

(71) Applicant: INVISTA North America S.á r.l., Wilmington, DE (US)

(72) Inventors: Alex Van Eck Conradie, Eaglescliffe (GB); Adriana Leonora Botes, Rosedale East (GB); Ramdane Haddouche, Middlesbrough (GB)

(73) Assignee: INVISTA NORTH AMERICA S.A.R.L., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/741,228

(22) Filed: Jun. 16, 2015

(65) Prior Publication Data

US 2015/0361466 A1 Dec. 17, 2015

Related U.S. Application Data

(60) Provisional application No. 62/012,666, filed on Jun. 16, 2014, provisional application No. 62/012,659, filed on Jun. 16, 2014, provisional application No. 62/012,604, filed on Jun. 16, 2014.

(51) Int. Cl.
| | |
|---|---|
| C12P 13/00 | (2006.01) |
| C12P 7/64 | (2006.01) |
| C12N 9/10 | (2006.01) |
| C12N 9/02 | (2006.01) |
| C12P 7/24 | (2006.01) |
| C07C 59/01 | (2006.01) |
| C08G 63/06 | (2006.01) |
| C12P 7/40 | (2006.01) |
| C12P 7/42 | (2006.01) |
| C07C 47/02 | (2006.01) |
| C07C 47/12 | (2006.01) |
| C07C 59/325 | (2006.01) |
| C07C 223/02 | (2006.01) |
| C12P 7/44 | (2006.01) |
| C12P 7/62 | (2006.01) |

(52) U.S. Cl.
CPC ............ *C12P 13/001* (2013.01); *C07C 47/02* (2013.01); *C07C 47/12* (2013.01); *C07C 59/01* (2013.01); *C07C 59/325* (2013.01); *C07C 223/02* (2013.01); *C08G 63/06* (2013.01); *C12N 9/0008* (2013.01); *C12N 9/0077* (2013.01); *C12N 9/1007* (2013.01); *C12N 9/1096* (2013.01); *C12P 7/24* (2013.01); *C12P 7/40* (2013.01); *C12P 7/42* (2013.01); *C12P 7/44* (2013.01); *C12P 7/62* (2013.01); *C12P 7/6409* (2013.01); *C12P 7/6436* (2013.01); *C12Y 102/99006* (2013.01); *C12Y 114/15001* (2013.01); *C12Y 114/15003* (2013.01); *C12Y 206/01018* (2013.01); *C12Y 206/01019* (2013.01); *C12Y 206/01029* (2013.01); *C12Y 206/01048* (2013.01); *C12Y 206/01082* (2013.01)

(58) Field of Classification Search
CPC .... C12P 7/62; C12N 9/18; C12N 1/32; C12Y 103/01008; C12Y 203/01016
See application file for complete search history.

(56) References Cited

U.S. PATENT DOCUMENTS

| | | | |
|---|---|---|---|
| 2,439,513 | A | 4/1948 | Hamblet et al. |
| 2,557,282 | A | 6/1951 | Hamblet et al. |
| 2,791,566 | A | 5/1957 | Jeffers |
| 2,840,607 | A | 6/1958 | Attane, Jr. et al. |
| 2,971,010 | A | 2/1961 | Gilby, Jr. et al. |
| 3,023,238 | A | 2/1962 | Chapman et al. |
| 3,338,959 | A | 8/1967 | Sciance et al. |
| 3,365,490 | A | 1/1968 | Arthur et al. |
| 3,515,751 | A | 6/1970 | Oberster |
| 3,719,561 | A | 3/1973 | Tanaka et al. |
| 4,058,555 | A | 11/1977 | Mims |
| 6,255,451 | B1 | 7/2001 | Koch et al. |
| 6,372,939 | B1 | 4/2002 | Bunel et al. |

(Continued)

FOREIGN PATENT DOCUMENTS

| | | |
|---|---|---|
| EP | 2647718 | 10/2013 |
| WO | WO 2008/006037 | 1/2008 |

(Continued)

OTHER PUBLICATIONS

"Metabolic engineering," Wikipedia, Jun. 8, 2014 (Jun. 8, 2014), XP002744570, Retrieved from the Internet: URL:https://en.wikipedia.org/w/index.php?title=Metabolicengineering&oldid=612026466 [retrieved on Sep. 15, 2015] last paragraph.
Akatsuka et al., "The Serratia marcescens bioH gene encodes an esterase," GENE, Jan. 2003, 302:185-192.
Eriksen et al., "Protein Design for Pathway Engineering," Journal of Structural Biology, Apr. 2013, 185(2):234-242.
Invitation to Pay Fees in International Application No. PCT/US2015/036015, dated Oct. 2, 2015, 9 pages.
Invitation to Pay Fees in International Application No. PCT/US2015/036067, dated Sep. 18, 2015, 12 pages.
Klapa and Stephanopoulos, "Bioreaction Engineering: Modeling and Control," 2000, Springer Verlag, Heidelberg, pp. 106-124.

(Continued)

*Primary Examiner* — Gregory Listvoyb
(74) *Attorney, Agent, or Firm* — Finnegan, Henderson, Farabow, Garrett & Dunner, LLP; Carla A. Mouta-Bellum

(57) ABSTRACT

This document describes biochemical pathways for producing 6-hydroxyhexanoate methyl ester and hexanoic acid hexyl ester using one or more of a fatty acid O-methyltransferase, an alcohol O-acetyltransferase and a monooxygenase, as well as recombinant hosts expressing one or more of such enzymes. 6-hydroxyhexanoate methyl esters and hexanoic acid hexyl ester can be enzymatically converted to adipic acid, adipate semialdehyde, 6-aminohexanoate, 6-hydroxyhexanoate, hexamethylenediamine, and 1,6-hexanediol.

19 Claims, 32 Drawing Sheets

(56) References Cited

U.S. PATENT DOCUMENTS

| | | |
|---|---|---|
| 8,088,607 B2 | 1/2012 | Burgard et al. |
| 8,361,769 B1 | 1/2013 | Koch et al. |
| 2004/0054235 A1 | 3/2004 | Fodor et al. |
| 2010/0035309 A1 | 2/2010 | Havemen et al. |
| 2010/0151536 A1* | 6/2010 | Baynes ............... C12P 7/18 435/128 |
| 2010/0203600 A1 | 8/2010 | Dubois |
| 2010/0298612 A1 | 11/2010 | Behrouzian et al. |
| 2010/0317069 A1 | 12/2010 | Burk et al. |
| 2011/0171699 A1 | 7/2011 | Raemakers-Franken et al. |
| 2011/0256599 A1 | 10/2011 | Hu et al. |
| 2012/0064252 A1 | 3/2012 | Beatty |
| 2012/0101009 A1 | 4/2012 | Beatty |
| 2013/0065279 A1 | 3/2013 | Burk et al. |
| 2013/0183728 A1 | 7/2013 | Botes |
| 2013/0210090 A1 | 8/2013 | Pearlman et al. |
| 2013/0217081 A1 | 8/2013 | Pearlman et al. |
| 2013/0224807 A1 | 8/2013 | Pearlman et al. |
| 2013/0267012 A1 | 10/2013 | Steen et al. |
| 2014/0186902 A1 | 7/2014 | Botes et al. |
| 2014/0186904 A1 | 7/2014 | Botes et al. |
| 2014/0193861 A1 | 7/2014 | Botes et al. |
| 2014/0193862 A1 | 7/2014 | Botes et al. |
| 2014/0193863 A1 | 7/2014 | Botes et al. |
| 2014/0193864 A1 | 7/2014 | Botes et al. |
| 2014/0193865 A1 | 7/2014 | Botes et al. |
| 2014/0196904 A1 | 7/2014 | Fontenelle et al. |
| 2014/0199737 A1 | 7/2014 | Botes et al. |
| 2014/0248673 A1 | 9/2014 | Botes et al. |
| 2015/0111262 A1 | 4/2015 | Botes et al. |
| 2015/0267211 A1 | 9/2015 | Botes et al. |

FOREIGN PATENT DOCUMENTS

| | | |
|---|---|---|
| WO | WO 2008/145737 | 12/2008 |
| WO | WO 2009/121066 | 1/2009 |
| WO | WO 2009/113853 | 9/2009 |
| WO | WO 2009/113855 | 9/2009 |
| WO | WO 2009/140159 | 11/2009 |
| WO | WO 2009/140695 | 11/2009 |
| WO | WO 2009/140696 | 11/2009 |
| WO | WO 2009/151728 | 12/2009 |
| WO | WO 2010/068944 | 6/2010 |
| WO | WO 2010/068953 | 6/2010 |
| WO | WO 2010/071759 | 6/2010 |
| WO | WO 2010/104390 | 9/2010 |
| WO | WO 2010/104391 | 9/2010 |
| WO | WO 2010/129936 | 11/2010 |
| WO | WO 2010/132845 | 11/2010 |
| WO | WO 2011/003034 | 1/2011 |
| WO | WO 2011/031146 | 3/2011 |
| WO | WO 2011/031147 | 3/2011 |
| WO | WO 2012/031910 | 3/2012 |
| WO | WO 2012/071439 | 5/2012 |
| WO | WO 2012/094425 | 7/2012 |
| WO | WO 2012/174430 | 12/2012 |
| WO | WO 2012/177721 | 12/2012 |
| WO | WO 2013/003744 | 1/2013 |
| WO | WO 2013/028519 | 2/2013 |
| WO | WO 2013/082542 | 6/2013 |
| WO | WO 2013/090837 | 6/2013 |
| WO | WO 2013/096898 | 6/2013 |
| WO | WO 2014/031724 | 2/2014 |
| WO | WO 2014/093865 | 6/2014 |
| WO | WO 2014/105788 | 7/2014 |
| WO | WO 2014/105793 | 7/2014 |
| WO | WO 2015/036050 | 3/2015 |

OTHER PUBLICATIONS

Moreno-Sanchez et al., "Experimental validation of metabolic pathway modeling—An illustration with glycolytic segments from Entamoeba histolytica," FEBS Journal, Jul. 2008, 275(13):3454-3469.

Palsson, "The challenges of in silico biology," Nature Biotechnology, Nature Publishing Group, US, Nov. 2000, 18(1):1147-1150.
Price et al., "Genome-scale models of microbial cells: evaluating the consequences of constraints," Nature Reviews. Microbiology, Nature Publishing Group, GB, Nov. 2004, 2(11):886-897.
Uniprot Accession No. 032472, Jun. 11, 2014, 2 pages.
Uniprot Accession No. P0A6RO, May 14, 2014, 5 pages.
Uniprot Accession No. P0A8ZO, Jun. 11, 2014, 3 pages.
Uniprot Accession No. P0AGG2, Jun. 11, 2014, 3 pages.
Uniprot Accession No. P0AEK4, Jun. 11, 2014, 6 pages.
Uniprot Accession No. P0A953, Jun. 11, 2014, 4 pages.
Uniprot Accession No. P0A6Q6, Jun. 11, 2014, 3 pages.
Uniprot Accession No. P0AEK2, May 14, 2014, 4 pages.
Uniprot Accession No. P13001, Jun. 11, 2014, 4 pages.
Uniprot Accession No. Q5EU90, Feb. 19, 2014, 2 pages.
Uniprot Accession No. Q73Q47, May 14, 2014, 2 pages.
Uniprot Accession No. Q818X2, Jun. 11, 2014, 2 pages.
Yadav et al., "The future of metabolic engineering and synthetic biology: Towards a systematic practice," Metabolic Engineering, Feb. 2012, 14(3):233-241.
Adkins, J. et al., "Engineering microbial chemical factories to produce renewable 'biomonomers'," *Front Microbiol.*, 2012, 3: 313 (12 pages).
Blombach, B. et al, "Current knowledge on isobutanol production with *Escherichia coli, Bacillus subtilis* and *Corynebacterium glutamicum*," *Bioeng Bugs.*, 2011, 2(6): 346-350.
Börnke, F, et al., "Tailoring plant metabolism for the production of novel polymers and platform chemicals," *Curr Opin Plant Biol.*, 2010, 13(3): 354-362.
Chan, S, et al., "Production of succinic acid from sucrose and sugarcane molasses by metabolically engineered *Escherichia coli*," *Bioresour Technol.*, 2012, 103(1): 329-336.
Choi, Y. J. et al., "Metabolic engineering of *Escherichia coli* for the production of 1-propanol," *Metab Eng.*, 2012, 14(5): 477-486.
Davids, T., et al., "Strategies for the discovery and engineering of enzymes for biocatalysis," *Curr. Opin. Chem. Biol.* 17(2):215-220 (2013).
ExPASy, "ENZYME entry: EC 1.1.1.35," archived Dec. 4, 2013, retrieved Jan. 15, 2017, Internet Archive, [http://web.archive.orgiweb/20131204110324/http://enzyme.expasy.org/EC/1.1.1.35] (3 pages).
ExPASy, "ENZYME entry: EC 1.1.1.100," archived Feb. 8, 2013, retrieved Jan. 15, 2017, Internet Archive, [http://web.archive.org/web/20130208105654/http://enzyme.expasy.org/EC/1.1.1.100] (2 pages).
ExPASy, "ENZYME entry: EC 1.2.1.3," archived Aug. 20, 2013, retrieved Jan. 15, 2017, Internet Archive, [http://web.archive.org/web/20130820074435/http://enzyme.expasy.org/EC/1.2.1.3] (2 pages).
ExPASy, "ENZYME entry: EC 1.2.1.10," archived Jun. 12, 2012, retrieved Jan. 15, 2017, Internet Archive, [http://web.archive.org/web/20120612031241/http://enzyme.expasy.org/EC/1.2.1.10] (3 pages).
ExPASy, "ENZYME entry: EC 1.3.1.8," archived Sep. 15, 2012, retrieved Jan. 15, 2017, Internet Archive, [http://web.archive.org/web/20120915015445/http://enzyme.expasy.org/EC/1.3.1.8] (2 pages).
ExPASy, "ENZYME entry: EC 1.14.15.1," archived Sep. 27, 2012, retrieved Jan. 15, 2017, Internet Archive, [http://web.archive.org/web/20120927192141/http://enzyme.expasy.org/EC/1.14.15.1] (2 pages).
ExPASy, "ENZYME entry: EC 2.1.1.15," archived Jun. 9, 2012, retrieved Jan. 15, 2017, Internet Archive, [http://web.archive.org/web/20120609122426/http://enzyme.expasy.org/EC/2.1.1.15] (2 pages).
ExPASy, "ENZYME entry: EC 2.3.1.9," archived May 29, 2013, retrieved Jan. 15, 2017, Internet Archive, [http://web.archive.org/web/20130529092636/http://enzyme.expasy.org/EC/2.3.1.9] (2 pages).
ExPASy, "ENZYME entry: EC 2.3.1.194," archived Nov. 9, 2014, retrieved Jan. 15, 2017, Internet Archive, [http://web.archive.org/web/20141109113828/http://enzyme.expasy.org/EC/2.3.1.194] (2 pages).

(56) References Cited

OTHER PUBLICATIONS

ExPASy, "ENZYME entry: EC 3.1.1.1," archived Dec. 4, 2013, retrieved Jan. 15, 2017, Internet Archive, [http://web.archive.org/web/20131204154025/http://enzyme.expasy.org/EC/3.1.1.1] (2 pages).
ExPASy, "ENZYME entry: EC 4.2.1.17," archived May 17, 2013, retrieved Jan. 15, 2017, Internet Archive, [http://web.archive.org/web/20130517111110/http://enzyme.expasy.org/EC/4.2.1.17] (3 pages).
ExPASy, "ENZYME entry: EC 6.4.1.2," archived Feb. 22, 2014, retrieved Jan. 5, 2017, Internet Archive, [http://web.archive.org/web/20140222190906/http://enzyme.expasy.org/EC/6.4.1.2] (8 pages).
Lee, S. et al., "Heterologous co-expression of accA, fabD, and thioesterase genes for improving long-chain fatty acid production in *Pseudomonas aeruginosa* and *Escherichia coli*," Appl Biochem Biotechnol., 2012, 167(1): 24-38.
Liang, J. et al., "Coordinated induction of multi-gene pathways in *Saccharomyces cerevisiae*," Nucleic Acids Res., 2013;41(4): e54, Epub Dec. 22, 2012 (10 pages).
Marchler-Bauer, A., et al., "CDD: specific functional annotation with the Conserved Domain Database," *Nucleic Acids Res.*, 37.suppl 1: D205-D210 (2009).
Rathnasingh, C. et al., "Development and evaluation of efficient recombinant *Escherichia coli* strains for the production of 3-hydroxypropionic acid from glycerol," Biotechnol Bioeng., 2009, 104(4): 729-739.
Xu, P. et al, "ePathBrick: a synthetic biology platform for engineering metabolic pathways in *E. coli,*" ACS Synth Biol., 2012, 1(7): 256-66.
International Search Report and Written Opinion in International Application No. PCT/US2015/036074, dated Sep. 9, 2015, 14 pages.
Invitation to Pay Fees in International Application No. PCT/US2015/036086, dated Sep. 16, 2015, 7 pages.
Invitation to Pay Fees in International Application No. PCT/US2015/036092, dated Sep. 21, 2015, 8 pages.
Uniprot Accession No. P69909, Jan. 4, 2005, 1 page.
"*Enterococcus faecalis* V583 bifuntional acetaldehyde-CoA/Alcohol Dehydrogenase" biocyc.org retrieved on Jun. 19, 2014, http://biocyc.org/EFAE226185/N_EW-IMAGE?type=ENZYME &object=GH11-877-MONOMER, 9 pages.
"Information on EC 1.2.57—butanal dehydrogenase," brenda-enzymes.org, retrieved on Jun. 19, 2014, http://www.brenda-enzymes.org/php/result_flat.php4?ecno=1.2.1.57, 6 pages.
"BRENDA—The comprehensive Enzyme Information System," Jul. 2011, retrieved on Sep. 19, 2014, http://web.archive.org/web/20111009205602/http://www.brenda-enzymes.org/, 1 page.
Aimin et al., "*Nocardia* sp. carboxylic acid reductase: cloning, expression, and characterization of a new aldehyde oxidoreductase family," Appl. Environ. Microbiol., 2004, 70:1874-1881.
Akita et al., "Highly stable meso-diaminopimelate dehydrogenase from an Ureibacillus thermosphaericus strain A1 isolated from a Japanese compost: purification, characterization and sequencing," AMB Express, 2011, 1:43, 8 pages.
Alber et al., "Malonyl-coenzyme A reductase in the modified 3-hydroxypropionate cycle for autotrophic carbon fixation in archaeal *Metallosphaera* and *Sulfolobus* spp," J. Bacteriology, 2006, 188:8551-8559.
Aloulou et al., "Purification and biochemical characterization of the LIP2 lipase from Yarrowia lipolytica," Biochim. Biophys. Acta, 2007, 1771:228-237.
Anton et al., Polyamides, Fibers, Encyclopedia of Polymer Science and Engineering, 2001, 11:409-445.
Atsumi et al., "Acetolactate synthase from *Bacillus subtilis*serves as a 2-ketoisovalerate decarboxylase from isobutanol synthesis in *Escherichi coli*," Applied and Environ. Microbiol., 2009, 75(19):6306-6311.

Aursnes et al., "Total Synthesis of the Lipid Mediator PD1(n-3 DPA): Configurational Assignments and Anti-Inflammatory and Pro-resolving Actions," Journal of Natural Products, Feb. 2014, 77:910-916.
Azuma et al., "Naphthalene—a constituent of Magnolia flowers," Phytochemistry, 1996, 42:999-1004.
Barker et al., "Enzymatic reactions in the degradation of 5-aminovalerate by Clostridium aminovalercum," J Biol Chem., 1987, 262(19):8994-9003.
Becker et al., "Metabolic flux engineering of L-lysine production in Corynebacterium glutamicum—over expression and modification of G6P dehydrogenase," J Biotechnol. 2007, 132(2):99-109.
Bellmann et al., "Expression control and specificity of the basic amino acid exporter LysE of Corynebacterium glutamicum," Microbiology 2001, 147:1765-1774.
Bennett et al., "Purification and properties of ϵ-caprolactone hydrolases from Acinetobacter NCIB 9871 and Nocardia globevula CL1," Journal of General Microbiology, 1988 134: 161-168.
Bergler et al., "Protein EnvM is the NADH-dependent enoyl-ACP reductase (FabI) of *Escherichia coli*," J. Bio Chem, 1993, 269(8):5493-5496.
Bernstein et al., "Transfer of the high-GC cyclohexane carboxylate degradation pathway from Rhodopseudomonas palustris to *Escherichia coli* for production of biotin," Metabolic Engineering, May 2008, 10(3-4):131-140.
Berthold et al., "Structure of the branched-chain keto acid decarboxylase (KdcA) from Lactococcus lactis provides insights into the structural basis for the chemoselective and enantioselective carboligation reaction," Acta Crystallographica Sec. D, 2007, D63:1217-1224.
Binieda et al., "Purification, characterization, DNA Sequence and cloning of a pimeloyl-CoA synthetase from Pseudomonas medocin 35," Biochem J., 1999, 340:793-801.
Bond-Watts et al., "Biochemical and Structural Characterization of the trans-Enoly-CoA Reductase from Treponema denticola," Biochemistry, 2012, 51:6827-6837.
Bordeaux et al., "Catalytic, Mild, and Selective Oxyfunctionalization of Linear Alkanes: Current challenges," Angew. Chem. Int. Ed., 2012, 51:10712-10723.
Bordes et al., " Isolation of a thermostable variant of Lip2 lipase from Yarrowia lipolytica by directed evolution and deeper insight into the denaturation mechanisms," Journal of Biotechnology, 2011, 156: 117-124.
Botting, "Substrate Specificity of the 3-Methylaspartate Ammonia-Lyase Reaction: Observation of Differential Relative Reaction Rates for Substrate-Product Pairs," Biochemistry, 1988, 27:2953-2955.
Boylan et al., "Functional identification of the fatty acid reductase components encoded in the luminescence operon of Vibrio fischeri," Journal of Bacteriology, 1985, 163(3):1186-1190.
Boylan et al., "Lux C, D and E genes of the Vibrio fischeri luminescence operon code for the reductase, transferase, and synthetase enzymes involved in aldehyde biosynthesis," Photochemistry and photobiology, 1989, 49:681-688.
Bramer et al., "The methylcitric acid pathway in Ralstonia eutropha: new genes identified involved in propionate metabolism," Microbiology 2001, 147:2203-2214.
Breithaupt et al., "Crystal structure of 12-oxophytodienoate reductase 3 from tomato: self-inhibition by dimerization," Proc Natl. Acad Sci. USA, 2006, 103:14337-14342.
Brigham et al., "Engineering Ralstonia eutropha for Production of Isobutanol from CO2, H2, and O2," Advanced Biofuels and Bioproducts 2013, Chapter 39, pp. 1065-1090.
Brzostowicz et al., " mRNA differential display in a microbial enrichment culture: simultaneous identification of three cyclohexanonemonooxygenases from three species," Applied and Environmental Microbiology, 2003, 69: 334-342.
Brzostowicz et al., "Identification of two gene clusters involved in cyclohexanone oxidation in Brevibacterium epidermidis strain HCU," Applied and Microbiological Biotechnology, 2002, 58:781-789.
Buckel et al., "Glutaconate CoA-transferase from Acidaminococcus fermentans," Eur J. Biochem, 1981, 118:315-321.

(56) References Cited

OTHER PUBLICATIONS

Budde et al., "Roles of Multiple Acetoacetyl Coenzyme A Reductases in Polyhydroxybutyrate Biosynthesis in Ralstonis eutropha H16," J Bacteriol. 2010, 192(20):5319-5328.

Bugg et al., "The emerging role for bacteria in lignin degradation and bio-product formation," Curr Opin Biotechnol 2011, 22(3):394-400.

Buhler et al., "Occurrence and the possible physiological role of 2-enoate reductases," FEBS Letters, 1980, 109:244-246.

Bult et al., "Complete genome sequence of the methanogenicarchaeon, Methanococcus jannaschii," Science, 1996, 273: 1058-1073.

Bunik et al., "Kinetic properties of the 2-oxoglutarate dehydrogenase complex from Azotobacter vinelandii evidence for the formation of a precatalytic complex with 2-oxoglutarate," Eur J Biochem., 267(12):3583-3591, Jun. 2000.

Cantu et al., "Thioesterases: A new perspective based on their primary and tertiary structures," Protein Science 2010, 19:1281-1295.

Chayabutra and Ju, "Degradation of n-hexadecane and its metabolites by Pseudomonas aeruginosa under microaerobic and anaerobic denitrifying conditions," Appl Environ Microbiol., 66(2):493-498, Feb. 2000.

Cheesbrough and Kolattukudy, "Alkane biosynthesis by decarbonylation of aldehydes catalyzed by a particulate preparation from Pisum sativum," PNAS USA, 1984, 81(21):6613-7.

Chen et al., "Termites fumigate their nests with naphthalene," Nature, 1998, 392:558-559.

Cheng et al., "Genetic Analysis of a Gene Cluster for Cyclohexanol Oxidation in *Acinetobacter* sp. Strain SE19 by In Vitro Transposition," Journal of Bacteriology, 2000, 182(17):4744-4751.

Clomburg et al., "Integrated engineering of Beta-oxidation reversal and omega-oxidation pathways for the synthesis of medium chain omega-functionalized carboxylic acids," Metabolic Engineering, Jan. 2015, 28:202-212.

Coon, "Omega oxygenases: nonheme-iron enzymes and P450 cytochromes," Biochemical & Biophysical Research Communications, 2005,338:378-385.

Cronan and Lin, "Synthesis of the α,ω-dicarboxylic acid precursor of biotin by the canonical fatty acid biosynthetic pathway," Current Opinion in Chem Biol., 2011, 15:407-413.

Cryle and Schlichting, "Structural insights from a P450 Carrier Protein complex reveal how specificity is achieved in the P450BioI ACP complex," Proceedings of the National Academy of Sciences, Oct. 2008, 105(41):15696-15701.

Cryle et al., "Carbon-carbon bond cleavage by cytochrome P450BioI (CYP107H1) E1," Chemical Communications, Jan. 2004, 86-87.

Cryle, "Selectivity in a barren landscape: the P450BioI-ACP complex," Biochemical Society Transactions, Aug. 2010, 38(4):934-939.

Da Silva et al., "Glycerol: A promising and abundant carbon source for industrial microbiology," Biotechnology Advances, 2009, 27:30-39.

Daisy et al., "Naphthalene, an insect repellent, is produced by *Muscodor vitigenus*, a novel endophytic fungus," Microbiology, 2002, 148:3737-3741.

Dalby, "Optimizing enzyme function by directed evolution," Current Opinion in Structural Biology, 2003, 13, 500-505.

Davis et al., "Overproduction of acetyl-CoA carboxylase activity increases the rate of fatty acid biosynthesis in *Escherichia coli*," J. Biol. Chem., 2000, 275(37): 28593-28598.

Day et al., "Partial purification and properties of acyl-CoA reductase from *Clostridum butyricum*," Archives of Biochemistry and Biophysics, 1978, 190(1):322-331.

Deana et al., "Substrate specificity of a dicarboxyl-CoA: Dicarboxylic acid coenzyme . A transferase from rat liver mitochondria," Biochem Int., 1992, 26:767-773.

Dekishima et al., "Extending Carbon Chain Length of 1-Butanol Pathway for 1-Hexanol Synthesis from Glucose by Engineered *Escherichia coli*," J. Am. Chem. Soc., Aug. 2011, 133(30):11399-11401.

Dellomonaco et al., "Engineered reversal of the [beta]-oxidation cycle for the synthesis of fuels and chemicals," Nature, Jan. 2011, 476(7360):355-359.

Deshmukh and Mungre, "Purification and properties of 2-aminoadipate: 2-oxoglutarate aminotransferase from bovine kidney," Biochem J, 1989, 261(3):761-768.

Doan et al., "Functional expression of five Arabidopsis fatty acyl-CoA reductase genes in *Escherichia coli*," J. Plant Physiology, 2009, 166:787-796.

Dobritzsch et al., "High resolution crystal structure of pyruvate decarboxylase from Zymomonas mobilis. Implications for substrate activation in pyruvate decarboxylases," J. Biol. Chem., 1998, 273:20196-20204.

Donoghue and Trudgill, "The Metabolism of Cyclohexanol by Acinetobacter NCIB9871," Eur J Bochem., 1975, 60:1-7.

Drevland et al., "Enzymology and Evolution of the Pyruvate Pathway to 2-Oxobutyrate in Methanocaldococcus jannaschii," J. Bacteriol., Apr. 2007, 189(12):4391-4400.

Drevland et al., "Methanogen homoaconitase catalyzes both hydrolyase reactions in coenzyme B biosynthesis," J Biol Chem., Oct. 2008, 283: 28888-28896.

Egmond et al., "Fusarium solani pisi cutinase," Biochimie, Nov. 2000, 82(11):1015-1021.

Eikmanns and Buckel, "Properties of 5-hydroxyvalerate CoA-transferase from *Clostridium aminovalericum*," Biol. Chem, 1990, 371:1077-1082.

Elkins et al., "Substrate Specificity of the RND-Type Multidrug Efflux Pumps AcrB and AcrD of *Esherichia coli* Is Determined Predominately by Two Large Periplasmic Looops," J Bacteriol. 2002, 184(23):6490-6499.

Elshahed et al., "Benzoate Fermentation by the Anaerobic bacterium *Syntrophus aciditrophicus* in the Absence of Hydrogen-Using Microorganisms," Applied and Environ Microbiology, 2001, 67(12):5520-5525.

Elshahed et al., "Metabolism of Benzoate, Cyclohex-1-ene Carboxylate, and Cyclohexane Carboxylate by Syntrophus aciditrophicus Strain SB in Syntrophic Association with H2-Using Microorganisms," Applied and Environ. Microbiol., Apr. 2001, 67(4):1728-1738.

Eurich et al., "Cloning and characterization of three fatty alcohol oxidase genes from Candida tropicalis strain ATCC 20336," Applied & Environmental Microbiology, 2004, 70(8): 4872-4879.

Ferreira et al. "A member of the sugar transporter family, Stl1p is the glycerol/H=symporter in *Saccharomyces cerevisiae*," Molecular Biology of the Cell, American Society for Cell Biology, Apr. 1, 2005, 16(4):2068-2076.

Fickers et al., "Carbon and nitrogen sources modulate lipase production in the yeast *Yarrowia lipolytica*," Journal of Applied Microbiology , 2004, 96:742-9.

Fickers et al., "The lipases from Yarrowia lipolytica: Genetics, production, regulation, biochemical characterization and biotechnological applications," Biotechnology Advances, 2011, 29: 632-644.

Fonknechten et al., "Clostridium sticklandii, a specialist in amino acid degradation: revisiting its metabolism through its genome sequence," BMC Genomics, 2010, 11:1-12.

Fuchs et al., "Microbial degradation of aromatic compounds—from one strategy to four," Nat Rev Microbiol., Oct. 3, 2011;9(11):803-816, Oct. 2011.

Fukui et al., "Expression and Characterization of ®-Specific Enoly Coenzyme A Hydratase Involved in Polyhydroxyalkanoate Biosynthesis by Aeromonas caviae," J Bacteriol. 1998, 180(3):667-673.

Funhoff et al., "CYP153A6, a Soluble P450 Oxygenase Catalyzing Terminal-Alkane Hydroxylation," J Bacteriol. 2006, 188(14):5220-5227.

Funhoff et al., "Expression and Characterization of (R)-Specific Enoyl Coenzyme A Hydratase Involved in Polyhydroxyalkanoate Biosynthesis by Aeromonas caviae," J. Bacteriol., 2006, 188(14):5220-5227.

(56) References Cited

OTHER PUBLICATIONS

Gallus and Schink, "Anaerobic degradation of pimelate by newly isolated denitrifying bacteria," Microbiology, 1994, 140:409-416.

Gao et al: "A novel meso-diaminopimelate dehydrogenase from Symbiobacterium themiophilum: overexpression, characterization, and potential for D-amino acid synthesis," Applied and Environmental Microbiology, 2012, 78:8595-8600.

Gasmi et al., "A molecular approach to optimize hIFN α2b expression and secretion in Yarrowia lipolytica," Appl Microbiol Biotechnol, 2011, 89:109-119.

GenBank Accession No. AAA23536, Apr. 26, 1993, 1 page.
GenBank Accession No. AAA24664.1, Mar. 25, 1993, 1 page.
Genbank Accession No. AAA24665.1, Apr. 26, 1993, 1 page.
Genbank Accession No. AAA57874.1, Nov. 21, 2011, 2 pages.
Genbank Accession No. AAA69178.1, Jul. 1, 1995, 1 page.
Genbank Accession No. AAA92347.1, Mar. 15, 1996, 1 page.
GenBank Accession No. AAB35106, Nov. 1995, 1 page.
GenBank Accession No. AAB60068.1, dated Jul. 1995, 1 page.
GenBank Accession No. AAB98494.1, Oct. 23, 2009, 2 pages.
GenBank Accession No. AAB99007.1, Oct 23, 2009, 2 pages.
GenBank Accession No. AAB99100, Aug. 27, 1996, 2 pages.
GenBank Accession No. AAB99277.1, Oct. 23, 2009.
GenBank Accession No. AAC23921, Apr. 23, 2003, 2 pages.
Genbank Accession No. AAC76437.1, dated Oct. 2010, 2 pages.
GenBank Accession No. AAF02538.1, Oct. 20, 1999, 2 pages.
Genbank Accession No. AAG08191.1, Jan. 31, 2014, 2 pages.
Genbank Accession No. AAK73167.2, retrieved May 19, 2014, 1 page.
Genbank Accession No. AAN37290.1, retrieved May 19, 2014, 1 page.
GenBank Accession No. AAO77182, Mar. 28, 2003, 1 page.
GenBank Accession No. AAQ59697.1, Jan. 31, 2014, 2 pages.
GenBank Accession No. AAS11092.1, Mar. 5, 2010, 1 page.
GenBank Accession No. AAS43086.1, dated Nov. 2011, 1 page.
Genbank Accession No. AAT43726, retrieved May 19, 2014, 1 page.
GenBank Accession No. AAW66853.1, Feb. 12, 2005, 1 page.
Genbank Accession No. AAY39893.1, Jan. 31, 2014, 2 pages.
GenBank Accession No. AB005294, Feb. 2000, 2 pages.
Genbank Accession No. ABA81135.1, Jan. 28, 2014, 2 pages.
GenBank Accession No. ABC76100.1, Mar. 11, 2010, 1 page.
GenBank Accession No. ABC76101.1, Mar. 11, 2010, 1 page.
GenBank Accession No. ABC76114.1, Mar. 11, 2010, 1 page.
GenBank Accession No. ABC76260.1, Mar. 11, 2010, 1 page.
GenBank Accession No. ABC76948.1, Mar. 11, 2010, 1 page.
GenBank Accession No. ABC76949.1, Mar. 11, 2010, 1 page.
GenBank Accession No. ABC77793.1, Mar. 11, 2010, 1 page.
GenBank Accession No. ABC77794.1, Mar. 11, 2010, 1 page.
GenBank Accession No. ABC77898.1, Mar. 11, 2010, 1 page.
GenBank Accession No. ABC77899.1, Mar. 11, 2010, 1 page.
GenBank Accession No. ABC77900.1, Mar. 11, 2010, 1 page.
GenBank Accession No. ABC78517.1, Mar. 11, 2010, 1 page.
GenBank Accession No. ABC78756.1, Mar. 11, 2010, 1 page.
GenBank Accession No. ABC78863.1, Mar. 11, 2010, 1 page.
GenBank Accession No. ABC78881.1, Mar. 11, 2010, 1 page.
GenBank Accession No. ABC78950.1, Mar. 11, 2010, 1 page.
Genbank Accession No. ABE47158.1, Jan. 26, 2014, 1 page.
Genbank Accession No. ABE47159.1, Jan. 28, 2014, 2 pages.
Genbank Accession No. ABE47160.1, Jan. 28, 2014, 1 page.
Genbank Accession No. AB183656.1, Jan. 3, 2007, 1 page.
Genbank Accession No. ABJ63754.1, dated Mar. 2010, 1 page.
Genbank Accession No. ABK71854.1, Jan. 31, 2014, 2 pages.
Genbank Accession No. ABK75684.1, Jan. 31, 2014, 2 pages.
Genbank Accession No. ACC40567.1, Jan. 31, 2014, 2 pages.
Genbank Accession No. ACJ06772.1, Dec. 4, 2009, 1 page.
Genbank Accession No. ADG98140.1, Jan. 28, 2014, 2 pages.
GenBank Accession No. ADK19581.1, Sep. 20, 2010, 2 pages.
GenBank Accession No. AE000666.1, Jan. 5, 2006, 309 pages.
GenBank Accession No. AEA39183.1, Apr. 4, 2011, 1 page.
GenBank Accession No. AJ012480.1, Apr. 2005, 2 pages.
GenBank Accession No. AY143338, Apr. 2003, 5 pages.
GenBank Accession No. AY495697, Mar. 2004, 3 pages.
Genbank Accession No. BAB91331.1, retrieved May 19, 2014, 1 page.
Genbank Accession No. BAC06606, Aug. 1, 2002, 1 page.
GenBank Accession No. BAD69624, Sep. 2005, 1 page.
GenBank Accession No. BAF92773, Nov. 27, 2007, 1 page.
Genbank Accession No. BAF94304.1, retrieved May 19, 2014, 1 page.
Genbank Accession No. CAA44858.1, Apr. 28, 1992, 1 page.
GenBank Accession No. CAA81612.1, Apr. 18, 2005, 2 pages.
GenBank Accession No. CAA90836.1, Apr. 18, 2005, 2 pages.
GenBank Accession No. CAB13029.2, Nov. 20, 1997, 2 pages.
GenBank Accession No. CAC48239.1, Apr. 15, 2005, 2 pages.
GenBank Accession No. CAE26094.1, Apr. 17, 2005, 2 pages.
GenBank Accession No. CAE26097.1, Apr. 17, 2005, 2 pages.
Genbank Accession No. CAH04396.1, Apr. 7, 2005, 1 page.
Genbank Accession No. CAH04397.1, Apr. 7, 2005, 2 pages.
Genbank Accession No. CAH04398.1, Apr. 7, 2005, 1 page.
GenBank Accession No. CCC78182.1, dated Jul. 2011, 1 page.
GenBank Accession No. D84432, replaced by Q9SKC9.1, Feb. 2005, 2 pages.
GenBank Accession No. D87518, Jul. 31, 1997, 2 pages.
GenBank Accession No. EFV11917.1, Sep. 9, 2013, 2 pages.
Genbank Accession No. EIV11143.1, Jun. 19, 2012, 2 pages.
GenBank Accession No. HQ418483.1, Apr. 4, 2011, 2 pages.
GenBank Accession No. JA114119.1, Apr. 19, 2011, 1 page.
GenBank Accession No. JA114148, Apr. 2011, 1 page.
GenBank Accession No. JA114151, Apr. 2011, 1 page.
GenBank Accession No. JA114154, Apr. 2011, 1 page.
GenBank Accession No. JA114157, Apr. 2011, 1 page.
GenBank Accession No. L42023, Oct. 2009, 285 pages.
GenBank Accession No. MJ0663, Oct. 1, 2014, 4 pages.
GenBank Accession No. NC_013156.1, Jun. 10, 2013, 2 pages.
GenBank Accession No. NC_014122.1, Jun. 10, 2013, 2 pages.
GenBank Accession No. NC_015562.1, Jun. 10, 2013, 2 Pages.
GenBank Accession No. NM_001246944, Dec. 2011, 2 pages.
GenBank Accession No. NM_001247852, Dec. 2011, 2 pages.
GenBank Accession No. NM_133240, Feb. 25, 2002, 2 pages.
GenBank Accession No. NP_247129, Jun. 10, 2013, 2 pages.
GenBank Accession No. NP_247250, Jun. 10, 2013, 2 pages.
GenBank Accession No. NP_247647, Jun. 10, 2013, 2 pages.
GenBank Accession No. P22822, Mar. 1, 1992, 1 page.
GenBank Accession No. P94129 (replaced by Q6F7B8), Mar. 1, 2004, 1 page.
GenBank Accession No. 548141, May 1993, 2 pages.
GenBank Accession No. XM_001827609, Mar. 2011, 2 pages.
GenBank Accession No. YP_001394144.1, Jul. 26, 2007, 1 page.
GenBank Accession No. YP_003127480, Jun. 10, 2013, 2 pages.
GenBank Accession No. YP_003128272, Jun. 10, 2013, 2 pages.
GenBank Accession No. YP_003615747, Jun. 10, 2013, 1 page.
GenBank Accession No. YP_003615922, Jun. 10, 2013, 2 pages.
GenBank Accession No. YP_004483786, Jul. 6, 2013, 2 pages.
GenBank Accession No. YP_400611, Nov. 10, 2005, 2 pages.
GenBank Accession No. YP_959486, Jan. 3, 2007, 2 pages.
GenBank Accession No. YP_959769, Jan. 3, 2007, 2 pages.

Gerbling et al., "A new acyl-CoA synthetase, located in higher plant cytosol," J Plant Physiol, 1994, 143:561-564.

Gloeckler et al., "Cloning and characterization of the *Bacillus sphaericus* genes controlling the bioconversion of pimlate into dethiobiotin," Gene, 1990, 87:63-70.

Gloerich et al., "Peroxisomal trans-2-enoyl-CoA reductase is involved in phytol degradation," FEBS Letters 2006, 580:2092-2096.

Gocke et al., "Comparative characterization of ThPP-dependent decarboxylases," J. Mol. Cat. B: Enzymatic, 2009, 61:30-35.

Gonzalez-Lopez, "Genetic control of extracellular protease synthesis in the yeast *Yarrowia lipolytica*," Genetics, 2002, 160: 417-427.

Graupner et al., "Identification of the gene encoding sulfopyruvate decarboxylase, an enzyme involved in biosynthesis of coenzyme M," J Bacterial., 2000, 182: 4862-4867.

(56) References Cited

OTHER PUBLICATIONS

Guerrillot et al., "Purification and Characterization of Two Aldehyde Dehydrogenases from Pseudomonas aeruginosa," Eur. J. Biochem. 1977, 81:185-192.
Hall, "The Contribution of Horizontal Gene Transfer to the Evolution of Fungi," Duke University Libraries, May 10, 2007, 163 pages.
Hall, "Asymmetric bioreduction of activated alkenes using cloned 12-oxophytodienoate reductase isoenzymes OPR-1 and OPR-3 from *Lycopersicon esculentum* (tomato): a striking change of stereoselectivity," Agnew Chem Int. Ed., 2007, 46:3934-3937.
Han et al., "Oxaloacetate hydrolase, the C—C bond lyase of oxalate secreting fungi," J. Biol. Chem. 2007, 282:9581-9590.
Harrison and Harwood, "The pimFABCDE operon from Phodopseudomonas palustris mediates dicarboxylic acid degradation and participates in anaerobic benzoate degradation," Microbiology, 2005, 151:727-736.
Harwood and Parales, "The beta-ketoadipate pathway and the biology of self-identity," Ann. Rev. Microbiol., 1996, 50:553-590.
Harwood et al., "Anaerobic metabolism of aromatic compounds via the benzoyl-CoA pathway," FEMS Microbiology Reviews, 1999, 22:439-458.
Hasson et al., "The crystal structure of benzoylformate decarboxylase at 1.6A resolution—Diversity of catalytic residues in ThDP-dependent enzymes," Biochemistry, 1998, 37:9918-9930.
Hayaishi et al., "Enzymatic Studies on the Metabolism of β-Alanine," J. Biol. Chem., 1961, 236, p. 781-790.
Haywood et al., "Characterization of two 3-ketothiolases possessing differing substrate specificities in the polyhydroxyalkanoate synthesizing organism *Alcaligenes eutrophus*," FEMS Microbiology Letters 1988, 52(1-2):91-96.
He et al., "*Nocardia* sp. carboxylic acid reductase: cloning, expression, and characterization of a new aldehyde oxidoreductase family," Applied and Environmental Microbiology, 2004, 70:1874-1881.
Heath et al., "The enoyl-[acyl-carrier-protein] reductases FabI and FabL from Bacillus subtilis," J Biol Chem., 275(51):40128-40133, Dec. 22, 2000.
Hermann et al, "Industrial production of amino acids by corynefoini bacteria," J Biotechnol. 2003, 104(1-3):155-172.
Hess et al., "Extremely thermostable esterases from the thermoacidophilic euryarchaeon *Picrophilus torridus*," Extremophiles, 2008, 12:351-364.
Ho and Weiner, "Isolation and characterization of an aldehyde dehydrogenase encoded by the aldB gene of *Escherichia coli*," J. Bacteriol., 2005, 187(3):1067-1073.
Hoffmeister et al., "Mitochondrial trans-2-enoyl-CoA reductase of wax ester fermentation from Euglena gracilis defines a new family of enzymes involved in lipid synthesis," J Biol Chem., 280(6):4329-4338. Epub Nov. 29, 2004.
Hofvander et al., "A prokaryotic acyl-CoA reductase performing reduction of fatty acyl-CoA to fatty alcohol," FEBS Letters, 2001, 585:3538-3543.
Holden et al., "Chorismate lyase: kinetics and engineering for stability," Biochim Biophys Acta., Jan. 31, 2002, 1594(1):160-167.
Hooks et al., "Long-chain acyl-CoA oxidases of Arabidopsis," Plant J., 1999, 20:1-13.
Horning et al., "α-Ketoglutaric Acid," Organic Syntheses, 1955, 3: 510-512.
Hotta et al., "Extremely Stable and Versatile Carboxylesterase from a Hyperthermophilic Archaeon," Applied and Environmental Microbiology, 2002, 68(8):3925-3931.
Howell et al., "Alpha-keto acid chain elongation reactions involved in the biosynthesis of coenzyme B (7-mercaptoheptanoyl threonine phosphate) in methanogenicArchaea," Biochemistry, 1989, 37: 10108-10117.
Howell et al., "Identification of enzymes homologous to isocitrate dehydrogenase that are involved in coenzyme Band leucine biosynthesis in methanoarchaea," J Bacteriol., Sep. 2000, 182: 5013-5016.
Hugler et al., "Malonyl-coenzyme A reductase from Chloroflexus aurantiacus, a key enzyme of the 3-hydroxypropionate cycle for autotrophic CO(2) fixaction," J. Bacteriology, 2002, 184:2404-2410.
Huhn et al., "Identification of the membrane protein SucE and its role in succinate transport in Corynebacterium glutamicum," Appl Microbiol Biotechnol. 2011, 89(2):327-335.
Hunt et al., "Characterization of an acyl-CoA thioesterase that functions as a major regulator of peroxisomal lipid metabolism," J. Biol Chem, 2002, 277:1128-1138.
International Preliminary Report on Patentability for International Application No. PCT/US2012/069934, dated Jun. 17, 2014, 15 pages.
International Preliminary Report on Patentability in International Application No. PCT/US 2012/042777, dated Jan. 10, 2013, 22 pages.
International Preliminary Report on Patentability in International Application No. PCT/US 2012/044984, dated Jan. 28, 2014, 11 pages.
International Preliminary Report on Patentability for International Application No. PCT/US2013/075058, dated Jun. 25, 2015, 11 pages.
International Preliminary Report on Patentability for International Application No. PCT/US2013/075087, dated Jun. 25, 2015, 11 pages.
International Preliminary Report on Patentability for International Application No. PCT/US2013/077445, dated Jul. 9, 2015, 11 pages.
International Preliminary Report on Patentability for International Application No. PCT/US2013/077420, dated Jul. 9, 2015, 14 pages.
International Preliminary Report on Patentability for International Application No. PCT/US2013/077419, dated Jul. 9, 2015, 13 pages.
International Preliminary Report on Patentability for International Application No. PCT/US2013/077430, dated Jul. 9, 2015, 18 pages.
International Preliminary Report on Patentability for International Application No. PCT/US2013/077413, dated Jul. 9, 2015, 13 pages.
International Preliminary Report on Patentability for International Application No. PCT/US2013/077411, dated Jul. 9, 2015, 12 pages.
International Preliminary Report on Patentability for International Application No. PCT/US2013/077423, dated Jul. 9, 2015, 14 pages.
International Search Report and Written Opinion in International Application No. PCT/US2014/052950, dated Dec. 3, 2014, 15 pages.
International Search Report and Written Opinion for International Application No. PCT/US2012/069934, dated Jan. 17, 2014, 21 pages.
International Search Report and Written Opinion in International Application No. PCT/US2012/042747, dated Jan. 14, 2013, 19 pages.
International Search Report and Written Opinion in International Application No. PCT/US 2012/042777, dated Sep. 11, 2012, 9 pages.
International Search Report and Written Opinion in International Application No. PCT/US 2012/044984, dated Dec. 17, 2013, 17 pages.
International Search Report and Written Opinion in International Application No. PCT/US 2012/071472, dated Dec. 17, 2013, 17 pages.
International Search Report and Written Opinion in International Application No. PCT/US2013/075058, dated Sep. 15, 2014, 17 pages.
International Search Report and Written Opinion in International Application No. PCT/US2013/075087, dated Aug. 4, 2014, 18 pages.
International Search Report and Written Opinion in International Application No. PCT/US2013/077411, dated Sep. 24, 2014, 18 pages.
International Search Report and Written Opinion in International Application No. PCT/US2013/077413, dated Jul. 22, 2014, 20 pages.
International Search Report and Written Opinion in International Application No. PCT/US2013/077419, dated Jun. 16, 2014, 19 pages.

(56) References Cited

OTHER PUBLICATIONS

International Search Report and Written Opinion in International Application No. PCT/US2013/077420, dated Jul. 21, 2014, 21 pages.
International Search Report and Written Opinion in International Application No. PCT/US2013/077423, dated Jul. 21, 2014, 22 pages.
International Search Report and Written Opinion in International Application No. PCT/US2013/077430, dated Nov. 10, 2014, 23 pages.
International Search Report and Written Opinion in International Application No. PCT/US2013/077445, dated Sep. 15, 2014, 17 pages.
International Search Report and Written Opinion in International Application No. PCT/US2014/053222, dated Mar. 4, 2015, 18 pages.
International Search Report and Written Opinion in International Application No. PCT/US2015/031227, dated Jul. 31, 2015, 40 pages.
International Search Report and Written Opinion in International Application No. PCT/US2015/036050, dated Aug. 14, 2015, 38 pages.
International Search Report and Written Opinion in International Application No. PCT/US2015/036057, dated Aug. 14, 2015, 74 pages.
Invitation to Pay Additional Fees in International Application No. PCT/US2013/075058, dated Jul. 7, 2014, 7 pages.
Invitation to Pay Additional Fees in International Application No. PCT/US2013/07745, dated Jul. 7, 2014, 9 pages.
Invitation to Pay Additional Fees in International Application No. PCT/US2014/053222, dated Dec. 15, 2014, 8 pages.
Invitation to Pay Fees in International Application No. PCT/US2013/075087, dated May 16, 2014, 9 pages.
Invitation to Pay Fees in International Application No. PCT/US2013/077411, dated Jul. 16, 2014, 9 pages.
Invitation to Pay Fees in International Application No. PCT/US2013/077413, dated May 12, 2014, 9 pages.
Invitation to Pay Fees in International Application No. PCT/US2013/077419, dated Apr. 16, 2014, 9 pages.
Invitation to Pay Fees in International Application No. PCT/US2013/077420, dated May 13, 2014, 9 pages.
Invitation to Pay Fees in International Application No. PCT/US2013/077423, dated May 13, 2014, 10 pages.
Invitation to Pay Fees in International Application No. PCT/US2013/077430, dated Aug. 25, 2014, 9 pages.
Ishige et al., "Wax Ester Production from n-Alkanes by *Acinetobacter* sp. Strain M-1: Ultrastructure of Cellular Inclusions and Role of Acyl Coenzyme A Reductase," Appl. Envtl. Microbiology, 2002, 68:1192-1195.
Ishikawa et al., "The pathway via D-galacturonate/L-galactonate is significant for ascorbate biosynthesis in Euglena gracilis: identification and functional characterization of aldonolactonase," Journal of Biologioal Chemistry, 2008, 283:31133-31141.
Iwaki et al., "Cloning and Characterization of a Gene Cluster Involved in Cyclopentanol Metabolism in *Comamonas* sp. Strain NCIMB 9872 and Biotransformations Effected by *Escherichia coli*-Expressed Cyclopentanone 1,2-Monooxygenase," Appl Environ Microbiol., 2002, 68(11):5671-5684, 14 pages.
Iwaki et al., "Identification of a Transcriptional Activator (ChnR) and a 6-Oxohexanoate Dehydrogenase (ChnE) in the Cyclohexanol Catabolic Pathway in *Acinetobacter* sp. Strain NCIMB 9871 and Localization of the Genes That Encode Them," Appl. Environ. Microbiol., 1999, 65(11):5158-5162.
Izumi et al., "Structure and Mechanism of HpcG, a Hydratase in the Homoprotocatechuate Degradation Pathway of *Escherichia coli*," J. Mol. Biol., 2007, 370:899-911.
Izumi et al., "The pimeloyl-CoA synthetase responsible for the first step in biotin biosynthesis by microorganisms," Agr. Biol. Chem., 1974, 38:2257-2262.

Jacob et al., "Glutaconate CoA-transferase from *Acidamiococcus fermentans*: the crystal structure reveals homology with other CoA-transferases," Structure, 1997, 5:415-426.
Jang et al., "Bio-based production of C2-C6 platform chemicals," Biotechnol. & Bioengineering, 2012, 109(10):2437-2459.
Jarboe, "YqhD: a broad-substrate range aldehyde reductase with various applications in production of biorenewable fuels and chemicals," Appl Microbiol Biotechnol., 2011, 89(2):249-257.
Jaremko et al., "The initial metabolic conversion of levulinic acid in Cupriavidus nectar," J. Biotechnol., 2011, 155(3):293-298.
Jeyakanthan et al., "Substrate specificity determinants of the methanogen homoaconitase enzyme: structure and function of the small subunit," Biochemistry, 2010, 49:2687-2696.
Jing et al., "Phylogenetic and experimental characterization of an acyl-ACP thioesterase family reveals significant diversity in enzymatic specificity and activity," BMC Biochemistry, 2011, 12:44, 16 pages.
Joon-Young et al., "Production of 1,2-Propanediol from Glycerol in *Saccharomyces cerevisiae*," J. Microbiology and Biotechnology, May 19, 2011, 21(8):846-853.
Kakugawa et al., "Purification and Characterization of a Lipase from the Glycolipid-Producing Yeast *Kurtzmanomyces* sp I-11," Bioscience Biotechnology Biochemistry, 2002, 66(5): 978-985.
Kato and Asano, "Cloning, nucleotide sequencing, and expression of the 2-methylasparatate ammonia-lyase gene from *Citrobacter amalonaticus* strain YG-1002," Appl. Microbiol Biotechnol, 1998, 50:468-474.
Kaulmann et al., "Substrate spectrum of omega-transaminase from Chromobacterium violaceum DSM30191 and its potential for biocatalysis," Enzyme Microb Technol. 2007, 41:628-637.
KEGG Enzyme 1.2.99.6 (last viewed on Aug. 17, 2015).
KEGG Enzyme 3.1.2.14 (last viewed on Aug. 17, 2015).
Kikuchi et al., "Characterization of a second lysine decarboxylase isolated from *Escherichia coli*," J Bacteriol, 1997, 179(14): 4486-4489.
Kim et al., "Cloning and characterization of a cyclohexanone monooxygenase gene from *Arthrobacter* sp. L661," Biotechnology Bioprocess Engineering, 2008, 13:40-47.
Kim, "Purification and properties of a diamine alpha-ketoglutarate transaminase from *Escherichia coli*," J Biol Chem 1964, 239(3):783-786.
Kitzing et al., "The 1.3 A crystal structure of the flavoprotein YqjM reveals a novel class of Old Yellow Enzymes," J. Biol. Chem., 2005, 280:27904-27913.
Kizer, "Application of Functional Genomics to Pathway Optimization for Increased Isoprenoid Production," Applied and Environmental Microbiology, 2008, 74(10)3229-3241.
Klatte et al., "Redox self-sufficient whole cell biotransformation for amination of alcohols," Bioorg & Medicinal Chem, May 2014, 22: 5578-5585.
Koch et al., "Products of Enzymatic Reduction of Benzoyl-CoA, A Key Reaction in Anaerobic Aromatic Metabolism," Eur. J. Biochemistry, Jan. 1993, 211(3):649-661.
Koch et al., "In Vivo Evolution of Butane Oxidation by Terminal Alkane Hydroxylases AlkB and CYP153A6," Appl. Environ. Microbiol., 2009, 75(2):337-344.
Kockelkorn and Fuchs, "Malonic semialdehyde reductase, succinic semialdehyde reductase, and succinyl-coenzyme A reductase from Metallosphaera sedula: enzymes of the autotrophic 3-hydroxypropionate/4-hydroxybutyrate cycle in Sulfolobales," J. Bacteriology, 2009, 191:6352-6362.
Kolattukudy, "Enzymatic synthesis of fatty alcohols in *Brassica oleracea*," Archives of Biochemistry and Biophysics, 1971, 142(2):701-709.
Köpke et al., "2,3-Butanediol Production by Acetogenic Bacteria, an Alternative Route to Chemical Synthesis, Using Industrial Waste Gas," Appl Environ Microbiol., 2011, 77(15):5467-5475.
Kulkarni and Kanekar, "Bioremediation of epsilon-caprolactam from nylon-6 waste water by use of Pseudomonas aeruginosa MCM B-407," Curr. Microbiol., 1998, 37:191-194.

(56) References Cited

OTHER PUBLICATIONS

Kung et al., "Cyclohexane carboxyl-coenzyme a (CoA) and cyclohex-1-ene-l-carboxyl-CoA dehydrogenases, two enzymes involved in the fermentation of benzoate and crotonate in Syntrophus aciditrophicus," J Bacteriol., 195(14):3193-3200, Epub May 10, 2013.
Lan et al., "Oxygen-tolerant coenzyme A-acylating aldehyde dehydrogenase facilitates efficient photosynthetic n-butanol biosynthesis in cyanobacteria," Energy Environ Sci, 2013, 6:2672-2681.
Larroy et al., "Characterization of the *Saccharomyces cerevisiae* YMR318C (ADH6) gene product as a broad specificity NADPH-dependent alcohol dehydrogenase: relevance in aldehyde reduction," Biochem J., 2002, 361(Pt 1):163-172.
Le Dall et al., "Multiple-copy integration in the yeast *Yarrowia lipolytica*," Current Genetics, 1994 26:38-44.
Lea et al., "Long-chain acyl-CoA dehydrogenase is a key enzyme in the mitochondrial B-oxidation of unsaturated fatty acids," Biochmica et Biophysica Acta, 2000, 1485: 121-128.
Lee and Meighen, "Cysteine-286 as the site of acylation of the Lux-specific fatty acyl-CoA reductase," Biochim Biophys Acta, 1997, 1338:215-222.
Lee et al., "Metabolic Engineering of Pentose Phosphate Pathway in Ralstonia eutropha for Enhanced Biosynthesis of Poly-β-hydroxybutyrate," Biotechnology Progress, 2003, 19(5):1444-1449.
Lee et al., "Synthesis of pure meso-2,3-butanediol from crude glycerol using an engineered metabolic pathway in *Escherichia coli*," Appl Biochem Biotechnol., 2012, 166(7):1801-1813.
Li et al., "Cupriavidus necator JMP 134 rapidly reduces furfural through a Zn-dependent alcohol dehydrogenase," Biodegradation, 2011, 22:1215-1225.
Lim et al., "Amplification of the NADPH-related genes zwf and gnd for the oddball biosynthesis of PHB in an *E. coli* transformant harboring a cloned phbCAB operon," J Bioscience and Bioengineering, 2002, 93(6):543-549.
Lin and Cronan, "Closing in on complete pathways of biotin biosynthesis," Molecular Biosystems, 2011, 7:1811-1821.
Lin et al., "Biotin Sythesis Begins by Hijacking the Fatty Acid Synthetic Pathway," Nature Chem Biol., Sep. 2010, 6:682-688.
Lin et al., "The BioC O-Methyltransferase Catalyzed Methyl Esterification of Malonyl-Acyl Carrier Protein, an Essential Step in Biotin Synthesis," Journal of Biological Chemistry, Sep. 2012, 287(44):37010-37020.
Lin, "Biotin Synthesis in *Escherichia coli*," PhD Dissertation, University of Illinois at Urbana-Champaign, 2012, 140 pages.
Liu and Chen, "Production and characterization of medium-chain-length polyhydroxyalkanoate with high 3-hydroxytetradecanoate monomer content by fadB and fadA knockout mutant of Pseudomonas putida KT2442," Appl. Microbiol. Biotechnol., 2007, 76(5):1153-1159.
Liu et al., "Two novel metal-independent long-chain alkyl alcohol dehydrogenases from Geobacillus thermodenitrificans NG80-2," Microbiology, 2009, 155:2078-2085.
Lopez-Sanchez et al., "Tetralin-Induced and ThnR-Regulated Aldehyde Dehydrogenase and β-Oxidation Genes in Sphingomonas macrogolitabida Strain TFA," Appl. Environ. Microbiol., 2010, 76(1):110-118.
Luo et al., "Production of 3-hydroxypropionic acid through propionaldehyde dehydrogenase PduP mediated biosynthetic pathway in Klebsiella pneumoniae," Bioresource Technology, 2012, 103:1-6.
Lütke-Eversloh & Steinbüchel, "Biochemical and molecular characterization of a succinate semialdehyde dehydrogenase involved in the catabolism of 4-hydroxybutyric acid in Ralstonia eutropha," FEMS Microbiology Letters, 1999, 181(1):63-71.
Mack and Buckel, "Conversion of glutaconate CoA-transferase from Acidaminococcus fermentans into an acyl-CoA hydrolase by site-directed mutagenesis," FEBS Letters, 1997, 405:209-212.
Maeda et al., "Purification and characterization of a biodegradable plastic-degrading enzyme from Aspergillus oryzae," Applied and Environmental Biotechnology, 2005, 67: 778-788.
Mahadik et al., "Production of acidic lipase by Aspergillus niger in solid state fermentation," Process Biochemistry, 2002, 38: 715-721.
Martin and Prather, "High-titer production of monomeric hydroxyvalerates from levulinic acide Pseudomonas putida," J. Biotechnol., 2009, 139: 61-67.
Martinez et al., "Fusarium solani cutinase is a lipolytic enzyme with a catalytic serine accessible to solvent," Nature, 1992, 356:615-618.
Matsumoto et al., "A new pathway for poly(3-hydroxybutyrate) production in *Escherichia coli* and *Corynebacterium glutamicum* by functional expression of a new acetoacetyl-coenzyme A synthase," Biosci. Biotechnol. Biochem., 2011, 75(2):364-366.
Mawal and Deshmukh, "Alpha-aminoadipate and kynurenine aminotransferase activities from rat kidney. Evidence for separate identity," J. Biol Chem, 1991, 266(4):2573-2575.
McAndrew et al., "Structural basis for substrate fatty acyl chain specificity: crystal structure of human very-long-chain acyl-CoA dehydrogenase," J. Biol. Chem., 2008, 283:9435-9443.
Meijnen et al., "Improved p-hydroxybenzoate production by engineered Pseudomonas putida S12 by using a mixed-substrate feeding strategy," Appl. Microbiol. Biotechnol., 2011, 90:885-893.
Mhetras et al., "Purification and characterization of acidic lipase from Aspergillus niger NCIM 1207," Bioresource Technology, 2009, 100: 1486-1490.
Millar et al., "CUT1, an *Arabidopsis* Gene Required for Cuticular Wax Biosynthesis and Pollen Fertility, Encodes a Very-Long-Chain Fatty Acid Condensing Enzyme," The Plant Cell, May 1999, 11(5):825-838, retrieved on Sep. 30, 2014, http://www.plantcell.org/content/11/5/825.full.
Miyazaki et al., "Alpha-Aminoadipate aminotransferase from an extremely thermophilic bacterium, *Thermus thermophilus*," Microbiology, 2004, 150(7): 2327-2334.
Mo et al., "Connecting extracellular metabolomic measurements to intracellular flux states in yeast," BMC Systems Biology, 2009, 3(37):1-17.
Mouttaki et al., "Cyclohexane Carboxylate and Benzoate Formation from Crotonate in Sytrophus aciditrophicus," Applied and Environ Microbiology, Feb. 2007, 73(3):930-938.
Murphy et al., "Fusarium polycaprolactone depolymerase is cutinase," Appl. Environm. Microbiol., 1996, 62:456-460.
Mutti et al., "Amination of ketones by employing two new (S)-selective w-transaminases and the His-tagged w-TA from Vibrio fluvialis," Eur. J. Org. Chem, 2012, 1003-1007 (Abstract).
Naggert et al., "Cloning, sequencing, and characterization of *Escherichia coli* thioesterase II," J. Biol. Chem., 1991, 266(17):11044-11050.
Neyfakh, "The Multidrug Efflux Transporter of Bacillus subtilis is a Structural and Functional Homolog of the *Staphylococcus* NorA Protein," Antimicrob Agents Chemother, 1992, 36(2):484-485.
Ng et al., "Quinolone Resistance Mediated by norA: Physiologic Characterization and Relationship to flqB, a Quinolone Resistance Locus on the *Staphylococcus aureus* Chromosome," Antimicrob Agents Chemother, 1994, 38(6):1345-1355.
Nicol et al., "Bioconversion of crude glycerol by fungi," Applied Microbiology and Biotechnology, Feb. 10, 2012, 93(5):1865-1875.
Nieder and Shapiro, "Physiological function of the Pseudomonas putida PpG6 (Pseudomonas oleovorans) alkane hydroxylase: monotetminal oxidation of alkanes and fatty acids," J. Bacteriol., 1975, 122(1):93-98.
Nishimaki et al., "Studies on the Metabolism of Unsaturated Fatty Acids. XIV.1 Purification and Properties of NADPH-Dependent trans-2-Enoyl-CoA Reductase of *Escherichia coli* K-12," J. Biochem., 1984, 95:1315-1321.
Nomura et al., "Expression of 3-Ketoacyl-Acyl Carrier Protein Reductase (fabG) Genes Enhances Production of Polyhydroxyalkanoate Copolymer from Glucose in Recombinant *Escherichia coli* JM109," Appl. Environ. Microbiol., 2005, 71(8):4297-4306.
Ohashi et al., "Continuous production of lactic acid from molasses by perfusion culture of Lactococcus lactis using a stirred ceramic membrane reactor," J. Bioscience and Bioengineering, 1999, 87(5):647-654.

(56) References Cited

OTHER PUBLICATIONS

Okuhara et al., "Formation of Glutaric and Adipic Acids from n-Alkanes with Odd and Even Numbers of Carbons by Candida tropicalis OH23," Agr. Biol. Chem., 1971, 35(9):1376-1380.
Onakunle et al., "The fomiation and substrate specificity of bacterial lactonases capable of enantioselective resolution of racemic lactones," Enzyme and Microbial Technology, 1997, 21: 245-251.
Oppenheim and Dickerson, "Adipic Acid," Kirk-Othmer Encyclopedia of Chemical Technology, 2003.
Ouchi et al., "Dual roles of a conserved pair, Arg23 and Ser20, in recognition of multiple substrates in alpha-aminoadipate aminotransferase from Thermus thermophilus," Biochem Biophys Res Commun, 2009, 388(1):21-27.
Palosaari and Rogers, "Purification and properties of the inducible coenzyme A-linked butyraldehyde dehydrogenase from Clostridium acetobutylicum," J. Bacteriol., 1988, 170(7):2971-2976.
Papanikolaou et al., "Citric acid production by Yarrowia lipolytica cultivated on olive-mill wastewater-based media," Bioresource Technol., 2008, 99(7):2419-2428.
Parthasarthy et al., "Substrate specificity of 2-hydroxyglutaryl-CoA dehydratase from *Clostiridium symbiosum*: Toward a bio-based production of adipic acid," Biochemistry, 2011, 50:3540-3550.
Pelletier and Harwood et al., "2-Hydroxycyclohexanecarboxyl coenzyme A dehydrogenase, an enzyme characteristic of the anaerobic benzoate degradation pathway used by Rhodopseudomonas palustris," J Bacteriol., 182(10):2753-2760, May 2000.
Pérez-Pantoja et al., "Metabolic reconstruction of aromatic compounds degradation from the genome of the amazing pollutant-degrading bacterium *Cupriavidus necator* JMP134," FEMS Microbiol. Rev., 2008, 32:736-794.
Peterson et al., "The Thermal Stability of the Fusarium solani pisi Cutinase as a Function of pH," BioMed Research International, 2001, 1.2:62-69.
Pignede et al., "Autocloning and Amplification of LIP2 in Yarrowia lipolytica,"Appl. Environ. Microbiol, 2000 66:3283-3289.
Pignede et al., "Characterization of an extracellular lipase encoded by LIP2 in Yarrowia lipolytica," Journal of Bacteriology, 2000, 182: 2802-2810.
Ploux et al., "Investigation of the first step of biotin biosynthesis in Bacillus sphaericus: Purification and characterization of the pimloyl-CoA synthase, and uptake of pimelate," Biochem J., 1992, 287:685-690.
Prabhu et al., "Lactate and Acrylate Metabolism by Megasphaera elsdenii under Batch and Steady-State Conditions," Applied and Environ. Microbiology, Sep. 2012, 78(24): 8564-8570.
Prather et al., "De novo biosynthetic pathways: rational design of microbial chemical factories," Current Opinion in Biotechnology, 2008, 19:468-474.
Prybylski et al., "Third-generation feed stocks for the clean and sustainable biotechnological production of bulk chemicals: synthesis of 2-hydroxyisobutyric acid," Energy, Sustainability and Society, 2012, 2:11.
Qian et al., "Metabolic engineering of *Escherichia coli* for the production of cadaverine: a five carbon diamine," Biotechnol Bioeng, 2011, 108(1):93-103.
Qiu et al., "Crystal structure and substrate specificity of the β-ketoacyl-acyl carrier protein synthase III (FabH) from *Staphylococcus aureus*," Protein Sci, 2005, 14(8):2087-2094.
Rajashekhara et al., "Propionyl-coenzyme A synthetases of *Ralstonia solanacearum* and *Salmonella choleraesuis* display atypical kenetics," FEBS Letters, 2004, 556:143-147.
Ramsay et al., "Use of a Nylon Manufacturing Waste as an Industrial Fermentation Substrate," Applied and Environmental Microbiology, 1986, 52(1):152-156.
Ray et al., "Cocrystal structures of diaminopimelate decarboxylase: mechanism, evolution, and inhibition of an antibiotic resistance accessory factor," Structure, 2002, 10(11):1499-1508.
Rea et al., "Structure and Mechanism of HpcH: A Metal Ion Dependent Class II Aldolase from the Homoprotocatechuate Degradation Pathway of *Escherichia coli*," J. Mol. Biol., 2007, 373:866-876.
Reiser and Somerville, "Isolation of mutants of *Acinetobacter calcoaceticus* deficient in wax ester synthesis and complementation of on mutation with gene encoding a fatty acyl coenzyme A reductase," J. Bacteriol., 1997, 179:2969-2975.
Rizzarelli et al., "Evidence for Selective Hydrolysis of Aliphatic Copolyesters Induced by Lipase Catalysis," Biomacromolecules, 2004, 5:433-444.
Rohdich et al., "Enoate reductases of Clostridia. Cloning, sequencing, and expression," J. Biol. Chem., 2001, 276:5779-5787.
Roje, "Vitamin B biosynthesis in plants," Phytochemistry, 2007, 68:1904-1921.
Roujeinikova et al., "Structural studies of fatty acyl-(acyl carrier protein) thioesters reveal a hydrophobic binding cavity that can expand to fit longer substrates," J Mol Biol., 365(1):135-145, Epub Sep. 23, 2006.
Ryu et al., "A novel synthesis of .beta.-trichlorostannyl ketones from siloxycyclopropanes and their facile dehydrostannation affording 2-methylene ketones," JOC, 1986, 51:2389-2391.
Salcher and Lingens, "Regulation of phospho-2-keto-3-deoxyheptonate aldolase (DAHP synthase) and anthranilate synthase of Pseudomonas aureofaciens," J Gen Microbiol., 121(2):473-476, Dec. 1980.
Sambrook et al., Molecular Cloning—a Laboratory Manual, Cold Spring Harbor Laboratory Press, 2001.
Samsonova et al., "Molecular cloning and characterization of *Escherichia coli* K12 ygjG gene," BMC Microbiology, 2003, 3:2.
Sanders et al., "Characterization of the human ω-oxidation pathway for ω-hydroxy-very-long-chain fatty acids," FASEB Journal, 2008, 22(6):2064-2071.
Sanders et al., "Evidence for two enzymatic pathways for ω-oxidation of docosanoic acid in rat liver microsomes," J. Lipid Research, 2005, 46(5):1001-1008.
Satoh et al., "Enzyme-catalyzed poly(3-hydroxybutyrate) synthesis from acetate with CoA recycling and NADPH regeneration in vitro," J Bioscience and Bioengineering, 2003, 95(4):335-341.
Scheller et al., "Generation of the Soluble and Functional Cytosolic Domain of Microsomal Cytochrome P450 52A3," J Biol Chem., 1994, 269(17):12779-12783.
Scheps et al., "Synthesis of omega-hydroxy dodecanoic acid based on an engineered CYP153A fusion construct," Microbial Biotechnology, 2013, 6:694-707.
Schirmer et al., "Microbial Biosynthesis of Alkanes," Science, 2010, 329:559-562.
Schwartz et al., "A proteomic view of the facultatively chemolithoautotrophic lifestyle of Ralstonia eutropha H16," Proteomics, 2009, 9:5132-5142.
Seedorf et al., "The genome of *Clostridium kluyveri*, a strict anaerobe with unique metabolic features," Proc. Natl. Acad. Sci. USA, 2008, 105(6):2128-2133.
Shapiro et al., "Remarkable Diversity in the Enzymes Catalyzing the Last Step in Synthesis of the Pimelate Moiety of Biotin," PLoSOne, Nov. 2012, 7(11):e49440, 11 pages.
Shen et al., "Driving Forces Enable High-Titer Anaerobic 1-Butanol Synthesis in *Escherichia coli*," Appl. Environ. Microbiol., 2011, 77(9):2905-2915.
Shikata et al., "A novel ADP-forming succinyl-CoA synthetase in Thermococcus kodakaraensis structurally related to the archaeal nucleoside diphosphate-foiiiiing acetyl-CoA synthetases," J. Biol. Chem, 2007, 282(37):26963-26970.
Siegert et al., "Exchanging the substrate specificities of pyruvate decarboxylase from Zymomonas mobilis and benzoylfolmate decarboxylase from Pseudomonas putida," Port. Eng. Des. Sel., 2005, 18:345-357.
Simon et al., "Chiral Compounds Synthesized by Biocatalytic Reductions [New Synthetic Methods (51)]," Angew Chem Ed Engl., 1985, 24:539-553.
Simon, "Properties and mechanistic aspects of newly found redox enzymes from anaerobes suitable for bioconversions on preparatory scale," Pure and Appl. Chem, 1992, 64:1181-1186.

(56) References Cited

OTHER PUBLICATIONS

Slater et al., "Multiple β-Ketothiolases Mediate Poly(β-Hydroxyalkanoate) Copolymer Synthesis in Ralstonia eutropha," J Bacteriol., 1998, 180(8):1979-1987.
Smith et al., "Complete genome sequence of Methanobacterium thermoautotrophicum deltaH: functional analysis and comparative genomics," J Bacteriol., 1997, 179: 7135-7155.
Smith et al., "Structural analysis of ligand binding and catalysis in chorismate lyase," Archives of Biochemistry and Biophysics, Jan. 2006, 445(1):72-80.
Stok et al., "Expression, Purification, and Characterization of BioI: A Carbon-Carbon Bond Cleaving Cytochrome P450 Involved in Biotin Biosynthesis in Bacillus Subtilis," Archives of Biochemistry and Biophysics, Dec. 2000, 384(2):351-360.
Strassner et al., "A homolog of old yellow enzyme in tomato. Spectral properties and substrate specificity of the recombinant protein," J. Biol. Chem. 1999, 274:35067-35073.
Stueckler, "Stereocomplementary bioreduction of alpha,beta-unsaturated dicarboxylic acids and dimethyl esters using enoate reductases: enzyme- and substrate-based stereocontrol," Org. Lett., 2007, 9:5409-5411.
Suzuki et al., "Acetylputrescine deacetylase from Micrococcus luteus K-11," BBA—General Subjects, 1986, 882(1):140-142.
Kobayashi et al., "Antimicrobial Activity of Meropenem Against Main Bacterial Species Isolated from Patient Blood in 2006," Jpn J. Antibiot. 2007, 60(6):378-86 (with English abstract).
Suzuki et al., "GriC and GriD Constitute a Carboxylic Acid Reductase Involved in Grixazone Biosynthesis in Streptomyces griseus," J. Antibiot., 2007, 60(6):380-387.
Tomita et al., "Mechanism for multiple-substrates recognition of alpha-aminoadipate aminotransferase from Thermus thermophilus," Proteins, 2009, 75(2):348-359.
Tseng et al., "Biosynthesis of chiral 3-hydroxyvalerate from single propionate-unrelated carbon sources in metabolically engineered E. coli," Microbial Cell Factories, 2010, 9:96.
Uniprot Accession No. I5YEB8, Sep. 5, 2012, 1 page.
U.S. Non-Final Office Action in U.S. Appl. No. 13/524,883, dated Nov. 29, 2013, 13 pages.
U.S. Non-Final Office Action in U.S. Appl. No. 13/715,981, dated Jun. 27, 2014, 23 pages.
U.S. Notice of Allowance in U.S. Appl. No. 13/524,883, dated May 29, 2014, 7 pages.
U.S. Notice of Allowance in U.S. Appl. No. 13/715,981, dated Dec. 16, 2014, 23 pages.
U.S. Notice of Allowance in U.S. Appl. No. 13/715,981, dated Apr. 6, 2015, 10 pages.
U.S. Non-Final Office Action in U.S. Appl. No. 13/715,826, dated Jan. 30, 2015, 24 pages.
U.S. Non-Final Office Action in U.S. Appl. No. 14/106,033, dated Apr. 6, 2015, 37 pages.
U.S. Non-Final Office Action in U.S. Appl. No. 14/138,827, dated Apr. 24, 2015, 35 pages.
U.S. Non-Final Office Action in U.S. Appl. No. 14/138,971, dated Jun. 9, 2015, 44 pages.
U.S. Non-Final Office Action in U.S. Appl. No. 14/138,904, dated Jun. 9, 2015, 50 pages.
U.S. Non-Final Office Action in U.S. Appl. No. 14/490,270, dated Jul. 17, 2015, 49 pages.
U.S. Non-Final Office Action in U.S. Appl. No. 14/130,117, dated Aug. 21, 2015, 49 pages.
U.S. Notice of Allowance in U.S. Appl. No. 14/106,124, dated Dec. 24, 2014, 31 pages.
Vamecq et al., "The microsomal dicarboxylyl-CoA synthetase," Biochem J., 1985, 230:683-693.
Van Beilen and Funhoff, "Expanding the alkane oxygenase toolbox: new enzymes and Applications," Curr. Opin. Biotechnol., 2005, 16:308-314.
Venkitasubramanian et al., "Aldehyde oxidoreductase as a biocatalyst: Reductions of vanillic acid," Enzyme and Microbial Technology, 2008, 42:130-137.
Vioque et al., Resolution and purification of an aldehyde-generating and an alcohol-generating fatty-acyl-CoA reductase from Pea leaves (*Pisum sativum* L),Archives of Biochemistry and Biophysics, 1997, 340(1):64-72.
Vyazmensky et al., "Isolation and Characterization of Subunits of Acetohydroxy Acid Synthase Isozyme III and Reconstruction of the Holoenzyme," Biochemistry, 1996, 35:10339-10346.
Wahlen et al., "Purification, characterization and potential bacterial wax production role of an NADPH-dependent fatty aldehyde reductase from Marinobacter aquaeolei VT8," Appl. Environ Microbiol, 2009, 75:2758-2764.
Wang and Kolattukudy, "Solubilization and purification of aldehyde-generation fatty acyl-CoA reductase from green alga *Botryococcus braunii*," FEBS Letters, 1995, 370:15-18.
Wee et al., "Biotechnological Production of Lactic Acid and Its Recent Applications," Food Technol. Biotechnol., 2006, 44(2):163-172.
Westin et al., "Molecular cloning and characterization of two mouse peroxisome proliferator-activated receptor alpha (PPARalpha)-regulated peroxisomal acyl-CoA thioesterases," J. Biol Chem, 2004, 279:21841-21848.
Westin et al., "The identification of a succinyl-CoA thioesterase suggests a novel pathway for succinate production in peroxisomes," J. Biol Chem, 2005, 280:38125-38132.
White and Kelly, "Purification and Properties of Diaminopimelate Decarboxylase From *Escherichia Coli*," Biochem J., 1965, 96:75-84.
White, "A novel biosynthesis of medium chain length alpha-ketodicarboxylic acids in methanogenic archaebacteria," Archivers of Biochemistry and Biophysics, 1989, 270: 691-697.
White, "Biosynthesis of the 7-mercaptoheptanoic acid subunit of component B [(7- mercaptoheptanoyl)threonine phosphate] of methanogenic bacteria," Biochemistry, 1989, 28: 860-865.
White et al., "Carboxylic acid reductase: a new tungsten enzyme catalyses the reduction of non-activated carboxylic acids to aldehydes," Eur. J. Biochem., 1989, 184(1):89-96.
White, "Steps in the conversion of a-ketosuberate to 7-mercaptoheptanoic acid in methanogenic bacteria," Biochemistry, 1989, 28: 9417-9423.
Widmann et al., "Structural classification by the Lipase Engineering Database: a case study of Candida antarctica lipase A," BMC Genomics, 2010, 11:123-130.
Willis et al., "Characterization of a fatty acyl-CoA reductase from *Marinobacter aquaeolei* VT8: a bacterial enzyme catalyzing the reduction of fatty acyl-CoA to fatty alcohol," Biochemistry, 2011, 50:10550-10558.
Wilson and Bouwer, "Biodegradation of aromatic compounds under mixed oxygen/denitrifying conditions: a review," J Ind Microbiol Biotechnol., 18(2-3):116-130, Feb.-Mar. 1997.
Wischgoll et al., "Structural basis for promoting and preventing decarboxylation in glutaryl-coenzyme, A dehydrogenases," Biochemistry, 2010, 49:5350-5357.
Woolridge et al., "Efflux of the natural polyamine spermidine facilitated by the Bacillus subtilis multidrug transporter Blt," J Biol Chem., 1997, 272(14):8864-8866.
Xiong et al., "A bio-catalytic approach to aliphatic ketones," Sci Rep., 2:311, Epub Mar. 13, 2012.
Yang et al., "Value-added uses for crude glycerol—a byproduct of biodiesel production," Biotechnology for Biofuels, 2012, 5:13.
Yonaha et al., "4-Aminobutyrate : 2-oxoglutarate aminotransferase of Streptomyces griseus: Purification and properties," Eur. J. Biochem., 1985, 146:101-106.
Zhang et al., "Expanding metabolism for biosynthesis of nonnatural alcohols," Proc Natl Acad Sci U S A., 105(52):20653-20658 Epub Dec. 8, 2008.
Zhao et al., "Prediction and characterization of enzymatic activities guided by sequence similarity and genome neighborhood networks," E-Life, Jun. 2014, 3: 1-32.
Zhuang et al., "Divergence of function in the hot dog fold enzyme superfamily: the bacterial thioesterase YciA," Biochemistry, 2008, 47(9):2789-2796.

(56) References Cited

OTHER PUBLICATIONS

Zomorrodi et al., "Improving the iMM904 S. Cerevisiae metabolic model using essentiality and synthetic lethality data," BMC Systems Biology, Dec. 2010, 4(1):1-15.

* cited by examiner

1st carboxyl group

2nd carboxyl group

1st amino group

2nd hydroxy group

FIGURE 9

| SEQ ID NO | Organism | GENBANK reference | Amino acid sequence |
|---|---|---|---|
| 1 | Escherichia coli | AAA24665.1 | MSQALKNLLTLNLEKIEEGLFRGQSEDLGLRQVFGGQVVGQALYAAKETVPEERLVHSFHSYFLRPGDSKKPIIYDVETLRDGNSFSARRVAAIQNGKPIFYMTASFQAPEAGFEHQKTMPSAPAPDGLPSETQIAQSLAHLLPPVLKDKFICDRPLEVRPVEFHNPLKGHVAEPHRQVWIRANGSVPDDLRVHQYLLGYASDLNFLPVALQPHGIGFLEPGIQIATIDHSMWFHRPFNLNEWLLYSVESTSASSARGFVRGEFYTQDGVLVASTVQEGVMRNHN |
| 2 | Mycobacterium marinum | ACC40567.1 | MSPITREERLERRIIQDLYANDPQFAAAKPATAITAAIERPGLPLPQIIETVMTGYADRPALAQRSVEFVTDAGTGHTTLRLLPHFETISYGELWDRISALADVLSTEQTVKPGDRVCLLGFNSVDYATIDMTLARLGAVAVPLQTSAAITQLQPIVAETQPTMIAASVDALADATELALSGQTATRVLVFDHHRQVDAHRAAVESARERLAGSAVVETLAEAIARGDVPRGASAGSAPGTDVSDDSLALLIYTSGSTGAPKGAMYPRRNVATFWRKRTWFEGGYEPSITLNFMPMSHVMGRQILYGTLCNGGTAYFVAKSDLSTLFEDLALVRPTELTFVPRVWDMVFDEFQSEVDRRLVDGADRVALEAQVKAEIRNDVLGGRYTSALTGSAPISDEMKAWVEELLDMHLVEGYGSTEAGMILIDGAIRRPAVLDYKLVDVPDLGYFLTDRPHPRGELLVKTDSLFPGYYQRAEVTADVFDADGFYRTGDIMAEVGPEQFVYLDRRNNVLKLSQGEFVTVSKLEAVFGDSPLVRQIYIYGNSARAYLLAVIVPTQEALDAVPVEELKARLGDSLQEVAKAAGIQSYEIPRDFIIETTPWTLENGLLTGIRKLARPQLKKHYGELLEQIYTDLAHGQADELRSLRQSGADAPVLVTVCRAAAALLGGSASDVQPDAHFTDLGGDSLSALSFTNLLHEIFDIEVPVGVIVSPANDLQALADYVEAARKPGSSRPTFASVHGASNGQVTEVHAGDLSLDKFIDAATLAEAPRLPAANTQVRTVLLTGATGFLGRYLALEWLERMDLVDGKLICLVRAKSDTEARARLDKTFDSGDPELLAHYRALAGDHLEVLAGDKGEADLGLDRQTWQRLADTVDLIVDPAALVNHVLPYSQLFGPNALGTAELLRLALTSKIKPYSYTSTIGVADQIPPSAFTEDADIRVISATRAVDDSYANGYSNSKWAGEVLLREAHDLCGLPVAVFRCDMILADTTWAGQLNVPDMFTRMILSLAATGIAPGSFYELAADGARQRAHYDGLPVEFIAEAISTLGAQSQDGFHTYHVMNPYDDGIGLDEFVDWLNESGCPIQRIADYGDWLQRFETALRALPDRQRHSSLLPLLHNYRQPERPVRGSIAPTDRFRAAVQEAKIGPDKIPHVGAPIIVKYVSDLRLLGLL |

FIGURE 9 (Continued)

| SEQ ID NO | Organism | GENBANK reference | Amino acid sequence |
|---|---|---|---|
| 3 | Mycobacterium smegmatis | ABK71854.1 | MTSDVHDATDGVTETALDDEQSTRRIAELYATDPEFAAAAPLPAVVDAAHKPGLRLAEIL QTLFTGYGDRPALGYRARELATDEGGRTVTRLLPRFDTLTYAQVWSRVQAVAAALRHNFA QPIYPGDAVATIGFASPDYLTLDLVCAYLGLVSVPLQHNAPVSRLAPILAEVEPRILTVS AEYLDLAVESVRDVNSVSQLVVFDHHPEVDDHRDALARAREQLAGKGIAVTTLDAIADEG AGLPAEPIYTADHDQRLAMILYTSGSTGAPKGAMYTEAMVARLWTMSFHTGDPTPVINVN FMPLNHLGGRIPISTAVQNGGTSYFVPESDMSTLFEDLALVRPTELGLVPRVADMLYQHH LATVDRLVTQGADELTAEKQAGAELREQVLGGRVITGFVSTAPLAAEMRAFLDITLGAHI VDGYGLTETGAVTRDGVIVRPPVIDYKLIDVPELGYFSTDKPYPRGELLVRSQTLTPGYY KRPEVTASVFDRDGSYYHTGDVMAETAPDHLVYVDRRNNVLKLAQGEFVAVANLEAVFSGA ALVRQIFVYGNSERSFLLAVVPTPEALEQYDPAALKAALADSLQRTARDAELQSYEVPA DFIVETEPFSAANGLLSGVGKLLRPNLKDRYGQRLEQMYADIAATQANQLRELRRAAATQ PVIDTLTQAAATILGTGSEVASDAHFTDLGGDSLSALTLSNLLSDFFGFEVPVGTIVNPA TNLAQLAQHIEAQRTAGDRRPSFTTVHGADATEIRASELTLDKFIDAETLRAAPGLPKVT TEPRTVLLSGANGWLGRFLTLQWLERLAPVGGTLTIVRGRDDAAARARLTQAYDTDPEL SRRFAELADRHLRVVAGDIGDPNLGLTPEIWHRLAAEVDLVVHPAALVNHVLPYRQLFGP NVVGTAEVIKLALTERIKPVTYLSTVSVAMGIPDFEEDGDIRTVSPVRPLDGGYANGYGN SKWAGEVLLREAHDLCGLPVATFRSDMILAHPRYRGQVNVPDMFTRLLLSLLITGVAPRS FYIGDGERPRAHYPGLTVDFVAEAVTTLGAQQREGYVSYDVMNPHDDGISLDVFVDWLIR AGHPIDRVDDYDDWVRRFETALTALPEKRRAQTVLPLLHAFRAPQAPLRGAPEPTEVFHA AVRTAKVGPGDIPHLDEALIDKYIRDLREFGLI |

FIGURE 9 (Continued)

| SEQ ID NO | Organism | GENBANK reference | Amino acid sequence |
|---|---|---|---|
| 4 | Segniliparus rugosus | EFV11917.1 | MGDGEERAKRFFQRIGELSATDPQFAAAAPDPAVVEAVSDPSLSFTRYLDTLMRGYAERP ALAHRVGAGYETISYGELWARVGAIAAAWQADGLAPGDFVATVGFTSPDYAVDLAAARS GLVSVPLQAGASLAQLVGILEETEPKVLAASASSLEGAVACALAAPSVQRLVVFDLRGPD ASESAADERRGALADAEEQLARAGRAVVVETLADLAARGEALPEAPLFEPAEGEDPLALL IYTSGSTGAPKGAMYSQRLVSQLWGRTPVVPGMPNISLHYMPLSHSYGRAVLAGALSAGG TAHFTANSDLSTLFEDIALARPTFLALVPRVCEMLFQESQRGQDVAELRERVLGGRLLVA VCGSAPLSPEMRAFMEEVLGPPLLDGYGSTEALGVMRNGIIQRPPVIDYKLVDVPELGYR TTDKPYPRGELCIRSTLSLSGYYKRPEITAEVFDAQGYYKTGDVMAEIAPDHLVYVDRSK NVLKLSQGEFVAVAKLEAAYGTSPYVKQJFVYGNSERSFLLAVVVPNAEVLGARDQEEAK PLIAASLQKIAKEAGLQSYEVPRDFLIETEPFTTQNGLLSEVGKLLRPKLKARYGEALEA RYDEIAHGQADELRALRDGAGQRPVVETVVRAAVAISGSEGAEVGPEANFADLGGDSLSA LSLANLLHDVFEVEVPVRIIIGPTASLAGIAKHIEAERAGASAPTAASVHGAGATRIRAS ELTLEKFLPEDLLAAAKGLPAADQVRTVLLTGANGWLGRFLALEQLERLARSGQDGGKLI CLVRGKDAAAARRIEETLGTDPALAARFAELAEGRLEVVPGDVGEPKFGLDDAAWDRLA EEVDVIVHPAALVNHVLPYHQLFGPNVVGTAEHRLATATAKRKPVTYLSTVAVAAGVEPS SFEEDGDIRAVVPERPLGDGYANGYGNSKWAGEVLLREAHELVGLPVAVFRSDMILAHTR YTGQLNVPDQFTRLVLSLLATGIAPKSFYQQGAAGERQRAHYDGIPVDFTAEAITTLGAE PSWFDGGAGFRSFDVFNPHHDGVGLDEFVDWLIEAGHPISRIDDHKEWFARFETAVRGLP EAQRQHSLLPLLRAYSFPHPPVDGSVYPTGKFQGAVKAAQVGSDHDVPHLGKALIVKYAD DLKALGLL |

FIGURE 9 (Continued)

| SEQ ID NO | Organism | GENBANK reference | Amino acid sequence |
|---|---|---|---|
| 5 | *Mycobacterium massiliense* | EIV11143.1 | MTNETNPQQEQLSRRIESLRESDPQFRAAQPDPAVAEQVLRPGLHLSEAIAALMTGYAER PALGERARELVIDQDGRTTLRLLPRFDTTYGELWSRTTSVAAAWHHDATHPVKAGDLVA TLGFTSIDYTVLDLAIMILGGVAVPLQTSAPASQWTTILAEAEPNTLAVSIELIGAAMES VRATPSIKQVVVFDYTPEVDDQREAFEAASTQLAGTGIALETLDAVIARGAALPAAPLYA PSAGDDPLALLIYTSGSTGAPKGAMHSENIVRRWWIREDVMAGTENLPMIGLNFMPMSH MGRGTLTSTLSTGGTGYFAASSDMSTLFEDMELIRPTALALVPRVCDMVFQRFQTEVDRR LASGDTASAEAVAAEVKADIRDNLFGGRVSAVMVGSAPLSEELGEFIESCFELNLTDGYG STEAGMVFRDGIVQRPPVIDYKLVDVPELLGYFSTDKPHPRGELLLKTDGMFLGYYKRPEV TASVFDADGFYMTGDIVAELAHDWIEIIDRRNNVLKLSQGEFVAVATLEAEYANSPVVHQ IYVYGSSERSYLLAVVVPTPEAVAAAKGDAAALKTTIADSLQDIAKEIQLQSYEVPRDFI IEPQPFTQGNGLLTGIAKLARPNLKAHYGPRLEQMYAEIAEQQAAELRALHGVDPDKPAL ETVLKAAQALLGVSSAELAADAHFTDLGGDSLSALSFSDLLRDIFAVEVPVGVIVSAAND LGGVAKFVDEQRHSGGTRPTAETVHGAGHTEIRAADLTLDKFIDEATLHAAPSLPKAAGI PHTVLLTGSNGYLGHYLALEWLERLDKTDGKLIVRGKNAEAAYGRLEEAFDTGDTELL AHFRSLADKHLEVLAGDIGDPNLGLDADTWQRLADTVDVIVHPAALVNHVLPYNQLFGPN VVGTAEIIKLAITTKIKPVTYLSTVAVAAYVDPTTFDEESDIRLISAVRPIDDGYANGYG NAKWAGEVLLREAHDLCGLPVAVFRSDMILAHSRYTGQLNVPDQFTRLILSLIATGIAPG SFYQAQTTGERPLAHYDGLPGDFTAEAITLGTQVPEGSEGFVTYDCVNPHADGISLDNF VDWLIEAGYPIARIDNYTEWFTRFDTAIRGLSEKQKQHSLLPLLHAFEQPSAAENHGVVP AKRFQHAVQAAGIGPVGQDGTTDJPHLSRRLIVKYAKDLEQLGLL |

FIGURE 9 (Continued)

| SEQ ID NO | Organism | GENBANK reference | Amino acid sequence |
|---|---|---|---|
| 6 | Segniliparus rotundus | ADG98140.1 | MTQSHTQGPQASAAHSRLARRAAELLATDPQAAATLPDPEVVRQATRPGLRLAERVDAIL SGYADRPALGQRSFQTVKDPITGRSSVELLPTFDTITYRELRERATAIASDLAHHPQAPA KPGDFLASIGFISVDYVAIDIAGVFAGLTAVPLQTGATLATLTAITAETAPTLFAASIEH LPTAVDAVLATPSVRRLLVFDYRAGSDEDREAVEAAKRKIADAGSSVLVDVLDEVIARGK SAPKAPLPPATDAGDDSLSLLIYTSGSTGTPKGAMYPERNVAHFWGGVWAAAFDEDAAPP VPAINITFLPLSHVASRLSLMPTLARGGLMHFVAKSDLSTLFEDLKLARPTNLFLVPRVV EMLYQHYQSELDRRGVQDGTREAEAVKDDLRTGLLGGRRITAGFGSAPLSAELAGFIESL LQIHLVDGYGSTEAGPVWRDGYLVKPPVTDYKLIDVPELGYFSTDSPHPRGELAIKTQTI LPGYYKRPETTAEVFDEDGFYLTGDVVAQIGPEQFAYVDRRKNVLKLSQGEFVTLAKLEA AYSSSPLVRQLFVYGSSERSYLLAVIVPTPDALKKFGVGEAAKAALGESLQKIARDEGLQ SYEVPRDFHETDPFTVENGLLSDARKSLRPKLKEHYGERLEAMYKELADGQANELRDIR RGVQQRPTLETVRRAAAAMLGASAAEIKPDAHFTDLGGDSLSALTFSNFLHDLFEVDVPV GVIVSAANTLGSVAEHIDAQLAGGRARPTFATVHGKGSTTIKASDLTLDKFIDEQTLEAA KHLPKPADPPRTVLLTGANGWLGRFLALEWLERLAPAGGKLITIVRGKDAAQAKARLDAA YESGDPKLAGHYQDLAATTLEVLAGDFSEPRLGLDEATWNRLADEVDFISHPGALVNHVL PYNQLFGPNVAGVAEIIKLANTTRIKPVTYLSTVAVAAGVEPSALDEDGDIRTVSAERSV DEGYANGYGNSKWGGEVLLREAHDRTGLPVRVFRSDMILAHQKYTGQVNATDQFTRLVQS LLATGLAPKSFYELDAQGNRQRAHYDGIPVDFTAESITTLGGDGLEGYRSYNVFNPHRDG VGLDEFVDWLIEAGHPITRIDDYDQWLSRFETSLRGLPESKRQASVLPLLHAFARPGPAV DGSPFRNTVFRTDVQKAKIGAEHDIPHLGKALVLKYADDIKQLGLL |
| 7 | Chromobacterium violaceum | AAQ59697.1 | MQKQRTTSQWRELDAAHHLHPFTDTASLNQAGARVMTRGEGVYLWDSEGNKIIDGMAGLW CVNVGYGRKDFAEAARRQMEELPFYNTFFKTTHPAVVELSSLLAEVTPAGFDRVFYTNSG SESVDTMIRMVRRYWDVQGKPEKKTLIGRWNGYHGSTIGGASLGGMKYMHEQGDLPIPGM AHIEQPWWYKHGKDMTPDEFGVAARWLEEKLEIGADKVAAFVGEPIQGAGGVIVPPAT YWPEIERICRKYDVLLVADEVICGFGRTGEWFGHQHFGQPDLFTAAKGLSSGYLPIGAV FVGKRVAEGLIAGGDFNHGFFTYSGHPVCAAVAHANVAALRDEGIVQRVKDDIGPYMQKRW RETFSRFEHVDDVRGVGMVQAFTLVKNKAKRELFPDFGEIGTLCRDIFFRNNLIMRACGD HIVSAPPLVMTRAEVDEMLAVAERCLEEFEQTLKARGLA |
| 8 | Pseudomonas aeruginosa | AAG08191.1 | MNARLHATSPLGDADLVRADQAHYMHGYHVFDDHRVNGSLNIAAGDGAYIYDTAGNRYLD AVGGMWCTNIGLGREEMARTVAEQTRLLAYSNPFCDMANPRAIELCRKLAELAPGDLHV FLTTGGSTAVDTAIRLMHYYQNCRGKRAKKHVITRINAYHGSTFLGMSLGGKSADRPAEF DFLDERIHHLACPYYYRAPEGLGEAEFLDGLVDEFERKILELGADRVGAFISEPVFGSGG VIVPPAGYHRRMWELCQRYDVLYISDEVVTSFGRLGHFFASQAVFGVQPDIILTAKGLTS GYQPLGACIFSRRIWEVIAEPDKGRCFSHGFFTYSGHPVACAAALKNIEIEREGLLAHAD EVGRYFEERLQSLRDLPIVGDVRGMRFMACVEFVADKASKALFPESLNIGEWVHLRAQKR GLLVRPIVHLNVMSPPLILTREQVDTVVRVLRESIEETVEDLVRAGHR |

FIGURE 9 (Continued)

| SEQ ID NO | Organism | GENBANK reference | Amino acid sequence |
|---|---|---|---|
| 9 | Pseudomonas syringae | AAY39893.1 | MSANNPQTLEWQALSSEHHLAPFSDYKQLKEKGPRHTRAEGVYLWDSEGNKILDGMSGL WCVAIGYGREELADAASKQMRELPYYNLFFQTAHPPVLELAKAISDIAPEGMNHVFFTGS GSEGNDTMLRMVRHYWALKGQPNKKTIISRVNGYHGSTVAGASLGGMTYMHEQGDLPIPG VVHPQPYWFGEGGDMTPDEFGIWAAEQLEKKILELGVENVGAFIAEPIQGAGGVIVPPD SYWPKIKEILSRYDILFAADEVICGFGRTSEWFGSDFYGLRPDMMTIAKGLTSGYVPMGG LIVRDEIVAVLNEGGDFNHGFTYSGHPVAAAVALENIRILREEKIVERVRSETAPYLQKR LRELSDHPLVGEVRGVGLLGAIELVKDKTTRERYTDKGAGMICRTFCFDNGLIMRAVGDT MIIAPPLVISFAQIDELVEKARTCLDLTLAVLQG |
| 10 | Rhodobacter sphaeroides | ABA81135.1 | MTRNDATNAAGAVGAAMRDHILLPAQEMAKLGKSAQPVLTHAEGIYVHTEDGRRLIDGPA GMWCAQVGYGRREIVDAMAHQAMVLPYASPWYMATSPAARLAEKIATLTPGDLNRIFFTT GGSTAVDSALRFSEFYNNVLGRPQKKRIIVRYDGYHGSTALTAACTGRTGNWPNFDIAQD RISFLSSPNPRHAGNRSQEAFLDDLVQEFEDRIESLGPDTIAAFLAEPILASGGVIIPPA GYHARFKAICEKHDILYISDEVVTGFGRCGEWFASEKVFGVVPDIITFAKGVTSGYVPLG GLAISEAVLARISGENAKGSWFTNGYTYSNQPVACAAALANIELMEREGIVDQAREMADY FAAALASLRDLPGVAETRSVGLVGCVQCLLDPTRADGTAEDKAFTLKIDERCFELGLIVR PLGDLCVISPPLIISRAQIDEMVAIMRQAITEVSAAHGLTAKEPAAV |
| 11 | Escherichia coli | AAA57874.1 | MNRLPSSASALACSAHALNLIEKRTLDHEEMKALNREVIEYFKEHVNPGFLEYRKSVTAG GDYGAVEWQAGSLNTLVDTQGQEFIDCLGGFGIFNVGHRNPVVVSAVQNQLAKQPLHSQE LLDPLRAMLAKTLAALTPGKLKYSFFCNSGTESVEAALKLAKAYQSPRGKFTFIATSGAF HGKSLGALSATAKSTFRKPFMPLLPGFRHVPFGNIEAMRTALNECKKTGDDVAAVILEPI QGEGGVILPPPGYLTAVRKLCDEFGALMILDEVQTGMGRTGKMFACEHENVQPDILCLAK ALGGGVMPIGATIATEEVFSVLFDNPFLHTTTFGGNPLACAAALATINVLLEQNLPAQAE QKGDMLLDGFRQLAREYPDLVQEARGKGMLMAIEFVDNEIGYNFASEMFRQRVLVAGTLN NAKTIREPPLTLTEQCELVIKAARKALAAMRVSVEEA |
| 12 | Vibrio Fluvialis | AEA39183.1 | MNKPQSWEARAETYSLYGFTDMPSLHQRGTVVTHGEGPYIVDVNGRRYLDANSGLWNMV AGFDHKGLIDAAKAQYERFPGYHAFFGRMSDQTVMLSEKLVEVSPFDSGRVFYTNSGSEA NDTMVKMLWFLHAAEGKPQKRKILTRWNAYHGVTAVSASMTGKPYNSVFGLPLPGFVHLT CPHYWRYGEEGETEEQFVARLARELEETIQREGADTIAGFFAEPVMGAGGVIPPAKGYFQ AILPILRKYDIPVISDEVICGFGRTGNTWGCVTYDFTPDAIISSKNLTAGFFPMGAVILG PELSKRLETAIEAIEEFPHGFTASGHPVGCAIALKAIDVVMNEGLAENVRRLAPRFEERL KHIAERPNIGEYRGIGFMWALEAVKDKASKTPFDGNLSVSERIANTCTDLGLICRPLGQS VVLCPPFILTEAQMDEMFDKLEKALDKVFAEVA |

FIGURE 9 (Continued)

| SEQ ID NO | Organism | GENBANK reference | Amino acid sequence |
|---|---|---|---|
| 13 | Polaromonas sp. JS666 | ABE47160.1 | MSEARVVNNQNDQSRAYAIPLEDIDVSNPELFRDNTMWGYFERLLRREDPVHYCKDSLFGP YWSVTKFKDIMQVETHPEIFSSEGNITIMESNAAVTLPMFIAMDPPKHDVQRMAVSPIVA PENLAKLEGLIRERTGRALDGLPINETFDWVKLVSINLTTQMLATLFDFPWEDRAKLTRW SDVATALVGTGIHDSEEQRMEELKGCVQYMTRLWNERVNVPPGNDLISMMAHTESMRNMT PEEFLGNIJLIVGGNDTTRNSMTGGVLALNENPDEYRKLCANPALIASMVPENVRWQTP LAHMRRTALQDTELGGKSIRKGDKVIHMWVSGNRDPEAIENPDAFIIDRAKPRHHLSFGF GIHRCVGNRLAELQLRIVWEELLKRWPNPGQIEVVSGAPERVLSPFVKGYESLPVRINA |
| 14 | Mycobacterium sp. HXN-1500 | CAH04396.1 | MTEMTVAASDATNAAYGMALEDIDVSNPVLFRDNTWHPYFKRLREEDPVHYCKSSMFGPY WSVTKYRDIMAVETNPKVFSSEAKSGGTIMDDNAAASLPMFIAMDPPKHDVQRKTVSPI VAPENLATMESVIRQRTADLLDGLPINEEFDWVHRVSIELTTKMLATLFDFPWDDRAKLT RWSDVTTALPGGGIIDSEEQRMAELMECATYFTELWNQRVNAEPKNDLISMMAHSESTRH MAPEEYLGNIVLLIVGGNDTTRNSMTGGVLALNEFPDEYRKLSANPALISSMVSEIIRWQ TPLSHMRRTALEDIEFGGKHIRQGDKVVMWYVSGNRDPEAIDNPDTFIIDRAKPRQHLSF GFGIHRCVGNRLAELQLNILWEEILKRWPDPLQIQVLQEPTRVLSPFVKGYESLPVRINA |
| 15 | Mycobacterium austroafricanum | ACJ06772.1 | MTEMTVAANDATNAAYGMALEDIDVSNPVLFRDNTWHPYFKRLREEDPVHYCKSSMFGPY WSVTKYRDIMAVETNPKVFSSEAKSGGTIMDDNAAASLPMFIAMDPPKHDVQRKTVSPI VAPENLATMESVIRQRTADLLDGLPINEEFDWVHRVSIDLTTKMLATLFDFPWDDRAKLT RWSDVTTALPGGGIIDSEEQRMAELMECATYFTELWNQRVNAEPKNDLISMMAHSESTRH MAPEEYLGNIVLLIVGGNDTTRNSMTGGVLALNEFPDEYRKLSANPALISSMVSEIIRWQ TPLSHMRRTALEDIEFGGKHIRQGDKVVMWYVSGNRDPEAIDNPDTFIIDRAKPRQHLSF GFGIHRCVGNRLAELQLNILWEEILKRWPDPLQIQVLQEPTRVLSPFVKGYESLPVRINA |
| 16 | Polaromonas sp. JS666 | ABE47159.1 | MSFTVIIAGAGQAAGQAAVASLRQEGFDGRIVLVGAEPVLPYQRPPLSKAFLAGTLPLERL FLKPPAFYEQARVDTLLGVAVTELDAARRQVRLDDGRELAFDHLLLATGGRARRLDCPGA DHPRLHYLRTVADVDGIRAALRPGARLVLIGGGYVGLEIAAVAAKIGLAVTVLEAAPTVL ARVTCPAVARFFESVHRQAGVTIRCATTVSGIEGDASLARVVTGDGERIDADLVIAGIGL LPNVELAQAAGLVCDNGIVVDEECRTSVPGIFAAGDCTQHPNAIYDSRLRLESVHNAIEQ GKTAAAAMCGKARPYRQVPWFWSDQYDLKLQTAGLNRGYDQVVMRGSTDNRSFAAFYLRD GRLLAVDAVNRPVEFMVAKALIANRTVIAPERLADERIAAKDLAG |
| 17 | Mycobacterium sp. HXN-1500 | CAH04397.1 | MIHTGVTEAVVVGAGQAGAQTVTSLRQRGFEGQJTLLGDEPALPYQRPPLSKAFLAGTL PLDRLYLRPAAFYQQAHVDVMVDTGVSELDTENRRIRLTDGRAISFDHLVLATGGRPRPL ACPGADHPRVHYLRTVTDVDRIRSQFHPGTRLVLVGGGYIGLEIAAVAAELGLTVTVLEA QTTVLARVTCPTVARFFEHTHRRAGVTIRCATTVTRIHDSSSTARIELDSGEYIDADLVI VGIGLLPNVDLASAAGLTCESGIVVDSRCQTSAPGIYAAGDCTQYPSPIYGRPLHLESVH NAIEQAKTAAAAILGRDEPFRQVPWFWSDQYNIKLQTAGVNEGYDDVIRGDPASASFAA FYLRAGKLLAVDAINRPREFMASKTLIAERAEVDPTQLADESLPPTALAAAVNGPTRATS PTSL |

FIGURE 9 (Continued)

| SEQ ID NO | Organism | GENBANK reference | Amino acid sequence |
|---|---|---|---|
| 18 | Polaromonas sp. JS666 | ABE47158.1 | MTKVTFIEHNGTVRNVDVDDGLSVMEAAVNNLVPGIDGDCGGACACATCHVHDAAWLDK LPPMEAMEKSMLEFAEGRNESSRLGCQJKLSPALDGIVVRTPLGQH |
| 19 | Mycobacterium sp. HXN-1500 | CAH04398.1 | MPKITYIDYTGTSRCVDAENGMSLMEIAINNNVPGIDGDCGGECACATCHVHVDADWLDK LPPSSDQEVSMLEFCDGVDHTSRLGCQJKICPTLDGIVVRTPAAQH |
| 20 | Bacillus subtilis | CAA44858.1 | MKIYGIYMDRPLSQEENERFMSFISPEKREKCRRFYHKEDAHRTLLGDVLVRSVISRQYQ LDKSDIRFSTQEYGKPCIPDLPDAHFNISHSGRWVICAFDSQPIGIDIEKTKPISLEJAK RFFSKTEYSDLLAKDKDEQTDYFYHLWSMKESFIKQEGKGLSLPLDSFSVRLHQDGQVSI ELPDSHSPCYIKTYEVDPGYKMAVCAAHPDFPEDITMVSYEELL |
| 21 | Nocardia sp. NRRL 5646 | ABI83656.1 | MIETILPAGVESAELLEYPEDLKAHPAEEHLIAKSVEKRRDFIGARHCARLALAELGEP PVAIGKGERGAPIWPRGVVGSLTHCDGYRAAAVAHKMRFRSIGIDAEPHATLPEGVLDSV SLPPEREWLKTTDSALHLDRILLFCAKEATYKAWWPLTARWLGFEEAHITFEIEDGSADSG NGTFHSELLVPGQTNDGGTPLLSFDGRWLIADGFILTAIAYA |
| 22 | Mycobacterium marinum | ACC41782.1 | MPREIRLPESSVVVRPAPMESATYSQSSRLQAAGLSPAITLFEKAAQTVPLPDAPQPVVI ADYGVATGHNSLKPMIMAAINALRRIREDRAIMVAHTDVPDNDFTALFRTLADDPDSYLH HDSASFASAVGRSFYTQILPSNTVSLGWSSWAIQWLSRIPAGAPELTDHVQVAYSKDERA RAAYAHQAATDWQDFLAFRGRELCPGGRLVVLTMALDEHGHFGYRPMNDALVAALNDQVR DGLLRPEELRRMAIPVVARAEKDLRAPFAPRGWFEGLTIEQLDVFNAEDRFWAAFQSDGD AESFGAQWAGFARAALFPTLAAALDCGTGDPRATAFIEQLEASVADRLASQPEPMRIPLA SLVLAKRA |
| 23 | Mycobacterium smegmatis | ABK73223.1 | MPKFRVAVDPEPDDPTPKMRAPRPHAAGLNSAIALLEEAARTVPLPEAPYPIVIADYGVG TGRNSMRRPIAAAIAALRGRTRPEHSVLVTHTDNADNPFTAVFRGLADNPDSYLRRDTSTY PSAVGRSFYTQILPSKSVHVGWSAWAIVRVGRMPMPVPDHVAASFSGDPQVVAAYARQAA FDWHEFVAFRGRELASGAQLVVLTAALGDDGDFGYRPLFAAVMDTLRELTADGVLRQDEL HRMSLPIVGRRANDFMAPFAPSGRFERLSISHLEVYDAEDVIYSSYQKDRDTDVFGLRWA DFCRFTFFSDLCTALDDDAARCTQFQDRLHAGIAARLSAQPEQMRIPLAQLVLERRRSG |
| 24 | Pseudomonas putida | CAA39234.1 | MLAQLPPALQSLHLPLRLKLWDGNOQFDLGPSPQVTILVKEPQLIGQLTHPSMEQLGTAFV EGKLELEGDIGEAIRVCDELSEALFTDEDEQPPERRSHDKRTDAEAISYHYDVSNAFYQL WLDQDMAYSCAYFREPDNTLDQAOQDKFDHLCRKLRLNAGDYLLDVGCGWGGLARFAARE YDAKVFGITLSKEQLKLGRQRVKAEGLTDKVDLQJLDYRDLPQDGRFDKVVSVGMFEHVG HANLALYCQKLFGAVREGGLVMNHGITAKHVDGRPVGRGAGEFIDRYVFPHGELPHLSMI SASICEAGLEVVDVESLRLHYAKTLHHWSENLENQLHKAAALVPEKTLRIWRLYLAGCAY AFEKGWINLHQILAVKPYADGHHDLPWTREDMYR |

FIGURE 9 (Continued)

| SEQ ID NO | Organism | GENBANK reference | Amino acid sequence |
|---|---|---|---|
| 25 | Saccharomyces cerevisiae | CAA85138.1 | MSEVSKWPAINPFHWGYNGTVSHIVGENGSIRLHLKDNKEQVDFDEFANKYVPTLKNGAQ FKLSPYLFTGILQTLYLGAADFSKKFPVFYGREIVKFSDGGVCTADWLIDSWKKDYEFDQ STTSFDKKKFDKDEKATHPEGWPRLLQPRTRYLKDNELEELREVDLPLVVILHGLAGGSHE PIIRSLAENLSRSGRFQVVVLNTRGCARSKITTRNLFTAYHTMDIREFLOREKQRHPDRK LYAVGCSFGATMLANYLGEEGDKSPLSAAATLCNPWDLLSAIRMSQDWWSRTLFSKNIA QFLTRTVQVNMGELGVPNGSLPDHPPTVKNPSFYMFTPENLIKAKSFKSTREFDEVVTAP ALGFPNAMEYYKAASSINRVDTIRVPTLVINSRDDPVVGPDQPYSIVEKNPRILYCRTDL GGHLAYLDKDNNSWATKAIAEFFTKFDELVV |
| 26 | Pseudomonas fluorescens | AAC60471.2 | MQIQGHYELQFEAVREAFAALFDDPQERGAGLCIQJGGETVVDLWAGTADKDGTEAWHSD TIVNLFSCTKTFTAVTALQLVAEGKLQLDAPVANYWPEFAAAGKEAITLRQLLCHQAGLP AIREMLPTEALYDWRLMVDTLAAEAPWWTPGQGHGYEAITYGWLVGELLRRADGRGPGES IVARVARPLGLDFHVGLADEEFYRVAHIARSKGNMGDEAAQRLLQVMMREPTAMTTRAFA NPPSILTSTNKPEWRRMQQPAANGHGNARSLAGFYSGLLDGSLLEADMLEQLTREHSIGP DKTLLTQTRFGLGCMLDQQQPQLPNATFGLGPRAFGHPRSAPVVRWVLPEHDVAFGFVTNT LGPVVLMDPRAQKLVGILAGCL |
| 27 | Pseudomonas putida | CAB51047.1 | MNGKSVVLDSAPEYVDKKYFWILSTFWPATPMIGIWLANETGWGIFYGLVLAVWYGVLP LLDAMFGEDFNNPPEEVVEKLEKERYYRVLTYLTVPMHYAALIVSAWWVGTQSMSWFEIV ALALSLGIVNGLALNTGHELGHKKEAFDRWMAKIVLAVVGYGHFFIEHNKGHHRDVATPM DPATSRMGENIYKFSTREIPGAFRRAWGLEEQRLSRRGQSVWSFDNEILQPMVITVVLYT LLAFFGPKMLVFLPIQMAFGWWQLTSANYIEHYGLLREKMADGRYEHQKPHHSWNSNHH VSNLVLFHLQRHSDHHAHPTRSYQSLRDFPGLPALPTGYPGAFLMAMIPQWFRSVMDPKV VNWANGDLSKIQIEDSMRAEYIKKFTHNVGADDKRGATAVAS |
| 28 | Candida maltose | BAA00371.1 | MAIEQIIEEVLPYLTKWYTILFGAAVTYFLSIALRNKFYEYKLKCENPVYFEDAGLFGIP ALIDIIKVRKAGQLADYTDTTFDKYPNLSSYMTVAGVLKIVFTVDPENIKAVLATQFNDF ALGARHAHFDPLLGDGIFTLDGEGWKLSRAMLRPQFAREQIAHVKALEPHVQILAKQIKL NKGKTFDLQELFFRFTVDTATEFLFGESVHSLYDEKLGIPAPNDIPGRENFAEAFNTSQH YLATRTYSQJFYWLTNPKEFRDCNAKVHKLAQYFVNTALNATEKEVEEKSKGGVFLYEL VKQTRDPKVLQDQLLNIMVAGRDTTAGLLSFAMFELARNPKIWNKLREEVEVNFGLGDEA RVDEISFETLKKCEYLKAVLNETLRMYPSVPINFRTATRDTTLPRGGGKDGNSPIFVPKG SSVVYSVYKTHRLKQFYGEDAYEFRPERWFEPSTRKLGWAYLPFNGGPRICLGQQFALTE ASYVIARLAQMFEHLESKDETYPPNKCIHLTMNHNEGVFISAK |

FIGURE 9 (Continued)

| SEQ ID NO | Organism | GENBANK reference | Amino acid sequence |
|---|---|---|---|
| 29 | Salmonella enterica subsp. enterica serovar Typhimurium | AAD39015.1 | MNTSELETLIRTILSEQLTTPAQTPVQPQGKGIFQSVSEAIDAAHQAFLRYQQCPLKTRS AIISAMRQELTPLLAPLAEESANETGMGNKEDKFLKNKAALDNTPGVEDLTTTALTGDGG MVLFEYSPFGVIGSVAPSTNPTETIRNNSISMLAAGNSIYFSPHPGAKKVSLKLISLIEE IAFRCCGIRNLVVTVAEPTFEATQQMMAHPRIAVLAITGGPGIVAMGKKSGKKVHGAGAG NPPCIVDETADLVKAAEDINGASFDYNLPCIAEKSLIVVESVAERLVQQMQTFGALLLS PADTDKLRAVCLPEGGANKKLVGKSPSAMLEAAGIAVPAKAPRLLIALVNADDPWVTSEQ LMPMLPVVKVSDFDSALALALKVEEGLHHTAIMHSQNVSRLNLAARTLQTSIFVKNGPSY AGIGVGGEGFTTFTIATPTGEGTTSARTFARSRRCVLTNGFSIR |
| 30 | Sphingomonas paucimobilis | BAD61059.1 | MSTPTNLEQVLAAGGNTVEMLRNSQIGAYVYPVVAPEFSNWRTEQWAWRNSAVLFDQTHH MVDLYIRGKDALKLLSDTMINSPKGWEPNKAKQYVPVTPYGHVIGDGIIFYLAEEEFVYV GRAPAANWLMYHAQTGGYNVDIVHDDRSPSRPMGKPVQRISWRFQIQGPKAWDVIEKLHG GTLEKLKFFNMAEMNIAGMKIRTLRHGMAGAPGLEIWGPYETQEKARNAILEAGKEFGLI PVGSRAYPSNTLESGWIPSPLPAIYTGDKLLKAYREWLPANSYEASGAIGGSFVSSNIEDY YVNPYEIGYGPFVKFDHDFIGRDALEAIDPATQRKKVTLAWNGDDMAKIYASLFDTEADA HYKFFDLPLANYANTNADAVLDAAGNVVGMSMFTGYSYNEKRALSLATIDHEIPVGTELT VLWGEENGGTRKTTVEPHKQMAVRAVVSPVPYSVTARETYEGGWRKAAVTA |
| 31 | Sphingomonas paucimobilis | BAC79257.1 | MAKSLQDVLDNAGNAVDFLRNQQTGPNVYPGVPAEYSNMWRNEQRAWAKTAVLFNQSYHMV ELMVEGPDAFAFLNYLGINSFKNFAPGKAKQWVPVTAEGYVIGDVILFYLAENQFNLVGR APAIEWAEFHAATGKWNVTLTRDERTALRTDGVRRHYRFQLQGPNAMAILTDAMGQTPPD LKFFNMADIQJAGKTVGALRHGMAGQPGYELYGPWADYEAVHSALVAAGKNHGLALVGGR AYSSNTLESGWVPSPFPGYLFGEGSADFRKWAGENSYGAKCSIGGSYVPESLEGYGLTPW DIGYGIIVKFDHDFIGKEALEKMANEPHLEKVTLALDDEDMLRVMSSYFSDSGRAKYFEF PSAVVSMHPYDSVLDGKHVGSTWVGYSSNEGKMLTLAMIDPKYAKPGTEVSLLWGEPN GGTSKPTVEPHEQTEIKAVVAPVPYSAVARTGYADSWRTKKA |
| 32 | Lactobacillus brevis | ABJ63754.1 | MAANEFSETHRVVYYEADDTGQLTLAMLINLFVLVSEDQNDALGLSTAFVQSHGVGWWVT QYHLHIDELPRTGAQVTIKTRATAYNRYFAYREYWLLDDAGQVLAYGEGIWVTMSYATRK ITTIPAEVMAPYHSEEQTRLPRLPRPDHFDEAVNQTLKPYTVRYFDIDGNGHVNNAHYFD WMLDVLPATFLRAHHPTDVKIRFENEVQYGHQVTSELSQAAALTTQHMIKVGDLTAVKAT IQWDNR |
| 33 | Lactobacillus plantarum | CCC78182.1 | MATLGANASLYSEQHRITYYECDRTGRATLTTLIDIAVLASEDQSDALGLTTEMVQSHGV GWVVTQYAIDITRMPRQDEVVTIAVRGSAYNPYFAYREFWIRDADGQQLAYITSIWVMMS QTTRRIVKILPELVAPYQSEVVKRIPRLPRPISFEATDTTITKPYHVRFFDIDPNRHVNN AHYFDWLVDTLPATFLLQHDLVHVDVRYENEVKYGQTVTAHANILPSEVADQVTTSHLIE VDDEKCCEVTIQWRTLPEPIQ |

METHODS, REAGENTS AND CELLS FOR BIOSYNTHESIZING COMPOUNDS

CROSS REFERENCE TO RELATED APPLICATIONS

This application claims the benefit of U.S. Provisional Application Ser. Nos. 62/012,659, filed Jun. 16, 2014, 62/012,666, filed Jun. 16, 2014, and 62/012,604, filed Jun. 16, 2014, the disclosure of each of which is incorporated herein by reference in its entirety.

TECHNICAL FIELD

This invention relates to methods for biosynthesizing 6-hydroxyhexanoate methyl ester and hexanoic acid hexyl ester using one or more isolated enzymes such as a fatty acid O-methyltransferase, an alcohol O-acetyltransferase and a monooxygenase, and to recombinant host cells expressing one or more such enzymes. This invention also relates to methods for enzymatically converting 6-hydroxyhexanoate methyl ester and hexanoic acid hexyl ester to 6-hydroxyhexanoate and 1,6-hexanediol using one or more enzymes such as an esterase, a monooxygenase and a demethylase. In addition, this invention relates to enzymatically converting 6-hydroxyhexanoate and/or 1,6-hexanediol to adipic acid, 6-aminohexanoic acid, hexamethylenediamine or 1,6-hexanediol (hereafter "C6 building blocks"), and recombinant hosts that produce such C6 building blocks.

BACKGROUND

Nylons are polyamides which are generally synthesized by the condensation polymerization of a diamine with a dicarboxylic acid. Similarly, Nylons may be produced by the condensation polymerization of lactams. A ubiquitous nylon is Nylon 6,6, which is produced by condensation polymerization of hexamethylenediamine (HMD) and adipic acid. Nylon 6 can be produced by a ring opening polymerization of caprolactam (Anton & Baird, Polyamides Fibers, Encyclopedia of Polymer Science and Technology, 2001).

Biotechnology offers an alternative approach to petrochemical processes via biocatalysis. Biocatalysis is the use of biological catalysts, such as enzymes, to perform biochemical transformations of organic compounds.

Both bioderived feedstocks and petrochemical feedstocks are viable starting materials for the biocatalysis processes.

Accordingly, against this background, it is clear that there is a need for sustainable methods for producing one or more of adipic acid, 6-hydroxyhexanoate, 6-aminohexanoate, hexamethylenediamine and 1,6-hexanediol (hereafter "C6 building blocks") wherein the methods are biocatalyst based.

However, no wild-type prokaryote or eukaryote naturally overproduces or excretes such C6 building blocks to the extracellular environment. Nevertheless, the metabolism of adipic acid has been reported.

The dicarboxylic acid adipic acid is converted efficiently as a carbon source by a number of bacteria and yeasts via β-oxidation into central metabolites. β-oxidation of Coenzyme A (CoA) activated adipate to CoA activated 3-oxoadipate facilitates further catabolism via, for example, pathways associated with aromatic substrate degradation. The catabolism of 3-oxoadipyl-CoA to acetyl-CoA and succinyl-CoA by several bacteria has been characterized comprehensively The optimality principle states that microorganisms regulate their biochemical networks to support maximum biomass growth. Beyond the need for expressing heterologous pathways in a host organism, directing carbon flux towards C6 building blocks that serve as carbon sources rather than as biomass growth constituents, contradicts the optimality principle. For example, transferring the 1-butanol pathway from *Clostridium* species into other production strains has often fallen short by an order of magnitude compared to the production performance of native producers (Shen et al., *Appl. Environ. Microbiol.*, 2011, 77(9):2905-2915).

The efficient synthesis of the seven carbon aliphatic backbone precursor is a key consideration in synthesizing one or more C6 building blocks prior to forming terminal functional groups, such as carboxyl, amine or hydroxyl groups, on the C6 aliphatic backbone.

SUMMARY

This document is based at least in part on the discovery that it is possible to construct biochemical pathways for producing a seven carbon chain aliphatic backbone precursor in which one or two functional groups, i.e., carboxyl, amine, or hydroxyl, can be formed, leading to the synthesis of one or more of adipic acid, 6-aminohexanoate, 6-hydroxyhexanoate, hexamethylenediamine, and 1,6-hexanediol (hereafter "C6 building blocks). Adipic acid and adipate, 6-hydroxyhexanoic acid and 6-hydroxyhexanoate, and 6-aminohexanoic and 6-aminohexanoate are used interchangeably herein to refer to the relevant compound in any of its neutral or ionized forms, including any salt forms thereof. It is understood by those skilled in the art that the specific form will depend on pH.

One of skill in the art understands that compounds containing carboxylic acid groups (including, but not limited to, organic monoacids, hydroxyacids, aminoacids, and dicarboxylic acids) are formed or converted to their ionic salt form when an acidic proton present in the parent compound either is replaced by a metal ion, e.g., an alkali metal ion, an alkaline earth ion, or an aluminum ion; or coordinates with an organic base. Acceptable organic bases include, but are not limited to, ethanolamine, diethanolamine, triethanolamine, tromethamine, N-methylglucamine, and the like. Acceptable inorganic bases include, but are not limited to, aluminum hydroxide, calcium hydroxide, potassium hydroxide, sodium carbonate, sodium hydroxide, and the like. A salt of the present invention is isolated as a salt or converted to the free acid by reducing the pH to below the pKa, through addition of acid or treatment with an acidic ion exchange resin.

One of skill in the art understands that compounds containing amine groups (including, but not limited to, organic amines, aminoacids, and diamines) are formed or converted to their ionic salt form, for example, by addition of an acidic proton to the amine to form the ammonium salt, formed with inorganic acids such as hydrochloric acid, hydrobromic acid, sulfuric acid, nitric acid, phosphoric acid, and the like; or formed with organic acids including, but not limited to, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3- hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. Acceptable inorganic bases include, but are not limited to, aluminum hydroxide, calcium hydroxide, potassium hydroxide, sodium carbonate, sodium hydroxide, and the like. A salt of the present invention is isolated as a salt or converted to the free amine by raising the pH to above the pKb through addition of base or treatment with a basic ion exchange resin.

One of skill in the art understands that compounds containing both amine groups and carboxylic acid groups (including, but not limited to, aminoacids) are formed or converted to their ionic salt form by either 1) acid addition salts, formed with inorganic acids including, but not limited to, hydrochloric acid, hydrobromic acid, sulfuric acid, nitric acid, phosphoric acid, and the like; or formed with organic acids including, but not limited to, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. Acceptable inorganic bases include, but are not limited to, aluminum hydroxide, calcium hydroxide, potassium hydroxide, sodium carbonate, sodium hydroxide, and the like, or 2) when an acidic proton present in the parent compound either is replaced by a metal ion, e.g., an alkali metal ion, an alkaline earth ion, or an aluminum ion; or coordinates with an organic base. Acceptable organic bases include, but are not limited to, ethanolamine, diethanolamine, triethanolamine, tromethamine, N-methylglucamine, and the like. Acceptable inorganic bases include, but are not limited to, aluminum hydroxide, calcium hydroxide, potassium hydroxide, sodium carbonate, sodium hydroxide, and the like. A salt can of the present invention is isolated as a salt or converted to the free acid by reducing the pH to below the pKa through addition of acid or treatment with an acidic ion exchange resin.

Pathways, metabolic engineering and cultivation strategies described herein rely on producing hexanoate methyl ester from hexanoate using, for example, a fatty acid O-methyltransferase and producing 6-hydroxyhexanoate methyl ester from hexanoate methyl ester using, for example, a monooxygenase. 6-hydroxyhexanoate can be produced from 6-hydroxyhexanoate methyl ester using, for example, a demethylase or an esterase.

Pathways, metabolic engineering and cultivation strategies described herein rely on producing hexanoic acid hexyl ester using, for example, an alcohol O-acetyltransferase and producing 6-hydroxyhexanoic acid hexyl ester, 6-hydroxyhexanoic acid 6-hydroxyhexyl ester and/or hexanoic acid 6-hydroxyhexyl ester from hexanoic acid hexyl ester using, for example, a monooxygenase. 6-hydroxyhexanoate can be produced from 6-hydroxyhexanoic acid hexyl ester and/or 6-hydroxyhexanoic acid 6-hydroxyhexyl ester using, for example, an esterase. 1,6-hexanediol can be produced from hexanoic acid 6-hydroxyhexyl ester and/or 6-hydroxyhexanoic acid 6-hydroxyhexyl ester using, for example, an esterase.

CoA-dependent elongation enzymes or homologs associated with the carbon storage pathways from polyhydroxyalkanoate accumulating bacteria are useful for producing precursor molecules. See, e.g., FIGS. 1-2.

In the face of the optimality principle, the inventors discovered surprisingly that appropriate non-natural pathways, feedstocks, host microorganisms, attenuation strategies to the host's biochemical network and cultivation strategies may be combined to efficiently produce one or more C6 building blocks.

In some embodiments, the C6 aliphatic backbone for conversion to a C6 building block can be formed from acetyl-CoA via two cycles of CoA-dependent carbon chain elongation using either NADH or NADPH dependent enzymes. See FIG. 1 and FIG. 2.

In some embodiments, an enzyme in the CoA-dependent carbon chain elongation pathway generating the C6 aliphatic backbone purposefully contains irreversible enzymatic steps.

In some embodiments, the terminal carboxyl groups can be enzymatically formed using a thioesterase, an aldehyde dehydrogenase, a 7-oxoheptanoate dehydrogenase, a 6-oxohexanoate dehydrogenase, a 5-oxopentanoate dehydrogenase or a monooxygenase. See FIG. 3 and FIG. 4.

In some embodiments, the terminal amine groups can be enzymatically formed using a ω-transaminase or a deacetylase. See FIG. 5 and FIG. 6.

In some embodiments, the terminal hydroxyl group can be enzymatically forming using a monooxygenase, an esterase or an alcohol dehydrogenase. See FIG. 3, FIG. 7 and FIG. 8. A monooxygenase (e.g., in combination with an oxidoreductase and/or ferredoxin) or an alcohol dehydrogenase can enzymatically form a hydroxyl group. The monooxygenase can have at least 70% sequence identity to any one of the amino acid sequences set forth in SEQ ID NOs: 13-15 or 27-28. An esterase can have at least 70% identity to the amino acid sequence set forth in SEQ ID NO: 26.

A ω-transaminase or a deacetylase can enzymatically form an amine group. The ω-transaminase can have at least 70% sequence identity to any one of the amino acid sequences set forth in SEQ ID NOs. 7-12.

A thioesterase, an aldehyde dehydrogenase, a 7-oxoheptanoate dehydrogenase, a 6-oxohexanoate dehydrogenase or a 5-oxopentanoate dehydrogenase can enzymatically form a terminal carboxyl group. The thioesterase can have at least 70% sequence identity to the amino acid sequence set forth in SEQ ID NO: 1.

A carboxylate reductase (e.g., in combination with a phosphopantetheinyl transferase) can form a terminal aldehyde group as an intermediate in forming the product. The carboxylate reductase can have at least 70% sequence identity to any one of the amino acid sequences set forth in SEQ ID NOs. 2-6.

Any of the methods can be performed in a recombinant host by fermentation. The host can be subjected to a cultivation strategy under aerobic, anaerobic, or micro-aerobic cultivation conditions. The host can be cultured under conditions of nutrient limitation such as phosphate, oxygen or nitrogen limitation. The host can be retained using a ceramic membrane to maintain a high cell density during fermentation.

In any of the methods, the host's tolerance to high concentrations of a C6 building block can be improved through continuous cultivation in a selective environment.

The principal carbon source fed to the fermentation can derive from biological or non-biological feedstocks. In some embodiments, the biological feedstock is, includes, or derives from, monosaccharides, disaccharides, lignocellulose, hemicellulose, cellulose, lignin, levulinic acid and formic acid, triglycerides, glycerol, fatty acids, agricultural waste, condensed distillers' solubles, or municipal waste.

In some embodiments, the non-biological feedstock is or derives from natural gas, syngas, $CO_2/H_2$, methanol, ethanol, benzoate, non-volatile residue (NVR) or a caustic wash waste stream from cyclohexane oxidation processes, or a terephthalic acid/isophthalic acid mixture waste stream.

This document also features a recombinant host that includes at least one exogenous nucleic acid encoding a fatty acid O-methyltransferase, and a monooxygenase, and produce 6-hydroxyhexanoate methyl ester. Such a host further can include a demethylase or esterase and further produce 6-hydroxyhexanoate. Such hosts further can include (i) a β-ketothiolase or an acetyl-CoA carboxylase and a β-ketoacyl-[acp] synthase, (ii) a 3-hydroxyacyl-CoA dehydrogenase or a 3-oxoacyl-CoA reductase, (iii) an enoyl-CoA hydratase, and (iv) a trans-2-enoyl-CoA reductase. The hosts also further can include one or more of a thioesterase, an aldehyde dehydrogenase, or a butanal dehydrogenase.

This document also features a recombinant host that includes at least one exogenous nucleic acid encoding an alcohol O-acetyltransferase and produce hexanoic acid hexyl ester. Such a host further can include a monooxygenase and an esterase and further produce 6-hydroxyhexanoate and/or 1,6-hexanediol. Such hosts further can include (i) a β-ketothiolase or an acetyl-CoA carboxylase and a β-ketoacyl-[acp] synthase, (ii) a 3-hydroxyacyl-CoA dehydrogenase or a 3-oxoacyl-CoA reductase, (iii) an enoyl-CoA hydratase, and (iv) a trans-2-enoyl-CoA reductase. The hosts also further can include one or more of a thioesterase, carboxylate reductase, an aldehyde dehydrogenase, a butanal or acetaldehyde dehydrogenase or an alcohol dehydrogenase.

A recombinant host producing 6-hydroxyhexanoate further can include one or more of a monooxygenase, an alcohol dehydrogenase, an aldehyde dehydrogenase, a 6-hydroxyhexanoate dehydrogenase, a 5-hydroxybutanoate dehydrogenase, a 4-hydroxybutyrate dehydrogenase, a 5-oxobutanoate dehydrogenase, a 6-oxohexanoate dehydrogenase, or a 7-oxoheptanoate dehydrogenase, the host further producing adipic acid or adipate semialdehyde.

A recombinant host producing 6-hydroxyhexanoate further can include one or more of a ω-transaminase, a 6-hydroxyhexanoate dehydrogenase, a 5-hydroxypentanoate dehydrogenase, a 4-hydroxybutyrate dehydrogenase, and an alcohol dehydrogenase, wherein the host further produces 6-aminohexanoate.

A recombinant host producing 6-aminohexanoic acid can include an amidohydrolase, wherein the host further produces caprolactam.

A recombinant host producing 6-hydroxyhexanoate or 6-aminohexanoate further can include one or more of a carboxylate reductase, a ω-transaminase, a deacetylase, a N-acetyl transferase, or an alcohol dehydrogenase, the host further producing hexamethylenediamine.

A recombinant host producing 6-hydroxyhexanoate further can include a carboxylate reductase or an alcohol dehydrogenase, wherein the host further produces 1,6-hexanediol.

The recombinant host can be a prokaryote, e.g., from the genus *Escherichia* such as *Escherichia coli*; from the genus *Clostridia* such as *Clostridium ljungdahlii*, *Clostridium autoethanogenum* or *Clostridium kluyveri*; from the genus *Corynebacteria* such as *Corynebacterium glutamicum*; from the genus *Cupriavidus* such as *Cupriavidus necator* or *Cupriavidus metallidurans*; from the genus *Pseudomonas* such as *Pseudomonas fluorescens*, *Pseudomonas putida* or *Pseudomonas oleavorans*; from the genus *Delftia acidovorans*, from the genus *Bacillus* such as *Bacillus subtillis*; from the genes *Lactobacillus* such as *Lactobacillus delbrueckii*; from the genus *Lactococcus* such as *Lactococcus lactis* or from the genus *Rhodococcus* such as *Rhodococcus equi*.

The recombinant host can be a eukaryote, e.g., a eukaryote from the genus *Aspergillus* such as *Aspergillus niger*; from the genus *Saccharomyces* such as *Saccharomyces cerevisiae*; from the genus *Pichia* such as *Pichia pastoris*; from the genus *Yarrowia* such as *Yarrowia lipolytica*, from the genus *Issatchenkia* such as *Issathenkia orientalis*, from the genus *Debaryomyces* such as *Debaryomyces hansenii*, from the genus *Arxula* such as *Arxula adenoinivorans*, or from the genus *Kluyveromyces* such as *Kluyveromyces lactis*.

In some embodiments, the host's endogenous biochemical network is attenuated or augmented to (1) ensure the intracellular availability of acetyl-CoA, (2) create a cofactor, i.e. NADH or NADPH, imbalance that may be balanced via the formation of a C6 Building Block, (3) prevent degradation of central metabolites, central precursors leading to and including C6 Building Blocks and (4) ensure efficient efflux from the cell.

Any of the recombinant hosts described herein further can include one or more of the following attenuated enzymes: polyhydroxyalkanoate synthase, an acetyl-CoA thioesterase, an acetyl-CoA specific β-ketothiolase, a phosphotransacetylase forming acetate, an acetate kinase, a lactate dehydrogenase, a menaquinol-fumarate oxidoreductase, a 2-oxoacid decarboxylase producing isobutanol, an alcohol dehydrogenase forming ethanol, a triose phosphate isomerase, a pyruvate decarboxylase, a glucose-6-phosphate isomerase, a transhydrogenase dissipating the cofactor imbalance, aglutamate dehydrogenase specific for the co-factor for which an imbalance is created, a NADH/NADPH-utilizing glutamate dehydrogenase, a pimeloyl-CoA dehydrogenase; an acyl-CoA dehydrogenase accepting C6 building blocks and central precursors as substrates; a glutaryl-CoA dehydrogenase; or a pimeloyl-CoA synthetase.

Any of the recombinant hosts described herein further can overexpress one or more genes encoding: an acetyl-CoA synthetase, a 6-phosphogluconate dehydrogenase; a transketolase; a feedback resistant threonine deaminase; a puridine nucleotide transhydrogenase; a formate dehydrogenase; a glyceraldehyde-3P-dehydrogenase; a malic enzyme; a glucose-6-phosphate dehydrogenase; a fructose 1,6 diphosphatase; a propionyl-CoA synthetase; a L-alanine dehydrogenase; a L-glutamate dehydrogenase; a L-glutamine synthetase; a lysine transporter; a dicarboxylate transporter; and/or a multidrug transporter.

This document also features methods of producing a ($C_{3-8}$ hydroxyalkyl)-C(=O)OCH$_3$ ester, the method including enzymatically converting a $C_{4-9}$ carboxylic acid to a ($C_{3-8}$ alkyl)-C(=O)OCH$_3$ ester; and enzymatically converting the ($C_{3-8}$ alkyl)-C(=O)OCH$_3$ ester to ($C_{3-8}$ hydroxyalkyl)-C(=O)OCH$_3$ ester.

In some embodiments, the $C_{4-9}$ carboxylic acid can be enzymatically converted to the ($C_{3-9}$ alkyl)-C(=O)OCH$_3$ ester using a polypeptide having fatty acid O-methyltransferase activity. In some embodiments, the polypeptide having fatty acid O-methyltransferase activity can have at least 70% sequence identity to an amino acid sequence set forth in SEQ ID NO:22, SEQ ID NO:23, and/or SEQ ID NO:24.

In some embodiments, the ($C_{3-8}$ alkyl)-C(=O)OCH$_3$ ester can be enzymatically converted to the ($C_{3-8}$ hydroxyalkyl)-C(=O)OCH$_3$ ester using a polypeptide having monooxygenase activity. In some embodiments, the monooxygenase is classified under EC 1.14.14.- or EC 1.14.15.-. In some embodiments, the monooxygenase can have at least 70% sequence identity to an amino acid sequence set forth in SEQ ID NO: 13-15, SEQ ID NO:27 and/or SEQ ID NO:28.

In some embodiments, the $C_{4-9}$ carboxylic acid can be enzymatically produced from a $C_{4-9}$ alkanoyl-CoA. In some embodiments, a polypeptide having thioesterase activity can enzymatically produce the $C_{4-9}$ carboxylic acid from the $C_{4-9}$ alkanoyl-CoA. In some embodiments, the thioesterase can have at least 70% sequence identity to the amino acid sequence set forth in SEQ ID NO:1, and/or SEQ ID NO: 32-33. In some embodiments, a polypeptide having butanal dehydrogenase activity and a polypeptide having aldehyde dehydrogenase activity enzymatically produce the $C_{4-9}$ carboxylic acid from $C_{4-9}$ alkanoyl-CoA.

This document also features methods of producing one or more hydroxy-substituted ($C_{4-9}$ alkyl)-OC(=O)—($C_{3-8}$ alkyl) esters. The method includes enzymatically converting a $C_{4-9}$ alkanoyl-CoA to a ($C_{4-9}$ alkyl)-OC(=O)—($C_{3-8}$ alkyl) ester; and enzymatically converting the ($C_{4-9}$ alkyl)-OC(=O)—($C_{3-8}$ alkyl) ester to any of ($C_{4-9}$ alkyl)-OC(=O)—($C_{3-8}$ hydroxyalkyl) ester, ($C_{4-9}$ hydroxyalkyl)-OC(=O)—($C_{3-8}$ hydroxyalkyl) ester, or ($C_{4-9}$ hydroxyalkyl)-OC(=O)—($C_{3-8}$ alkyl) ester.

In some embodiments, the $C_{4-9}$ alkanoyl-CoA can be enzymatically converted to the ($C_{4-9}$ alkyl)-OC(=O)—($C_{3-8}$ alkyl) ester using a polypeptide having alcohol O-acetyltransferase activity. In some embodiments, the alcohol O-acetyltransferase can have at least 70% sequence identity to the amino acid sequence set forth in SEQ ID NO: 25.

In some embodiments, ($C_{4-9}$ alkyl)-OC(=O)—($C_{3-8}$ alkyl) ester is enzymatically converted to any of ($C_{4-9}$ alkyl)-OC(=O)—($C_{3-8}$ hydroxyalkyl) ester, ($C_{4-9}$ hydroxyalkyl)-OC(=O)—($C_{3-8}$ hydroxyalkyl) ester, or ($C_{4-9}$ hydroxyalkyl)-OC(=O)—($C_{3-8}$ alkyl) ester using a polypeptide having monooxygenase activity. In some embodiments, said polypeptide having monooxygenase activity is classified under EC 1.14.14.- or EC 1.14.15.-.

In some embodiments, the method further can include enzymatically converting the ($C_{4-9}$ hydroxyalkyl)-OC(=O)—($C_{3-8}$ hydroxyalkyl) ester or ($C_{4-9}$ alkyl)-OC(=O)—($C_{3-8}$ hydroxyalkyl) ester to a $C_{4-9}$ hydroxyalkanoate. In some embodiments, a polypeptide having esterase activity enzymatically converts the ($C_{4-9}$ hydroxyalkyl)-OC(=O)—($C_{3-8}$ hydroxyalkyl) ester or ($C_{4-9}$ alkyl)-OC(=O)—($C_{3-8}$ hydroxyalkyl) ester to the $C_{4-9}$ hydroxyalkanoate.

In one aspect, this document features a method for producing a bioderived 6-carbon compound. The method for producing a bioderived six carbon compound can include culturing or growing a recombinant host as described herein under conditions and for a sufficient period of time to produce the bioderived six carbon compound, wherein, optionally, the bioderived six carbon compound is selected from the group consisting of adipic acid, adipate semialdehyde, 6-aminohexanoic acid, 6-hydroxyhexanoic acid, caprolactam, hexamethylenediamine, 1,6-hexanediol, and combinations thereof.

In one aspect, this document features composition comprising a bioderived six carbon compound as described herein and a compound other than the bioderived six carbon compound, wherein the bioderived six carbon compound is selected from the group consisting of adipic acid, adipate semialdehyde, 6-aminohexanoic acid, 6-hydroxyhexanoic acid, caprolactam, hexamethylenediamine, 1,6-hexanediol, and combinations thereof. For example, the bioderived six carbon compound is a cellular portion of a host cell or an organism.

This document also features a biobased polymer comprising the bioderived adipic acid, adipate semialdehyde, 6-aminohexanoic acid, 6-hydroxyhexanoic acid, caprolactam, hexamethylenediamine, 1,6-hexanediol, and combinations thereof.

This document also features a biobased resin comprising the bioderived adipic acid, adipate semialdehyde, 6-aminohexanoic acid, 6-hydroxyhexanoic acid, caprolactam, hexamethylenediamine, 1,6-hexanediol, and combinations thereof, as well as a molded product obtained by molding a biobased resin.

In another aspect, this document features a process for producing a biobased polymer that includes chemically reacting the bioderived adipic acid, adipate semialdehyde, 6-aminohexanoic acid, 6-hydroxyhexanoic acid, caprolactam, hexamethylenediamine, and/or 1,6-hexanediol, with itself or another compound in a polymer producing reaction.

In another aspect, this document features a process for producing a biobased resin that includes chemically reacting the bioderived adipic acid, adipate semialdehyde, 6-aminohexanoic acid, 6-hydroxyhexanoic acid, caprolactam, hexamethylenediamine, and/or 1,6-hexanediol, with itself or another compound in a resin producing reaction.

In another aspect, this document provides a bio-derived product, bio-based product or fermentation-derived product, wherein said product comprises:

(i) a composition comprising at least one bio-derived, bio-based or fermentation-derived compound provided herein or in any one of FIGS. 1-8, or any combination thereof;

(ii) a bio-derived, bio-based or fermentation-derived polymer comprising the bio-derived, bio-based or fermentation-derived composition or compound of (i), or any combination thereof;

(iii) a bio-derived, bio-based or fermentation-derived resin comprising the bio-derived, bio-based or fermentation-derived compound or bio-derived, bio-based or fermentation-derived composition of (i) or any combination thereof or the bio-derived, bio-based or fermentation-derived polymer of (ii) or any combination thereof;

(iv) a molded substance obtained by molding the bio-derived, bio-based or fermentation-derived polymer of (ii) or the bio-derived, bio-based or fermentation-derived resin of (iii), or any combination thereof;

(v) a bio-derived, bio-based or fermentation-derived formulation comprising the bio-derived, bio-based or fermentation-derived composition of (i), bio-derived, bio-based or fermentation-derived compound of (i), bio-derived, bio-based or fermentation-derived polymer of (ii), bio-derived, bio-based or fermentation-derived resin of (iii), or bio-derived, bio-based or fermentation-derived molded substance of (iv), or any combination thereof; or (vi) a bio-derived, bio-based or fermentation-derived semi-solid or a non-semi-solid stream, comprising the bioderived, bio-based or fermentation-derived composition of (i), bio-derived, bio-based or fermentation-derived compound of (i), bio-derived, bio-based or fermentation-derived polymer of (ii), bio-derived, bio-based or fermentation-derived resin of (iii), bio-derived, bio-based or fermentation-derived formulation of (v), or bio-derived, bio-based or fermentation-derived molded substance of (iv), or any combination thereof.

Also, described herein is a biochemical network comprising at least one exogenous nucleic acid encoding a polypeptide having (i) fatty acid O-methyltransferase activity or alcohol O-acetyltransferase activity, (ii) monooxygenase activity, and (iii) esterase or demethylase activity.

Also, described herein is a biochemical network comprising at least one exogenous nucleic acid encoding a polypeptide having fatty acid O-methyltransferase activity and a polypeptide having monooxygenase activity, wherein the biochemical network enzymatically produces 6-hydroxyhexanoate methyl ester. The biochemical network can further include a polypeptide having demethylase activity or a polypeptide having esterase activity, wherein the polypeptide having demethylase activity or a polypeptide having esterase activity enzymatically produce 6-hydroxyhexanoate.

The biochemical network can further include at least one exogenous nucleic acid encoding a polypeptide having β-ketothiolase activity or a polypeptide having acetyl-CoA carboxylase activity and a polypeptide having β-ketoacyl-[acp] synthase activity, a polypeptide having 3-hydroxyacyl-CoA dehydrogenase activity or a polypeptide having 3-oxoacyl-CoA reductase activity, a polypeptide having enoyl-CoA hydratase activity, and a polypeptide having trans-2-enoyl-CoA reductase activity, wherein the polypeptide having β-ketothiolase activity or a polypeptide having acetyl-CoA carboxylase activity and a polypeptide having β-ketoacyl-[acp] synthase activity, a polypeptide having 3-hydroxyacyl-CoA dehydrogenase activity or a polypeptide having 3-oxoacyl-CoA reductase activity, a polypeptide having enoyl-CoA hydratase activity, and a polypeptide having trans-2-enoyl-CoA reductase activity enzymatically produce C6 precursor molecules such as hexanoyl-CoA.

The biochemical network can further one or more of an exogenous polypeptide having thioesterase activity, a polypeptide having aldehyde dehydrogenase activity, or a polypeptide having butanal dehydrogenase activity, wherein the polypeptide having thioesterase activity, a polypeptide having aldehyde dehydrogenase activity, or a polypeptide having butanal dehydrogenase activity enzymatically produce hexanoate as a C6 precursor molecule.

Also, described herein is a biochemical network comprising at least one exogenous nucleic acid encoding a polypeptide having alcohol O-acetyltransferase activity and a polypeptide having monooxygenase activity, wherein the biochemical network produces hexanoic acid hexyl ester. The biochemical network can further include an esterase, wherein the esterase enzymatically converts hexanoic acid hexyl ester to 6-hydroxyhexanoate and/or 1,6-hexanediol.

The biochemical network can further include at least one exogenous nucleic acid encoding a polypeptide having β-ketothiolase activity or a polypeptide having acetyl-CoA carboxylase activity and a polypeptide having β-ketoacyl-[acp] synthase activity, a polypeptide having 3-hydroxyacyl-CoA dehydrogenase activity or a polypeptide having 3-oxoacyl-CoA reductase activity, a polypeptide having enoyl-CoA hydratase activity, and a polypeptide having trans-2-enoyl-CoA reductase activity, wherein the polypeptide having β-ketothiolase activity or a polypeptide having acetyl-CoA carboxylase activity and a polypeptide having β-ketoacyl-[acp] synthase activity, a polypeptide having 3-hydroxyacyl-CoA dehydrogenase activity or a polypeptide having 3-oxoacyl-CoA reductase activity, a polypeptide having enoyl-CoA hydratase activity, and a polypeptide having trans-2-enoyl-CoA reductase activity enzymatically produce C6 precursor molecules such as hexanoyl-CoA. The biochemical network can further include one or more of an exogenous a polypeptide having aldehyde dehydrogenase activity, a polypeptide having alcohol dehydrogenase activity, a polypeptide having butanal dehydrogenase activity, a polypeptide having carboxylate reductase activity or a polypeptide having thioesterase activity, wherein the polypeptide having aldehyde dehydrogenase activity, a polypeptide having alcohol dehydrogenase activity, a polypeptide having butanal dehydrogenase activity, a polypeptide having carboxylate reductase activity or a polypeptide having thioesterase activity enzymatically produce hexanol as a C6 precursor molecule.

A biochemical network producing 6-hydroxyhexanoate can further include one or more of a polypeptide having monooxygenase activity, a polypeptide having alcohol dehydrogenase activity, a polypeptide having aldehyde dehydrogenase activity, a polypeptide having 7-oxohexanoate dehydrogenase activity, a polypeptide having 6-oxohexanoate dehydrogenase activity, a polypeptide having 5-hydroxypentanoate dehydrogenase activity, a polypeptide having 4-hydroxybutyrate dehydrogenase activity or a polypeptide having 6-hydroxyhexanoate dehydrogenase activity, wherein the polypeptide having monooxygenase activity, a polypeptide having alcohol dehydrogenase activity, a polypeptide having aldehyde dehydrogenase activity, a polypeptide having 7-oxohexanoate dehydrogenase activity, a polypeptide having 6-oxohexanoate dehydrogenase activity, a polypeptide having 5-hydroxypentanoate dehydrogenase activity, a polypeptide having 4-hydroxybutyrate dehydrogenase activity or a polypeptide having 6-hydroxyhexanoate dehydrogenase activity enzymatically convert 6-hydroxyhexanoate to adipic acid or adipate semialdehyde.

A biochemical network producing 6-hydroxyhexanoate can further include one or more of a polypeptide having ω-transaminase activity, a polypeptide having 6-hydroxyhexanoate dehydrogenase activity, a polypeptide having 5-hydroxybutanoate dehydrogenase activity, a polypeptide having 4-hydroxybutyrate dehydrogenase activity and a polypeptide having alcohol dehydrogenase activity, wherein the polypeptide having ω-transaminase activity, a polypeptide having 6-hydroxyhexanoate dehydrogenase activity, a polypeptide having 5-hydroxybutanoate dehydrogenase activity, a polypeptide having 4-hydroxybutyrate dehydrogenase activity and a polypeptide having alcohol dehydrogenase activity enzymatically convert 6-hydroxyhexanoate to 6-aminohexanoate.

A biochemical network producing 6-aminohexanoate, 6-hydroxyhexanoate, adipate semialdehyde, or 1,6-hexanediol can further include one or more of a polypeptide having carboxylate reductase activity, a polypeptide having ω-transaminase activity, a polypeptide having deacetylase activity, a polypeptide having N-acetyl transferase activity, or a polypeptide having alcohol dehydrogenase activity, wherein the a polypeptide having carboxylate reductase activity, a polypeptide having ω-transaminase activity, a polypeptide having deacetylase activity, a polypeptide having N-acetyl transferase activity, or a polypeptide having alcohol dehydrogenase activity, enzymatically convert 6-aminohexanoate, 6-hydroxyhexanoate, adipate semialdehyde, or 1,6-hexanediol to hexamethylenediamine.

A biochemical network producing 6-hydroxyhexanoate can further include one or more of a polypeptide having carboxylate reductase activity and a polypeptide having alcohol dehydrogenase activity, wherein the polypeptide having carboxylate reductase activity and a polypeptide having alcohol dehydrogenase activity enzymatically convert 6-hydroxyhexanoic acid to 1,6-hexanediol.

Also, described herein is a means for obtaining 6-hydroxyhexanoate using (i) a polypeptide having fatty acid O-methyltransferase activity and a polypeptide having monooxygenase activity and (ii) a polypeptide having demethylase activity or a polypeptide having esterase activity. The means can further include means for converting 6-hydroxyhexanoate to at least one of adipic acid, 6-aminohexanoic acid, caprolactam, hexamethylenediamine, 6-hydroxyhexanoic acid, and 1,6-hexanediol. The means can include a polypeptide having aldehyde dehydrogenase activity, a polypeptide having 7-oxohexanoate dehydrogenase activity, a polypeptide having 6-oxohexanoate dehydrogenase activity, a polypeptide having 5-hydroxypentanoate dehydrogenase activity, a polypeptide having 4-hydroxybutyrate dehydrogenase activity or a polypeptide having 6-hydroxyhexanoate dehydrogenase activity.

Also, described herein is a means for obtaining 6-hydroxyhexanoate using (i) a polypeptide having alcohol O-acetyltransferase and a polypeptide having monooxygenase activity and (ii) a polypeptide having demethylase activity or a polypeptide having esterase activity. The means can further include means for converting 6-hydroxyhexanoate to at least one of adipic acid, 6-aminohexanoic acid, caprolactam, hexamethylenediamine, 6-hydroxyhexanoic acid, and 1,6-hexanediol. The means can include a polypeptide having aldehyde dehydrogenase activity, a polypeptide having 7-oxohexanoate dehydrogenase activity, a polypeptide having 6-oxohexanoate dehydrogenase activity, a polypeptide having 5-hydroxypentanoate dehydrogenase activity, a polypeptide having 4-hydroxybutyrate dehydrogenase activity or a polypeptide having 6-hydroxyhexanoate dehydrogenase activity.

Also described herein is (i) a step for obtaining 6-hydroxyhexanoate using a polypeptide having alcohol O-acetyltransferase, a polypeptide having monooxygenase activity, and a polypeptide having demethylase activity or a polypeptide having esterase activity, and (ii) a step for obtaining adipic acid, 6-aminohexanoate, adipate semialdehyde 1,6-hexanediol, hexamethylenediamine using a polypeptide having carboxylate reductase activity, a polypeptide having alcohol dehydrogenase activity, a polypeptide having ω-transaminase activity, a polypeptide having deacetylase activity, a polypeptide having N-acetyl transferase activity, a polypeptide having 6-hydroxyhexanoate dehydrogenase activity, a polypeptide having 5-hydroxybutanoate dehydrogenase activity, a polypeptide having 4-hydroxybutyrate dehydrogenase activity, a polypeptide having aldehyde dehydrogenase activity, a polypeptide having 7-oxohexanoate dehydrogenase activity, a polypeptide having 6-oxohexanoate dehydrogenase activity, a polypeptide having 5-hydroxypentanoate dehydrogenase activity, a polypeptide having 4-hydroxybutyrate dehydrogenase activity or a polypeptide having 6-hydroxyhexanoate dehydrogenase activity.

In another aspect, this document features a composition comprising 6-hydroxyhexanoate and a polypeptide having alcohol O-acetyltransferase, a polypeptide having monooxygenase activity, and a polypeptide having demethylase activity or a polypeptide having esterase activity complex. The composition can be cellular. The composition can further include a polypeptide having carboxylate reductase activity, a polypeptide having alcohol dehydrogenase activity, a polypeptide having ω-transaminase activity, a polypeptide having deacetylase activity, a polypeptide having N-acetyl transferase activity, a polypeptide having 6-hydroxyhexanoate dehydrogenase activity, a polypeptide having 5-hydroxybutanoate dehydrogenase activity, a polypeptide having 4-hydroxybutyrate dehydrogenase activity, a polypeptide having aldehyde dehydrogenase activity, a polypeptide having 7-oxohexanoate dehydrogenase activity, a polypeptide having 6-oxohexanoate dehydrogenase activity, a polypeptide having 5-hydroxypentanoate dehydrogenase activity, a polypeptide having 4-hydroxybutyrate dehydrogenase activity or a polypeptide having 6-hydroxyhexanoate dehydrogenase activity, and at least one of adipic acid, 6-aminohexanoic acid, caprolactam, hexamethylenediamine, 6-hydroxyhexanoic acid, and 1,6-hexanediol. The composition can be cellular.

The reactions of the pathways described herein can be performed in one or more cell (e.g., host cell) strains (a) naturally expressing one or more relevant enzymes, (b) genetically engineered to express one or more relevant enzymes, or (c) naturally expressing one or more relevant enzymes and genetically engineered to express one or more relevant enzymes. Alternatively, relevant enzymes can be extracted from of the above types of host cells and used in a purified or semi-purified form. Extracted enzymes can optionally be immobilized to the floors and/or walls of appropriate reaction vessels. Moreover, such extracts include lysates (e.g. cell lysates) that can be used as sources of relevant enzymes. In the methods provided by the document, all the steps can be performed in cells (e.g., host cells), all the steps can be performed using extracted enzymes, or some of the steps can be performed in cells and others can be performed using extracted enzymes.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein including GenBank and NCBI submissions with accession numbers are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and the drawings, and from the claims. The word "comprising" in the claims may be replaced by "consisting essentially of" or with "consisting of," according to standard practice in patent law.

DESCRIPTION OF DRAWINGS

FIG. 7 also contains an exemplary biochemical pathway leading to 6-hydroxyhexanoate using 1,6-hexanediol as a central precursor.

FIG. 9 contains the amino acid sequences of an *Escherichia coli* thioesterase encoded by tesB (See GenBank Accession No. AAA24665.1, SEQ ID NO: 1), a *Mycobacterium marinum* carboxylate reductase (See Genbank Accession No. ACC40567.1, SEQ ID NO: 2), a *Mycobacterium smegmatis* carboxylate reductase (See Genbank Accession No. ABK71854.1, SEQ ID NO: 3), a *Segniliparus rugosus* carboxylate reductase (See Genbank Accession No. EFV11917.1, SEQ ID NO: 4), a *Mycobacterium massiliense* carboxylate reductase (See Genbank Accession No. EIV11143.1, SEQ ID NO: 5), a *Segniliparus rotundus* carboxylate reductase (See Genbank Accession No. ADG98140.1, SEQ ID NO: 6), a *Chromobacterium violaceum* ω-transaminase (See Genbank Accession No. AAQ59697.1, SEQ ID NO: 7), a *Pseudomonas aeruginosa* ω-transaminase (See Genbank Accession No. AAG08191.1, SEQ ID NO: 8), a *Pseudomonas syringae* ω-transaminase (See Genbank Accession No. AAY39893.1, SEQ ID NO: 9), a *Rhodobacter sphaeroides* ω-transaminase (See Genbank Accession No. ABA81135.1, SEQ ID NO: 10), an *Escherichia coli* w-transaminase (See Genbank Accession No. AAA57874.1, SEQ ID NO: 11) and a *Vibrio Fluvialis* ω-transaminase (See Genbank Accession No. AEA39183.1, SEQ ID NO: 12), a *Polaromonas* sp. JS666 monooxygenase (See Genbank Accession No. ABE47160.1, SEQ ID NO:13), a *Mycobacterium* sp. HXN-1500 monooxygenase (See Genbank Accession No. CAH04396.1, SEQ ID NO:14), a *Mycobacterium austroafricanum* monooxygenase (See Genbank Accession No. ACJ06772.1, SEQ ID NO:15), a *Polaromonas* sp. JS666 oxidoreductase (See Genbank Accession No. ABE47159.1, SEQ ID NO:16), a *Mycobacterium* sp. HXN-1500 oxidoreductase (See Genbank Accession No. CAH04397.1, SEQ ID NO:17), a *Polaromonas* sp. JS666 ferredoxin (See Genbank Accession No. ABE47158.1, SEQ ID NO:18), a *Mycobacterium* sp. HXN-1500 ferredoxin (See Genbank Accession No. CAH04398.1, SEQ ID NO:19), *Bacillus subtilis* phosphopantetheinyl transferase (See Genbank Accession No. CAA44858.1, SEQ ID NO:20), *Nocardia* sp. NRRL 5646 phosphopantetheinyl transferase (See Genbank Accession No. ABI83656.1, SEQ ID NO:21), a *Mycobacterium marinum* fatty acid O-methyltransferase (GenBank Accession No. ACC41782.1; SEQ ID NO:22), a *Mycobacterium smegmatis* str. MC2 fatty acid O-methyltransferase (GenBank Accession No. ABK73223.1; SEQ ID NO:23), a *Pseudomonas putida* fatty acid O-methyltransferase (GenBank Accession No. CAA39234.1; SEQ ID NO:24), a *Saccharomyces cerevisiae* alcohol O-acetyltransferase (Genbank Accession No: CAA85138.1, SEQ ID NO: 25), a *Pseudomonas fluorescens* carboxylesterase (Genbank Accession No. AAC60471.2, SEQ ID NO: 26), a *Pseudomonas putida* alkane 1-monooxygenase (Genbank Accession No. CAB51047.1, SEQ ID NO: 27), a *Candida maltose* cytochrome P450 (Genbank Accession Nos: BAA00371.1, SEQ ID NO: 28), a *Salmonella enterica* subsp. *enterica* serovar *Typhimurium* butanal dehydrogenase (GenBank Accession No. AAD39015, SEQ ID NO:29), a *Sphingomonas paucimobilis* demethylase (GenBank Accession No. BAD61059.1 and GenBank Accession No. BAC79257.1, SEQ ID NOs: 30 and 31, respectively), a *Lactobacillus brevis* thioesterase (GenBank Accession No. ABJ63754.1, SEQ ID NO:32), and a *Lactobacillus plantarum* thioesterase (GenBank Accession No. CCC78182.1, SEQ ID NO:33).

DETAILED DESCRIPTION

Figure 1:
FIG. 1 is a schematic of exemplary biochemical pathways leading to hexanoyl-CoA using NADH-dependent enzymes and acetyl-CoA as central metabolites.

This document provides enzymes, non-natural pathways, cultivation strategies, feedstocks, central precursors, host microorganisms and attenuations to the host's biochemical network, which generate a six carbon chain aliphatic backbone (which can be bound to a coenzyme A moiety) from central metabolites in which two terminal functional groups may be formed leading to the synthesis of one or more of adipic acid, 6-hydroxyhexanoate, 6-aminohexanoate, caprolactam, hexamethylenediamine or 1,6-hexanediol (referred to as "C6 building blocks" herein). As used herein, the term "central precursor" is used to denote any metabolite in any metabolic pathway shown herein leading to the synthesis of a C6 building block. The term "central metabolite" is used herein to denote a metabolite that is produced in all microorganisms to support growth.

Host microorganisms described herein can include endogenous pathways that can be manipulated such that one or more C6 building blocks or central precursors thereof can be produced. In an endogenous pathway, the host microorganism naturally expresses all of the enzymes catalyzing the reactions within the pathway. A host microorganism containing an engineered pathway does not naturally express all of the enzymes catalyzing the reactions within the pathway but has been engineered such that all of the enzymes within the pathway are expressed in the host.

The term "exogenous" as used herein with reference to a nucleic acid (or a protein) and a host refers to a nucleic acid that does not occur in (and cannot be obtained from) a cell of that particular type as it is found in nature or a protein encoded by such a nucleic acid. Thus, a non-naturally-occurring nucleic acid is considered to be exogenous to a host once in the host. It is important to note that non-naturally-occurring nucleic acids can contain nucleic acid subsequences or fragments of nucleic acid sequences that are found in nature provided the nucleic acid as a whole does not exist in nature. For example, a nucleic acid molecule containing a genomic DNA sequence within an expression vector is non-naturally-occurring nucleic acid, and thus is exogenous to a host cell once introduced into the host, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular host microorganism. For example, an entire chromosome isolated from a cell of yeast x is an exogenous nucleic acid with respect to a cell of yeast y once that chromosome is introduced into a cell of yeast y.

In contrast, the term "endogenous" as used herein with reference to a nucleic acid (e.g., a gene) (or a protein) and a host refers to a nucleic acid (or protein) that does occur in (and can be obtained from) that particular host as it is found in nature. Moreover, a cell "endogenously expressing" a nucleic acid (or protein) expresses that nucleic acid (or protein) as does a host of the same particular type as it is found in nature. Moreover, a host "endogenously producing" or that "endogenously produces" a nucleic acid, protein, or other compound produces that nucleic acid, protein, or compound as does a host of the same particular type as it is found in nature.

For example, depending on the host and the compounds produced by the host, one or more of the following polypeptides may be expressed in the host in addition to a polypeptide having fatty acid O-methyltransferase activity or a polypeptide having alcohol O-acetyltransferase activity: a polypeptide having monooxygenase activity, a polypeptide having esterase activity, a polypeptide having demethylase activity, a polypeptide having β-ketothiolase activity, a polypeptide having acetyl-CoA carboxylase activity, a polypeptide having β-ketoacyl-[acp] synthase activity, a polypeptide having 3-hydroxyacyl-CoA dehydrogenase activity, a polypeptide having 3-oxoacyl-CoA reductase activity, a polypeptide having enoyl-CoA hydratase activity, a polypeptide having trans-2-enoyl-CoA reductase activity, a polypeptide having thioesterase activity, a polypeptide having aldehyde dehydrogenase activity, a polypeptide having butanal dehydrogenase activity, a polypeptide having monooxygenase activity in, for example, the CYP4F3B family, a polypeptide having alcohol dehydrogenase activity, a polypeptide having 5-oxopentanoate dehydrogenase activity, a polypeptide having 6-oxohexanoate dehydrogenase activity, a polypeptide having 7-oxoheptanoate dehydrogenase activity, a polypeptide having ω-transaminase activity, a polypeptide having 6-hydroxyhexanoate dehydrogenase activity, a polypeptide having 5-hydroxybutanoate dehydrogenase activity, a polypeptide having 4-hydroxybutyrate dehydrogenase activity, a polypeptide having carboxylate reductase activity, a polypeptide having deacetylase activity, a polypeptide having N-acetyl transferase activity, or a polypeptide having amidohydrolase activity. In recombinant hosts expressing a polypeptide having carboxylate reductase activity, a polypeptide having phosphopantetheinyl transferase activity also can be expressed as it enhances activity of the polypeptide having carboxylate reductase activity. In recombinant hosts expressing a polypeptide having monooxygenase activity, an electron transfer chain protein such as a polypeptide having oxidoreductase activity and/or a polypeptide having ferredoxin polypeptide activity also can be expressed.

In some embodiments, a recombinant host can include at least one exogenous nucleic acid encoding a polypeptide having (i) fatty acid O-methyltransferase activity or a polypeptide having alcohol O-acetyltransferase activity, (ii) a polypeptide having monooxygenase activity, and (iii) a polypeptide having esterase activity or a polypeptide having demethylase activity.

In some embodiments, a recombinant host can include at least one exogenous nucleic acid encoding a polypeptide having fatty acid O-methyltransferase activity and a polypeptide having monooxygenase activity, wherein the host produces 6-hydroxyhexanoate methyl ester. Such a host further can include a polypeptide having demethylase activity or a polypeptide having esterase activity and further produce 6-hydroxyhexanoate. In some embodiments, the recombinant host also can include at least one exogenous nucleic acid encoding a polypeptide having β-ketothiolase activity or a polypeptide having acetyl-CoA carboxylase activity and a polypeptide having β-ketoacyl-[acp] synthase activity, a polypeptide having 3-hydroxyacyl-CoA dehydrogenase activity or a polypeptide having 3-oxoacyl-CoA reductase activity, a polypeptide having enoyl-CoA hydratase activity, and a polypeptide having trans-2-enoyl-CoA reductase activity to produce C6 precursor molecules such as hexanoyl-CoA. Such a host further can include one or more of (e.g., two or three of) an exogenous polypeptide having thioesterase activity, a polypeptide having aldehyde dehydrogenase activity, or a polypeptide having butanal dehydrogenase activity, and produce hexanoate as a C6 precursor molecule.

In some embodiments, a recombinant host can include at least one exogenous nucleic acid encoding a polypeptide having alcohol O-acetyltransferase activity and a polypeptide having monooxygenase activity, wherein the host produces hexanoic acid hexyl ester. Such a host further can include a polypeptide having esterase activity and further produce 6-hydroxyhexanoate and/or 1,6-hexanediol. In some embodiments, the recombinant host also can include at least one exogenous nucleic acid encoding a polypeptide having β-ketothiolase activity or a polypeptide having acetyl-CoA carboxylase activity and a polypeptide having β-ketoacyl-[acp] synthase activity, a polypeptide having 3-hydroxyacyl-CoA dehydrogenase activity or a polypeptide having 3-oxoacyl-CoA reductase activity, a polypeptide having enoyl-CoA hydratase activity, and a polypeptide having trans-2-enoyl-CoA reductase activity to produce C6 precursor molecules such as hexanoyl-CoA. Such a host further can include one or more of (e.g., two or three of) an exogenous a polypeptide having aldehyde dehydrogenase activity, a polypeptide having alcohol dehydrogenase activity, a polypeptide having butanal dehydrogenase activity, a polypeptide having carboxylate reductase activity or a polypeptide having thioesterase activity and produce hexanol as a C6 precursor molecule.

A recombinant host producing 6-hydroxyhexanoate further can include one or more of a polypeptide having monooxygenase activity (e.g., in the CYP4F3B family), a polypeptide having alcohol dehydrogenase activity, a polypeptide having aldehyde dehydrogenase activity, a polypeptide having 7-oxohexanoate dehydrogenase activity, a polypeptide having 6-oxohexanoate dehydrogenase activity, a polypeptide having 5-hydroxypentanoate dehydrogenase activity, a polypeptide having 4-hydroxybutyrate dehydrogenase activity or a polypeptide having 6-hydroxyhexanoate dehydrogenase activity, and produce adipic acid or adipate semialdehyde. For example, a recombinant host further can include a polypeptide having monooxygenase activity and produce adipic acid or adipate semialdehyde. As another example, a recombinant host further can include (i) a polypeptide having alcohol dehydrogenase activity, a polypeptide having 6-hydroxyhexanoate dehydrogenase activity, a polypeptide having 5-hydroxybutanoate dehydrogenase activity, or a polypeptide having 4-hydroxybutyrate dehydrogenase activity or (ii) a polypeptide having aldehyde dehydrogenase activity, a polypeptide having 5-oxobutanoate dehydrogenase activity, a polypeptide having 6-oxo-hexanoate dehydrogenase activity, or a polypeptide having 7-oxohexanoate dehydrogenase activity, and produce adipic acid.

A recombinant host producing 6-hydroxyhexanoate further can include one or more of a polypeptide having transaminase activity, a polypeptide having 6-hydroxyhexanoate dehydrogenase activity, a polypeptide having 5-hydroxybutanoate dehydrogenase activity, a polypeptide having 4-hydroxybutyrate dehydrogenase activity and a polypeptide having alcohol dehydrogenase activity, and produce 6-aminohexanoate. For example, a recombinant host producing 6-hydroxyhexanoate further can include a polypeptide having ω-transaminase activity and either a polypeptide having 6-hydroxyhexanoate dehydrogenase activity or polypeptide having alcohol dehydrogenase activity.

A recombinant host producing 6-aminohexanoate, 6-hydroxyhexanoate, adipate semialdehyde or 1,6-hexanediol further can include one or more of a polypeptide having carboxylate reductase activity, a polypeptide having ω-transaminase activity, a polypeptide having deacetylase activity, a polypeptide having N-acetyl transferase activity, or a polypeptide having alcohol dehydrogenase activity, and produce hexamethylenediamine. In some embodiments, a recombinant host further can include each of a polypeptide having carboxylate reductase activity, a polypeptide having ω-transaminase activity, a polypeptide having deacetylase activity, and a polypeptide having N-acetyl transferase activity. In some embodiments, a recombinant host further can include a polypeptide having carboxylate reductase activity and a polypeptide having ω-transaminase activity. In some embodiments, a recombinant host further can include a polypeptide having carboxylate reductase activity, a polypeptide having ω-transaminase activity, and a polypeptide having alcohol dehydrogenase activity. In the embodiments in which the recombinant host produces 6-aminohexanoate, an additional polypeptide having ω-transaminase activity may not be necessary to produce hexamethylenediamine. In some embodiments, the host includes a second exogenous polypeptide having ω-transaminase activity that differs from the first exogenous polypeptide having ω-transaminase activity.

A recombinant host producing 6-hydroxyhexanoic acid further can include one or more of a polypeptide having carboxylate reductase activity and a polypeptide having alcohol dehydrogenase activity, and produce 1,6-hexanediol.

Within an engineered pathway, the enzymes can be from a single source, i.e., from one species or genus, or can be from multiple sources, i.e., different species or genera. Nucleic acids encoding the enzymes described herein have been identified from various organisms and are readily available in publicly available databases such as GenBank or EMBL. In recombinant hosts containing an exogenous enzyme, the hosts contain an exogenous nucleic acid encoding the enzyme.

Any of the enzymes described herein that can be used for production of one or more C6 building blocks can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of the corresponding wild-type enzyme. It will be appreciated that the sequence identity can be determined on the basis of the mature enzyme (e.g., with any signal sequence removed) or on the basis of the immature enzyme (e.g., with any signal sequence included).

For example, a polypeptide having thioesterase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of an *Escherichia coli* thioesterase encoded by tesB (see GenBank Accession No. AAA24665.1, SEQ ID NO: 1), to the amino acid sequence of a *Lactobacillus brevis* thioesterase (GenBank Accession No. ABJ63754.1, SEQ ID NO:32) or a *Lactobacillus plantarum* thioesterase (GenBank Accession No. CCC78182.1, SEQ ID NO:33). See FIG. 9.

For example, a polypeptide having carboxylate reductase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Mycobacterium marinum* (see Genbank Accession No. ACC40567.1, SEQ ID NO: 2), a *Mycobacterium smegmatis* (see Genbank Accession No. ABK71854.1, SEQ ID NO: 3), a *Segniliparus rugosus* (see Genbank Accession No. EFV11917.1, SEQ ID NO: 4), a *Mycobacterium massiliense* (see Genbank Accession No. EIV11143.1, SEQ ID NO: 5), or a *Segniliparus rotundus* (see Genbank Accession No. ADG98140.1, SEQ ID NO: 6) carboxylate reductase. See, FIG. 9.

For example, a polypeptide having ω-transaminase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Chromobacterium violaceum* (see Genbank Accession No. AAQ59697.1, SEQ ID NO: 7), a *Pseudomonas aeruginosa* (see Genbank Accession No. AAG08191.1, SEQ ID NO: 8), a *Pseudomonas syringae* (see Genbank Accession No. AAY39893.1, SEQ ID NO: 9), a *Rhodobacter sphaeroides* (see Genbank Accession No. ABA81135.1, SEQ ID NO: 10), an *Escherichia coli* (see Genbank Accession No. AAA57874.1, SEQ ID NO: 11), or a *Vibrio fluvialis* (see Genbank Accession No. AEA39183.1, SEQ ID NO: 12) ω-transaminase. Some of these ω-transaminases are diamine ω-transaminases. See, FIG. 9.

For example, a polypeptide having monooxygenase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Polaromonas* sp. JS666 monooxygenase (see Genbank Accession No. ABE47160.1, SEQ ID NO:13), a *Mycobacterium* sp. HXN-1500 monooxygenase (see Genbank Accession No. CAH04396.1, SEQ ID NO:14), or a *Mycobacterium austroafricanum* monooxygenase (See Genbank Accession No. ACJ06772.1, SEQ ID NO:15). See, FIG. 9.

For example, a polypeptide having oxidoreductase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Polaromonas* sp. JS666 oxidoreductase (see Genbank Accession No. ABE47159.1, SEQ ID NO:16) or a *Mycobacterium* sp. HXN-1500 oxidoreductase (see Genbank Accession No. CAH04397.1, SEQ ID NO:17). See, FIG. 9.

For example, a polypeptide having ferredoxin activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Polaromonas* sp. JS666 ferredoxin (see Genbank Accession No. ABE47158.1, SEQ ID NO:18) or a *Mycobacterium* sp. HXN-1500 ferredoxin (see Genbank Accession No. CAH04398.1, SEQ ID NO:19). See, FIG. 9.

For example, a polypeptide having phosphopantetheinyl transferase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Bacillus subtilis* phosphopantetheinyl transferase (see Genbank Accession No. CAA44858.1, SEQ ID NO:20) or a *Nocardia* sp. NRRL 5646 phosphopantetheinyl transferase (see Genbank Accession No. ABI83656.1, SEQ ID NO:21). See FIG. 9.

For example, a polypeptide having fatty acid O-methyltransferase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Mycobacterium marinum* (see GenBank Accession No. ACC41782.1, SEQ ID NO: 22), a *Mycobacterium smegmatis* (see GenBank Accession No. ABK73223.1, SEQ ID NO: 23), or a *Pseudomonas putida* (see GenBank Accession No. CAA39234.1, SEQ ID NO: 24) methyltransferase. See FIG. 9.

For example, a polypeptide having alcohol O-acetyltransferase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Saccharomyces cerevisiae* (see GenBank Accession No. CAA85138.1, SEQ ID NO: 25) alcohol O-acetyltransferase. See FIG. 9.

For example, a polypeptide having esterase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Pseudomonas fluorescens* (see GenBank Accession No. AAC60471.2, SEQ ID NO: 26) esterase. See FIG. 9.

For example, a polypeptide having alkane 1-monooxygenase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Pseudomonas putida* alkane 1-monooxygenase (Genbank Accession No. CAB51047.1, SEQ ID NO: 27).

For example, a polypeptide having cytochrome P450 monooxygenase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Candida maltose* cytochrome P450 (Genbank Accession No: BAA00371.1, SEQ ID NO: 28).

For example, a polypeptide having butanal dehydrogenase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Salmonella enterica* subsp. *enterica* serovar *Typhimurium* butanal dehydrogenase (see GenBank Accession No. AAD39015, SEQ ID NO:29).

For example, a polypeptide having syringate O-demethylase activity described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Sphingomonas paucimobilis* demethylase (see, GenBank Accession No. BAD61059.1 and GenBank Accession No. BAC79257.1, SEQ ID NOs: 30 and 31, respectively).

The percent identity (homology) between two amino acid sequences can be determined as follows. First, the amino acid sequences are aligned using the BLAST 2 Sequences (Bl2seq) program from the stand-alone version of BLASTZ containing BLASTP version 2.0.14. This stand-alone version of BLASTZ can be obtained from Fish & Richardson's web site (e.g., www.fr.com/blast/) or the U.S. government's National Center for Biotechnology Information web site (www.ncbi.nlm.nih.gov). Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq-i c:\seq1.txt-j c:\seq2.txt-p blastp-o c:\output.txt. If the two compared sequences share homology (identity), then the designated output file will present those regions of homology as aligned sequences. If the two compared sequences do not share homology (identity), then the designated output file will not present aligned sequences. Similar procedures can be following for nucleic acid sequences except that blastn is used.

Once aligned, the number of matches is determined by counting the number of positions where an identical amino acid residue is presented in both sequences. The percent identity (homology) is determined by dividing the number of matches by the length of the full-length polypeptide amino acid sequence followed by multiplying the resulting value by 100. It is noted that the percent identity (homology) value is rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given enzyme can be modified such that optimal expression in a particular species (e.g., bacteria or fungus) is obtained, using appropriate codon bias tables for that species.

Functional fragments of any of the enzymes described herein can also be used in the methods of the document. The term "functional fragment" as used herein refers to a peptide fragment of a protein that is shorter than the full-length immature protein and has at least 25% (e.g., at least: 30%; 40%; 50%; 60%; 70%; 75%; 80%; 85%; 90%; 91%; 92%; 93%; 94%; 95%; 96%; 97%; 98%; 99%; 100%; or even greater than 100%) of the activity of the corresponding mature, full-length, wild-type protein. The functional fragment can generally, but not always, be comprised of a continuous region of the protein, wherein the region has functional activity.

This document also provides (i) functional variants of the enzymes used in the methods of the document and (ii) functional variants of the functional fragments described above. Functional variants of the enzymes and functional fragments can contain additions, deletions, or substitutions relative to the corresponding wild-type sequences. Enzymes with substitutions will generally have not more than 50 (e.g., not more than one, two, three, four, five, six, seven, eight, nine, ten, 12, 15, 20, 25, 30, 35, 40, or 50) amino acid substitutions (e.g., conservative substitutions). This applies to any of the enzymes described herein and functional fragments. A conservative substitution is a substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution. By contrast, a nonconservative substitution is a substitution of one amino acid for another with dissimilar characteristics.

Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. Additions (addition variants) include fusion proteins containing: (a) any of the enzymes described herein or a fragment thereof; and (b) internal or terminal (C or N) irrelevant or heterologous amino acid sequences. In the context of such fusion proteins, the term "heterologous amino acid sequences" refers to an amino acid sequence other than (a). A heterologous sequence can be, for example a sequence used for purification of the recombinant protein (e.g., FLAG, polyhistidine (e.g., hexahistidine), hemagglutinin (HA), glutathione-S-transferase (GST), or maltosebinding protein (MBP)). Heterologous sequences also can be proteins useful as detectable markers, for example, luciferase, green fluorescent protein (GFP), or chloramphenicol acetyl transferase (CAT). In some embodiments, the fusion protein contains a signal sequence from another protein. In certain host cells (e.g., yeast host cells), expression and/or secretion of the target protein can be increased through use of a heterologous signal sequence. In some embodiments, the fusion protein can contain a carrier (e.g., KLH) useful, e.g., in eliciting an immune response for antibody generation) or ER or Golgi apparatus retention signals. Heterologous sequences can be of varying length and in some cases can be a longer sequences than the full-length target proteins to which the heterologous sequences are attached.

Engineered hosts can naturally express none or some (e.g., one or more, two or more, three or more, four or more, five or more, or six or more) of the enzymes of the pathways described herein. Thus, a pathway within an engineered host can include all exogenous enzymes, or can include both endogenous and exogenous enzymes. Endogenous genes of the engineered hosts also can be disrupted to prevent the formation of undesirable metabolites or prevent the loss of intermediates in the pathway through other enzymes acting on such intermediates. Engineered hosts can be referred to as recombinant hosts or recombinant host cells. As described herein recombinant hosts can include nucleic acids encoding one or more of a polypeptide having fatty acid O-methyltransferase activity, a polypeptide having alcohol O-acetyltransferase activity, a polypeptide having dehydrogenase activity, a polypeptide having β-ketothiolase activity, a polypeptide having β-ketoacyl-[acp] synthase activity, a polypeptide having carboxylase activity, a polypeptide having reductase activity, a polypeptide having hydratase activity, a polypeptide having thioesterase activity, a polypeptide having monooxygenase activity, a polypeptide having demethylase activity, a polypeptide having esterase activity, or a polypeptide having transaminase activity as described herein.

In addition, the production of one or more C6 building blocks can be performed in vitro using the isolated enzymes described herein, using a lysate (e.g., a cell lysate) from a host microorganism as a source of the enzymes, or using a plurality of lysates from different host microorganisms as the source of the enzymes.

Biosynthetic Methods

The present document provides methods of producing a ($C_{3-8}$ hydroxyalkyl)-C(=O)OCH$_3$ ester. As used herein, the term ($C_{3-8}$ hydroxyalkyl)-C(=O)OCH$_3$ ester refers to a compound having the following formula:

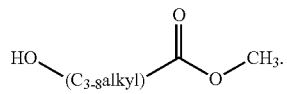

As used herein, the term "$C_{3-8}$ hydroxyalkyl" refers to a saturated hydrocarbon group that may be straight-chain or branched, and is substituted by at least one hydroxyl (i.e., hydroxy or OH) group. In some embodiments, the $C_{3-8}$ hydroxyalkyl refers to refers to a saturated hydrocarbon group that may be straight-chain or branched, and is substituted by at least one terminal hydroxyl (OH) group. In some embodiments, the alkyl group contains 4 to 8, 4 to 7, 4 to 6, 4 to 5, 5 to 8, 5 to 7, 5 to 6, 6 to 8, 6 to 7, or 7 to 8 carbon atoms. In some embodiments, the $C_{3-8}$ hydroxyalkyl is a group of the following formula:

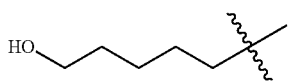 [SMILES: *CCCCCO]

In some embodiments, the method comprises:
a) enzymatically converting a $C_{3-8}$ carboxylic acid to a ($C_{3-8}$ alkyl)-C(=O)OCH$_3$ ester; and
b) enzymatically converting the ($C_{3-8}$ alkyl)-C(=O)OCH$_3$ ester to ($C_{3-8}$ hydroxyalkyl)-C(=O)OCH$_3$ ester.

As used herein, the term "$C_{4-9}$ carboxylic acid" refers to a compound having the formula R—C(=O)OH, wherein R is a refers to a saturated hydrocarbon group (i.e., an alkyl group) that may be straight-chain or branched, wherein the compound has from 4 to 9 carbon atoms. In some embodiments, the $C_{4-9}$ carboxylic acid group contains 4 to 9, 4 to 8, 4 to 7, 4 to 6, 4 to 5, 5 to 9, 5 to 8, 5 to 7, 5 to 6, 6 to 9, 6 to 8, 6 to 7, 7 to 9, 7 to 8, or 8 to 9 carbon atoms. Exemplary $C_{4-9}$ carboxylic acids include butanoic acid (i.e., butanoate), pentanoic acid (i.e., pentanoate), hexanoic acid (i.e., hexanoate), heptanoic acid (i.e., heptanoate), octanoic acid (e.g., octanoate), nonanoic acid (i.e., nonanoate), 2-methylhexanoic acid (i.e., 2-methylhexanoate), 3-methylhexanoic acid (i.e., 3-methylhexanoate), 4-methylhexanoic acid (i.e., 4-methylhexanoate), and 5-methylhexanoic acid (i.e., 5-methylhexanoate). In some embodiments, the $C_{4-9}$ carboxylic acid is hexanoate (i.e., hexanoic acid).

As used herein, the term "($C_{3-8}$ alkyl)-C(=O)OCH$_3$ ester" refers to a compound having the following formula:

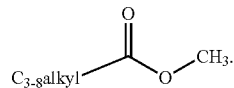

As used herein, the term "$C_{3-8}$ alkyl" refers to a saturated hydrocarbon group that may be straight-chain or branched, having 3 to 9 carbon atoms. In some embodiments, the alkyl group contains 4 to 8, 4 to 7, 4 to 6, 4 to 5, 5 to 8, 5 to 7, 5 to 6, 6 to 8, 6 to 7, or 7 to 8, carbon atoms. Example alkyl moieties include n-butyl, isobutyl, sec-butyl, tert-butyl, n-pentyl, iso-pentyl, neo-pentyl, n-hexyl, n-heptyl, n-octyl. In some embodiments, the $C_{3-8}$ alkyl is a group of the following formula:

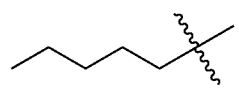 [SMILES: *CCCCC]

In some embodiments, the method comprises:
a) enzymatically converting a $C_{4-9}$ carboxylic acid to a ($C_{3-8}$ alkyl)-C(=O)OCH$_3$ ester; and
b) enzymatically converting the ($C_{3-8}$ alkyl)-C(=O)OCH$_3$ ester to ($C_{3-8}$ hydroxyalkyl)-C(=O)OCH$_3$ ester.

In some embodiments, the $C_{4-9}$ carboxylic acid is enzymatically converted to the ($C_{3-8}$ alkyl)-C(=O)OCH$_3$ ester using a polypeptide having fatty acid O-methyltransferase activity. In some embodiments, the polypeptide having fatty acid O-methyltransferase activity has at least 70% sequence identity to an amino acid sequence set forth in SEQ ID NO:23, SEQ ID NO:24, or SEQ ID NO:25.

In some embodiments, the ($C_{3-8}$ alkyl)-C(=O)OCH$_3$ ester is enzymatically converted to the ($C_{3-8}$ hydroxyalkyl)-C(=O)OCH$_3$ ester using a polypeptide having monooxygenase activity. In some embodiments, the monooxygenase is classified under EC 1.14.14.- or EC 1.14.15.-. In some embodiments, the monooxygenase has at least 70% sequence identity to an amino acid sequence set forth in SEQ ID NO: 13-15, SEQ ID NO:27 and/or, SEQ ID NO:28.

In some embodiments, the $C_{4-9}$ carboxylic acid is enzymatically produced from $C_{4-9}$ alkanoyl-CoA. As used herein, the term "$C_{4-9}$ alkanoyl-CoA" refers to a compound having the following formula:

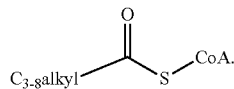

wherein the $C_{3-8}$ alkyl group is as defined herein. In some embodiments, the $C_{3-8}$ alkyl is a group of the following formula:

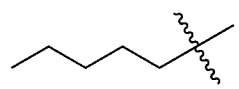 [SMILES: *CCCCC]

In some embodiments, a polypeptide having thioesterase activity enzymatically produces the $C_{4-9}$ carboxylic acid from $C_{4-9}$ alkanoyl-CoA. In some embodiments, the thioesterase has at least 70% sequence identity to the amino acid sequence set forth in SEQ ID NO:1.

In some embodiments, a polypeptide having butanal dehydrogenase activity and a polypeptide having aldehyde dehydrogenase activity enzymatically produces the $C_{4-9}$ carboxylic acid from the $C_{4-9}$ alkanoyl-CoA.

In some embodiments, the method of producing a ($C_{3-8}$ hydroxyalkyl)-C(=O)OCH$_3$ ester is a method of producing 6-hydroxyhexanoate methyl ester, said method comprising:

a) enzymatically converting hexanoate to hexanoate methyl ester; and b) enzymatically converting the hexanoate methyl ester to 6-hydroxyhexanoate methyl ester.

In some embodiments, hexanoate is enzymatically converted to hexanoate methyl ester using a polypeptide having fatty acid O-methyltransferase activity. In some embodiments, the polypeptide having fatty acid O-methyltransferase activity has at least 70% sequence identity to an amino acid sequence set forth in SEQ ID NO:22, SEQ ID NO:23, or SEQ ID NO:24.

In some embodiments, hexanoate methyl ester is enzymatically converted to 6-hydroxyhexanoate methyl ester using a polypeptide having monooxygenase activity. In some embodiments, the polypeptide having monooxygenase activity has at least 70% sequence identity to an amino acid sequence set forth in SEQ ID NO: 13-15, SEQ ID NO:27 and/or SEQ ID NO:28. In some embodiments, the polypeptide having monooxygenase activity is classified under EC 1.14.14.- or EC 1.14.15.-.

In some embodiments, hexanoate is enzymatically produced from hexanoyl-CoA. In some embodiments, a polypeptide having thioesterase activity enzymatically produces hexanoate from hexanoyl-CoA. In some embodiments, the polypeptide having thioesterase activity has at least 70% sequence identity to the amino acid sequence set forth in SEQ ID NO:1, and/or SEQ ID NO: 32-33.

In some embodiments, a polypeptide having butanal dehydrogenase activity and a polypeptide having aldehyde dehydrogenase activity enzymatically produces hexanoate from hexanoyl-CoA.

The present document further provides methods of producing one or more terminal hydroxy-substituted ($C_{4-9}$ alkyl)-OC(=O)—($C_{3-8}$ alkyl) esters. As used herein, the term ($C_{4-9}$ alkyl)-OC(=O)—($C_{3-8}$ alkyl) ester" refers to a compound having the following formula:

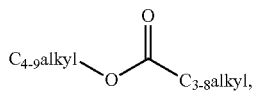

wherein the $C_{3-8}$ alkyl group is as defined herein. As used herein the term "terminal hydroxy-substituted "($C_{4-9}$ alkyl)-OC(=O)—($C_{3-8}$ alkyl) ester" refers to a compound having the following formula:

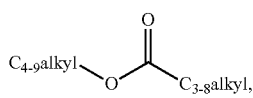

wherein at least one of the alkyl groups (i.e., at least one of the $C_{4-9}$ alkyl and $C_{3-8}$ alkyl groups) is substituted by at least one terminal hydroxy (—OH) group, and the $C_{3-8}$ alkyl is as defined herein. As used herein, the term "$C_{4-9}$ alkyl" refers to a saturated hydrocarbon group that may be straight-chain or branched, having 4 to 9 carbon atoms. In some embodiments, the alkyl group contains 4 to 9, 4 to 8, 4 to 7, 4 to 6, 4 to 5, 5 to 9, 5 to 8, 5 to 7, 5 to 6, 6 to 9, 6 to 8, 6 to 7, 7 to 9, 7 to 8, or 8 to 9 carbon atoms. Example alkyl moieties include n-butyl, isobutyl, sec-butyl, tert-butyl, n-pentyl, iso-pentyl, neo-pentyl, n-hexyl, n-heptyl, n-octyl, and n-nonyl. In some embodiments, one of the alkyl groups is substituted by at least one terminal hydroxy group. In some embodiments, each of the alkyl groups is substituted by at least one terminal hydroxy group. In some embodiments, one of the alkyl groups is substituted by one terminal hydroxy group. In some embodiments, each of the alkyl groups is substituted by one terminal hydroxy group. In some embodiments, the terminal hydroxy-substituted ($C_{4-9}$ alkyl)-OC(=O)—($C_{3-8}$ alkyl) ester is selected from the group consisting of:

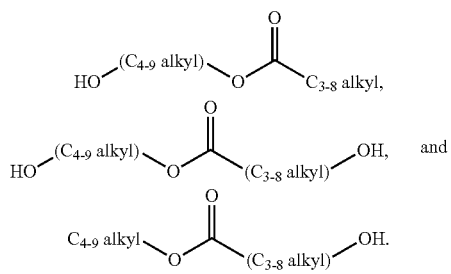

In some embodiments, the method includes:

a) enzymatically converting $C_{4-9}$ alkanoyl-CoA to a ($C_{4-9}$ alkyl)-OC(=O)—(C3-8 alkyl) ester; and b) enzymatically converting the ($C_{4-9}$ alkyl)-OC(=O)—($C_{3-8}$ alkyl) ester to any of ($C_{4-9}$ alkyl)-OC(=O)—($C_{3-8}$ hydroxyalkyl) ester, ($C_{4-9}$ hydroxyalkyl)-OC(=O)—($C_{3-8}$ hydroxyalkyl) ester, or ($C_{4-9}$ hydroxyalkyl)-OC(=O)—($C_{3-8}$ alkyl) ester.

In some embodiments, $C_{4-9}$ alkanoyl-CoA is enzymatically converted to the ($C_{4-9}$ alkyl)-OC(=O)—($C_{3-8}$ alkyl) ester using a polypeptide having alcohol O-acetyltransferase activity. In some embodiments, the alcohol O-acetyltransferase has at least 70% sequence identity to the amino acid sequence set forth in SEQ ID NO: 25.

In some embodiments, the ($C_{4-9}$ alkyl)-OC(=O)—($C_{3-8}$ alkyl) ester is enzymatically converted to any of ($C_{4-9}$ alkyl)-OC(=O)—($C_{3-8}$ hydroxyalkyl) ester, ($C_{4-9}$ hydroxyalkyl)-OC(=O)—($C_{3-8}$ hydroxyalkyl) ester, or ($C_{4-9}$ hydroxyalkyl)-OC(=O)—($C_{3-8}$ alkyl) ester using a polypeptide having monooxygenase activity. In some embodiments, the polypeptide having monooxygenase activity is classified under EC 1.14.14.- or EC 1.14.15.-.

In some embodiments, the method further includes enzymatically converting ($C_{4-9}$ hydroxyalkyl)-OC(=O)—($C_{3-8}$ hydroxyalkyl) ester or ($C_{4-9}$ alkyl)-OC(=O)—($C_{3-8}$ hydroxyalkyl) ester to a $C_{4-9}$ hydroxyalkanoate. In some embodiments, a polypeptide having esterase activity enzymatically converts ($C_{4-9}$ hydroxyalkyl)-OC(=O)—($C_{3-8}$ hydroxyalkyl) ester or ($C_{4-9}$ alkyl)-OC(=O)—($C_{3-8}$ hydroxyalkyl) ester to the $C_{4-9}$ hydroxyalkanoate.

As used herein, the term $C_{4-9}$ hydroxyalkanoate refers to a compound having the following formula:

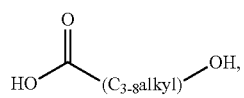

wherein the $C_{3-8}$ hydroxyalkyl is as defined herein. Example $C_{4-9}$ hydroxyalkanoates include, but are not limited to, 6-hydroxyhexanoate (i.e., 6-hydroxyhexanoic acid), 5-hydroxyhexanoate (i.e., 5-hydroxyhexanoic acid), 4-hydroxyhexanoate (i.e., 4-hydroxyhexanoic acid), 3-hydroxyhexanoate (i.e., 3-hydroxyhexanoic acid), and the like. It is understood by those skilled in the art that the specific form will depend on pH (e.g., neutral or ionized forms, including any salt forms thereof). In some embodiments, the $C_{3-8}$ hydroxyalkyl is a group having the following formula:

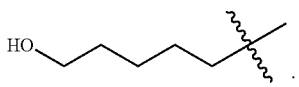 [SMILES: *CCCCCO]

In some embodiments, the method of producing one or more hydroxy-substituted $(C_{4-9}$ alkyl)-OC(=O)—$(C_{3-8}$ alkyl) esters is a method of producing one or more hexanoic acid hexyl hydroxyl esters. In some embodiments, the method includes:

a) enzymatically converting hexanoyl-CoA to hexanoic acid hexyl ester; and b) enzymatically converting hexanoic acid hexyl ester to any of 6-hydroxyhexanoic acid hexyl ester, 6-hydroxyhexanoic acid 6-hydroxyhexyl ester, or hexanoic acid 6-hydroxyhexyl ester.

In some embodiments, hexanoyl-CoA is enzymatically converted to hexanoic acid hexyl ester using a polypeptide having alcohol O-acetyltransferase activity. In some embodiments, the polypeptide having alcohol O-acetyltransferase activity has at least 70% sequence identity to the amino acid sequence set forth in SEQ ID NO: 25.

In some embodiments, hexanoic acid hexyl ester is enzymatically converted to any of 6-hydroxyhexanoic acid hexyl ester, 6-hydroxyhexanoic acid 6-hydroxyhexyl ester and/or hexanoic acid 6-hydroxyhexyl ester using a polypeptide having monooxygenase activity. In some embodiments, the polypeptide having monooxygenase activity is classified under EC 1.14.14.- or EC 1.14.15.-.

In some embodiments, the method further includes enzymatically converting 6-hydroxyhexanoic acid 6-hydroxyhexyl ester or 6-hydroxyhexanoic acid hexyl ester to 6-hydroxyhexanoate. In some embodiments, a polypeptide having esterase activity enzymatically converts 6-hydroxyhexanoic acid 6-hydroxyhexyl ester or 6-hydroxyhexanoic acid hexyl ester to 6-hydroxyhexanoate.

In some embodiments, the method further includes enzymatically converting 6-hydroxyhexanoic acid 6-hydroxyhexyl ester or hexanoic acid 6-hydroxyhexyl ester to 1,6-hexanediol. In some embodiments, a polypeptide having esterase activity enzymatically converts 6-hydroxyhexanoic acid 6-hydroxyhexyl ester or hexanoic acid 6-hydroxyhexyl ester to 1,6-hexanediol.

In some embodiments, the method can include enzymatically converting 6-hydroxyhexanoic acid hexyl ester, 6-hydroxyhexanoic acid 6-hydroxyhexyl ester, or hexanoic acid 6-hydroxyhexyl ester to 6-hydroxyhexanoate and/or 1,6-hexanediol. In some embodiments, a polypeptide having esterase activity enzymatically converts 6-hydroxyhexanoic acid hexyl ester, 6-hydroxyhexanoic acid 6-hydroxyhexyl ester, or hexanoic acid 6-hydroxyhexyl ester to 6-hydroxyhexanoate and/or 1,6-hexanediol.

In some embodiments, the method further includes enzymatically converting 1,6-hexanediol to 6-hydroxyhexanal.

In some embodiments, a polypeptide having alcohol dehydrogenase activity enzymatically converts 1,6-hexanediol to 6-hydroxyhexanal.

In some embodiments, the method further includes enzymatically converting 6-hydroxyhexanal to 6-hydroxyhexanoate. In some embodiments, a polypeptide having aldehyde dehydrogenase activity enzymatically converts 6-hydroxyhexanal to 6-hydroxyhexanoate.

In some embodiments, the method further includes enzymatically converting 6-hydroxyhexanoate methyl ester to 6-hydroxyhexanoate. In some embodiments, a polypeptide having demethylase or esterase activity enzymatically converts 6-hydroxyhexanoate methyl ester to 6-hydroxyhexanoate.

In some embodiments, the method further includes enzymatically converting 6-hydroxyhexanoate to a product selected from the group consisting of adipic acid, adipate semialdehyde, 6-aminohexanoate, hexamethylenediamine, and 1,6-hexanediol.

In some embodiments, the method includes enzymatically converting 6-hydroxyhexanoate to adipate semialdehyde using a polypeptide having alcohol dehydrogenase activity, a polypeptide having 6-hydroxyhexanoate dehydrogenase activity, a polypeptide having 5-hydroxypentanoate dehydrogenase activity, a polypeptide having 4-hydroxybutyrate dehydrogenase activity, or a polypeptide having monooxygenase activity.

In some embodiments, the method further the enzymatically converting adipate semialdehyde to adipic acid using a polypeptide having 5-oxopentanoate dehydrogenase activity, a polypeptide having 6-oxohexanoate dehydrogenase activity, a polypeptide having 7-oxoheptanoate dehydrogenase activity, a polypeptide having aldehyde dehydrogenase activity, or a polypeptide having monooxygenase activity.

In some embodiments, the method further includes enzymatically converting adipate semialdehyde to 6-aminohexanoate. In some embodiments, a polypeptide having ω-transaminase activity enzymatically converts adipate semialdehyde to 6-aminohexanoate.

In some embodiments, the method further includes enzymatically converting 6-aminohexanoate to hexamethylenediamine. In some embodiments, the method further includes enzymatically converting adipate semialdehyde to hexamethylenediamine. In some embodiments, adipate semialdehyde or 6-aminohexanoate is enzymatically converted to hexamethylenediamine using a polypeptide having carboxylate reductase activity and/or a polypeptide having ω-transaminase activity and optionally one or more of a polypeptide having N-acetyl transferase activity, a polypeptide having acetylputrescine deacetylase activity, and a polypeptide having alcohol dehydrogenase activity.

In some embodiments, said method comprises enzymatically converting 6-hydroxyhexanoate to 1,6-hexanediol using a polypeptide having carboxylate reductase activity and a polypeptide having alcohol dehydrogenase activity.

In some embodiments, said method further comprises enzymatically converting 1,6-hexanediol to hexamethylenediamine. In some embodiments, a polypeptide having alcohol dehydrogenase activity and a polypeptide having ω-transaminase activity enzymatically converts 1,6-hexanediol hexamethylenediamine.

In some embodiments, a polypeptide having carboxylate reductase activity, a polypeptide having ω-transaminase activity, and a polypeptide having alcohol dehydrogenase activity enzymatically converts 6-hydroxyhexanoate to hexamethylenediamine.

In some embodiments, the polypeptide having ω-transaminase activity has at least 70% sequence identity to any one of the amino acid sequences set forth in SEQ ID NO. 7-12.

In some embodiments, hexanoyl-CoA is produced from acetyl-CoA via two cycles of CoA-dependent carbon chain elongation. In some embodiments, each of said two cycles of CoA-dependent carbon chain elongation comprises using a polypeptide having β-ketothiolase activity or a polypeptide having acetyl-CoA carboxylase activity and a polypeptide having β-ketoacyl-[acp] synthase activity, a polypeptide having 3-hydroxyacyl-CoA dehydrogenase activity or a polypeptide having 3-oxoacyl-CoA reductase activity, a polypeptide having enoyl-CoA hydratase activity, and a polypeptide having trans-2-enoyl-CoA reductase activity to form hexanoyl-CoA from acetyl-CoA.

Enzymes Converting Hexanoate or Hexanoyl-CoA to 6-Hydroxyhexanoate

Figure 7:
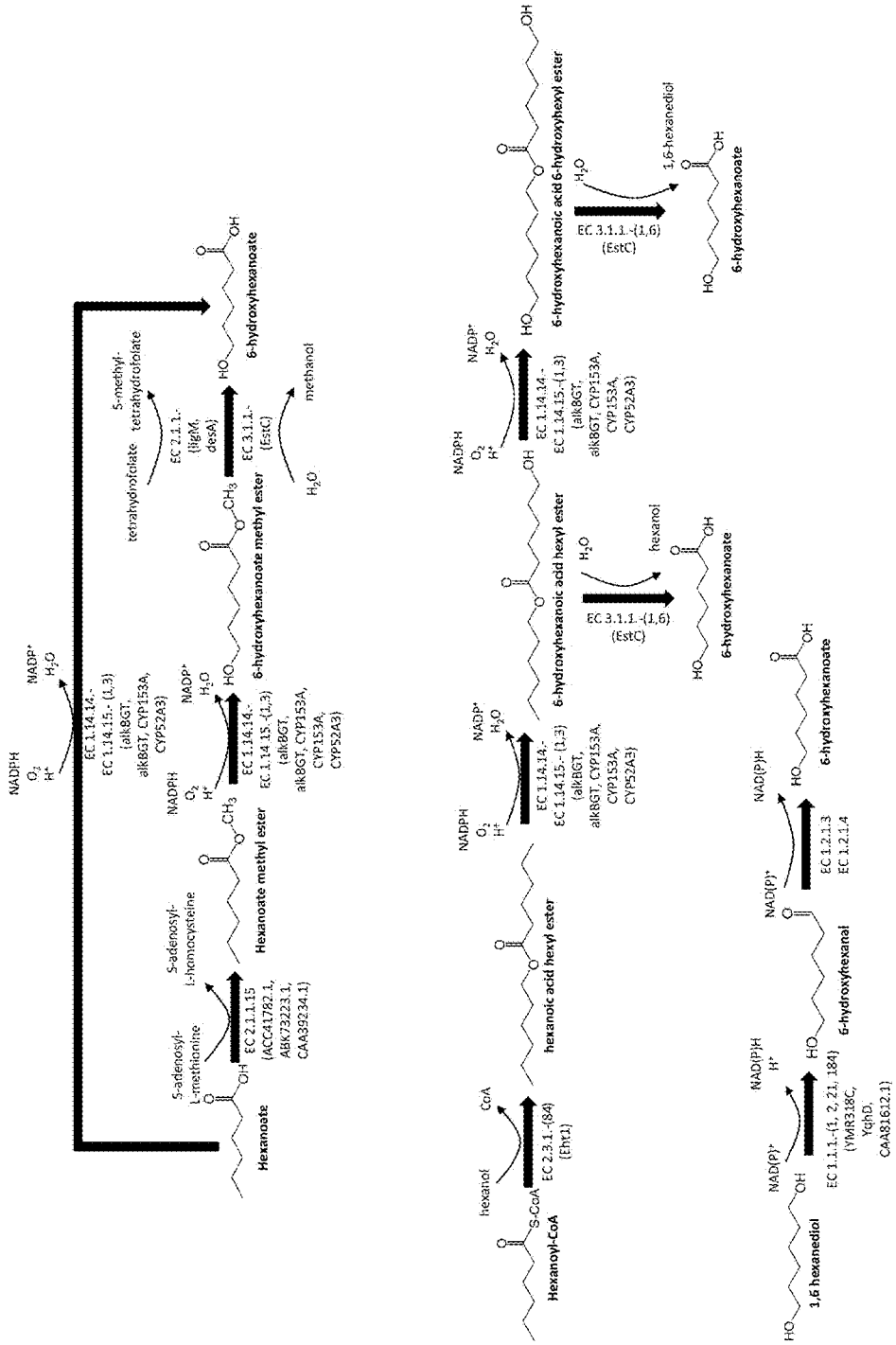
FIG. 7 is a schematic of exemplary biochemical pathways leading to 6-hydroxyhexanoate via ester intermediates using hexanoate or hexanoyl-CoA as a central precursor.

As depicted in FIG. 7, hexanoate methyl ester can be formed from hexanoate using a polypeptide having fatty acid O-methyltransferase activity, such as the polypeptide having fatty acid O-methyltransferase activity classified, for example, under EC 2.1.1.15. For example, the polypeptide having fatty acid O-methyltransferase activity can be obtained from *Mycobacterium marinum* (GenBank Accession No. ACC41782.1. SEQ ID NO:22); *Mycobacterium smegmatis* (see GenBank Accession No. ABK73223.1, SEQ ID NO: 23), or *Pseudomonas putida* (see GenBank Accession No. CAA39234.1, SEQ ID NO: 24).

Hexanoate methyl ester can be converted to 6-hydroxyhexanoate methyl ester using a polypeptide having monooxygenase activity classified, for example, under EC 1.14.14.- or EC 1.14.15.-(1,3) For example, a polypeptide having monooxygenase activity can be, for example, from the CYP153A family (SEQ ID NO:13-15), the CYP52A3 family (See Genbank Accession No: BAA00371.1, SEQ ID NO: 28) or the alkB family such as the gene product of alkBGT from *Pseudomonas putida* (See Genbank Accession No. CAB51047.1, SEQ ID NO: 27). See, FIG. 7.

6-hydroxyhexanoate methyl ester can be converted to 6-hydroxyhexanoate using a polypeptide having demethylase activity classified, for example, under EC 2.1.1.- such as the gene product of ligM (see GenBank Accession No. BAD61059.1; SEQ ID NO:30) or desA (GenBank Accession No. BAC79257.1; SEQ ID NO:31) or using a polypeptide having esterase activity classified, for example under EC 3.1.1.- such as the gene product of EstC (see GenBank Accession No. AAC60471.2, SEQ ID NO: 26).

As depicted in FIG. 7, hexanoyl-CoA can be converted to hexanoic acid hexyl ester using a polypeptide having alcohol O-acetyltransferase activity classified, for example, under EC 2.3.1.-(84) such as the gene product of Eht1 (Genbank Accession No: CAA85138.1, SEQ ID NO: 25).

Hexanoic acid hexyl ester can be converted to 6-hydroxyhexanoic acid hexyl ester and/or 6-hydroxyhexanoic acid 6-hydroxyhexyl ester using a polypeptide having monooxygenase activity classified, for example, under EC 1.14.14.- or EC 1.14.15.-(1,3) For example, a polypeptide having monooxygenase activity can be, for example, from the CYP153A family, the CYP52A3 family (Genbank Accession No: BAA00371.1, SEQ ID NO: 28) or the alkB family such as the gene product of alkBGT from *Pseudomonas putida* (Genbank Accession No. CAB51047.1, SEQ ID NO: 27). See, FIG. 7.

6-hydroxyhexanoic acid hexyl ester and 6-hydroxyhexanoic acid 6-hydroxyhexyl ester can be converted to 6-hydroxyhexanoate using a polypeptide having esterase activity classified, for example, under EC 3.1.1.-(1,6) such as the gene product of EstC (see GenBank Accession No. AAC60471.2, SEQ ID NO: 26).

For example, the monooxygenase CYP153A family classified, for example, under EC 1.14.15.-(1,3) is soluble and has regio-specificity for terminal hydroxylation, accepting medium chain length substrates (see, e.g., Koch et al., *Appl. Environ. Microbiol.*, 2009, 75(2), 337-344; Funhoff et al., 2006, *J. Bacteriol.*, 188(44): 5220-5227; Van Beilen & Funhoff, *Current Opinion in Biotechnology*, 2005, 16, 308-314; Nieder and Shapiro, *J. Bacteriol.*, 1975, 122(1), 93-98). Although non-terminal hydroxylation is observed in vitro for CYP153A, in vivo only 1-hydroxylation occurs (see, Funhoff et al., 2006, supra).

The substrate specificity and activity of terminal monooxygenases has been broadened via successfully, reducing the chain length specificity of CYP153A to below C8 (Koch et al., 2009, supra).

Figure 3:
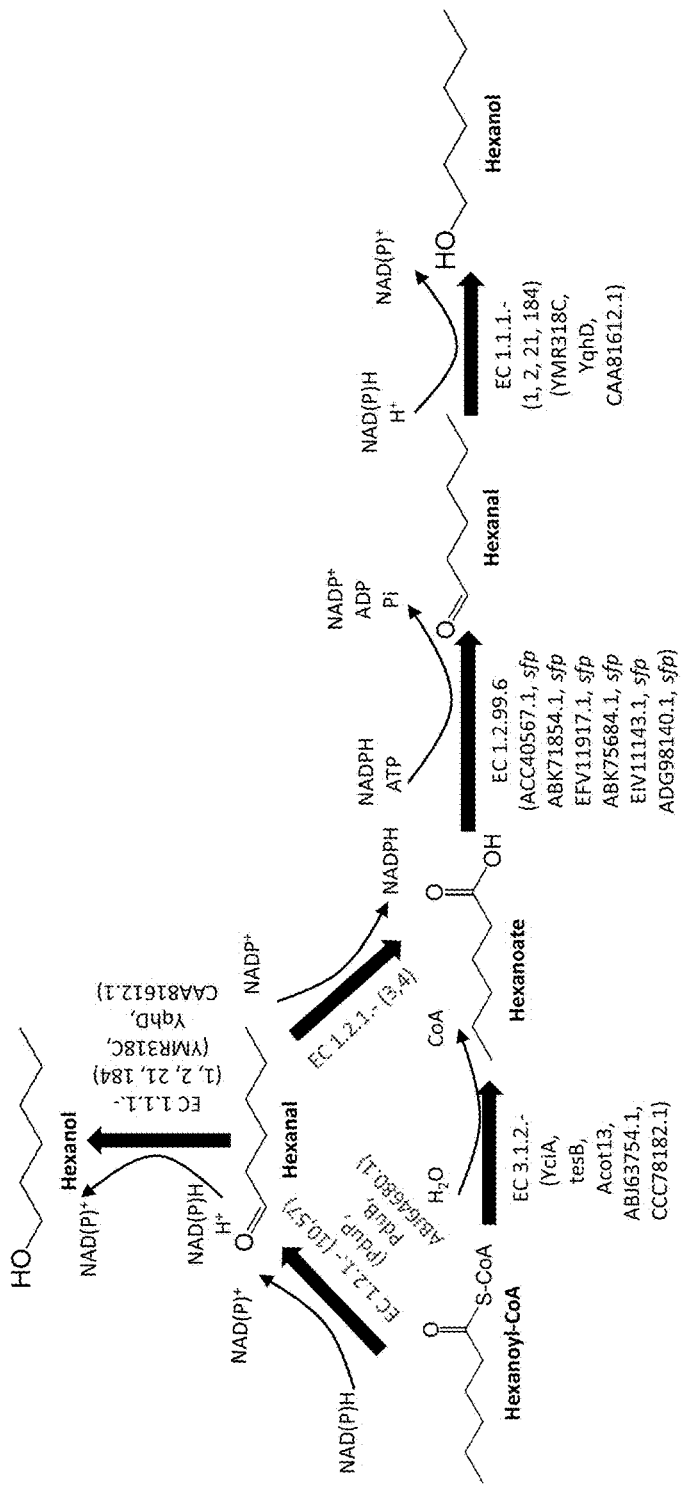
FIG. 3 is a schematic of exemplary biochemical pathways leading to hexanoate and hexanol using hexanoyl-CoA as a central precursor.

In some embodiments, hexanoate can be enzymatically formed from hexanoyl-CoA using a polypeptide having thioesterase activity classified under EC 3.1.2.-, such as the gene product of YciA, tesB (GenBank Accession No. AAA24665.1, SEQ ID NO: 1), Acot13 (Cantu et al., *Protein Science*, 2010, 19, 1281-1295; Zhuang et al., *Biochemistry*, 2008, 47(9):2789-2796; Naggert et al., *J. Biol. Chem.*, 1991, 266(17):11044-11050), the acyl-[acp] thioesterase from a *Lactobacillus brevis* (GenBank Accession No. ABJ63754.1, SEQ ID NO:32), or a *Lactobacillus plantarum* (GenBank Accession No. CCC78182.1, SEQ ID NO:33). Such acyl-[acp] thioesterases have C6-C8 chain length specificity (see, for example, Jing et al., 2011, *BMC Biochemistry*, 12(44)). See, FIG. 3.

In some embodiments, hexanoate can be enzymatically formed from hexanoyl-CoA using a polypeptide having butanal dehydrogenase activity classified, for example, under EC 1.2.1.- such as EC 1.2.1.10 or EC 1.2.1.57 (see, e.g., GenBank Accession No. AAD39015, SEQ ID NO:29 or GenBank Accession No. ABJ64680.1) such as the gene product of PduP or PduB and an aldehyde dehydrogenase classified, for example, under EC 1.2.1.- (e.g., EC 1.2.1.3 or EC 1.2.1.4) (see, Ho & Weiner, *J. Bacteriol.*, 2005, 187(3): 1067-1073). See, FIG. 3.

Enzymes Generating Hexanoyl-CoA for Conversion to a C6 Building Block

Figure 2:
FIG. 2 is a schematic of exemplary biochemical pathways leading to hexanoyl-CoA using NADPH-dependent enzymes and acetyl-CoA as central metabolites.

As depicted in FIG. 1 and FIG. 2, hexanoyl-CoA can be formed from acetyl-CoA via two cycles of CoA-dependent carbon chain elongation using either NADH or NADPH dependent enzymes.

In some embodiments, a CoA-dependent carbon chain elongation cycle comprises using a polypeptide having β-ketothiolase activity or a polypeptide having acetyl-CoA carboxylase activity and a polypeptide having β-ketoacyl-[acp] synthase activity, a polypeptide having 3-hydroxyacyl-CoA dehydrogenase activity or a polypeptide having 3-oxoacyl-CoA reductase activity, a polypeptide having enoyl-CoA hydratase activity and a polypeptide having trans-2-enoyl-CoA reductase activity. A polypeptide having β-ketothiolase activity can convert acetyl-CoA to 3-oxobutanoyl-CoA and can convert butanoyl-CoA to 3-oxohexanoyl-CoA. A polypeptide having acetyl-CoA carboxylase activity can convert acetyl-CoA to malonyl-CoA. A polypeptide having acetoacetyl-CoA synthase activity can convert malonyl-CoA to acetoacetyl-CoA. A polypeptide having 3-hydroxybutyryl-CoA dehydrogenase activity can convert 3-oxobutanoyl-CoA to 3-hydroxybutanoyl CoA. A polypeptide having 3-oxoacyl-CoA reductase/3-hydroxyacyl-CoA dehydrogenase activity can convert 3-oxohexanoyl-CoA to 3-hydroxyhexanoyl-CoA. A polypeptide having enoyl-CoA hydratase activity can convert 3-hydroxybutanoyl-CoA to but-2-enoyl-CoA and can convert 3-hydroxyhexanoyl-CoA to hex-2-enoyl-CoA. A polypeptide having trans-2-enoyl-CoA reductase activity can convert but-2-enoyl-CoA to butanoyl-CoA and can convert hex-2-enoyl-CoA to hexanoyl-CoA. See FIGS. 1 and 2.

In some embodiments, a polypeptide having β-ketothiolase activity can be classified under EC 2.3.1.16, such as the gene product of bktB (See, e.g., Genbank Accession No. AAC38322.1). The polypeptide having β-ketothiolase activity encoded by bktB from *Cupriavidus necator* accepts butanoyl-CoA as substrates. When butanoyl-CoA is the substrate, the CoA-activated C6 aliphatic backbone (3-oxohexanoyl-CoA) is produced (see, e.g., Haywood et al., *FEMS Microbiology Letters*, 1988, 52:91-96; Slater et al., *J. Bacteriol.*, 1998, 180(8):1979-1987). The polypeptide having β-ketothiolase activity encoded by paaJ (See, e.g., Genbank Accession No. AAC74479.1), catF and pcaF can be classified under, for example, EC 2.3.1.174. The polypeptide having β-ketothiolase activity encoded by paaJ condenses acetyl-CoA and succinyl-CoA to 3-oxoadipyl-CoA (see, for example, Fuchs et al., 2011, *Nature Reviews Microbiology*, 9, 803-816; Gael et al., 2002, *J. Bacteriol.*, 184(1), 216-223) See FIGS. 1 and 2.

In some embodiments, a polypeptide having acetyl-CoA carboxylase activity can be classified, for example, under EC 6.4.1.2. In some embodiments, a polypeptide having β-ketoacyl-[acp] synthase activity can be classified, for example, under 2.3.1.180 such as the gene product of FabH from *Staphylococcus aereus* (Qiu et al., 2005, *Protein Science*, 14: 2087-2094). See FIGS. 1 and 2.

In some embodiments, a polypeptide having 3-hydroxyacyl-CoA dehydrogenase activity or a polypeptide having 3-oxoacyl-CoA dehydrogenase activity can be classified under EC 1.1.1.-. For example, the polypeptide having 3-hydroxyacyl-CoA dehydrogenase activity can be classified under EC 1.1.1.35, such as the gene product of fadB (FIG. 1); classified under EC 1.1.1.157, such as the gene product of hbd (can be referred to as a 3-hydroxybutyryl-CoA dehydrogenase) (FIG. 1); or classified under EC 1.1.1.36, such as the acetoacetyl-CoA reductase gene product of phaB (Liu & Chen, *Appl. Microbiol. Biotechnol.*, 2007, 76(5):1153-1159; Shen et al., *Appl. Environ. Microbiol.*, 2011, 77(9):2905-2915; Budde et al., *J. Bacteriol.*, 2010, 192(20):5319-5328) (FIG. 2).

In some embodiments, a polypeptide having 3-oxoacyl-CoA reductase activity can be classified under EC 1.1.1.100, such as the gene product of fabG (Budde et al., *J. Bacteriol.*, 2010, 192(20):5319-5328; Nomura et al., *Appl. Environ. Microbiol.*, 2005, 71(8):4297-4306). FIG. 2.

In some embodiments, a polypeptide having enoyl-CoA hydratase activity can be classified under EC 4.2.1.17, such as the gene product of crt (Genbank Accession No. AAA95967.1) (FIG. 1), or classified under EC 4.2.1.119, such as the gene product of phaJ (Genbank Accession No. BAA21816.1) (FIG. 2) (Shen et al., 2011, supra; Fukui et al., *J. Bacteriol.*, 1998, 180(3):667-673).

In some embodiments, a polypeptide having trans-2-enoyl-CoA reductase activity can be classified under EC 1.3.1.38 (FIG. 2), EC 1.3.1.8 (FIG. 2), or EC 1.3.1.44 (FIG. 1), such as the gene product of ter (Genbank Accession No. AAW66853.1) (Nishimaki et al., *J. Biochem.*, 1984, 95:1315-1321; Shen et al., 2011, supra) or tdter (Genbank Accession No. AAS11092.1) (Bond-Watts et al., *Biochemistry*, 2012, 51:6827-6837).

Figure 4:
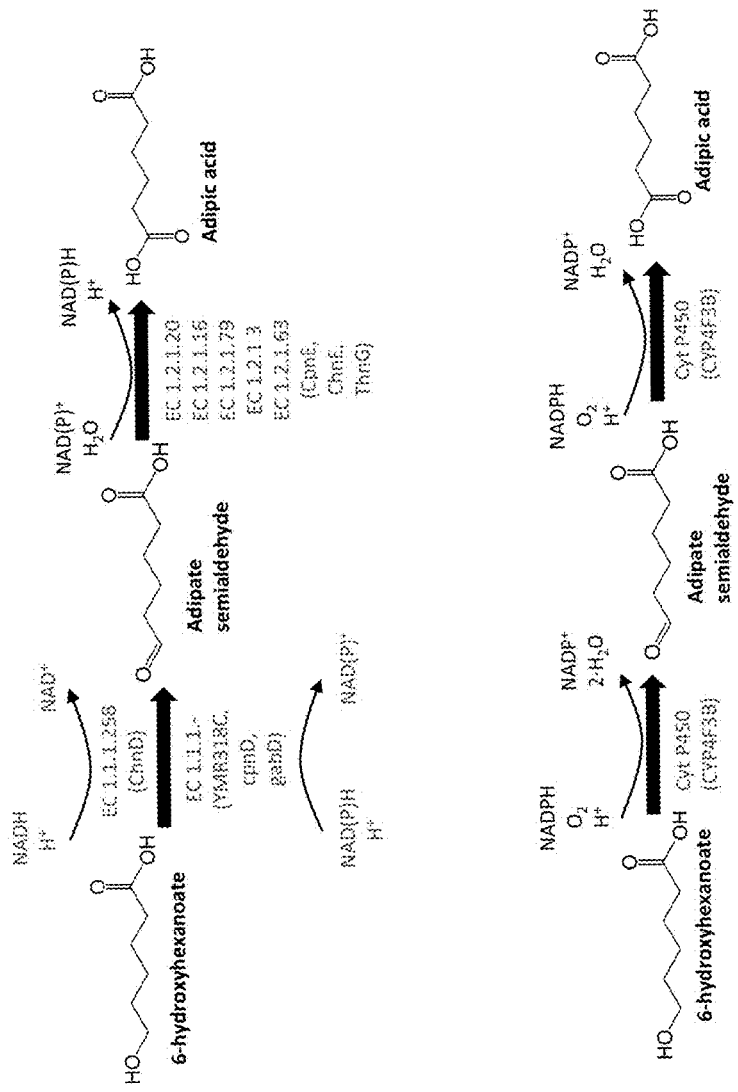
FIG. 4 is a schematic of an exemplary biochemical pathway leading to adipic acid using 6-hydroxyhexanoate as a central precursor.
Figure 5:
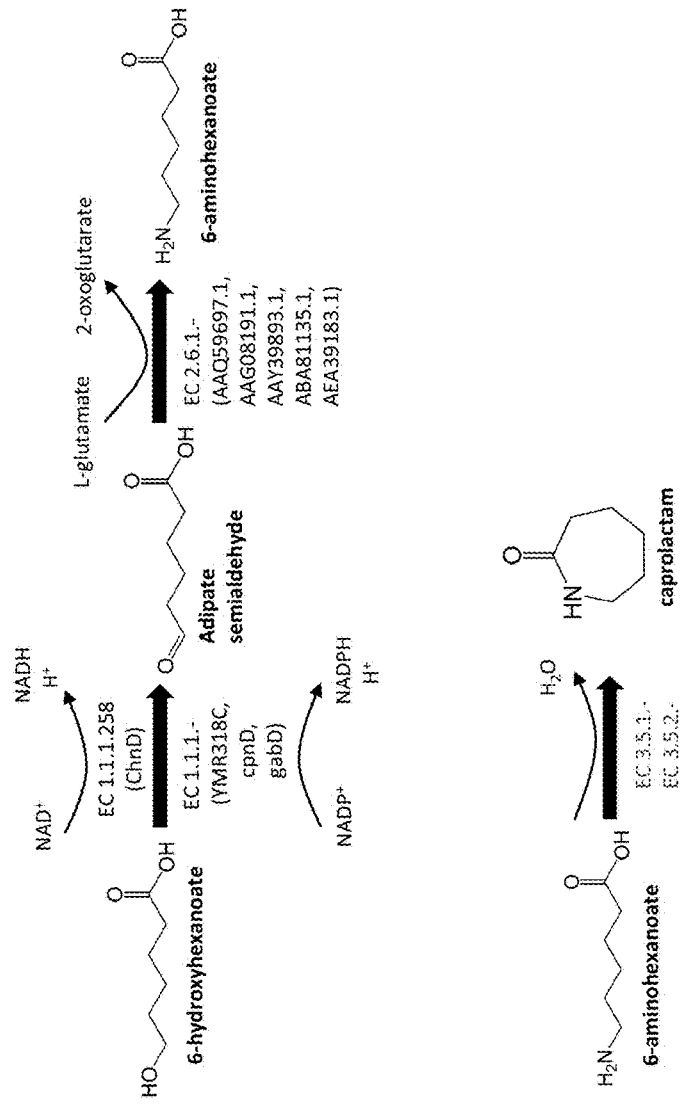
FIG. 5 is a schematic of exemplary biochemical pathways leading to 6-aminohexanoate and caprolactam using 6-hydroxyhexanoate as a central precursor.

Enzymes Generating the Terminal Carboxyl Groups in the Biosynthesis of a C6 Building Block As depicted in FIGS. 4, 5, and 7, a terminal carboxyl group can be enzymatically formed using a polypeptide having thioesterase activity, a polypeptide having aldehyde dehydrogenase activity, a polypeptide having 7-oxoheptanoate dehydrogenase activity, a polypeptide having 6-oxohexanoate dehydrogenase activity, a polypeptide having 5-oxopentanoate dehydrogenase activity, a polypeptide having monooxygenase activity, a polypeptide having esterase activity or a polypeptide having demethylase activity.

In some embodiments, the first terminal carboxyl group is enzymatically formed by a polypeptide having syringate O-demethylase activity classified under EC 2.1.1.- such as the gene products of ligM (see GenBank Accession No. BAD61059.1; SEQ ID NO:30) or desA (GenBank Accession No. BAC79257.1; SEQ ID NO:31) or a polypeptide having esterase activity classified under EC 3.1.1.- such as the gene product of EstC (see, e.g., GenBank Accession No. AAC60471.2, SEQ ID NO: 26). See, e.g., FIG. 7.

In some embodiments, the first terminal carboxyl group is enzymatically formed by a polypeptide having aldehyde dehydrogenase activity classified, for example, under EC 1.2.1.3 or EC 1.2.1.4.

In some embodiments, the second terminal carboxyl group leading to the synthesis of adipic acid is enzymatically formed by a polypeptide having aldehyde dehydrogenase activity classified, for example, under EC 1.2.1.3 (see, Guerrillot & Vandecasteele, *Eur. J. Biochem.*, 1977, 81, 185-192). See FIG. 4.

In some embodiments, the second terminal carboxyl group leading to the synthesis of adipic acid is enzymatically formed by a polypeptide having dehydrogenase activity classified under EC 1.2.1.- such as a polypeptide having 5-oxopentanoate dehydrogenase activity (e.g., the gene product of CpnE), a polypeptide having 6-oxohexanoate dehydrogenase activity (e.g., the gene product of ChnE from *Acinetobacter* sp.), a polypeptide having 7-oxoheptanoate dehydrogenase activity (e.g., the gene product of ThnG from *Sphingomonas macrogolitabida*) (Iwaki et al., *Appl. Environ. Microbiol.*, 1999, 65(11), 5158-5162; López-Sánchez et al., *Appl. Environ. Microbiol.*, 2010, 76(1), 110-118). For example, a polypeptide having 5-oxopentanoate dehydrogenase activity can be classified under EC 1.2.1.20. For example, a polypeptide having 6-oxohexanoate dehydrogenase activity can be classified under EC 1.2.1.63. For example, a polypeptide having 7-oxoheptanoate dehydrogenase activity can be classified under EC 1.2.1.-. See, FIG. 4.

In some embodiments, the second terminal carboxyl group leading to the synthesis of adipic acid is enzymatically formed by a polypeptide having monooxygenase activity in the cytochrome P450 family such as CYP4F3B (see, e.g., Sanders et al., *J. Lipid Research*, 2005, 46(5):1001-1008; Sanders et al., *The FASEB Journal*, 2008, 22(6):2064-2071). See, FIG. 4.

The utility of ω-oxidation in introducing carboxyl groups into alkanes has been demonstrated in the yeast *Candida tropicalis*, leading to the synthesis of adipic acid (Okuhara et al., *Agr. Biol. Chem.*, 1971, 35(9), 1376-1380).

Figure 6:
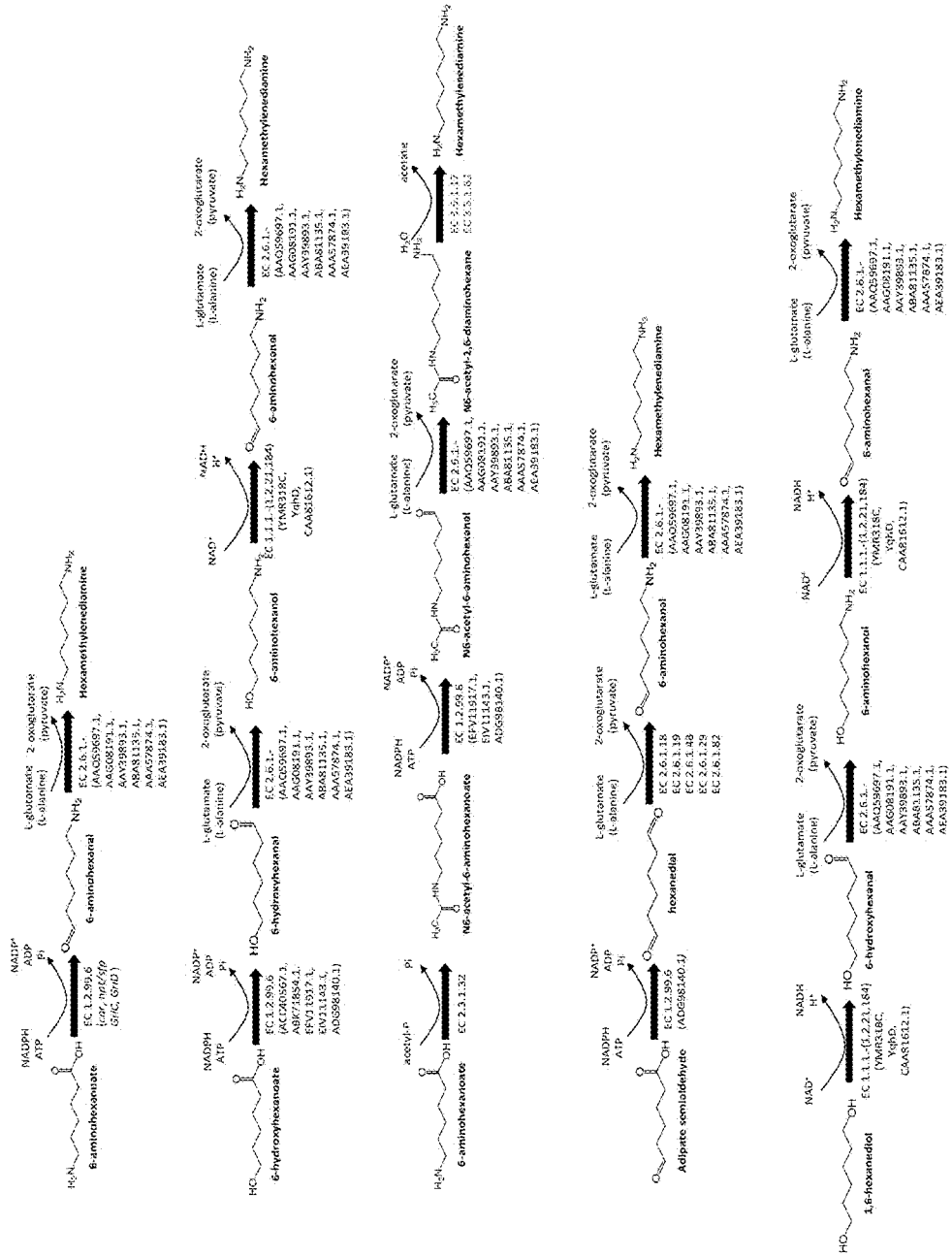
FIG. 6 is a schematic of exemplary biochemical pathways leading to hexamethylenediamine using 6-aminohexanoate, 6-hydroxyhexanoate, adipate semialdehyde or 1,6-hexanediol as a central precursor.

Enzymes Generating the Terminal Amine Groups in the Biosynthesis of a C6 Building Block As depicted in FIG. 5 and FIG. 6, terminal amine groups can be enzymatically formed using a polypeptide having ω-transaminase activity or a polypeptide having deacetylase activity.

In some embodiments, the first terminal amine group leading to the synthesis of 6-aminohexanoic acid, 6-aminohexanal, or 6-aminohexanol is enzymatically formed by a ω-transaminase classified, for example, under EC 2.6.1.- such as EC 2.6.1.18, EC 2.6.1.19, EC 2.6.1.29, EC 2.6.1.48, or EC 2.6.1.82 such as that obtained from *Chromobacterium violaceum* (Genbank Accession No. AAQ59697.1, SEQ ID NO: 7), *Pseudomonas aeruginosa* (Genbank Accession No. AAG08191.1, SEQ ID NO: 8), *Pseudomonas syringae* (Genbank Accession No. AAY39893.1, SEQ ID NO: 9), *Rhodobacter sphaeroides* (Genbank Accession No. ABA81135.1, SEQ ID NO: 10), *Vibrio Fluvialis* (Genbank Accession No. AAA57874.1, SEQ ID NO: 12), *Streptomyces griseus*, or *Clostridium viride*. An additional polypeptide having ω-transaminase activity that can be used in the methods and hosts described herein is from *Escherichia coli* (Genbank Accession No. AAA57874.1, SEQ ID NO: 11). Some of the polypeptides having ω-transaminase activity classified, for example, under EC 2.6.1.29 or EC 2.6.1.82 are polypeptides having diamine ω-transaminase activity (e.g., SEQ ID NO:11). See, e.g., FIGS. 5 and 6.

The reversible polypeptide having ω-transaminase activity from *Chromobacterium violaceum* (Genbank Accession No. AAQ59697.1, SEQ ID NO: 7) has demonstrated analogous activity accepting 6-aminohexanoic acid as amino donor, thus forming the first terminal amine group in adipate semialdehyde (Kaulmann et al., *Enzyme and Microbial Technology*, 2007, 41, 628-637).

The reversible polypeptide having 4-aminobutyrate:2-oxoglutarate transaminase activity from *Streptomyces griseus* has demonstrated analogous activity for the conversion of 6-aminohexanoate to adipate semialdehyde (Yonaha et al., *Eur. J. Biochem.*, 1985, 146, 101-106).

The reversible polypeptide having 5-aminovalerate transaminase activity from *Clostridium viride* has demonstrated analogous activity for the conversion of 6-aminohexanoate to adipate semialdehyde (Barker et al., *J. Biol. Chem.*, 1987, 262(19), 8994-9003).

In some embodiments, the second terminal amine group leading to the synthesis of hexamethylenediamine is enzymatically formed by a polypeptide having diamine transaminase activity. For example, the second terminal amino group can be enzymatically formed by a polypeptide having diamine transaminase activity classified, for example, under EC 2.6.1.-, e.g., EC 2.6.1.29 or classified, for example, under EC 2.6.1.82, such as the gene product of YgjG from *E. coli* (Genbank Accession No. AAA57874.1, SEQ ID NO: 12). See, FIG. 6.

The gene product of ygjG accepts a broad range of diamine carbon chain length substrates, such as putrescine, cadaverine and spermidine (Samsonova et al., *BMC Microbiology*, 2003, 3:2).

The polypeptide having diamine transaminase activity from *E. coli* strain B has demonstrated activity for 1,7 diaminoheptane (Kim, *The Journal of Chemistry*, 1964, 239(3), 783-786).

In some embodiments, the second terminal amine group leading to the synthesis of hexamethylenediamine is enzymatically formed by a polypeptide having deacetylase activity classified, for example, under EC 3.5.1.62 such as a polypeptide having acetylputrescine deacetylase activity. The polypeptide having acetylputrescine deacetylase activity from *Micrococcus luteus* K-11 accepts a broad range of carbon chain length substrates, such as acetylputrescine, acetylcadaverine and $N^8$-acetylspermidine (see, for example, Suzuki et al., 1986, *BBA—General Subjects*, 882 (1):140-142).

Figure 8:
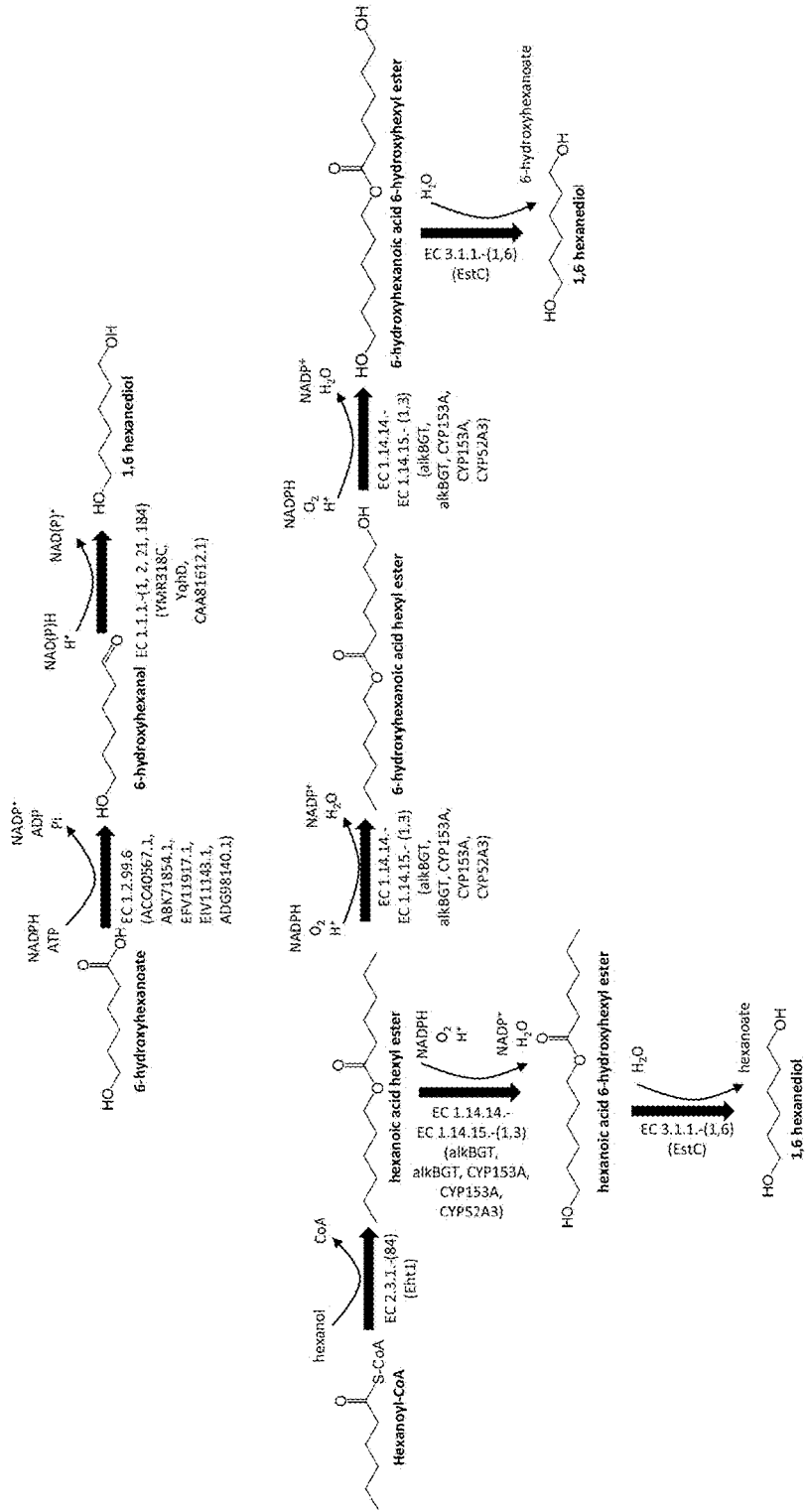
FIG. 8 is a schematic of exemplary biochemical pathways leading to 1,6-hexanediol using 6-hydroxyhexanoate or hexanoyl-CoA as a central precursor.
Figure 10:
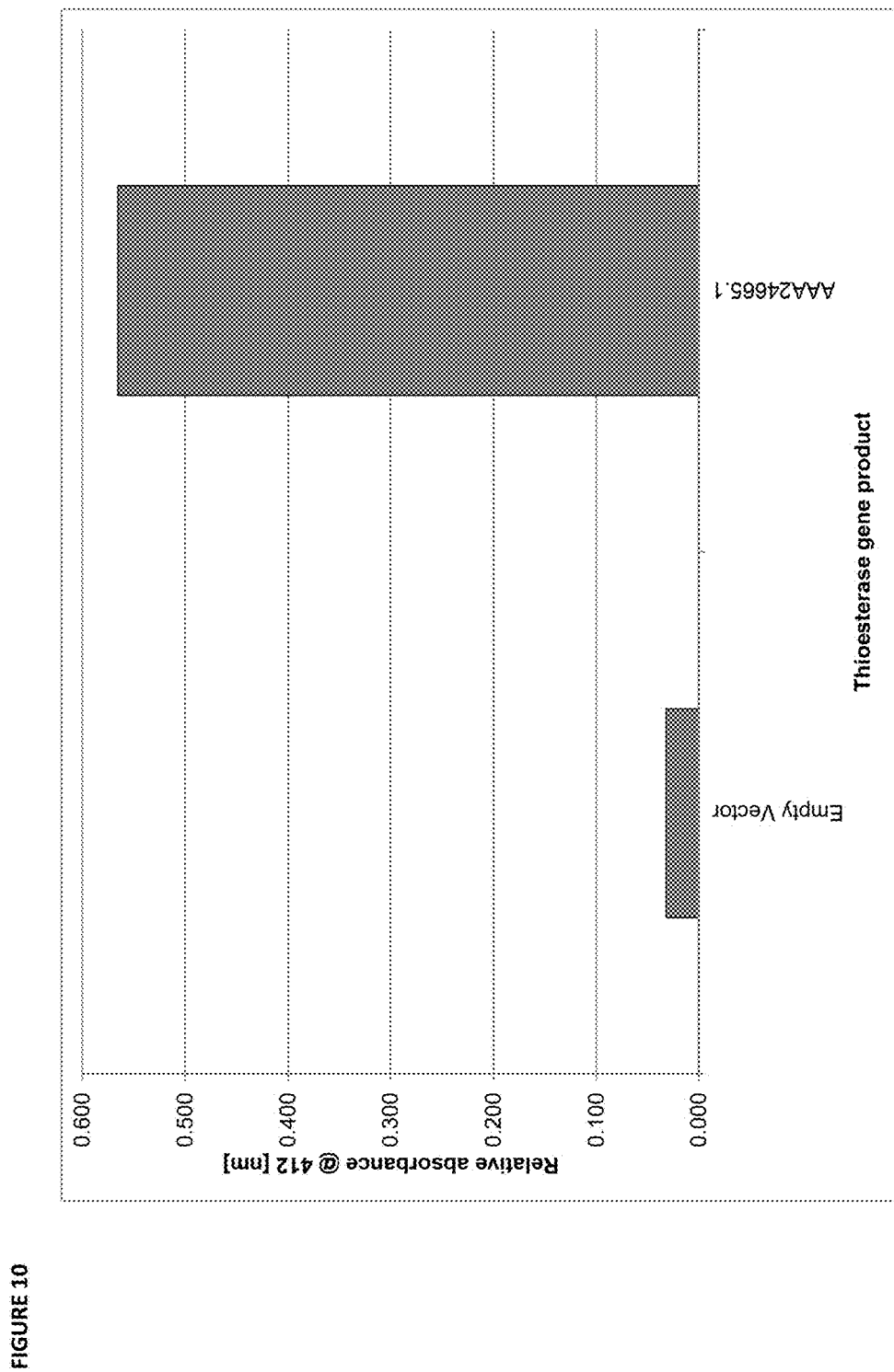
FIG. 10 is a bar graph of the relative absorbance at 412 nm of released CoA as a measure of the activity of a thioesterase for converting hexanoyl-CoA to hexanoate relative to the empty vector control.

Enzymes Generating the Terminal Hydroxyl Groups in the Biosynthesis of a C6 Building Block As depicted in FIG. 8, a terminal hydroxyl group can be enzymatically forming using a polypeptide having alcohol dehydrogenase activity. For example, the second terminal hydroxyl group leading to the synthesis of 1,6 hexanediol can be enzymatically formed by a polypeptide having alcohol dehydrogenase activity classified under EC 1.1.1.- (e.g., EC 1.1.1.1, 1.1.1.2, 1.1.1.21, or 1.1.1.184). A first terminal hydroxyl group can be enzymatically formed with a polypeptide having monoxygenase activity as discussed above with respect to the formation of 6-hydroxyhexanoate methyl ester in FIG. 7.

As depicted in FIG. 8, hexanoyl-CoA can be converted to hexanoic acid hexyl ester using a polypeptide having alcohol O-acetyltransferase activity classified, for example, under EC 2.3.1.-(84) such as the gene product of Eht1 (Genbank Accession No: CAA85138.1, SEQ ID NO: 25).

Hexanoic acid hexyl ester can be converted to 6-hydroxyhexanoic acid 6-hydroxyhexyl ester using a polypeptide having monooxygenase activity classified, for example, under EC 1.14.14.- or EC 1.14.15.-(1,3). Hexanoic acid hexyl ester can be converted to hexanoic acid 6-hydroxyhexyl ester using a polypeptide having monooxygenase activity classified, for example, under EC 1.14.14.- or EC 1.14.15.-(1,3). For example, a polypeptide having monooxygenase activity can be, for example, from the CYP153A family, the CYP52A3 family or the alkB family such as the gene product of alkBGT from *Pseudomonas putida*. See, FIG. 7.

Hexanoic acid 6-hydroxyhexyl ester and 6-hydroxyhexanoic acid 6-hydroxyhexyl can be converted to 1,6-hexanediol using a polypeptide having esterase activity classified, for example, under EC 3.1.1.- (e.g., EC 3.1.1.1 or EC 3.1.1.6) such as the gene product of EstC (see GenBank Accession No. AAC60471.2, SEQ ID NO: 26).

Biochemical Pathways
Pathways to Hexanoyl-CoA as Central Precursor to C6 Building Blocks In some embodiments, hexanoyl-CoA is synthesized from acetyl-CoA by conversion of acetyl-CoA to 3-oxobutanoyl-CoA by a polypeptide having β-ketothiolase activity classified, for example, under EC 2.3.1.9, such as the gene product of phaA or atoB; followed by conversion of 3-oxobutanoyl-CoA to (S) 3-hydroxybutanoyl-CoA by a polypeptide having 3-hydroxyacyl-CoA dehydrogenase activity classified, for example, under EC 1.1.1.35, such as the gene product of fadB or classified, for example, under EC 1.1.1.157 such as the gene product of hbd; followed by conversion of (S) 3-hydroxybutanoyl-CoA to but-2-enoyl-CoA by a polypeptide having enoyl-CoA hydratase activity classified, for example, under EC 4.2.1.17 such as the gene product of crt (Genbank Accession No. AAA95967.1); followed by conversion of but-2-enoyl-CoA to butanoyl-CoA by a polypeptide having trans-2-enoyl-CoA reductase activity classified, for example, under EC 1.3.1.44 such as the gene product of ter (Genbank Accession No. AAW66853.1) or tdter (Genbank Accession No. AAS11092.1); followed by conversion of butanoyl-CoA to 3-oxo-hexanoyl-CoA by a polypeptide having β-ketothiolase activity classified, for example, under EC 2.3.1.16 such as the gene product of bktB (Genbank Accession No. AAC38322.1) or classified, for example, under EC 2.3.1.174 such as the gene product of paaJ (Genbank Accession No. AAC74479.1); followed by conversion of 3-oxo-hexanoyl-CoA to (S) 3-hydroxyhexanoyl-CoA by a polypeptide having 3-hydroxyacyl-CoA dehydrogenase activity classified, for example, under EC 1.1.1.35 such as the gene product of fadB or by a polypeptide having 3-hydroxyacyl-CoA dehydrogenase activity classified, for example, under EC 1.1.1.157 such as the gene product of hbd; followed by conversion of (S) 3-hydroxyhexanoyl-CoA to hex-2-enoyl-CoA by a polypeptide having enoyl-CoA hydratase activity classified, for example, under EC 4.2.1.17 such as the gene product of crt (Genbank Accession No. AAA95967.1); followed by conversion of hex-2-enoyl-CoA to hexanoyl-CoA by a polypeptide having trans-2-enoyl-CoA reductase activity classified, for example, under EC 1.3.1.44 such as the gene product of ter (Genbank Accession No. AAW66853.1) or tdter (Genbank Accession No. AAS11092.1). See FIG. 1.

In some embodiments, hexanoyl-CoA is synthesized from the central metabolite, acetyl-CoA, by conversion of acetyl-CoA to 3-oxobutanoyl-CoA by a polypeptide having β-ketothiolase activity classified, for example, under EC 2.3.1.9, such as the gene product of phaA or atoB; followed by conversion of 3-oxobutanoyl-CoA to (R) 3-hydroxybutanoyl-CoA by a polypeptide having 3-oxoacyl-CoA reductase activity classified, for example, under EC 1.1.1.100, such as the gene product of fadG or by a polypeptide having acetoacetyl-CoA reductase activity classified, for example, under EC 1.1.1.36 such as the gene product of phaB; followed by conversion of (R) 3-hydroxybutanoyl-CoA to but-2-enoyl-CoA by a polypeptide having enoyl-CoA hydratase activity classified, for example, under EC 4.2.1.119 such as the gene product of phaJ (Genbank Accession No. BAA21816.1); followed by conversion of but-2enoyl-CoA to butanoyl-CoA by a polypeptide having trans-2-enoyl-CoA reductase activity classified, for example, under EC 1.3.1.38 or a polypeptide having acyl-CoA dehydrogenase activity classified, for example, under EC 1.3.1.8; followed by conversion of butanoyl-CoA to 3-oxo-hexanoyl-CoA by a polypeptide having β-ketothiolase activity classified, for example, under EC 2.3.1.16 such as the gene product of bktB (Genbank Accession No. AAC38322.1) or classified, for example, under EC 2.3.1.174 such as the gene product of paaJ (Genbank Accession No. AAC74479.1); followed by conversion of 3-oxo-hexanoyl-CoA to (R) 3-hydroxyhexanoyl-CoA by a polypeptide having 3-oxoacyl-CoA reductase activity classified, for example, under EC 1.1.1.100 such as the gene product of fabG; followed by conversion of (R) 3-hydroxyhexanoyl-CoA to hex-2-enoyl-CoA by a polypeptide having enoyl-CoA hydratase activity classified, for example, under EC 4.2.1.119 such as the gene product of phaJ (Genbank Accession No. BAA21816.1); followed by conversion of hex-2-enoyl-CoA to hexanoyl-CoA by a polypeptide having trans-2-enoyl-CoA reductase activity classified, for example, under EC 1.3.1.38 or a polypeptide having acyl-CoA dehydrogenase activity classified, for example, under EC 1.3.1.8. See FIG. 2.

In some embodiments, 3-oxobutanoyl-CoA can be synthesized from acetyl-CoA. A polypeptide having acetyl-CoA carboxylase activity classified, for example, under EC 6.4.1.2 can be used to convert acetyl-CoA to malonyl-CoA, which can be converted to 3-oxobutanoyl-CoA using a polypeptide having acetoacetyl-CoA synthase activity classified, for example, under EC 2.3.1.194 such as the gene product of fabH. See, FIG. 1 and FIG. 2.

Pathways Using Hexanoyl-CoA to Produce the Central Precursor Hexanoate

In some embodiments, hexanoate is synthesized from hexanoyl-CoA by conversion of hexanoyl-CoA to hexanoate by a polypeptide having thioesterase activity classified, for example, under EC 3.1.2.- such as the gene product of YciA, tesB, Acot13, a *Lactobacillus brevis* acyl-[acp] thioesterase (GenBank Accession No. ABJ63754.1, SEQ ID NO:32) or a *Lactobacillus plantarum* acyl-[acp] thioesterase (GenBank Accession No. CCC78182.1, SEQ ID NO:33). See, FIG. 3.

In some embodiments, hexanoyl-CoA is converted to hexanal by a polypeptide having butanal dehydrogenase activity classified, for example, under EC 1.2.1.57 (see, e.g., GenBank Accession No. AAD39015, SEQ ID NO:29) or EC 1.2.1.10 or the gene products of PduP or PduB; followed by conversion of hexanal to hexanoate by a polypeptide having aldehyde dehydrogenase activity classified, for example, under EC 1.2.1.4 or EC 1.2.1.3. See FIG. 3.

The conversion of hexanoyl-CoA to hexanal has been demonstrated using both NADH and NADPH as co-factors (see Palosaari and Rogers, *J. Bacteriol.*, 1988, 170(7): 2971-2976).

Pathways Using Hexanoyl-CoA to Produce the Central Precursor Hexanol

In some embodiments, hexanoate is synthesized from hexanoyl-CoA by conversion of hexanoyl-CoA to hexanoate by a polypeptide having thioesterase activity classified, for example, under EC 3.1.2.- such as the gene product of YciA, tesB or Acot13, a *Lactobacillus brevis* acyl-[acp] thioesterase (GenBank Accession No. ABJ63754.1, SEQ ID NO:32) or a *Lactobacillus plantarum* acyl-[acp] thioesterase (GenBank Accession No. CCC78182.1, SEQ ID NO:33); followed by conversion of hexanoate to hexanal by a polypeptide having carboxylate reductase activity classified, for example, under EC 1.2.99.6, such as the gene product of car enhanced by the gene product of sfp; followed by conversion of hexanal to hexanol by a polypeptide having alcohol dehydrogenase activity classified, for example, under EC 1.1.1.- such as EC 1.1.1.1, EC 1.1.1.2, EC 1.1.1.21, or EC 1.11184) such as the gene product of YMR318C (Genbank Accession No. CAA90836.1) or YqhD (from *E. coli*, GenBank Accession No. AAA69178.1) (see, e.g., Liu et al., *Microbiology*, 2009, 155, 2078-2085; Larroy et al., 2002, *Biochem J.*, 361(Pt 1), 163-172; or Jarboe, 2011, *Appl. Microbiol. Biotechnol.*, 89(2), 249-257) or the protein having GenBank Accession No. CAA81612.1 (from *Geobacillus stearothermophilus*). See, FIG. 3.

In some embodiments, hexanoyl-CoA is converted to hexanal by a polypeptide having butanal dehydrogenase activity classified, for example, under EC 1.2.1.57 (see, e.g, GenBank Accession No. BAD61059.1, SEQ ID NO:30); followed by conversion of hexanal to hexanol by a polypeptide having alcohol dehydrogenase activity classified, for example, under EC 1.1.1.- such as EC 1.1.1.1, EC 1.1.1.2, EC 1.1.1.21, or EC 1.1.1.184) such as the gene product of YMR318C (Genbank Accession No. CAA90836.1) or YqhD (from *E. coli*, GenBank Accession No. AAA69178.1) (see, e.g., Liu et al., *Microbiology*, 2009, 155, 2078-2085; Larroy et al., 2002, *Biochem J.*, 361(Pt 1), 163-172; or Jarboe, 2011, *Appl. Microbiol. Biotechnol.*, 89(2), 249-257) or the protein having GenBank Accession No. CAA81612.1 (from *Geobacillus stearothermophilus*). See, FIG. 3.

Pathways Using Hexanoate or Hexanoyl-CoA as Central Precursor to 6-Hydroxyhexanoate In some embodiments, 6-hydroxyhexanoate is synthesized from the central precursor, hexanoate, by conversion of hexanoate to hexanoate methyl ester using a polypeptide having fatty acid O-methyltransferase activity classified, for example, under EC 2.1.1.15 (e.g., the fatty acid O-methyltransferase from *Mycobacterium marinum* (GenBank Accession No. ACC41782.1. SEQ ID NO:22), *Mycobacterium smegmatis* (see GenBank Accession No. ABK73223.1, SEQ ID NO: 23), or *Pseudomonas putida* (see GenBank Accession No. CAA39234.1, SEQ ID NO: 24); followed by conversion to 6-hydroxyhexanoate methyl ester using a polypeptide having monooxygenase activity classified, for example, under EC 1.14.14.- or EC 1.14.15.-(1,3) such as a polypeptide having monooxygenase activity in the CYP153A, the CYP52A3 family or alkB family; followed by conversion to 6-hydroxyhexanoate using a polypeptide having syringate O-demethylase activity classified under EC 2.1.1.- such as the gene products of ligM (see GenBank Accession No. BAD61059.1; SEQ ID NO:30) or desA (GenBank Accession No. BAC79257.1; SEQ ID NO:31) or using a polypeptide having esterase activity classified under EC 3.1.1.- such as the gene product of EstC (see GenBank Accession No. AAC60471.2, SEQ ID NO: 26) (Kim et al., 1994, Biosci. Biotech. Biochem, 58(1), 111-116).

In some embodiments, hexanoate can be enzymatically converted to 6-hydroxyhexanoate by a polypeptide having monooxygenase activity (classified, for example, under EC 1.14.14.- or EC 1.14.15.- (e.g., EC 1.14.15.1 or EC 1.14.15.3 such as a monooxygenase in the CYP153A, theCYP52A3 family or/and the alkB family).

In some embodiments, hexanoyl-CoA can be converted to hexanoic acid hexyl ester using a polypeptide having alcohol O-acetyltransferase activity classified, for example, under EC 2.3.1.-(84) such as the gene product of Eht1 (Genbank Accession No: CAA85138.1, SEQ ID NO: 25); followed by conversion to 6-hydroxyhexanoic acid hexyl ester and/or 6-hydroxyhexanoic acid 6-hydroxyhexyl ester using a polypeptide having monooxygenase activity classified, for example, under EC 1.14.14.- or EC 1.14.15.-(1,3). For example, a polypeptide having monooxygenase activity can be, for example, from the CYP153A family, the CYP52A3 family (Genbank Accession No: BAA00371.1, SEQ ID NO: 28) or the alkB family such as the gene product of alkBGT from *Pseudomonas putida* (Genbank Accession No. CAB51047.1, SEQ ID NO: 27); followed by conversion of 6-hydroxyhexanoic acid hexyl ester and/or 6-hydroxyhexanoic acid 6-hydroxyhexyl to 6-hydroxyhexanoate using a polypeptide having esterase activity classified, for example, under EC 3.1.1.-(1,6) such as the gene product of EstC (see GenBank Accession No. AAC60471.2, SEQ ID NO: 26) (Kim et al., 1994, Biosci. Biotech. Biochem, 58(1), 111-116). See FIG. 7.

Pathways Using 6-Hydroxyhexanoate as Central Precursor to Adipate

Adipate semialdehyde can be synthesized by enzymatically converting 6-hydroxyhexanoate to adipate semialdehyde using a polypeptide having alcohol dehydrogenase activity classified, for example, under EC 1.1.1.- such as the gene product of YMR318C (classified, for example, under EC 1.1.1.2, see Genbank Accession No. CAA90836.1) (Larroy et al., 2002, Biochem J., 361 (Pt 1), 163-172), cpnD (Iwaki et al., 2002, Appl. Environ. Microbiol., 68(11):5671-5684) or gbd, a polypeptide having 6-hydroxyhexanoate dehydrogenase activity classified, for example, under EC 1.1.1.258 such as the gene product of ChnD (Iwaki et al., Appl. Environ. Microbiol., 1999, 65(11):5158-5162), or a polypeptide having cytochrome P450 activity (Sanders et al., J. Lipid Research, 2005, 46(5), 1001-1008; Sanders et al., The FASEB Journal, 2008, 22(6), 2064-2071). See, FIG. 4. The polypeptide having alcohol dehydrogenase activity encoded by YMR318C has broad substrate specificity, including the oxidation of C6 alcohols.

Adipate semialdehyde can be enzymatically converted to adipic acid using a polypeptide having aldehyde dehydrogenase activity classified, for example, under EC 1.2.1.-(3, 16, 20, 63, 79) such as a polypeptide having 7-oxoheptanoate dehydrogenase activity (e.g., the gene product of ThnG), a polypeptide having 6-oxohexanoate dehydrogenase activity (e.g., the gene product of ChnE). See FIG. 4.

Pathway Using 6-Hydroxyhexanoate as Central Precursor to 6-Aminohexanoate

In some embodiments, 6-aminohexanoate is synthesized from 6-hydroxyhexanoate by conversion of 6-hydroxyhexanoate to adipate semialdehyde using a polypeptide having alcohol dehydrogenase activity classified, for example, under EC 1.1.1.- such as the gene product of YMR318C (classified, for example, under EC 1.1.1.2, see Genbank Accession No. CAA90836.1) (Larroy et al., 2002, Biochem J., 361(Pt 1), 163-172), cpnD (Iwaki et al., 2002, Appl. Environ. Microbiol., 68(11):5671-5684), or gbd, or a 6-hydroxyhexanoate dehydrogenase classified, for example, under EC 1.1.1.258 such as the gene product of ChnD (Iwaki et al., Appl. Environ. Microbiol., 1999, 65(11):5158-5162); followed by conversion to 6-aminohexanoate by a polypeptide having ω-transaminase activity classified, for example, under EC 2.6.1.18, EC 2.6.1.19, EC 2.6.1.29, EC 2.6.1.48, EC 2.6.1.82 such as from a *Chromobacterium violaceum* (see Genbank Accession No. AAQ59697.1, SEQ ID NO: 7), a *Pseudomonas aeruginosa* (see Genbank Accession No. AAG08191.1, SEQ ID NO: 8), a *Pseudomonas syringae* (see Genbank Accession No. AAY39893.1, SEQ ID NO: 9), a *Rhodobacter sphaeroides* (see Genbank Accession No. ABA81135.1, SEQ ID NO: 10), or a *Vibrio fluvialis* (see Genbank Accession No. AEA39183.1, SEQ ID NO: 12). See FIG. 5.

Pathway Using 6-Aminohexanoate, 6-Hydroxyhexanoate, or Adipate Semialdehyde as Central Precursor to Hexamethylenediamine In some embodiments, hexamethylenediamine is synthesized from the central precursor 6-aminohexanoate by conversion of 6-aminohexanoate to 6-aminohexanal by a polypeptide having carboxylate reductase activity classified, for example, under EC 1.2.99.6 such as the gene product of car in combination with a phosphopantetheine transferase enhancer (e.g., encoded by a sfp gene from *Bacillus subtilis* or npt gene from *Nocardia*) or the gene products of GriC and GriD from *Streptomyces griseus*; followed by conversion of 6-aminohexanal to hexamethylenediamine by a polypeptide having ω-transaminase activity classified, for example, under EC 2.6.1.- such as 2.6.1.18, EC 2.6.1.19, EC 2.6.1.29, EC 2.6.1.48, or EC 2.6.1.82 such as from a *Chromobacterium violaceum* (see Genbank Accession No. AAQ59697.1, SEQ ID NO: 7), a *Pseudomonas aeruginosa* (see Genbank Accession No. AAG08191.1, SEQ ID NO: 8), a *Pseudomonas syringae* (see Genbank Accession No. AAY39893.1, SEQ ID NO: 9), a *Rhodobacter sphaeroides* (see Genbank Accession No. ABA81135.1, SEQ ID NO: 10), an *Escherichia coli* (see Genbank Accession No. AAA57874.1, SEQ ID NO: 11), or a *Vibrio fluvialis* (see Genbank Accession No. AEA39183.1, SEQ ID NO: 12). See FIG. 6.

The polypeptide having carboxylate reductase activity encoded by the gene product of car and enhancer npt or sfp has broad substrate specificity, including terminal difunctional C4 and C5 carboxylic acids (Venkitasubramanian et al., Enzyme and Microbial Technology, 2008, 42, 130-137).

In some embodiments, hexamethylenediamine is synthesized from the central precursor 6-hydroxyhexanoate (which can be produced as described in FIG. 7), by conversion of 6-hydroxyhexanoate to 6-hydroxyhexanal by a polypeptide having carboxylate reductase activity classified, for example, under EC 1.2.99.6 such as from *Mycobacterium marinum* (Genbank Accession No. ACC40567.1, SEQ ID NO: 2), *Mycobacterium smegmatis* (Genbank Accession No.

ABK71854.1, SEQ ID NO: 3), *Segniliparus rugosus* (Genbank Accession No. EFV11917.1, SEQ ID NO: 4), *Mycobacterium massiliense* (Genbank Accession No. EIV11143.1, SEQ ID NO: 5), or *Segniliparus rotundus* (Genbank Accession No. ADG98140.1, SEQ ID NO: 6) in combination with a phosphopantetheine transferase enhancer (e.g., encoded by a sfp (Genbank Accession No. CAA44858.1, SEQ ID NO:20) gene from *Bacillus subtilis* or npt (Genbank Accession No. ABI83656.1, SEQ ID NO:21) gene from *Nocardia*), or the gene products of GriC and GriD from *Streptomyces griseus*; followed by conversion of 6-oxohexanol to 6-aminohexanol by a polypeptide having ω-transaminase activity classified, for example, under EC 2.6.1.- such as 2.6.1.18, EC 2.6.1.19, EC 2.6.1.29, EC 2.6.1.48, or EC 2.6.1.82 such as from a *Chromobacterium violaceum* (see Genbank Accession No. AAQ59697.1, SEQ ID NO: 7), a *Pseudomonas aeruginosa* (see Genbank Accession No. AAG08191.1, SEQ ID NO: 8), a *Pseudomonas syringae* (see Genbank Accession No. AAY39893.1, SEQ ID NO: 9), a *Rhodobacter sphaeroides* (see Genbank Accession No. ABA81135.1, SEQ ID NO: 10), an *Escherichia coli* (see Genbank Accession No. AAA57874.1, SEQ ID NO: 11), or a *Vibrio fluvialis* (see Genbank Accession No. AEA39183.1, SEQ ID NO: 12); followed by conversion to 6-aminohexanal by a polypeptide having alcohol dehydrogenase activity classified, for example, under EC 1.1.1.- (e.g., EC 1.1.1.1, EC 1.1.1.2, EC 1.1.1.21, or EC 1.1.1.184) such as the gene product of YMR318C (Genbank Accession No. CAA90836.1) or YqhD (from *E. coli*, GenBank Accession No. AAA69178.1) (Liu et al., *Microbiology*, 2009, 155, 2078-2085; Larroy et al., 2002, *Biochem J.*, 361(Pt 1), 163-172; Jarboe, 2011, *Appl. Microbiol. Biotechnol.*, 89(2), 249-257) or the protein having GenBank Accession No. CAA81612.1; followed by conversion to hexamethylenediamine by a polypeptide having ω-transaminase activity classified, for example, under EC 2.6.1.- such as 2.6.1.18, EC 2.6.1.19, EC 2.6.1.29, EC 2.6.1.48, or EC 2.6.1.82 such as from a *Chromobacterium violaceum* (see Genbank Accession No. AAQ59697.1, SEQ ID NO: 7), a *Pseudomonas aeruginosa* (see Genbank Accession No. AAG08191.1, SEQ ID NO: 8), a *Pseudomonas syringae* (see Genbank Accession No. AAY39893.1, SEQ ID NO: 9), a *Rhodobacter sphaeroides* (see Genbank Accession No. ABA81135.1, SEQ ID NO: 10), an *Escherichia coli* (see Genbank Accession No. AAA57874.1, SEQ ID NO: 11), or a *Vibrio fluvialis* (see Genbank Accession No. AEA39183.1, SEQ ID NO: 12). See FIG. 6.

In some embodiments, hexamethylenediamine is synthesized from the central precursor 6-aminohexanoate by conversion of 6-aminohexanoate to N6-acetyl-6-aminohexanoate by a polypeptide having N-acetyltransferase activity such as a polypeptide having lysine N-acetyltransferase activity classified, for example, under EC 2.3.1.32; followed by conversion to N6-acetyl-6-aminohexanal by a polypeptide having carboxylate reductase activity classified, for example, under EC 1.2.99.6 such as from *Segniliparus rugosus* (Genbank Accession No. EFV11917.1, SEQ ID NO: 4), *Mycobacterium massiliense* (Genbank Accession No. EIV11143.1, SEQ ID NO: 5), or *Segniliparus rotundus* (Genbank Accession No. ADG98140.1, SEQ ID NO: 6) in combination with a phosphopantetheine transferase enhancer (e.g., encoded by a sfp (Genbank Accession No. CAA44858.1, SEQ ID NO:20) gene from *Bacillus subtilis* or npt (Genbank Accession No. ABI83656.1, SEQ ID NO:21) gene from *Nocardia*), or the gene products of GriC and GriD from *Streptomyces griseus*; followed by conversion to N6-acetyl-1,6-diaminohexane by a polypeptide having ω-transaminase activity classified, for example, under EC 2.6.1.- such as 2.6.1.18, EC 2.6.1.19, EC 2.6.1.29, EC 2.6.1.48, or EC 2.6.1.82 such as from a *Chromobacterium violaceum* (see Genbank Accession No. AAQ59697.1, SEQ ID NO: 7), a *Pseudomonas aeruginosa* (see Genbank Accession No. AAG08191.1, SEQ ID NO: 8), a *Pseudomonas syringae* (see Genbank Accession No. AAY39893.1, SEQ ID NO: 9), a *Rhodobacter sphaeroides* (see Genbank Accession No. ABA81135.1, SEQ ID NO: 10), an *Escherichia coli* (see Genbank Accession No. AAA57874.1, SEQ ID NO: 11), or a *Vibrio fluvialis* (see Genbank Accession No. AEA39183.1, SEQ ID NO: 12); followed by conversion to hexamethylenediamine by a polypeptide having acetylputrescine deacetylase activity classified, for example, under EC 3.5.1.17 or EC 3.5.1.62. See, FIG. 6.

In some embodiments, hexamethylenediamine is synthesized from the central precursor adipate semialdehyde by conversion of adipate semialdehyde to hexanedial by a polypeptide having carboxylate reductase activity classified, for example, under EC 1.2.99.6 such as from *Segniliparus rotundus* (Genbank Accession No. ADG98140.1, SEQ ID NO: 6) in combination with a phosphopantetheine transferase enhancer (e.g., encoded by a sfp (Genbank Accession No. CAA44858.1, SEQ ID NO:20) gene from *Bacillus subtilis* or npt (Genbank Accession No. ABI83656.1, SEQ ID NO:21) gene from *Nocardia*), or the gene products of GriC and GriD from *Streptomyces griseus*; followed by conversion to 6-aminohexanal by a polypeptide having ω-transaminase activity classified, for example, under EC 2.6.1.18, EC 2.6.1.19, EC 2.6.1.29, EC 2.6.1.48 or EC 2.6.1.82; followed by conversion to hexamethylenediamine by a activity ω-transaminase classified, for example, under EC 2.6.1.18, EC 2.6.1.19, EC 2.6.1.29, EC 2.6.1.48, or EC 2.6.1.82 such as SEQ ID NOs:7-12. See FIG. 6.

In some embodiments, hexamethylenediamine is synthesized from the central precursor 1,6-hexanediol by conversion of 1,6-hexanediol to 6-hydroxyhexanal by a a polypeptide having alcohol dehydrogenase activity classified, for example, under EC 1.1.1.- (e.g., EC 1.1.1.1, EC 1.1.1.2, EC 1.1.1.21, or EC 1.1.1.184) such as the gene product of YMR318C (Genbank Accession No. CAA90836.1) or YqhD (from *E. coli*, GenBank Accession No. AAA69178.1) (Liu et al., *Microbiology*, 2009, 155, 2078-2085; Larroy et al., 2002, *Biochem J.*, 361(Pt 1), 163-172; Jarboe, 2011, *Appl. Microbiol. Biotechnol.*, 89(2), 249-257) or the protein having GenBank Accession No. CAA81612.1; followed by conversion of 6-oxohexanal to 6-aminohexanol by a polypeptide having ω-transaminase activity classified, for example, under EC 2.6.1.- such as 2.6.1.18, EC 2.6.1.19, EC 2.6.1.29, EC 2.6.1.48, or EC 2.6.1.82 such as from a *Chromobacterium violaceum* (see Genbank Accession No. AAQ59697.1, SEQ ID NO: 7), a *Pseudomonas aeruginosa* (see Genbank Accession No. AAG08191.1, SEQ ID NO: 8), a *Pseudomonas syringae* (see Genbank Accession No. AAY39893.1, SEQ ID NO: 9), a *Rhodobacter sphaeroides* (see Genbank Accession No. ABA81135.1, SEQ ID NO: 10), an *Escherichia coli* (see Genbank Accession No. AAA57874.1, SEQ ID NO: 11), or a *Vibrio fluvialis* (see Genbank Accession No. AEA39183.1, SEQ ID NO: 12); followed by conversion to 6-aminohexanal by a polypeptide having alcohol dehydrogenase activity classified, for example, under EC 1.1.1.- (e.g., EC 1.1.1.1, EC 1.1.1.2, EC 1.1.1.21, or EC 1.1.1.184) such as the gene product of YMR318C (Genbank Accession No. CAA90836.1) or YqhD (from *E. coli*, GenBank Accession No. AAA69178.1) (Liu et al., *Microbiology*, 2009, 155, 2078-2085; Larroy et al., 2002, Biochem J., 361(Pt 1), 163-172; Jarboe, 2011, Appl. Microbiol. Biotechnol., 89(2), 249-257) or the protein having GenBank Accession No. CAA81612.1; followed by conversion to hexamethylenediamine classified, for example, under EC 2.6.1.- such as 2.6.1.18, EC 2.6.1.19, EC 2.6.1.29, EC 2.6.1.48, or EC 2.6.1.82 such as from a *Chromobacterium violaceum* (see Genbank Accession No. AAQ59697.1, SEQ ID NO: 7), a *Pseudomonas aeruginosa* (see Genbank Accession No. AAG08191.1, SEQ ID NO: 8), a *Pseudomonas syringae* (see Genbank Accession No. AAY39893.1, SEQ ID NO: 9), a *Rhodobacter sphaeroides* (see Genbank Accession No. ABA81135.1, SEQ ID NO: 10), an *Escherichia coli* (see Genbank Accession No. AAA57874.1, SEQ ID NO: 11), or a *Vibrio fluvialis* (see Genbank Accession No. AEA39183.1, SEQ ID NO: 12). See FIG. 6.

Pathways Using 6-Hydroxyhexanoate and Hexanoyl-CoA as Central Precursor to 1,6-Hexanediol In some embodiments, 1,6 hexanediol is synthesized from the central precursor 6-hydroxyhexanoate by conversion of 6-hydroxyhexanoate to 6-hydroxyhexanal by a polypeptide having carboxylate reductase activity classified, for example, under EC 1.2.99.6 such as from *Mycobacterium marinum* (Genbank Accession No. ACC40567.1, SEQ ID NO: 2), *Mycobacterium smegmatis* (Genbank Accession No. ABK71854.1, SEQ ID NO: 3), *Segniliparus rugosus* (Genbank Accession No. EFV11917.1, SEQ ID NO: 4), *Mycobacterium massiliense* (Genbank Accession No. EIV11143.1, SEQ ID NO: 5), or *Segniliparus rotundus* (Genbank Accession No. ADG98140.1, SEQ ID NO: 6) in combination with a phosphopantetheine transferase enhancer (e.g., encoded by a sfp (Genbank Accession No. CAA44858.1, SEQ ID NO:20) gene from *Bacillus subtilis* or npt (Genbank Accession No. ABI83656.1, SEQ ID NO:21) gene from *Nocardia*), or the gene products of GriC and GriD from *Streptomyces griseus* (Suzuki et al., *J. Antibiot.*, 2007, 60(6), 380-387); followed by conversion of 7-hydroxyhexanal to 1,6 hexanediol by a polypeptide having alcohol dehydrogenase activity classified, for example, under EC 1.1.1.- such as EC 1.1.1.1, EC 1.1.1.2, EC 1.1.1.21, or EC 1.1.1.184 such as the gene product of YMR318C (Genbank Accession No. CAA90836.1) or YqhD (from *E. coli*, GenBank Accession No. AAA69178.1) (from *E. coli*, GenBank Accession No. AAA69178.1) (see, e.g., Liu et al., *Microbiology*, 2009, 155, 2078-2085; Larroy et al., 2002, *Biochem J.*, 361(Pt 1), 163-172; or Jarboe, 2011, *Appl. Microbiol. Biotechnol.*, 89(2), 249-257) or the protein having GenBank Accession No. CAA81612.1 (from *Geobacillus stearothermophilus*). See, FIG. 8.

In some embodiments, hexanoyl-CoA can be converted to hexanoic acid hexyl ester using a polypeptide having alcohol O-acetyltransferase activity classified, for example, under EC 2.3.1.-(84) such as the gene product of Eht1 (Genbank Accession No: CAA85138.1, SEQ ID NO: 25); followed by conversion to hexanoic acid 6-hydroxy hexyl ester and/or 6-hydroxyhexanoic acid 6-hydroxyhexyl ester using a polypeptide having monooxygenase activity classified, for example, under EC 1.14.14.- or EC 1.14.15.-(1,3). For example, a polypeptide having monooxygenase activity can be, for example, from the CYP153A family, the CYP52A3 (Genbank Accession No: BAA00371.1, SEQ ID NO: 28) family or the alkB family such as the gene product of alkBGT from *Pseudomonas putida* (Genbank Accession No. CAB51047.1, SEQ ID NO: 27); followed by conversion of hexanoic acid 6-hydroxy hexyl ester and/or 6-hydroxyhexanoic acid 6-hydroxyhexyl to 1,6-hexanediol using a polypeptide having esterase activity classified, for example, under EC 3.1.1.-(1,6) such as the gene product of EstC (see GenBank Accession No. AAC60471.2, SEQ ID NO: 26). See FIG. 8.

Cultivation Strategy

In some embodiments, the cultivation strategy entails achieving an aerobic, anaerobic, micro-aerobic, or mixed oxygen/denitrification cultivation condition. Enzymes characterized in vitro as being oxygen sensitive require a micro-aerobic cultivation strategy maintaining a very low dissolved oxygen concentration (See, for example, Chayabatra & Lu-Kwang, *Appl. Environ. Microbiol.*, 2000, 66(2), 493 0 498; Wilson and Bouwer, 1997, *Journal of Industrial Microbiology and Biotechnology*, 18(2-3), 116-130).

In some embodiments, the cultivation strategy entails nutrient limitation such as nitrogen, phosphate or oxygen limitation.

In some embodiments, a final electron acceptor other than oxygen such as nitrates can be utilized.

In some embodiments, a cell retention strategy using, for example, ceramic membranes can be employed to achieve and maintain a high cell density during either fed-batch or continuous fermentation.

In some embodiments, the principal carbon source fed to the fermentation in the synthesis of one or more C6 building blocks can derive from biological or non-biological feedstocks.

In some embodiments, the biological feedstock can be or can derive from, monosaccharides, disaccharides, lignocellulose, hemicellulose, cellulose, lignin, levulinic acid and formic acid, triglycerides, glycerol, fatty acids, agricultural waste, condensed distillers' solubles, or municipal waste.

The efficient catabolism of crude glycerol stemming from the production of biodiesel has been demonstrated in several microorganisms such as *Escherichia coli*, *Cupriavidus necator*, *Pseudomonas oleavorans*, *Pseudomonas putida* and *Yarrowia lipolytica* (Lee et al., *Appl. Biochem. Biotechnol.*, 2012, 166:1801-1813; Yang et al., *Biotechnology for Biofuels*, 2012, 5:13; Meijnen et al., *Appl. Microbiol. Biotechnol.*, 2011, 90:885-893).

The efficient catabolism of lignocellulosic-derived levulinic acid has been demonstrated in several organisms such as *Cupriavidus necator* and *Pseudomonas putida* in the synthesis of 3-hydroxyvalerate via the precursor propanoyl-CoA (Jaremko and Yu, 2011, supra; Martin and Prather, *J. Biotechnol.*, 2009, 139:61-67).

The efficient catabolism of lignin-derived aromatic compounds such as benzoate analogues has been demonstrated in several microorganisms such as *Pseudomonas putida*, *Cupriavidus necator* (Bugg et al., *Current Opinion in Biotechnology*, 2011, 22, 394-400; Pérez-Pantoja et al., *FEMS Microbiol. Rev.*, 2008, 32, 736-794).

The efficient utilization of agricultural waste, such as olive mill waste water has been demonstrated in several microorganisms, including *Yarrowia lipolytica* (Papanikolaou et al., *Bioresour. Technol.*, 2008, 99(7):2419-2428).

The efficient utilization of fermentable sugars such as monosaccharides and disaccharides derived from cellulosic, hemicellulosic, cane and beet molasses, cassava, corn and other agricultural sources has been demonstrated for several microorganism such as *Escherichia coli*, *Corynebacterium glutamicum* and *Lactobacillus delbrueckii* and *Lactococcus lactis* (see, e.g., Hermann et al, *J. Biotechnol.*, 2003, 104: 155-172; Wee et al., *Food Technol. Biotechnol.*, 2006, 44(2):163-172; Ohashi et al., *J. Bioscience and Bioengineering*, 1999, 87(5):647-654).

The efficient utilization of furfural, derived from a variety of agricultural lignocellulosic sources, has been demonstrated for *Cupriavidus necator* (Li et al., *Biodegradation*, 2011, 22:1215-1225).

In some embodiments, the non-biological feedstock can be or can derive from natural gas, syngas, $CO_2/H_2$, methanol, ethanol, benzoate, non-volatile residue (NVR) or a caustic wash waste stream from cyclohexane oxidation processes, or terephthalic acid/isophthalic acid mixture waste streams.

The efficient catabolism of methanol has been demonstrated for the methylotrophic yeast *Pichia pastoris*.

The efficient catabolism of ethanol has been demonstrated for *Clostridium kluyveri* (Seedorf et al., *Proc. Natl. Acad. Sci. USA*, 2008, 105(6) 2128-2133).

The efficient catabolism of $CO_2$ and $H_2$, which may be derived from natural gas and other chemical and petrochemical sources, has been demonstrated for *Cupriavidus necator* (Prybylski et al., *Energy, Sustainability and Society*, 2012, 2:11).

The efficient catabolism of syngas has been demonstrated for numerous microorganisms, such as *Clostridium ljungdahlii* and *Clostridium autoethanogenum* (Kopke et al., *Applied and Environmental Microbiology*, 2011, 77(15): 5467-5475).

The efficient catabolism of the non-volatile residue waste stream from cyclohexane processes has been demonstrated for numerous microorganisms, such as *Delftia acidovorans* and *Cupriavidus necator* (Ramsay et al., *Applied and Environmental Microbiology*, 1986, 52(1):152-156).

In some embodiments, the host microorganism is a prokaryote. For example, the prokaryote can be a bacterium from the genus *Escherichia* such as *Escherichia coli*; from the genus *Clostridia* such as *Clostridium ljungdahlii*, *Clostridium* autoethanogenum or *Clostridium kluyveri*; from the genus *Corynebacteria* such as *Corynebacterium glutamicum*; from the genus *Cupriavidus* such as *Cupriavidus necator* or *Cupriavidus metallidurans*; from the genus *Pseudomonas* such as *Pseudomonas fluorescens, Pseudomonas putida* or *Pseudomonas oleavorans*; from the genus *Delftia* such as *Delftia acidovorans*; from the genus *Bacillus* such as *Bacillus subtillis*; from the genus *Lactobacillus* such as *Lactobacillus delbrueckii*; or from the genus *Lactococcus* such as *Lactococcus lactis*. Such prokaryotes also can be a source of genes to construct recombinant host cells described herein that are capable of producing one or more C6 building blocks.

In some embodiments, the host microorganism is a eukaryote. For example, the eukaryote can be a filamentous fungus, e.g., one from the genus *Aspergillus* such as *Aspergillus niger*. Alternatively, the eukaryote can be a yeast, e.g., one from the genus *Saccharomyces* such as *Saccharomyces cerevisiae*; from the genus *Pichia* such as *Pichia pastoris*; or from the genus *Yarrowia* such as *Yarrowia lipolytica*; from the genus *Issatchenkia* such as Issathenkia *orientalis*; from the genus *Debaryomyces* such as *Debaryomyces hansenii*; from the genus *Arxula* such as *Arxula adenoinivorans*; or from the genus *Kluyveromyces* such as *Kluyveromyces lactis*. Such eukaryotes also can be a source of genes to construct recombinant host cells described herein that are capable of producing one or more C6 building blocks.

Metabolic Engineering

The present document provides methods involving less than all the steps described for all the above pathways. Such methods can involve, for example, one, two, three, four, five, six, seven, eight, nine, ten, eleven, twelve or more of such steps. Where less than all the steps are included in such a method, the first, and in some embodiments the only, step can be any one of the steps listed.

Furthermore, recombinant hosts described herein can include any combination of the above enzymes such that one or more of the steps, e.g., one, two, three, four, five, six, seven, eight, nine, ten, or more of such steps, can be performed within a recombinant host. This document provides host cells of any of the genera and species listed and genetically engineered to express one or more (e.g., two, three, four, five, six, seven, eight, nine, 10, 11, 12 or more) recombinant forms of any of the enzymes recited in the document. Thus, for example, the host cells can contain exogenous nucleic acids encoding enzymes catalyzing one or more of the steps of any of the pathways described herein.

In addition, this document recognizes that where enzymes have been described as accepting CoA-activated substrates, analogous enzyme activities associated with [acp]-bound substrates exist that are not necessarily in the same enzyme class.

Also, this document recognizes that where enzymes have been described accepting (R)-enantiomers of substrate, analogous enzyme activities associated with (S)-enantiomer substrates exist that are not necessarily in the same enzyme class.

This document also recognizes that where an enzyme is shown to accept a particular co-factor, such as NADPH, or co-substrate, such as acetyl-CoA, many enzymes are promiscuous in terms of accepting a number of different co-factors or co-substrates in catalyzing a particular enzyme activity. Also, this document recognizes that where enzymes have high specificity for e.g., a particular co-factor such as NADH, an enzyme with similar or identical activity that has high specificity for the co-factor NADPH may be in a different enzyme class. In addition, enzymes in a pathway that require a particular co-factor can be replaced with an enzyme that has similar or identical activity and specificity for a different co-factor. For example, one or more steps in a pathway that use an enzyme with specificity for NADH can be replaced with an enzyme having similar or identical activity and specificity for NADPH. Similarly, one or more steps in a pathway that use an enzyme with specificity for NADPH can be replaced with an enzyme having similar or identical activity and specificity for NADH.

In some embodiments, the enzymes in the pathways outlined herein are the result of enzyme engineering via non-direct or rational enzyme design approaches with aims of improving activity, improving specificity, reducing feedback inhibition, reducing repression, improving enzyme solubility, changing stereo-specificity, or changing co-factor specificity.

In some embodiments, the enzymes in the pathways outlined here can be gene dosed, i.e., overexpressed, into the resulting genetically modified organism via episomal or chromosomal integration approaches.

In some embodiments, genome-scale system biology techniques such as Flux Balance Analysis can be utilized to devise genome scale attenuation or knockout strategies for directing carbon flux to a C6 building block.

Attenuation strategies include, but are not limited to; the use of transposons, homologous recombination (double cross-over approach), mutagenesis, enzyme inhibitors and RNAi interference.

In some embodiments, fluxomic, metabolomic and transcriptomal data can be utilized to inform or support genome-scale system biology techniques, thereby devising genome scale attenuation or knockout strategies in directing carbon flux to a C6 building block.

In some embodiments, the host microorganism's tolerance to high concentrations of a C6 building block can be improved through continuous cultivation in a selective environment.

In some embodiments, the host microorganism's endogenous biochemical network can be attenuated or augmented to (1) ensure the intracellular availability of acetyl-CoA, (2) create an NADH or NADPH imbalance that may be balanced via the formation of one or more C6 building blocks, (3) prevent degradation of central metabolites, central precursors leading to and including one or more C6 building blocks and/or (4) ensure efficient efflux from the cell.

In some embodiments requiring intracellular availability of acetyl-CoA for C6 building block synthesis, endogenous enzymes catalyzing the hydrolysis of propionoyl-CoA and acetyl-CoA such as short-chain length polypeptides having thioesterase activity can be attenuated in the host organism.

In some embodiments requiring the intracellular availability of acetyl-CoA for C6 building block synthesis, an endogenous polypeptide having phosphotransacetylase activity generating acetate such as pta can be attenuated (Shen et al., *Appl. Environ. Microbiol.*, 2011, 77(9):2905-2915).

In some embodiments requiring the intracellular availability of acetyl-CoA for C6 building block synthesis, an endogenous gene in an acetate synthesis pathway encoding a polypeptide having acetate kinase activity, such as ack, can be attenuated.

In some embodiments requiring the intracellular availability of acetyl-CoA and NADH for C6 building block synthesis, an endogenous gene encoding an enzyme that catalyzes the degradation of pyruvate to lactate such as a polypeptide having lactate dehydrogenase activity encoded by ldhA can be attenuated (Shen et al., 2011, supra).

In some embodiments requiring the intracellular availability of acetyl-CoA and NADH for C6 building block synthesis, endogenous genes encoding enzymes, such as polypeptide having menaquinol-fumarate oxidoreductase activity, that catalyze the degradation of phophoenolpyruvate to succinate such as frdBC can be attenuated (see, e.g., Shen et al., 2011, supra).

In some embodiments requiring the intracellular availability of acetyl-CoA and NADH for C6 building block synthesis, an endogenous gene encoding an enzyme that catalyzes the degradation of acetyl-CoA to ethanol such as the polypeptide having alcohol dehydrogenase activity encoded by adhE can be attenuated (Shen et al., 2011, supra).

In some embodiments, where pathways require excess NADH co-factor for C6 building block synthesis, a recombinant polypeptide having formate dehydrogenase activity gene can be overexpressed in the host organism (Shen et al., 2011, supra).

In some embodiments, where pathways require excess NADH or NADPH co-factor for C6 building block synthesis, a polypeptide having transhydrogenase activity dissipating the cofactor imbalance can be attenuated.

In some embodiments, an endogenous gene encoding an enzyme that catalyzes the degradation of pyruvate to ethanol such as polypeptide having pyruvate decarboxylase activity can be attenuated.

In some embodiments, an endogenous gene encoding an enzyme that catalyzes the generation of isobutanol such as a polypeptide having 2-oxoacid decarboxylase activity can be attenuated.

In some embodiments requiring the intracellular availability of acetyl-CoA for C6 building block synthesis, a recombinant polypeptide having acetyl-CoA synthetase activity such as the gene product of acs can be overexpressed in the microorganism (Satoh et al., *J. Bioscience and Bioengineering*, 2003, 95(4):335-341).

In some embodiments, carbon flux can be directed into the butose phosphate cycle to increase the supply of NADPH by attenuating an endogenous polypeptide having glucose-6-phosphate isomerase activity (EC 5.3.1.9).

In some embodiments, carbon flux can be redirected into the butose phosphate cycle to increase the supply of NADPH by overexpression a polypeptide having 6-phosphogluconate dehydrogenase activity and/or a polypeptide having transketolase activity (Lee et al., 2003, *Biotechnology Progress*, 19(5), 1444-1449).

In some embodiments, where pathways require excess NADPH co-factor in the synthesis of a C6 building block, a gene such as UdhA encoding a polypeptide having puridine nucleotide transhydrogenase activity can be overexpressed in the host organisms (Brigham et al., *Advanced Biofuels and Bioproducts*, 2012, Chapter 39, 1065-1090).

In some embodiments, where pathways require excess NADPH co-factor in the synthesis of a C6 Building Block, a recombinant polypeptide having glyceraldehyde-3-phosphate-dehydrogenase activity gene such as GapN can be overexpressed in the host organisms (Brigham et al., 2012, supra).

In some embodiments, where pathways require excess NADPH co-factor in the synthesis of a C6 building block, a recombinant malic enzyme gene such as macA or maeB can be overexpressed in the host organisms (Brigham et al., 2012, supra).

In some embodiments, where pathways require excess NADPH co-factor in the synthesis of a C6 building block, a recombinant polypeptide having glucose-6-phosphate dehydrogenase activity gene such as zwf can be overexpressed in the host organisms (Lim et al., *J. Bioscience and Bioengineering*, 2002, 93(6), 543-549).

In some embodiments, where pathways require excess NADPH co-factor in the synthesis of a C6 building block, a recombinant polypeptide having fructose 1,6 diphosphatase activity such as fbp can be overexpressed in the host organisms (Becker et al., *J. Biotechnol.*, 2007, 132:99-109).

In some embodiments, where pathways require excess NADPH co-factor in the synthesis of a C6 building block, endogenous polypeptide having triose phosphate isomerase activity (EC 5.3.1.1) can be attenuated.

In some embodiments, where pathways require excess NADPH co-factor in the synthesis of a C6 building block, a recombinant polypeptide having glucose dehydrogenase activity such as the gene product of gdh can be overexpressed in the host organism (Satoh et al., *J. Bioscience and Bioengineering*, 2003, 95(4):335-341).

In some embodiments, endogenous enzymes facilitating the conversion of NADPH to NADH can be attenuated, such as the NADH generation cycle that may be generated via inter-conversion of polypeptides having glutamate dehydrogenase activity classified under EC 1.4.1.2 (NADH-specific) and EC 1.4.1.4 (NADPH-specific).

In some embodiments, an endogenous polypeptide having glutamate dehydrogenase activity (EC 1.4.1.3) that utilizes both NADH and NADPH as co-factors can be attenuated.

In some embodiments, a membrane-bound polypeptide having cytochrome P450 activity such as CYP4F3B can be solubilized by only expressing the cytosolic domain and not the N-terminal region that anchors the P450 to the endoplasmic reticulum (see, for example, Scheller et al., *J. Biol. Chem.*, 1994, 269(17):12779-12783).

In some embodiments, a membrane-bound polypeptide having enoyl-CoA reductase activity can be solubilized via expression as a fusion protein to a small soluble protein such as a maltose binding protein (Gloerich et al., *FEBS Letters*, 2006, 580, 2092-2096).

In some embodiments using hosts that naturally accumulate polyhydroxyalkanoates, the endogenous polypeptides having polyhydroxyalkanoate synthase activity can be attenuated in the host strain.

In some embodiments requiring the intracellular availability of butanoyl-CoA for C6 building block synthesis, a recombinant polypeptide having propionyl-CoA synthetase activity such as the gene product of PrpE-RS can be overexpressed in the microorganism (Rajashekhara & Watanabe, *FEBS Letters*, 2004, 556:143-147).

In some embodiments, a polypeptide having L-alanine dehydrogenase activity can be overexpressed in the host to regenerate L-alanine from pyruvate as an amino donor for ω-transaminase reactions.

In some embodiments, a polypeptide having L-glutamate dehydrogenase activity, a polypeptide having L-glutamine synthetase activity, or a polypeptide having glutamate synthase activity can be overexpressed in the host to regenerate L-glutamate from 2-oxoglutarate as an amino donor for ω-transaminase reactions.

In some embodiments, enzymes such as polypeptide having pimeloyl-CoA dehydrogenase activity classified under, EC 1.3.1.62; a polypeptide having acyl-CoA dehydrogenase activity classified, for example, under EC 1.3.8.7 or EC 1.3.8.1; and/or a polypeptide having glutaryl-CoA dehydrogenase activity classified, for example, under EC 1.3.8.6 that degrade central metabolites and central precursors leading to and including C6 building blocks can be attenuated.

In some embodiments, endogenous enzymes activating C6 building blocks via Coenzyme A esterification such as polypeptide having CoA-ligases activity (e.g., a pimeloyl-CoA synthetase) classified under, for example, EC 6.2.1.14 can be attenuated.

In some embodiments, the efflux of a C6 building block across the cell membrane to the extracellular media can be enhanced or amplified by genetically engineering structural modifications to the cell membrane or increasing any associated transporter activity for a C6 building block.

The efflux of hexamethylenediamine can be enhanced or amplified by overexpressing broad substrate range multi-drug transporters such as Blt from *Bacillus subtilis* (Woolridge et al., 1997, *J. Biol. Chem.*, 272(14):8864-8866); AcrB and AcrD from *Escherichia coli* (Elkins & Nikaido, 2002, *J. Bacteriol.*, 184(23), 6490-6499), NorA from *Staphylococcus aereus* (Ng et al., 1994, *Antimicrob Agents Chemother*, 38(6), 1345-1355), or Bmr from *Bacillus subtilis* (Neyfakh, 1992, *Antimicrob Agents Chemother*, 36(2), 484-485).

The efflux of 6-aminohexanoate and hexamethylenediamine can be enhanced or amplified by overexpressing the solute transporters such as the lysE transporter from *Corynebacterium glutamicum* (Bellmann et al., 2001, *Microbiology*, 147, 1765-1774).

The efflux of adipic acid can be enhanced or amplified by overexpressing a dicarboxylate transporter such as the SucE transporter from *Corynebacterium glutamicum* (Huhn et al., *Appl. Microbiol. & Biotech.*, 89(2), 327-335).

Producing C6 Building Blocks Using a Recombinant Host

Typically, one or more C6 building blocks can be produced by providing a host microorganism and culturing the provided microorganism with a culture medium containing a suitable carbon source as described above. In general, the culture media and/or culture conditions can be such that the microorganisms grow to an adequate density and produce a C6 building block efficiently. For large-scale production processes, any method can be used such as those described elsewhere (Manual of Industrial Microbiology and Biotechnology, 2$^{nd}$ Edition, Editors: A. L. Demain and J. E. Davies, ASM Press; and Principles of Fermentation Technology, P. F. Stanbury and A. Whitaker, Pergamon). Briefly, a large tank (e.g., a 100 gallon, 200 gallon, 500 gallon, or more tank) containing an appropriate culture medium is inoculated with a particular microorganism. After inoculation, the microorganism is incubated to allow biomass to be produced. Once a desired biomass is reached, the broth containing the microorganisms can be transferred to a second tank. This second tank can be any size. For example, the second tank can be larger, smaller, or the same size as the first tank. Typically, the second tank is larger than the first such that additional culture medium can be added to the broth from the first tank. In addition, the culture medium within this second tank can be the same as, or different from, that used in the first tank.

Once transferred, the microorganisms can be incubated to allow for the production of a C6 building block. Once produced, any method can be used to isolate C6 building blocks. For example, C6 building blocks can be recovered selectively from the fermentation broth via adsorption processes. In the case of adipic acid and 6-aminohexanoic acid, the resulting eluate can be further concentrated via evaporation, crystallized via evaporative and/or cooling crystallization, and the crystals recovered via centrifugation. In the case of hexamethylenediamine and 1,6-hexanediol, distillation may be employed to achieve the desired product purity.

The invention is further described in the following examples, which do not limit the scope of the invention described in the claims.

EXAMPLES

Example 1

Enzyme Activity of ω-Transaminase Using Adipate Semialdehyde as Substrate and Forming 6-Aminohexanoate A nucleotide sequence encoding a His-tag was added to the genes from *Chromobacterium violaceum*, *Pseudomonas aeruginosa*, *Pseudomonas syringae*, *Rhodobacter sphaeroides*, and *Vibrio fluvialis* encoding the ω-transaminases of SEQ ID NOs: 7, 8, 9, 10 and 12, respectively (see FIG. 9) such that N-terminal HIS tagged w-transaminases could be produced. Each of the resulting modified genes was cloned into a pET21a expression vector under control of the T7 promoter and each expression vector was transformed into a BL21[DE3] *E. coli* host. The resulting recombinant *E. coli* strains were cultivated at 37° C. in a 250 mL shake flask culture containing 50 mL LB media and antibiotic selection pressure, with shaking at 230 rpm. Each culture was induced overnight at 16° C. using 1 mM IPTG.

The pellet from each induced shake flask culture was harvested via centrifugation. Each pellet was resuspended and lysed via sonication. The cell debris was separated from the supernatant via centrifugation and the cell free extract was used immediately in enzyme activity assays.

Enzyme activity assays in the reverse direction (i.e., 6-aminohexanoate to adipate semialdehyde) were performed in a buffer composed of a final concentration of 50 mM HEPES buffer (pH=7.5), 10 mM 6-aminohexanoate, 10 mM pyruvate and 100 µM pyridoxyl 5' phosphate. Each enzyme activity assay reaction was initiated by adding cell free extract of the ω-transaminase gene product or the empty vector control to the assay buffer containing the 6-aminohexanoate and incubated at 25° C. for 24 h, with shaking at 250 rpm. The formation of L-alanine from pyruvate was quantified via RP-HPLC.

Figure 16:
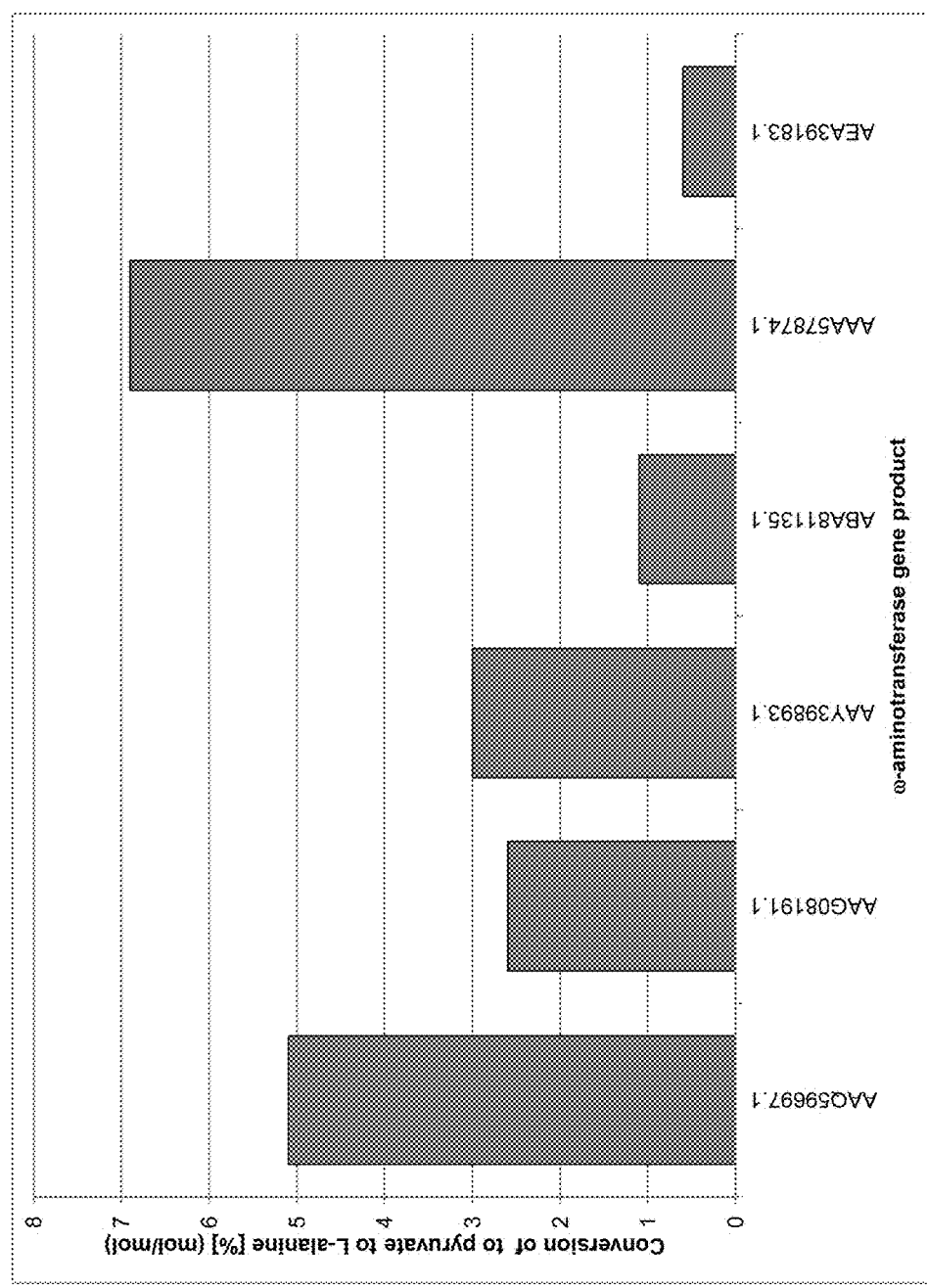
FIG. 16 is a bar graph summarizing the percent conversion after 4 hours of pyruvate to L-alanine (mol/mol) as a measure of the ω-transaminase activity of the enzyme only controls (no substrate).
Figure 17:
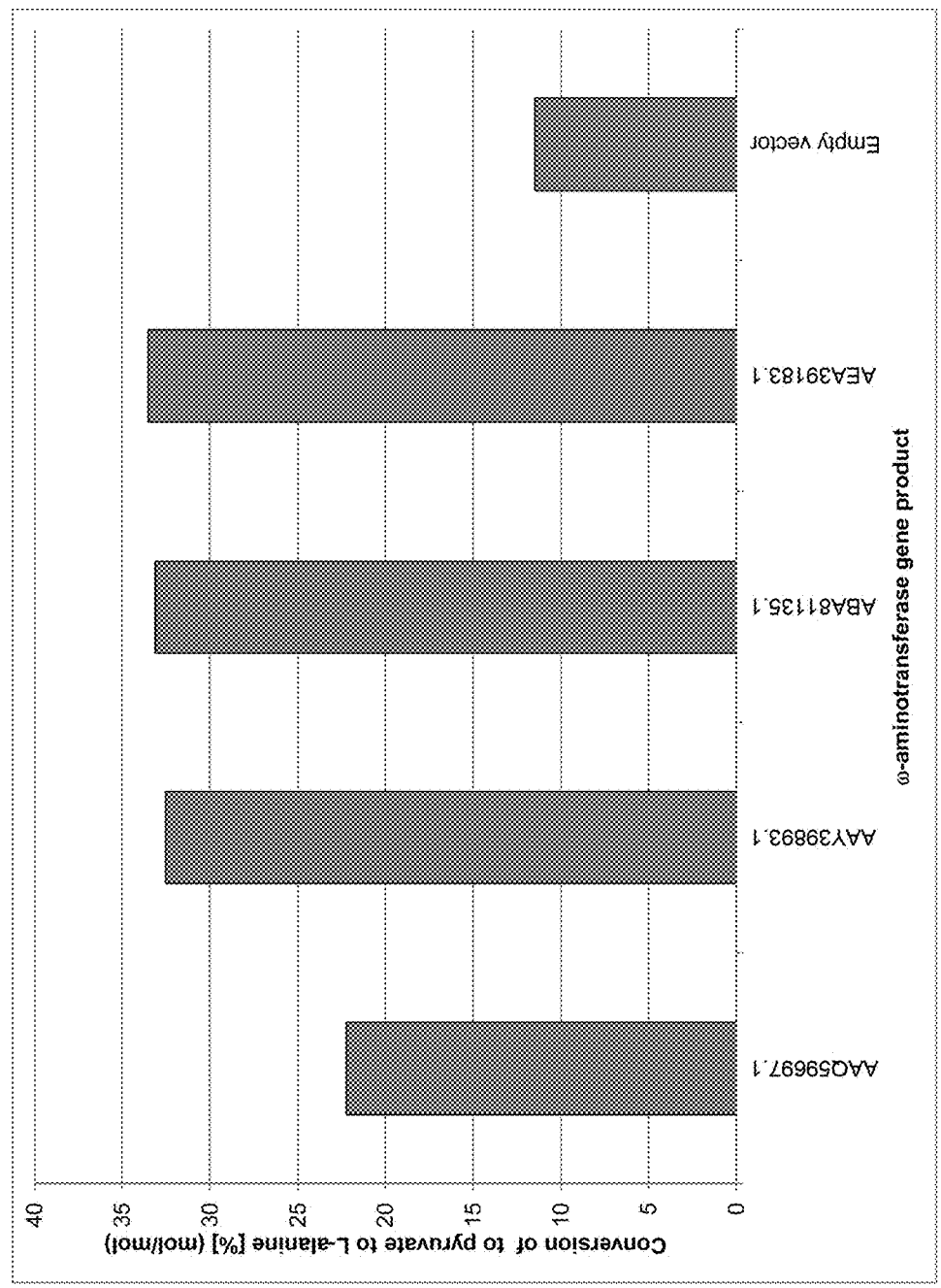
FIG. 17 is a bar graph of the percent conversion after 24 hours of pyruvate to L-alanine (mol/mol) as a measure of the ω-transaminase activity for converting 6-aminohexanoate to adipate semialdehyde relative to the empty vector control.

Each enzyme only control without 6-aminoheptanoate demonstrated low base line conversion of pyruvate to L-alanine See FIG. 16. The gene product of SEQ ID NO 7, SEQ ID NO 9, SEQ ID NO 10 and SEQ ID NO 12 accepted 6-aminohexanote as substrate as confirmed against the empty vector control. See FIG. 17.

Enzyme activity in the forward direction (i.e., adipate semialdehyde to 6-aminohexanoate) was confirmed for the transaminases of SEQ ID NO 7, SEQ ID NO 8, SEQ ID NO 9, SEQ ID NO 10 and SEQ ID NO 12. Enzyme activity assays were performed in a buffer composed of a final concentration of 50 mM HEPES buffer (pH=7.5), 10 mM adipate semialdehyde, 10 mM L-alanine and 100 µM pyridoxyl 5' phosphate. Each enzyme activity assay reaction was initiated by adding a cell free extract of the ω-transaminase gene product or the empty vector control to the assay buffer containing the adipate semialdehyde and incubated at 25° C. for 4 h, with shaking at 250 rpm. The formation of pyruvate was quantified via RP-HPLC.

Figure 18:
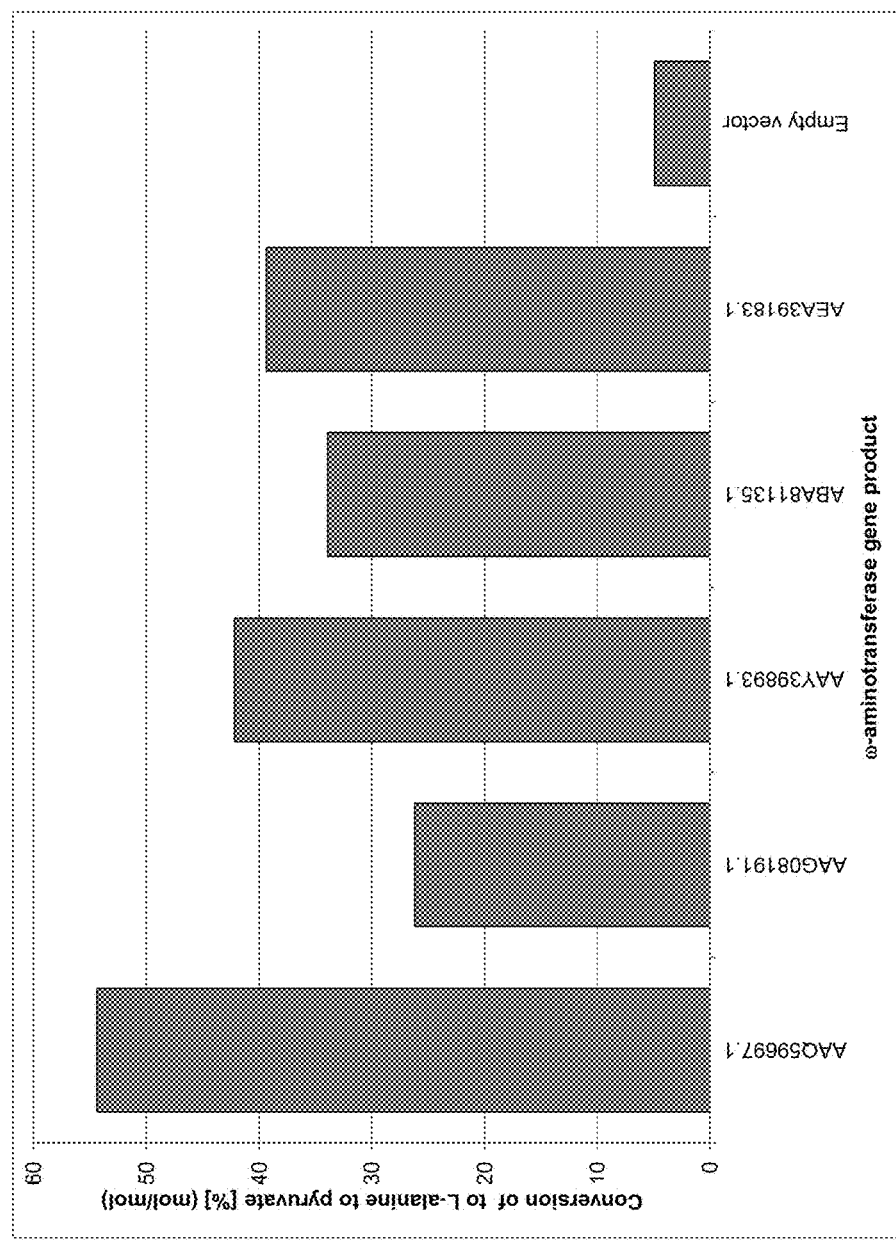
FIG. 18 is a bar graph of the percent conversion after 4 hours of L-alanine to pyruvate (mol/mol) as a measure of the ω-transaminase activity for converting adipate semialdehyde to 6-aminohexanoate relative to the empty vector control.

The gene product of SEQ ID NO 7, SEQ ID NO 8, SEQ ID NO 9, SEQ ID NO 10 and SEQ ID NO 12 accepted adipate semialdehyde as substrate as confirmed against the empty vector control. See FIG. 18. The reversibility of the ω-transaminase activity was confirmed, demonstrating that the ω-transaminases of SEQ ID NO 7, SEQ ID NO 8, SEQ ID NO 9, SEQ ID NO 10 and SEQ ID NO 12 accepted adipate semialdehyde as substrate and synthesized 6-aminohexanoate as a reaction product.

Example 2

Enzyme Activity of Carboxylate Reductase Using Adipate as Substrate and Forming Adipate Semialdehyde A sequence encoding a HIS-tag was added to the genes from *Segniliparus rugosus* and *Segniliparus rotundus* that encode the carboxylate reductases of SEQ ID NOs: 4 and 6, respectively (see FIG. 9), such that N-terminal HIS tagged carboxylate reductases could be produced. Each of the modified genes was cloned into a pET Duet expression vector along with a sfp gene encoding a HIS-tagged phosphopantetheine transferase from *Bacillus subtilis*, both under the T7 promoter. Each expression vector was transformed into a BL21[DE3] *E. coli* host and the resulting recombinant *E. coli* strains were cultivated at 37° C. in a 250 mL shake flask culture containing 50 mL LB media and antibiotic selection pressure, with shaking at 230 rpm. Each culture was induced overnight at 37° C. using an auto-induction media.

The pellet from each induced shake flask culture was harvested via centrifugation. Each pellet was resuspended and lysed via sonication, and the cell debris was separated from the supernatant via centrifugation. The carboxylate reductases and phosphopantetheine transferases were purified from the supernatant using Ni-affinity chromatography, diluted 10-fold into 50 mM HEPES buffer (pH=7.5), and concentrated via ultrafiltration.

Figure 11:
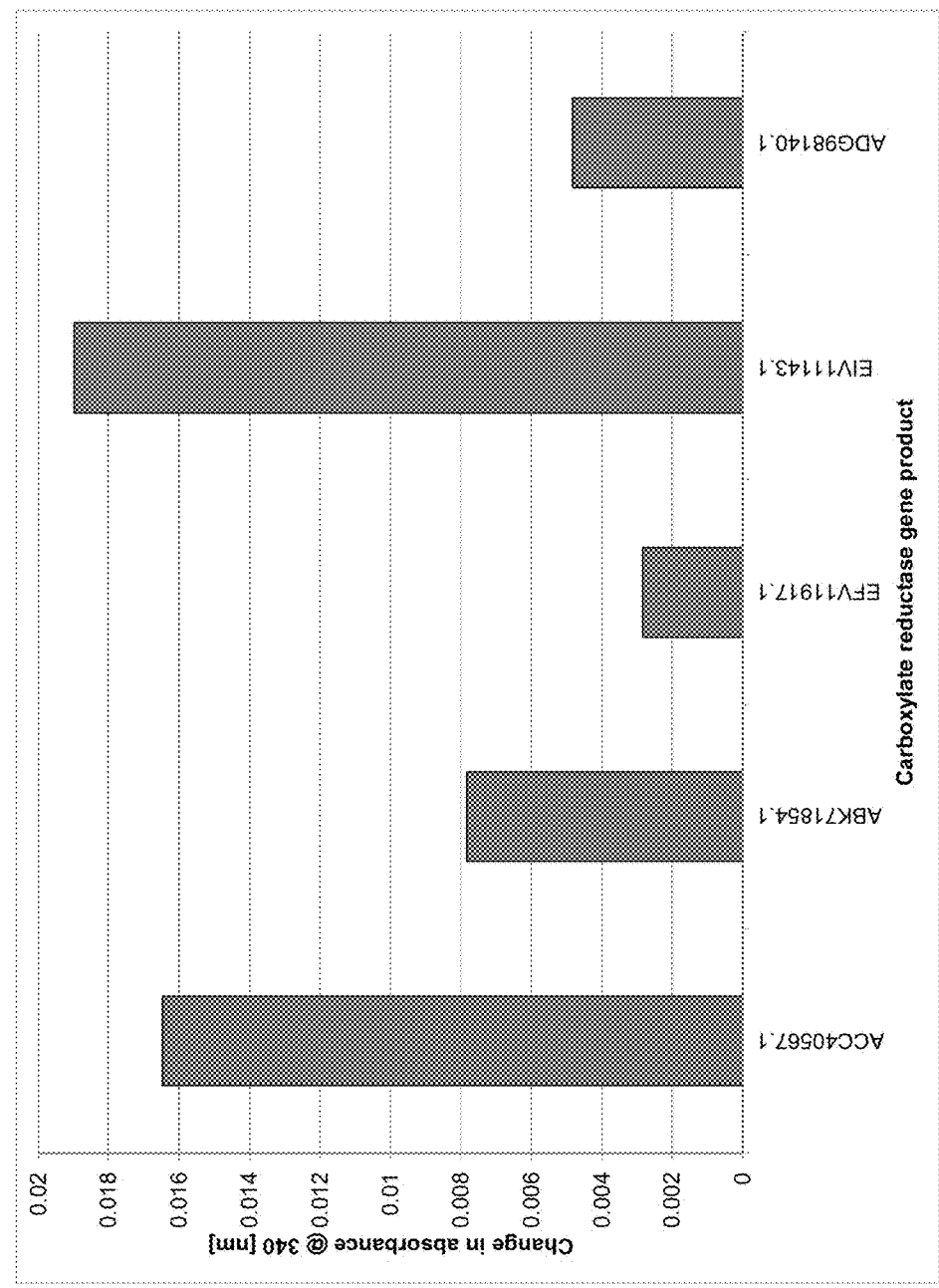
FIG. 11 is a bar graph summarizing the change in absorbance at 340 nm after 20 min, which is a measure of the consumption of NADPH and the activity of the carboxylate reductases with no substrate (enzyme only controls).

Enzyme activity assays (i.e., from adipate to adipate semialdehyde) were performed in triplicate in a buffer composed of a final concentration of 50 mM HEPES buffer (pH=7.5), 2 mM adipate, 10 mM MgCl$_2$, 1 mM ATP and 1 mM NADPH. Each enzyme activity assay reaction was initiated by adding purified carboxylate reductase and phosphopantetheine transferase gene products or the empty vector control to the assay buffer containing the adipate and then incubated at room temperature for 20 min. The consumption of NADPH was monitored by absorbance at 340 nm. Each enzyme only control without adipate demonstrated low base line consumption of NADPH. See FIG. 11.

Figure 12:
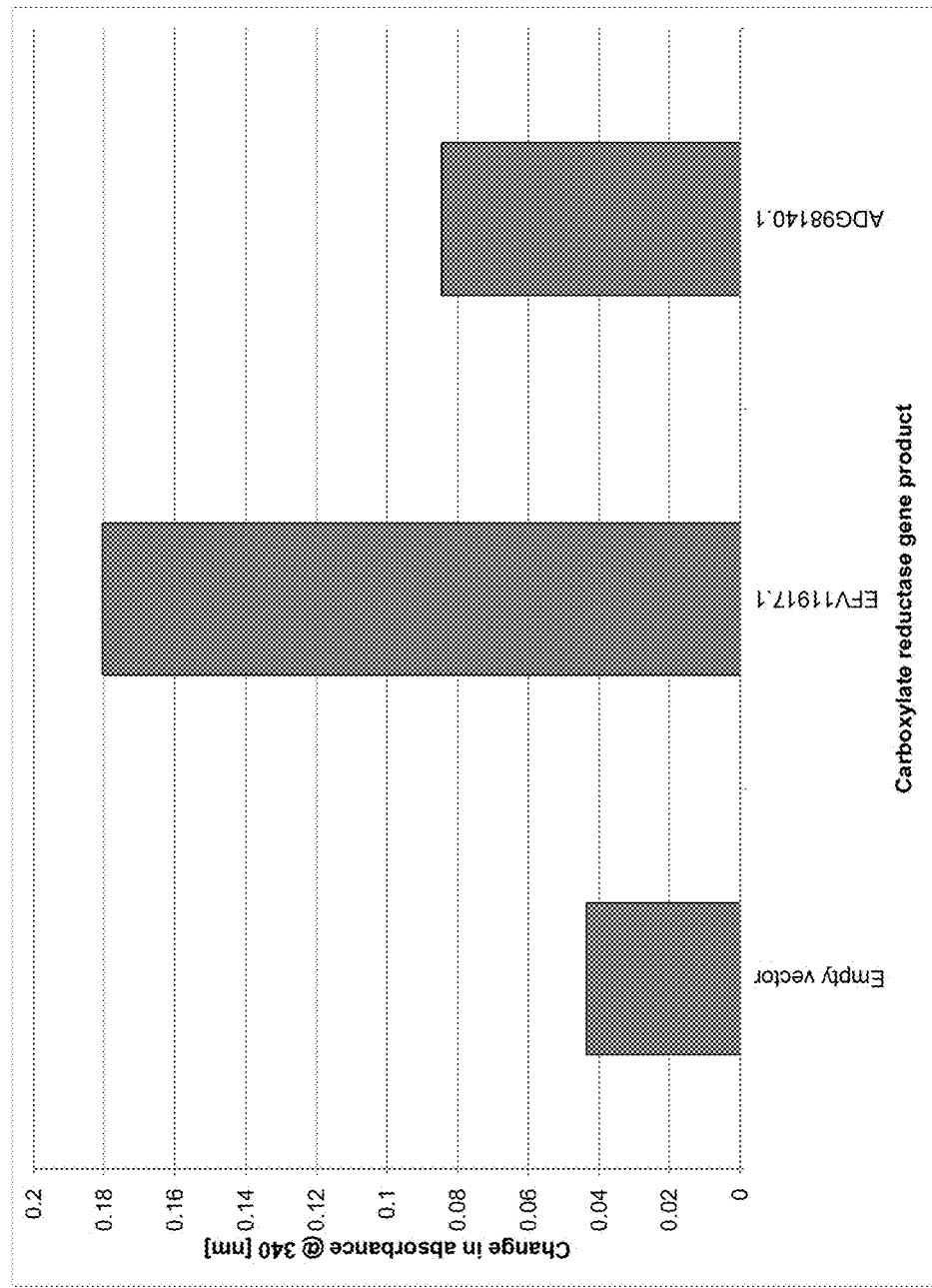
FIG. 12 is a bar graph of the change in absorbance at 340 nm after 20 min, which is a measure of the consumption of NADPH and the activity of carboxylate reductases for converting adipate to adipate semialdehyde relative to the empty vector control.

The gene products of SEQ ID NO 4 and SEQ ID NO 6, enhanced by the gene product of sfp, accepted adipate as substrate, as confirmed against the empty vector control (see FIG. 12), and synthesized adipate semialdehyde.

Example 3

Enzyme Activity of Carboxylate Reductase Using 6-Hydroxyhexanoate as Substrate and Forming 6-Hydroxyhexanal A sequence encoding a His-tag was added to the genes from *Mycobacterium marinum*, *Mycobacterium smegmatis*, *Segniliparus rugosus*, *Mycobacterium massiliense*, and *Segniliparus rotundus* that encode the carboxylate reductases of SEQ ID NOs: 2-6, respectively (see FIG. 9) such that N-terminal HIS tagged carboxylate reductases could be produced. Each of the modified genes was cloned into a pET Duet expression vector alongside a sfp gene encoding a His-tagged phosphopantetheine transferase from *Bacillus subtilis*, both under control of the T7 promoter. Each expression vector was transformed into a BL21[DE3] *E. coli* host along with the expression vectors from Example 1. Each resulting recombinant *E. coli* strain was cultivated at 37° C. in a 250 mL shake flask culture containing 50 mL LB media and antibiotic selection pressure, with shaking at 230 rpm. Each culture was induced overnight at 37° C. using an auto-induction media.

The pellet from each induced shake flask culture was harvested via centrifugation. Each pellet was resuspended and lysed via sonication. The cell debris was separated from the supernatant via centrifugation. The carboxylate reductases and phosphopantetheine transferase were purified from the supernatant using Ni-affinity chromatography, diluted 10-fold into 50 mM HEPES buffer (pH=7.5) and concentrated via ultrafiltration.

Enzyme activity (i.e., 6-hydroxyhexanoate to 6-hydroxyhexanal) assays were performed in triplicate in a buffer composed of a final concentration of 50 mM HEPES buffer (pH=7.5), 2 mM 6-hydroxyhexanal, 10 mM MgCl$_2$, 1 mM ATP, and 1 mM NADPH. Each enzyme activity assay reaction was initiated by adding purified carboxylate reductase and phosphopantetheine transferase or the empty vector control to the assay buffer containing the 6-hydroxyhexanoate and then incubated at room temperature for 20 min. The consumption of NADPH was monitored by absorbance at 340 nm. Each enzyme only control without 6-hydroxyhexanoate demonstrated low base line consumption of NADPH. See FIG. 11.

Figure 13:
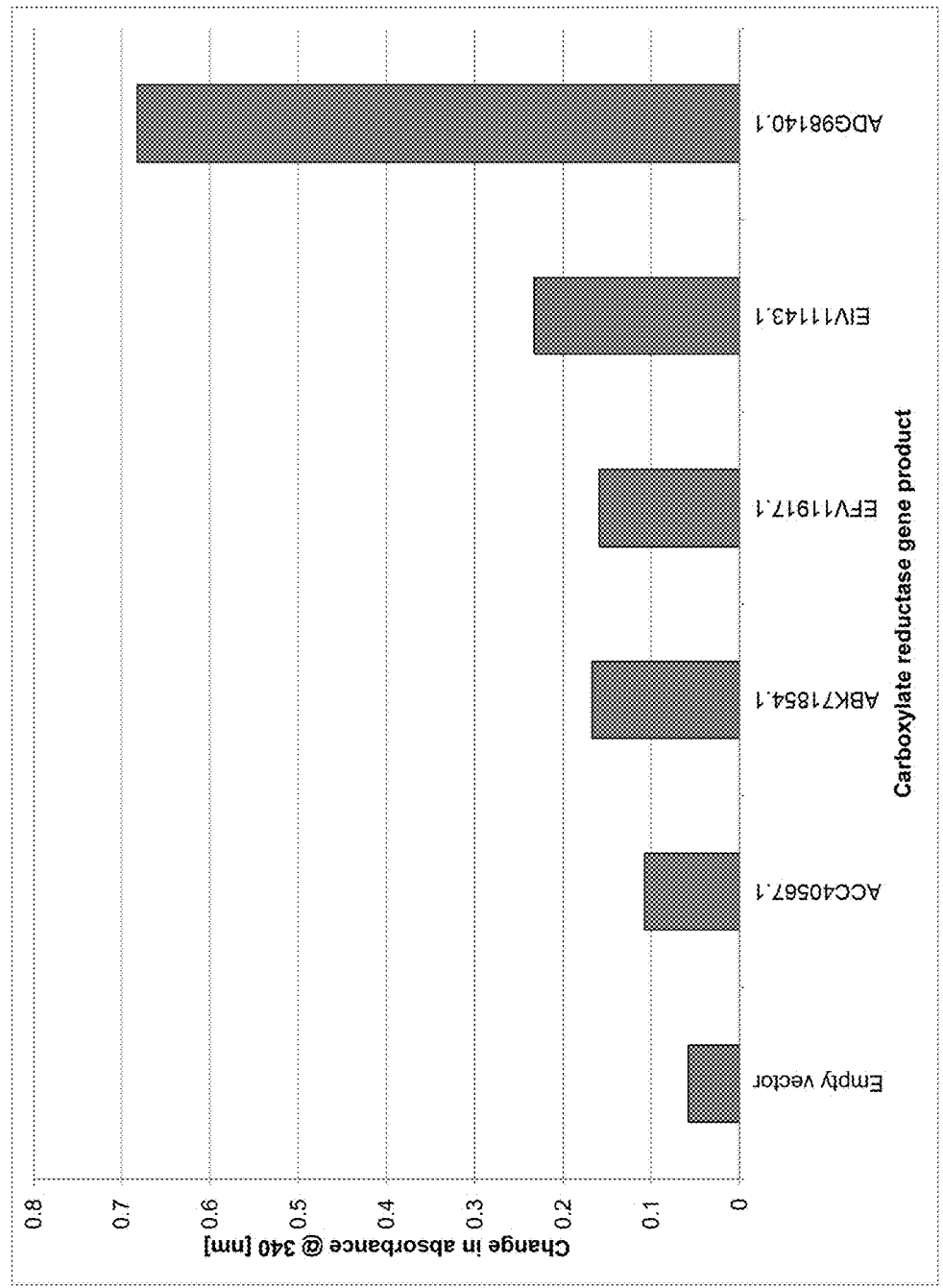
FIG. 13 is a bar graph of the change in absorbance at 340 nm after 20 min, which is a measure of the consumption of NADPH and the activity of carboxylate reductases for converting 6-hydroxyhexanoate to 6-hydroxyhexanal relative to the empty vector control.

The gene products of SEQ ID NO 2-6, enhanced by the gene product of sfp, accepted 6-hydroxyhexanoate as substrate as confirmed against the empty vector control (see FIG. 13), and synthesized 6-hydroxyhexanal.

Example 4

Enzyme Activity of ω-Transaminase for 6-Aminohexanol, Forming 6-Oxohexanol

A sequence encoding an N-terminal His-tag was added to the *Chromobacterium violaceum*, *Pseudomonas aeruginosa*,

*Pseudomonas syringae, Rhodobacter sphaeroides, Escherichia coli,* and *Vibrio fluvialis* genes encoding the ω-transaminases of SEQ ID NOs: 7-12, respectively (see FIG. 9) such that N-terminal HIS tagged ω-transaminases could be produced. The modified genes were cloned into a pET21a expression vector under the T7 promoter. Each expression vector was transformed into a BL21[DE3] *E. coli* host. Each resulting recombinant *E. coli* strain were cultivated at 37° C. in a 250 mL shake flask culture containing 50 mL LB media and antibiotic selection pressure, with shaking at 230 rpm. Each culture was induced overnight at 16° C. using 1 mM IPTG.

The pellet from each induced shake flask culture was harvested via centrifugation. Each pellet was resuspended and lysed via sonication. The cell debris was separated from the supernatant via centrifugation and the cell free extract was used immediately in enzyme activity assays.

Enzyme activity assays in the reverse direction (i.e., 6-aminohexanol to 6-oxohexanol) were performed in a buffer composed of a final concentration of 50 mM HEPES buffer (pH=7.5), 10 mM 6-aminohexanol, 10 mM pyruvate, and 100 μM pyridoxyl 5' phosphate. Each enzyme activity assay reaction was initiated by adding cell free extract of the ω-transaminase gene product or the empty vector control to the assay buffer containing the 6-aminohexanol and then incubated at 25° C. for 4 h, with shaking at 250 rpm. The formation of L-alanine was quantified via RP-HPLC.

Each enzyme only control without 6-aminohexanol had low base line conversion of pyruvate to L-alanine See FIG. 16.

Figure 21:
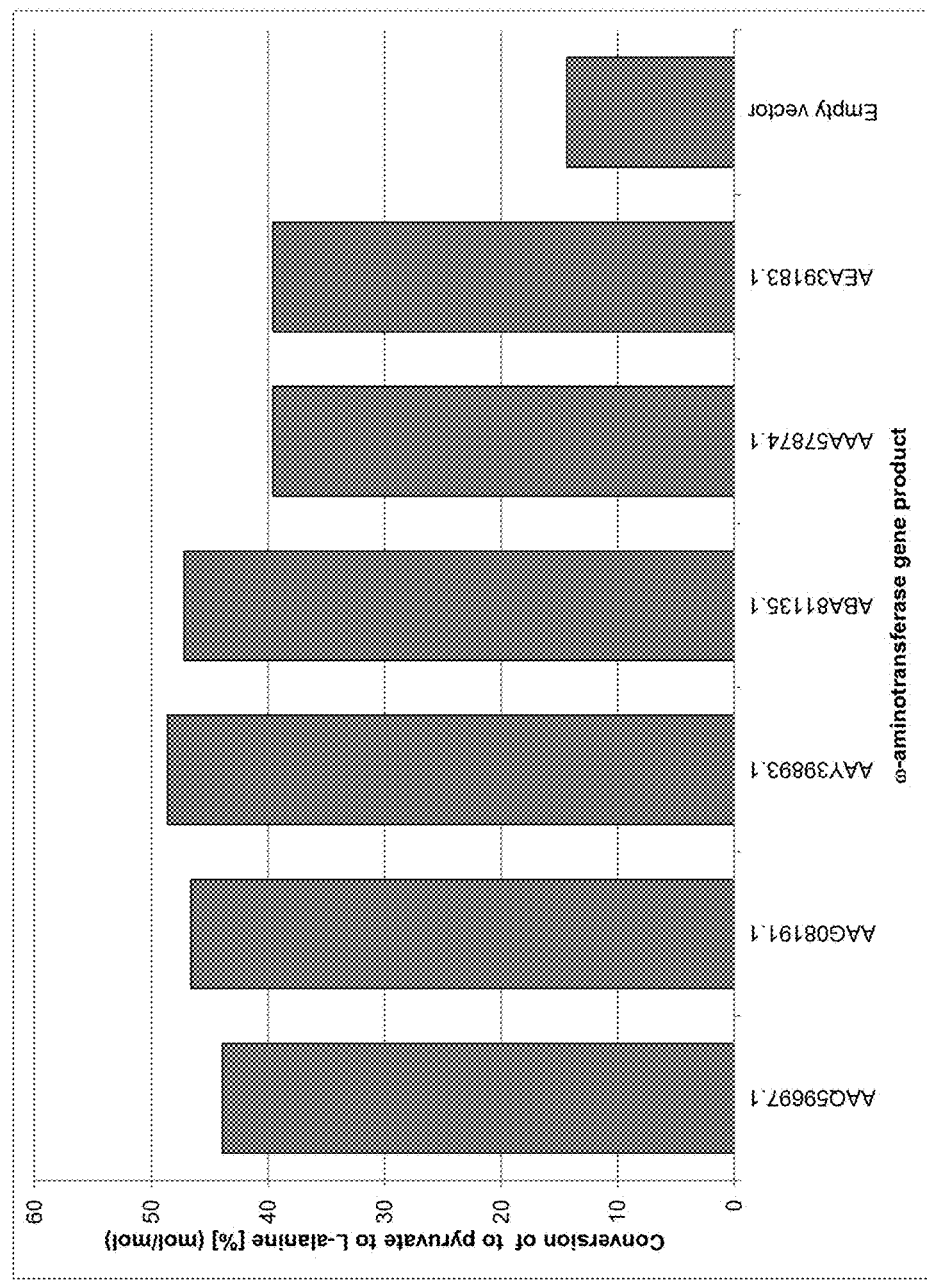
FIG. 21 is a bar graph of the percent conversion after 4 hours of pyruvate to L-alanine (mol/mol) as a measure of the ω-transaminase activity for converting 6-aminohexanol to 6-oxohexanol relative to the empty vector control.

The gene products of SEQ ID NOs: 7-12 accepted 6-aminohexanol as substrate as confirmed against the empty vector control (see FIG. 21) and synthesized 6-oxohexanol as reaction product. Given the reversibility of the ω-transaminase activity (see Example 2), it can be concluded that the gene products of SEQ ID NOs: 7-12 accept 6-aminohexanol as substrate and form 6-oxohexanol.

Example 5

Enzyme Activity of ω-Transaminase Using Hexamethylenediamine as Substrate and Forming 6-Aminohexanal A sequence encoding an N-terminal His-tag was added to the *Chromobacterium violaceum, Pseudomonas aeruginosa, Pseudomonas syringae, Rhodobacter sphaeroides, Escherichia coli,* and *Vibrio fluvialis* genes encoding the ω-transaminases of SEQ ID NOs: 7-12, respectively (see FIG. 9) such that N-terminal HIS tagged ω-transaminases could be produced. The modified genes were cloned into a pET21a expression vector under the T7 promoter. Each expression vector was transformed into a BL21[DE3] *E. coli* host. Each resulting recombinant *E. coli* strain were cultivated at 37° C. in a 250 mL shake flask culture containing 50 mL LB media and antibiotic selection pressure, with shaking at 230 rpm. Each culture was induced overnight at 16° C. using 1 mM IPTG.

The pellet from each induced shake flask culture was harvested via centrifugation. Each pellet was resuspended and lysed via sonication. The cell debris was separated from the supernatant via centrifugation and the cell free extract was used immediately in enzyme activity assays.

Enzyme activity assays in the reverse direction (i.e., hexamethylenediamine to 6-aminohexanal) were performed in a buffer composed of a final concentration of 50 mM HEPES buffer (pH=7.5), 10 mM hexamethylenediamine, 10 mM pyruvate, and 100 μM pyridoxyl 5' phosphate. Each enzyme activity assay reaction was initiated by adding cell free extract of the ω-transaminase gene product or the empty vector control to the assay buffer containing the hexamethylenediamine and then incubated at 25° C. for 4 h, with shaking at 250 rpm. The formation of L-alanine was quantified via RP-HPLC.

Each enzyme only control without hexamethylenediamine had low base line conversion of pyruvate to L-alanine See FIG. 16.

Figure 19:
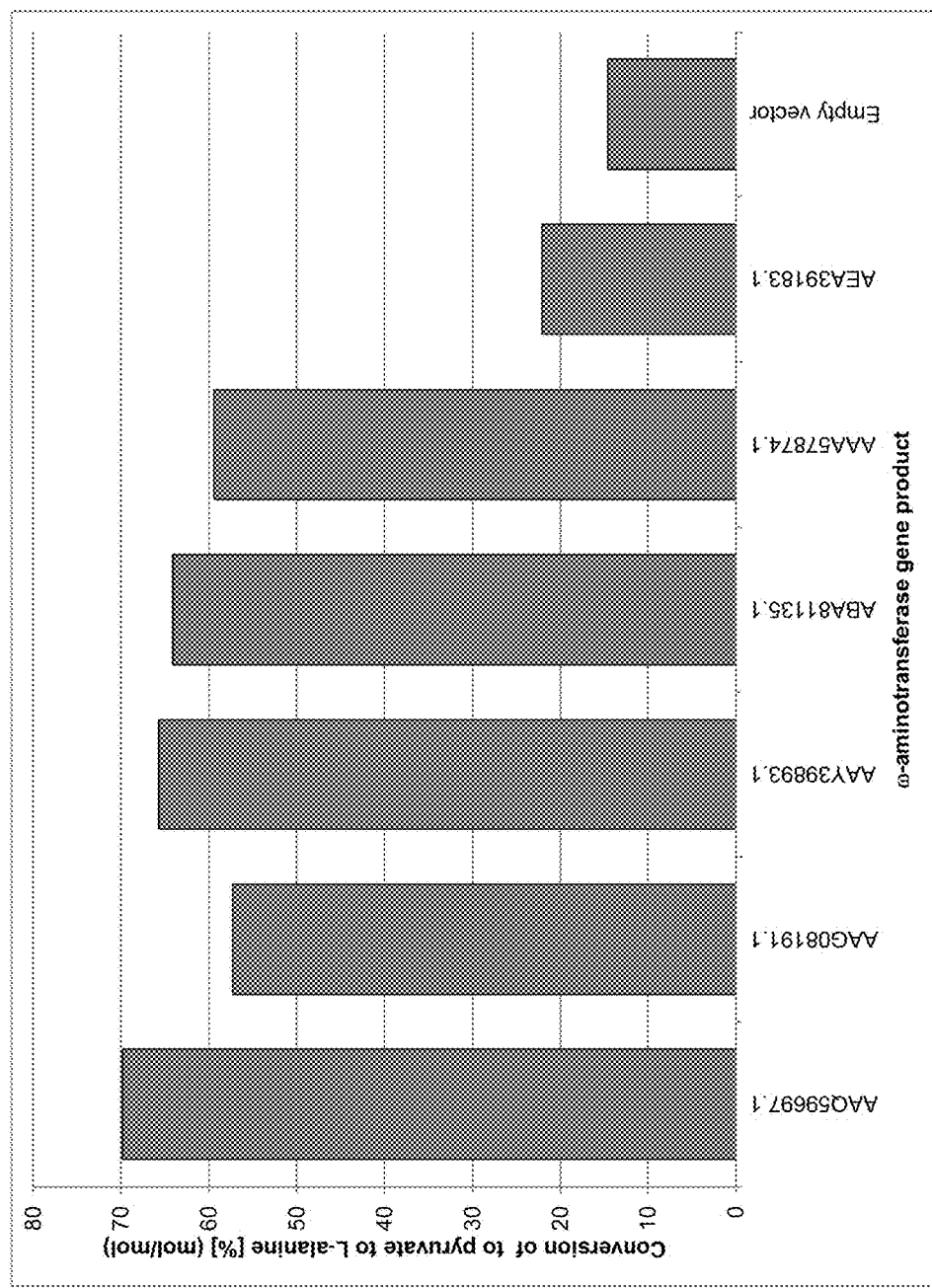
FIG. 19 is a bar graph of the percent conversion after 4 hours of pyruvate to L-alanine (mol/mol) as a measure of the ω-transaminase activity for converting hexamethylenediamine to 6-aminohexanal relative to the empty vector control.

The gene products of SEQ ID NOs: 7-12 accepted hexamethylenediamine as substrate as confirmed against the empty vector control (see FIG. 19) and synthesized 6-aminohexanal as reaction product. Given the reversibility of the ω-transaminase activity (see Example 2), it can be concluded that the gene products of SEQ ID NOs: 7-12 accept 6-aminohexanal as substrate and form hexamethylenediamine.

Example 6

Enzyme Activity of Carboxylate Reductase for N6-Acetyl-6-Aminohexanoate, Forming N6-Acetyl-6-Aminohexanal The activity of each of the N-terminal His-tagged carboxylate reductases of SEQ ID NOs: 4-6 (see Examples 2 and 3, and FIG. 9) for converting N6-acetyl-6-aminohexanoate to N6-acetyl-6-aminohexanal was assayed in triplicate in a buffer composed of a final concentration of 50 mM HEPES buffer (pH=7.5), 2 mM N6-acetyl-6-aminohexanoate, 10 mM MgCl$_2$, 1 mM ATP, and 1 mM NADPH. The assays were initiated by adding purified carboxylate reductase and phosphopantetheine transferase or the empty vector control to the assay buffer containing the N6-acetyl-6-aminohexanoate then incubated at room temperature for 20 min. The consumption of NADPH was monitored by absorbance at 340 nm. Each enzyme only control without N6-acetyl-6-aminohexanoate demonstrated low base line consumption of NADPH. See FIG. 11.

The gene products of SEQ ID NO 4-6, enhanced by the gene product of sfp, accepted N6-acetyl-6-aminohexanoate as substrate as confirmed against the empty vector control (see FIG. 14), and synthesized N6-acetyl-6-aminohexanal.

Example 7

Enzyme Activity of ω-Transaminase Using N6-Acetyl-1,6-Diaminohexane, and Forming N6-Acetyl-6-Aminohexanal The activity of the N-terminal His-tagged ω-transaminases of SEQ ID NOs: 7-12 (see Example 4, and FIG. 9) for converting N6-acetyl-1,6-diaminohexane to N6-acetyl-6-aminohexanal was assayed using a buffer composed of a final concentration of 50 mM HEPES buffer (pH=7.5), 10 mM N6-acetyl-1,6-diaminohexane, 10 mM pyruvate and 100 μM pyridoxyl 5' phosphate. Each enzyme activity assay reaction was initiated by adding a cell free extract of the ω-transaminase or the empty vector control to the assay buffer containing the N6-acetyl-1,6-diaminohexane then incubated at 25° C. for 4 h, with shaking at 250 rpm. The formation of L-alanine was quantified via RP-HPLC.

Figure 14:
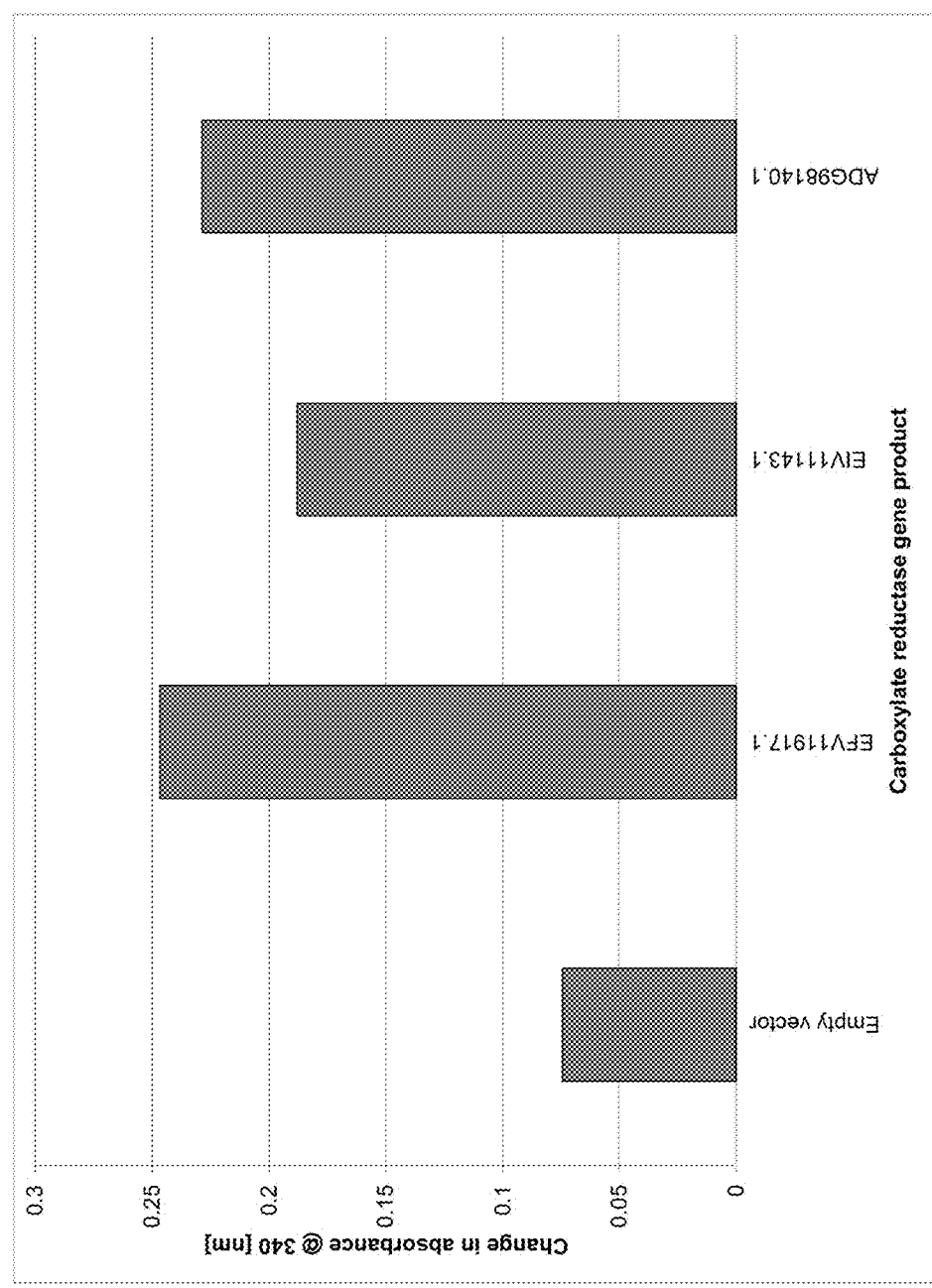
FIG. 14 is a bar graph of the change in absorbance at 340 nm after 20 min, which is a measure of the consumption of NADPH and the activity of carboxylate reductases for converting N6-acetyl-6-aminohexanoate to N6-acetyl-6-aminohexanal relative to the empty vector control.

Each enzyme only control without N6-acetyl-1,6-diaminohexane demonstrated low base line conversion of pyruvate to L-alanine See FIG. 14.

Figure 20:
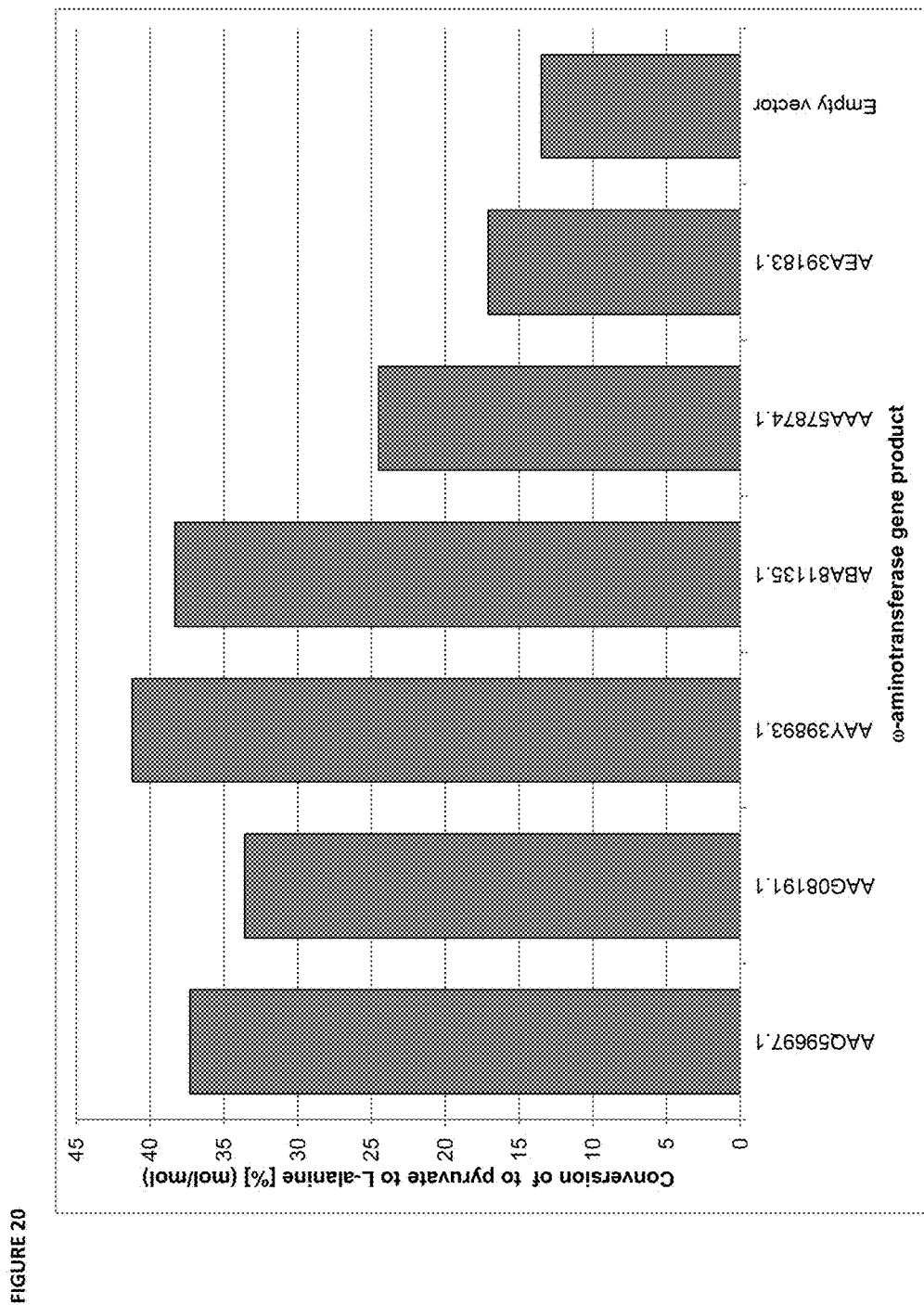
FIG. 20 is a bar graph of the percent conversion after 4 hours of pyruvate to L-alanine (mol/mol) as a measure of the ω-transaminase activity for converting N6-acetyl-1,6-diaminohexane to N6-acetyl-6-aminohexanal relative to the empty vector control.

The gene product of SEQ ID NOs: 7-12 accepted N6-acetyl-1,6-diaminohexane as substrate as confirmed against the empty vector control (see FIG. 20) and synthesized N6-acetyl-6-aminohexanal as reaction product.

Given the reversibility of the ω-transaminase activity (see Example 2), the gene products of SEQ ID NOs: 7-12 accept N6-acetyl-6-aminohexanal as substrate forming N6-acetyl-1,6-diaminohexane.

Example 8

Enzyme Activity of Carboxylate Reductase Using Adipate Semialdehyde as Substrate and Forming Hexanedial The N-terminal His-tagged carboxylate reductase of SEQ ID NO 6 (see Example 2, Example 3 and FIG. 9) was assayed using adipate semialdehyde as substrate. The enzyme activity assay was performed in triplicate in a buffer composed of a final concentration of 50 mM HEPES buffer (pH=7.5), 2 mM adipate semialdehyde, 10 mM $MgCl_2$, 1 mM ATP and 1 mM NADPH. The enzyme activity assay reaction was initiated by adding purified carboxylate reductase and phosphopantetheine transferase or the empty vector control to the assay buffer containing the adipate semialdehyde and then incubated at room temperature for 20 min. The consumption of NADPH was monitored by absorbance at 340 nm. The enzyme only control without adipate semialdehyde demonstrated low base line consumption of NADPH. See FIG. 11.

Figure 15:
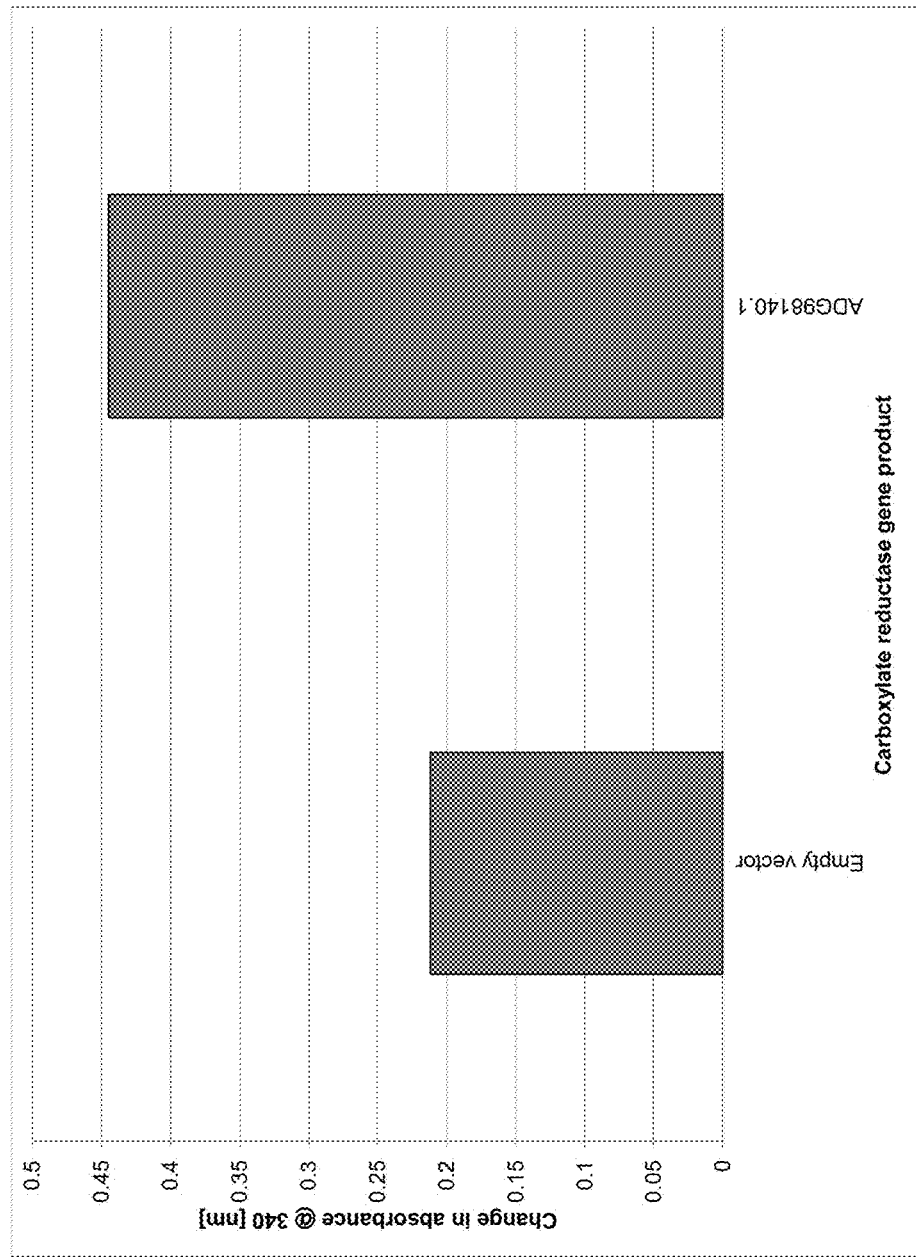
FIG. 15 is a bar graph of the change in absorbance at 340 nm after 20 min, which is a measure of the consumption of NADPH and activity of carboxylate reductases for converting adipate semialdehyde to hexanedial relative to the empty vector control.

The gene product of SEQ ID NO: 6, enhanced by the gene product of sfp, accepted adipate semialdehyde as substrate as confirmed against the empty vector control (see FIG. 15) and synthesized hexanedial.

Example 9

Enzyme Activity of CYP153 Monooxygenase Using Hexanoate as Substrate in Forming 6-Hydroxyhexanoate A sequence encoding a HIS tag was added to the *Polaromonas* sp. JS666, *Mycobacterium* sp. HXN-1500 and *Mycobacterium austroafricanum* genes respectively encoding (1) the monooxygenases (SEQ ID NOs: 13-15), (2) the associated ferredoxin reductase partner (SEQ ID NOs: 16-17) and the specie's ferredoxin (SEQ ID NOs: 18-19). For the *Mycobacterium austroafricanum* monooxygenase, *Mycobacterium* sp. HXN-1500 oxidoreductase and ferredoxin partners were used. The three modified protein partners were cloned into a pgBlue expression vector under a hybrid pTac promoter. Each expression vector was transformed into a BL21[DE3] *E. coli* host. Each resulting recombinant *E. coli* strain were cultivated at 37° C. in a 500 mL shake flask culture containing 50 mL LB media and antibiotic selection pressure. Each culture was induced for 24 h at 28° C. using 1 mM IPTG.

The pellet from each induced shake flask culture was harvested via centrifugation. Each pellet was resuspended and the cells made permeable using Y-Per™ solution (ThermoScientific, Rockford, Ill.) at room temperature for 20 min. The permeabilized cells were held at 0° C. in the Y-Per™ solution.

Enzyme activity assays were performed in a buffer composed of a final concentration of 25 mM potassium phosphate buffer (pH=7.8), 1.7 mM $MgSO_4$, 2.5 mM NADPH and 30 mM hexanoate. Each enzyme activity assay reaction was initiated by adding a fixed mass of wet cell weight of permeabilized cells suspended in the Y-Per™ solution to the assay buffer containing the heptanoate and then incubated at 28° C. for 24 h, with shaking at 1400 rpm in a heating block shaker. The formation of 7-hydroxyheptanoate was quantified via LC-MS.

Figure 22:
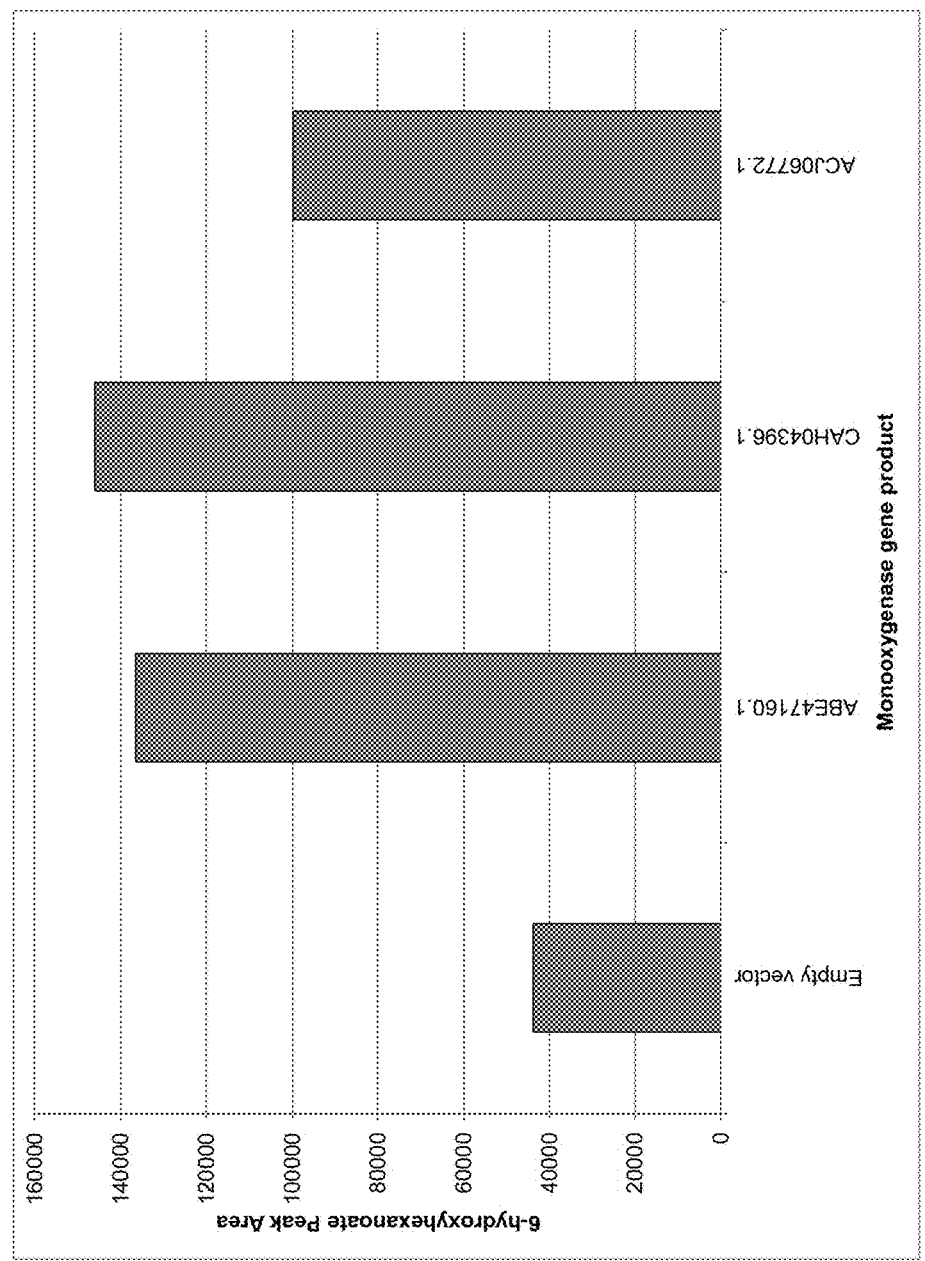
FIG. 22 is a bar graph of the change in peak area for 6-hydroxyhexanoate as determined via LC-MS, as a measure of the monooxygenase activity for converting hexanoate to 6-hydroxyhexanoate relative to the empty vector control.
Figure 23:
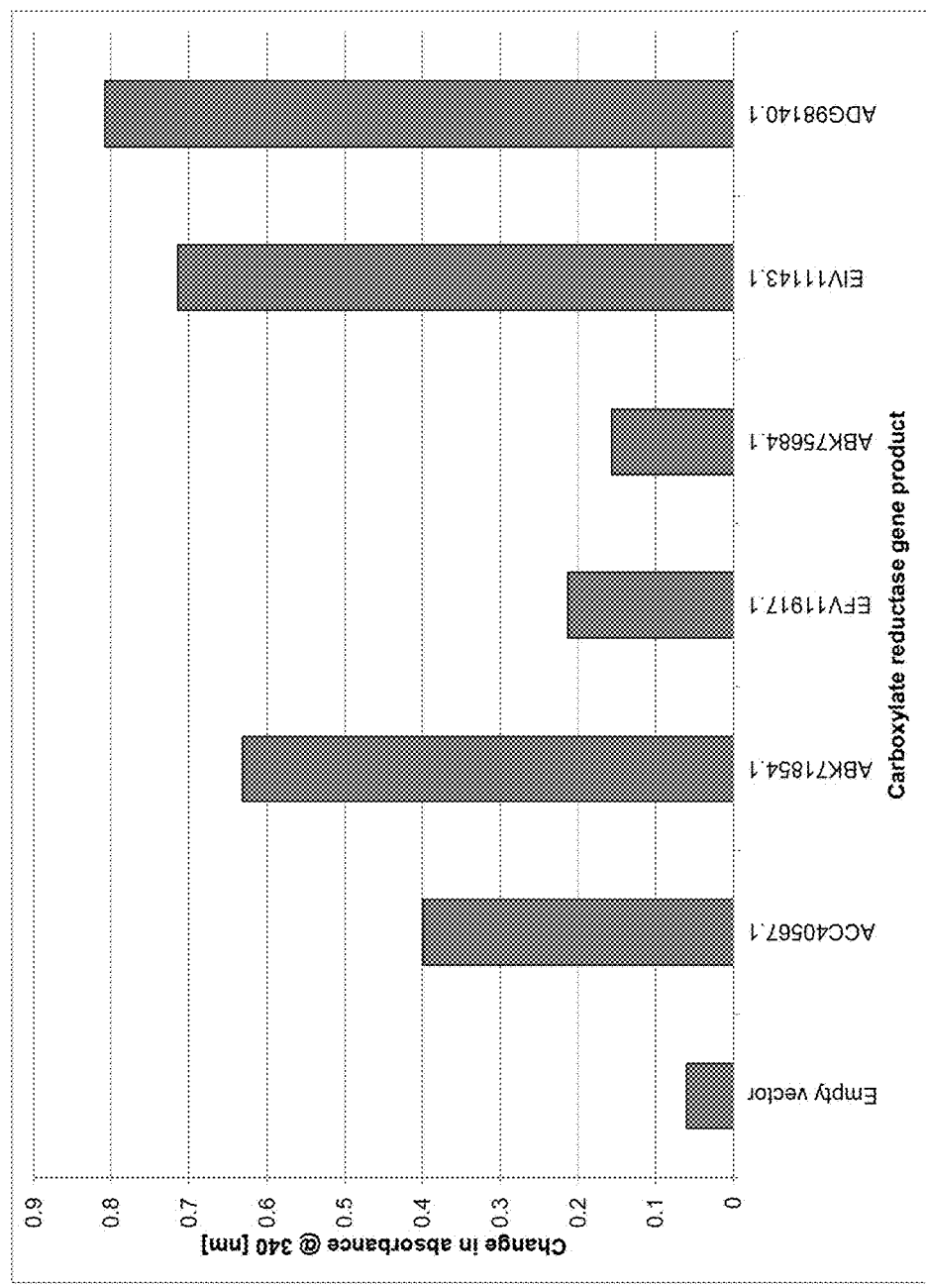
FIG. 23 is a bar graph of the change in absorbance at 340 nm after 20 min, which is a measure of the consumption of NADPH and activity of carboxylate reductases for converting hexanoic acid to hexanal relative to the empty vector control.

The monooxygenase gene products of SEQ ID NO 13-15 along with reductase and ferredoxin partners, accepted hexanoate as substrate as confirmed against the empty vector control (see FIG. 22) and synthesized 6-hydroxyhexanoate as reaction product.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of producing a terminal hydroxyl ($C_{3-8}$ hydroxyalkyl)-C(=O)OCH$_3$ ester in a recombinant host, said method comprising:
   a) enzymatically converting a $C_{4-9}$ carboxylic acid to a ($C_{3-8}$ alkyl)-C(=O)OCH$_3$ ester using a polypeptide having fatty acid O-methyltransferase activity classified under EC 2.1.1.15; and
   b) enzymatically converting the ($C_{3-8}$ alkyl)-C(=O)OCH$_3$ ester to a terminal hydroxyl ($C_{3-8}$ hydroxyalkyl)-C(=O)OCH$_3$ ester using a polypeptide having monooxygenase activity classified under EC 1.14.14.- or EC 1.14.15.-,
   wherein the $C_{4-9}$ carboxylic acid is enzymatically produced from a $C_{4-9}$ alkanoyl-CoA using:
   a polypeptide having thioesterase activity classified under EC 3.1.2.-; or
   a polypeptide having butanal dehydrogenase activity classified under EC 1.2.1.10 or EC 1.2.1.57 and a polypeptide having aldehyde dehydrogenase activity classified under EC 1.2.1.3 or EC 1.2.1.4.

2. The method of claim 1, said method further comprising enzymatically converting the terminal hydroxyl ($C_{3-8}$ hydroxyalkyl)-C(=O)OCH$_3$ ester to a terminal hydroxyl $C_{4-9}$ hydroxyalkanoate using a polypeptide having demethylase activity classified under EC 2.1.1.- and/or a polypeptide having esterase activity classified under EC 3.1.1.-.

3. The method of claim 1, wherein $C_{4-9}$ carboxylic acid is hexanoate, and is enzymatically converted to hexanoate methyl ester; and the hexanoate methyl ester is enzymatically converted to 6-hydroxyhexanoate methyl ester.

4. The method of claim 1, wherein the $C_{4-9}$ alkanoyl-CoA is hexanoyl-CoA, and hexanoate is enzymatically produced from hexanoyl-CoA.

5. The method of claim 3, said method further comprising enzymatically converting 6-hydroxyhexanoate methyl ester to 6-hydroxyhexanoate using a polypeptide having demethylase activity classified under EC 2.1.1.- or a polypeptide having esterase activity classified under EC 3.1.1.-.

6. The method of claim 4, wherein hexanoyl-CoA is produced from acetyl-CoA via two cycles of CoA-dependent carbon chain elongation, wherein each of said two cycles of CoA-dependent carbon chain elongation comprises using (i) a polypeptide having β-ketothiolase activity classified under EC 2.3.1.9, EC 2.3.1.16, or EC 2.3.1.174 or a polypeptide having acetyl-CoA carboxylase activity classified under EC 6.4.1.2 and a polypeptide having acetoacetyl-CoA synthase activity classified under EC 2.3.1.194, (ii) a polypeptide having 3-hydroxyacyl-CoA dehydrogenase activity classified under EC 1.1.1.35, EC 1.1.1.36, or EC 1.1.1.157 or a polypeptide having 3-oxoacyl-CoA reductase activity classified under EC 1.1.1.100, (iv) a polypeptide having enoyl-CoA hydratase activity classified under EC 4.2.1.17 or EC 4.2.1.119, and (v) a polypeptide having trans-2-enoyl-CoA reductase activity classified under EC 1.3.1.8, EC 1.3.1.38, or EC 1.3.1.44 to form hexanoyl-CoA from acetyl-CoA.

7. A method of enzymatically producing 6-hydroxyhexanoate, the method comprising:
  a) enzymatically converting hexanoate to hexanoate methyl ester using a polypeptide having fatty acid O-methyltransferase activity classified under EC 2.1.1.15;
  b) enzymatically converting hexanoate methyl ester to 6-hydroxyhexanoate methyl ester using a polypeptide having monooxygenase activity classified under EC 1.14.14.- or EC 1.14.15.-; and
  c) enzymatically converting 6-hydroxyhexanoate methyl ester to 6-hydroxyhexanoate using a polypeptide having demethylase activity classified under EC 2.1.1.- or a polypeptide having esterase activity classified under EC 3.1.1.-.

8. The method of claim 1, wherein said recombinant host is subjected to a cultivation strategy under aerobic, anaerobic or, micro-aerobic cultivation conditions.

9. The method of claim 8, wherein said recombinant host is cultured under conditions of nutrient limitation.

10. The method of claim 8, wherein said recombinant host is retained using a ceramic membrane to maintain a high cell density during fermentation.

11. The method of claim 8, wherein the principal carbon source fed to the recombinant host derives from a biological feedstock.

12. The method of claim 11, wherein the biological feedstock is, or derives from, monosaccharides, disaccharides, lignocellulose, hemicellulose, cellulose, lignin, levulinic acid, formic acid, triglycerides, glycerol, fatty acids, agricultural waste, condensed distillers' solubles, or municipal waste.

13. The method of claim 8, wherein the principal carbon source fed to the recombinant host derives from a non-biological feedstock.

14. The method of claim 13, wherein the non-biological feedstock is, or derives from, natural gas, syngas, $CO_2/H_2$, methanol, ethanol, benzoate, non-volatile residue (NVR) caustic wash waste stream from cyclohexane oxidation processes, or terephthalic acid/isophthalic acid mixture waste streams.

15. The method of claim 9, wherein the recombinant host is a prokaryote selected from *Escherichia, Clostridia, Corynebacteria, Cupriavidus, Pseudomonas, Delftia, Bacillus, Lactobacillus, Lactococcus*, and *Rhodococcus*, or a eukaryote selected from *Aspergillus, Saccharomyces, Pichia, Yarrowia, Issatchenkia, Debaryomyces, Arxula*, and *Kluveromyces*.

16. The method of claim 3, wherein the polypeptide having fatty acid O-methyltransferase activity classified under EC 2.1.1.15 has at least 85% sequence identity to an amino acid sequence set forth in SEQ ID NO:22, SEQ ID NO:23, or SEQ ID NO:24; and the polypeptide having monooxygenase activity classified under EC 1.14.14.- or EC 1.14.15.- has at least 85% sequence identity to an amino acid sequence set forth in SEQ ID NO: 13-15, SEQ ID NO:27 or SEQ ID NO:28.

17. The method of claim 4, wherein the polypeptide having thioesterase activity classified under EC 3.1.2.- has at least 85% sequence identity to the amino acid sequence set forth in SEQ ID NO:1, SEQ ID NO:32, or SEQ ID NO:33.

18. The method of claim 5, wherein the polypeptide having demethylase activity classified under EC 2.1.1.- has at least 85% sequence identity to the amino acid sequence set forth in SEQ ID NO: 30 or SEQ ID NO: 31 and the polypeptide having esterase activity classified under EC 3.1.1.- has at least 85% sequence identity to the amino acid sequence set forth in SEQ ID NO: 26.

19. The method of claim 8, wherein said recombinant host is cultured under conditions of phosphate, nitrogen, or oxygen limitation.

* * * * *

UNITED STATES PATENT AND TRADEMARK OFFICE
CERTIFICATE OF CORRECTION

PATENT NO. : 9,816,117 B2  
APPLICATION NO. : 14/741228  
DATED : November 14, 2017  
INVENTOR(S) : Alex Van Eck Conradie et al.

Page 1 of 1

It is certified that error appears in the above-identified patent and that said Letters Patent is hereby corrected as shown below:

Claim 15, Column 142, Line 14, "The method of claim 9" should read -- The method of claim 8 --.

Claim 16, Column 142, Line 29, "SEQ ID NO: 13-15" should read -- SEQ ID NOs:13-15 --.

Claim 18, Column 142, Line 38, "SEQ ID NO: 31" should read -- SEQ ID NO:31 --.

Claim 18, Column 142, Line 41, "SEQ ID NO: 26" should read -- SEQ ID NO:26 --.

Signed and Sealed this  
Eighth Day of May, 2018

Andrei Iancu  
*Director of the United States Patent and Trademark Office*

SEQUENCE LISTING

```
<160> NUMBER OF SEQ ID NOS: 33

<210> SEQ ID NO 1
<211> LENGTH: 286
<212> TYPE: PRT
<213> ORGANISM: Escherichia coli

<400> SEQUENCE: 1

Met Ser Gln Ala Leu Lys Asn Leu Leu Thr Leu Leu Asn Leu Glu Lys
1               5                   10                  15

Ile Glu Glu Gly Leu Phe Arg Gly Gln Ser Glu Asp Leu Gly Leu Arg
            20                  25                  30

Gln Val Phe Gly Gly Gln Val Val Gly Gln Ala Leu Tyr Ala Ala Lys
        35                  40                  45

Glu Thr Val Pro Glu Glu Arg Leu Val His Ser Phe His Ser Tyr Phe
    50                  55                  60

Leu Arg Pro Gly Asp Ser Lys Lys Pro Ile Ile Tyr Asp Val Glu Thr
```

```
                65                   70                  75                  80
Leu Arg Asp Gly Asn Ser Phe Ser Ala Arg Arg Val Ala Ala Ile Gln
                    85                  90                  95

Asn Gly Lys Pro Ile Phe Tyr Met Thr Ala Ser Phe Gln Ala Pro Glu
                100                 105                 110

Ala Gly Phe Glu His Gln Lys Thr Met Pro Ser Ala Pro Ala Pro Asp
                115                 120                 125

Gly Leu Pro Ser Glu Thr Gln Ile Ala Gln Ser Leu Ala His Leu Leu
            130                 135                 140

Pro Pro Val Leu Lys Asp Lys Phe Ile Cys Asp Arg Pro Leu Glu Val
145                 150                 155                 160

Arg Pro Val Glu Phe His Asn Pro Leu Lys Gly His Val Ala Glu Pro
                165                 170                 175

His Arg Gln Val Trp Ile Arg Ala Asn Gly Ser Val Pro Asp Asp Leu
                180                 185                 190

Arg Val His Gln Tyr Leu Leu Gly Tyr Ala Ser Asp Leu Asn Phe Leu
            195                 200                 205

Pro Val Ala Leu Gln Pro His Gly Ile Gly Phe Leu Glu Pro Gly Ile
        210                 215                 220

Gln Ile Ala Thr Ile Asp His Ser Met Trp Phe His Arg Pro Phe Asn
225                 230                 235                 240

Leu Asn Glu Trp Leu Leu Tyr Ser Val Glu Ser Thr Ser Ala Ser Ser
                245                 250                 255

Ala Arg Gly Phe Val Arg Gly Glu Phe Tyr Thr Gln Asp Gly Val Leu
                260                 265                 270

Val Ala Ser Thr Val Gln Glu Gly Val Met Arg Asn His Asn
            275                 280                 285

<210> SEQ ID NO 2
<211> LENGTH: 1174
<212> TYPE: PRT
<213> ORGANISM: Mycobacterium marinum

<400> SEQUENCE: 2

Met Ser Pro Ile Thr Arg Glu Glu Arg Leu Glu Arg Arg Ile Gln Asp
  1               5                  10                  15

Leu Tyr Ala Asn Asp Pro Gln Phe Ala Ala Ala Lys Pro Ala Thr Ala
                 20                  25                  30

Ile Thr Ala Ala Ile Glu Arg Pro Gly Leu Pro Leu Pro Gln Ile Ile
             35                  40                  45

Glu Thr Val Met Thr Gly Tyr Ala Asp Arg Pro Ala Leu Ala Gln Arg
         50                  55                  60

Ser Val Glu Phe Val Thr Asp Ala Gly Thr Gly His Thr Thr Leu Arg
 65                  70                  75                  80

Leu Leu Pro His Phe Glu Thr Ile Ser Tyr Gly Glu Leu Trp Asp Arg
                 85                  90                  95

Ile Ser Ala Leu Ala Asp Val Leu Ser Thr Glu Gln Thr Val Lys Pro
                100                 105                 110

Gly Asp Arg Val Cys Leu Leu Gly Phe Asn Ser Val Asp Tyr Ala Thr
            115                 120                 125

Ile Asp Met Thr Leu Ala Arg Leu Gly Ala Val Ala Val Pro Leu Gln
        130                 135                 140

Thr Ser Ala Ala Ile Thr Gln Leu Gln Pro Ile Val Ala Glu Thr Gln
145                 150                 155                 160
```

```
Pro Thr Met Ile Ala Ser Val Asp Ala Leu Ala Asp Ala Thr Glu
            165                 170                 175

Leu Ala Leu Ser Gly Gln Thr Ala Thr Arg Val Leu Val Phe Asp His
            180                 185                 190

His Arg Gln Val Asp Ala His Arg Ala Ala Val Glu Ser Ala Arg Glu
            195                 200                 205

Arg Leu Ala Gly Ser Ala Val Val Glu Thr Leu Ala Glu Ala Ile Ala
            210                 215                 220

Arg Gly Asp Val Pro Arg Gly Ala Ser Ala Gly Ser Ala Pro Gly Thr
225                 230                 235                 240

Asp Val Ser Asp Asp Ser Leu Ala Leu Leu Ile Tyr Thr Ser Gly Ser
                    245                 250                 255

Thr Gly Ala Pro Lys Gly Ala Met Tyr Pro Arg Arg Asn Val Ala Thr
            260                 265                 270

Phe Trp Arg Lys Arg Thr Trp Phe Glu Gly Gly Tyr Glu Pro Ser Ile
            275                 280                 285

Thr Leu Asn Phe Met Pro Met Ser His Val Met Gly Arg Gln Ile Leu
            290                 295                 300

Tyr Gly Thr Leu Cys Asn Gly Gly Thr Ala Tyr Phe Val Ala Lys Ser
305                 310                 315                 320

Asp Leu Ser Thr Leu Phe Glu Asp Leu Ala Leu Val Arg Pro Thr Glu
                    325                 330                 335

Leu Thr Phe Val Pro Arg Val Trp Asp Met Val Phe Asp Glu Phe Gln
            340                 345                 350

Ser Glu Val Asp Arg Arg Leu Val Asp Gly Ala Asp Arg Val Ala Leu
            355                 360                 365

Glu Ala Gln Val Lys Ala Glu Ile Arg Asn Asp Val Leu Gly Gly Arg
            370                 375                 380

Tyr Thr Ser Ala Leu Thr Gly Ser Ala Pro Ile Ser Asp Glu Met Lys
385                 390                 395                 400

Ala Trp Val Glu Glu Leu Leu Asp Met His Leu Val Glu Gly Tyr Gly
                    405                 410                 415

Ser Thr Glu Ala Gly Met Ile Leu Ile Asp Gly Ala Ile Arg Arg Pro
            420                 425                 430

Ala Val Leu Asp Tyr Lys Leu Val Asp Val Pro Asp Leu Gly Tyr Phe
            435                 440                 445

Leu Thr Asp Arg Pro His Pro Arg Gly Glu Leu Leu Val Lys Thr Asp
            450                 455                 460

Ser Leu Phe Pro Gly Tyr Tyr Gln Arg Ala Glu Val Thr Ala Asp Val
465                 470                 475                 480

Phe Asp Ala Asp Gly Phe Tyr Arg Thr Gly Asp Ile Met Ala Glu Val
                    485                 490                 495

Gly Pro Glu Gln Phe Val Tyr Leu Asp Arg Arg Asn Asn Val Leu Lys
            500                 505                 510

Leu Ser Gln Gly Glu Phe Val Thr Val Ser Lys Leu Glu Ala Val Phe
            515                 520                 525

Gly Asp Ser Pro Leu Val Arg Gln Ile Tyr Ile Tyr Gly Asn Ser Ala
            530                 535                 540

Arg Ala Tyr Leu Leu Ala Val Ile Val Pro Thr Gln Glu Ala Leu Asp
545                 550                 555                 560

Ala Val Pro Val Glu Glu Leu Lys Ala Arg Leu Gly Asp Ser Leu Gln
                    565                 570                 575

Glu Val Ala Lys Ala Ala Gly Leu Gln Ser Tyr Glu Ile Pro Arg Asp
```

```
                580               585               590
Phe Ile Ile Glu Thr Thr Pro Trp Thr Leu Glu Asn Gly Leu Leu Thr
            595               600               605

Gly Ile Arg Lys Leu Ala Arg Pro Gln Leu Lys Lys His Tyr Gly Glu
610               615               620

Leu Leu Glu Gln Ile Tyr Thr Asp Leu Ala His Gly Gln Ala Asp Glu
625               630               635               640

Leu Arg Ser Leu Arg Gln Ser Gly Ala Asp Ala Pro Val Leu Val Thr
            645               650               655

Val Cys Arg Ala Ala Ala Ala Leu Leu Gly Gly Ser Ala Ser Asp Val
            660               665               670

Gln Pro Asp Ala His Phe Thr Asp Leu Gly Gly Asp Ser Leu Ser Ala
            675               680               685

Leu Ser Phe Thr Asn Leu Leu His Glu Ile Phe Asp Ile Glu Val Pro
690               695               700

Val Gly Val Ile Val Ser Pro Ala Asn Asp Leu Gln Ala Leu Ala Asp
705               710               715               720

Tyr Val Glu Ala Ala Arg Lys Pro Gly Ser Ser Arg Pro Thr Phe Ala
            725               730               735

Ser Val His Gly Ala Ser Asn Gly Gln Val Thr Glu Val His Ala Gly
            740               745               750

Asp Leu Ser Leu Asp Lys Phe Ile Asp Ala Ala Thr Leu Ala Glu Ala
            755               760               765

Pro Arg Leu Pro Ala Ala Asn Thr Gln Val Arg Thr Val Leu Leu Thr
770               775               780

Gly Ala Thr Gly Phe Leu Gly Arg Tyr Leu Ala Leu Glu Trp Leu Glu
785               790               795               800

Arg Met Asp Leu Val Asp Gly Lys Leu Ile Cys Leu Val Arg Ala Lys
            805               810               815

Ser Asp Thr Glu Ala Arg Ala Arg Leu Asp Lys Thr Phe Asp Ser Gly
            820               825               830

Asp Pro Glu Leu Leu Ala His Tyr Arg Ala Leu Ala Gly Asp His Leu
            835               840               845

Glu Val Leu Ala Gly Asp Lys Gly Glu Ala Asp Leu Gly Leu Asp Arg
850               855               860

Gln Thr Trp Gln Arg Leu Ala Asp Thr Val Asp Leu Ile Val Asp Pro
865               870               875               880

Ala Ala Leu Val Asn His Val Leu Pro Tyr Ser Gln Leu Phe Gly Pro
            885               890               895

Asn Ala Leu Gly Thr Ala Glu Leu Leu Arg Leu Ala Leu Thr Ser Lys
            900               905               910

Ile Lys Pro Tyr Ser Tyr Thr Ser Thr Ile Gly Val Ala Asp Gln Ile
            915               920               925

Pro Pro Ser Ala Phe Thr Glu Asp Ala Asp Ile Arg Val Ile Ser Ala
            930               935               940

Thr Arg Ala Val Asp Asp Ser Tyr Ala Asn Gly Tyr Ser Asn Ser Lys
945               950               955               960

Trp Ala Gly Glu Val Leu Leu Arg Glu Ala His Asp Leu Cys Gly Leu
            965               970               975

Pro Val Ala Val Phe Arg Cys Asp Met Ile Leu Ala Asp Thr Thr Trp
            980               985               990

Ala Gly Gln Leu Asn Val Pro Asp Met Phe Thr Arg Met Ile Leu Ser
            995               1000              1005
```

-continued

```
Leu Ala Ala Thr Gly Ile Ala Pro Gly Ser Phe Tyr Glu Leu Ala Ala
    1010                1015                1020

Asp Gly Ala Arg Gln Arg Ala His Tyr Asp Gly Leu Pro Val Glu Phe
1025                1030                1035                1040

Ile Ala Glu Ala Ile Ser Thr Leu Gly Ala Gln Ser Gln Asp Gly Phe
                1045                1050                1055

His Thr Tyr His Val Met Asn Pro Tyr Asp Asp Gly Ile Gly Leu Asp
                1060                1065                1070

Glu Phe Val Asp Trp Leu Asn Glu Ser Gly Cys Pro Ile Gln Arg Ile
            1075                1080                1085

Ala Asp Tyr Gly Asp Trp Leu Gln Arg Phe Glu Thr Ala Leu Arg Ala
            1090                1095                1100

Leu Pro Asp Arg Gln Arg His Ser Ser Leu Leu Pro Leu Leu His Asn
1105                1110                1115                1120

Tyr Arg Gln Pro Glu Arg Pro Val Arg Gly Ser Ile Ala Pro Thr Asp
                1125                1130                1135

Arg Phe Arg Ala Ala Val Gln Glu Ala Lys Ile Gly Pro Asp Lys Asp
                1140                1145                1150

Ile Pro His Val Gly Ala Pro Ile Ile Val Lys Tyr Val Ser Asp Leu
            1155                1160                1165

Arg Leu Leu Gly Leu Leu
    1170

<210> SEQ ID NO 3
<211> LENGTH: 1173
<212> TYPE: PRT
<213> ORGANISM: Mycobacterium smegmatis

<400> SEQUENCE: 3

Met Thr Ser Asp Val His Asp Ala Thr Asp Gly Val Thr Glu Thr Ala
1               5                   10                  15

Leu Asp Asp Glu Gln Ser Thr Arg Arg Ile Ala Glu Leu Tyr Ala Thr
            20                  25                  30

Asp Pro Glu Phe Ala Ala Ala Pro Leu Pro Ala Val Val Asp Ala
        35                  40                  45

Ala His Lys Pro Gly Leu Arg Leu Ala Glu Ile Leu Gln Thr Leu Phe
    50                  55                  60

Thr Gly Tyr Gly Asp Arg Pro Ala Leu Gly Tyr Arg Ala Arg Glu Leu
65                  70                  75                  80

Ala Thr Asp Glu Gly Gly Arg Thr Val Thr Arg Leu Leu Pro Arg Phe
                85                  90                  95

Asp Thr Leu Thr Tyr Ala Gln Val Trp Ser Arg Val Gln Ala Val Ala
            100                 105                 110

Ala Ala Leu Arg His Asn Phe Ala Gln Pro Ile Tyr Pro Gly Asp Ala
        115                 120                 125

Val Ala Thr Ile Gly Phe Ala Ser Pro Asp Tyr Leu Thr Leu Asp Leu
    130                 135                 140

Val Cys Ala Tyr Leu Gly Leu Val Ser Val Pro Leu Gln His Asn Ala
145                 150                 155                 160

Pro Val Ser Arg Leu Ala Pro Ile Leu Ala Glu Val Glu Pro Arg Ile
                165                 170                 175

Leu Thr Val Ser Ala Glu Tyr Leu Asp Leu Ala Val Glu Ser Val Arg
            180                 185                 190

Asp Val Asn Ser Val Ser Gln Leu Val Val Phe Asp His His Pro Glu
```

-continued

```
            195                 200                 205
Val Asp Asp His Arg Asp Ala Leu Ala Arg Ala Arg Glu Gln Leu Ala
210                 215                 220
Gly Lys Gly Ile Ala Val Thr Thr Leu Asp Ala Ile Ala Asp Glu Gly
225                 230                 235                 240
Ala Gly Leu Pro Ala Glu Pro Ile Tyr Thr Ala Asp His Asp Gln Arg
                245                 250                 255
Leu Ala Met Ile Leu Tyr Thr Ser Gly Ser Thr Gly Ala Pro Lys Gly
                260                 265                 270
Ala Met Tyr Thr Glu Ala Met Val Ala Arg Leu Trp Thr Met Ser Phe
                275                 280                 285
Ile Thr Gly Asp Pro Thr Pro Val Ile Asn Val Asn Phe Met Pro Leu
290                 295                 300
Asn His Leu Gly Gly Arg Ile Pro Ile Ser Thr Ala Val Gln Asn Gly
305                 310                 315                 320
Gly Thr Ser Tyr Phe Val Pro Glu Ser Asp Met Ser Thr Leu Phe Glu
                325                 330                 335
Asp Leu Ala Leu Val Arg Pro Thr Glu Leu Gly Leu Val Pro Arg Val
                340                 345                 350
Ala Asp Met Leu Tyr Gln His His Leu Ala Thr Val Asp Arg Leu Val
                355                 360                 365
Thr Gln Gly Ala Asp Glu Leu Thr Ala Glu Lys Gln Ala Gly Ala Glu
                370                 375                 380
Leu Arg Glu Gln Val Leu Gly Arg Val Ile Thr Gly Phe Val Ser
385                 390                 395                 400
Thr Ala Pro Leu Ala Ala Glu Met Arg Ala Phe Leu Asp Ile Thr Leu
                405                 410                 415
Gly Ala His Ile Val Asp Gly Tyr Gly Leu Thr Glu Thr Gly Ala Val
                420                 425                 430
Thr Arg Asp Gly Val Ile Val Arg Pro Pro Val Ile Asp Tyr Lys Leu
                435                 440                 445
Ile Asp Val Pro Glu Leu Gly Tyr Phe Ser Thr Asp Lys Pro Tyr Pro
450                 455                 460
Arg Gly Glu Leu Leu Val Arg Ser Gln Thr Leu Thr Pro Gly Tyr Tyr
465                 470                 475                 480
Lys Arg Pro Glu Val Thr Ala Ser Val Phe Asp Arg Asp Gly Tyr Tyr
                485                 490                 495
His Thr Gly Asp Val Met Ala Glu Thr Ala Pro Asp His Leu Val Tyr
                500                 505                 510
Val Asp Arg Arg Asn Asn Val Leu Lys Leu Ala Gln Gly Glu Phe Val
                515                 520                 525
Ala Val Ala Asn Leu Glu Ala Val Phe Ser Gly Ala Ala Leu Val Arg
                530                 535                 540
Gln Ile Phe Val Tyr Gly Asn Ser Glu Arg Ser Phe Leu Leu Ala Val
545                 550                 555                 560
Val Val Pro Thr Pro Glu Ala Leu Glu Gln Tyr Asp Pro Ala Ala Leu
                565                 570                 575
Lys Ala Ala Leu Ala Asp Ser Leu Gln Arg Thr Ala Arg Asp Ala Glu
                580                 585                 590
Leu Gln Ser Tyr Glu Val Pro Ala Asp Phe Ile Val Glu Thr Glu Pro
                595                 600                 605
Phe Ser Ala Ala Asn Gly Leu Leu Ser Gly Val Gly Lys Leu Leu Arg
610                 615                 620
```

```
Pro Asn Leu Lys Asp Arg Tyr Gly Gln Arg Leu Glu Gln Met Tyr Ala
625                 630                 635                 640

Asp Ile Ala Ala Thr Gln Ala Asn Gln Leu Arg Glu Leu Arg Arg Ala
            645                 650                 655

Ala Ala Thr Gln Pro Val Ile Asp Thr Leu Thr Gln Ala Ala Ala Thr
        660                 665                 670

Ile Leu Gly Thr Gly Ser Glu Val Ala Ser Asp Ala His Phe Thr Asp
    675                 680                 685

Leu Gly Gly Asp Ser Leu Ser Ala Leu Thr Leu Ser Asn Leu Leu Ser
690                 695                 700

Asp Phe Phe Gly Phe Glu Val Pro Val Gly Thr Ile Val Asn Pro Ala
705                 710                 715                 720

Thr Asn Leu Ala Gln Leu Ala Gln His Ile Glu Ala Gln Arg Thr Ala
            725                 730                 735

Gly Asp Arg Arg Pro Ser Phe Thr Thr Val His Gly Ala Asp Ala Thr
        740                 745                 750

Glu Ile Arg Ala Ser Glu Leu Thr Leu Asp Lys Phe Ile Asp Ala Glu
    755                 760                 765

Thr Leu Arg Ala Ala Pro Gly Leu Pro Lys Val Thr Thr Glu Pro Arg
770                 775                 780

Thr Val Leu Leu Ser Gly Ala Asn Gly Trp Leu Gly Arg Phe Leu Thr
785                 790                 795                 800

Leu Gln Trp Leu Glu Arg Leu Ala Pro Val Gly Gly Thr Leu Ile Thr
            805                 810                 815

Ile Val Arg Gly Arg Asp Asp Ala Ala Ala Arg Ala Arg Leu Thr Gln
        820                 825                 830

Ala Tyr Asp Thr Asp Pro Glu Leu Ser Arg Arg Phe Ala Glu Leu Ala
    835                 840                 845

Asp Arg His Leu Arg Val Val Ala Gly Asp Ile Gly Asp Pro Asn Leu
850                 855                 860

Gly Leu Thr Pro Glu Ile Trp His Arg Leu Ala Ala Glu Val Asp Leu
865                 870                 875                 880

Val Val His Pro Ala Ala Leu Val Asn His Val Leu Pro Tyr Arg Gln
            885                 890                 895

Leu Phe Gly Pro Asn Val Val Gly Thr Ala Glu Val Ile Lys Leu Ala
        900                 905                 910

Leu Thr Glu Arg Ile Lys Pro Val Thr Tyr Leu Ser Thr Val Ser Val
    915                 920                 925

Ala Met Gly Ile Pro Asp Phe Glu Glu Asp Gly Asp Ile Arg Thr Val
930                 935                 940

Ser Pro Val Arg Pro Leu Asp Gly Gly Tyr Ala Asn Gly Tyr Gly Asn
945                 950                 955                 960

Ser Lys Trp Ala Gly Glu Val Leu Leu Arg Glu Ala His Asp Leu Cys
            965                 970                 975

Gly Leu Pro Val Ala Thr Phe Arg Ser Asp Met Ile Leu Ala His Pro
        980                 985                 990

Arg Tyr Arg Gly Gln Val Asn Val Pro Asp Met Phe Thr Arg Leu Leu
    995                 1000                1005

Leu Ser Leu Leu Ile Thr Gly Val Ala Pro Arg Ser Phe Tyr Ile Gly
        1010                1015                1020

Asp Gly Glu Arg Pro Arg Ala His Tyr Pro Gly Leu Thr Val Asp Phe
1025                1030                1035                1040
```

```
Val Ala Glu Ala Val Thr Thr Leu Gly Ala Gln Gln Arg Glu Gly Tyr
                1045                1050                1055

Val Ser Tyr Asp Val Met Asn Pro His Asp Asp Gly Ile Ser Leu Asp
            1060                1065                1070

Val Phe Val Asp Trp Leu Ile Arg Ala Gly His Pro Ile Asp Arg Val
            1075                1080                1085

Asp Asp Tyr Asp Asp Trp Val Arg Arg Phe Glu Thr Ala Leu Thr Ala
            1090                1095                1100

Leu Pro Glu Lys Arg Arg Ala Gln Thr Val Leu Pro Leu Leu His Ala
1105                1110                1115                1120

Phe Arg Ala Pro Gln Ala Pro Leu Arg Gly Ala Pro Glu Pro Thr Glu
                1125                1130                1135

Val Phe His Ala Ala Val Arg Thr Ala Lys Val Gly Pro Gly Asp Ile
                1140                1145                1150

Pro His Leu Asp Glu Ala Leu Ile Asp Lys Tyr Ile Arg Asp Leu Arg
                1155                1160                1165

Glu Phe Gly Leu Ile
            1170

<210> SEQ ID NO 4
<211> LENGTH: 1148
<212> TYPE: PRT
<213> ORGANISM: Segniliparus rugosus

<400> SEQUENCE: 4

Met Gly Asp Gly Glu Glu Arg Ala Lys Arg Phe Phe Gln Arg Ile Gly
1               5                   10                  15

Glu Leu Ser Ala Thr Asp Pro Gln Phe Ala Ala Ala Pro Asp Pro
            20                  25                  30

Ala Val Val Glu Ala Val Ser Asp Pro Ser Leu Ser Phe Thr Arg Tyr
            35                  40                  45

Leu Asp Thr Leu Met Arg Gly Tyr Ala Glu Arg Pro Ala Leu Ala His
        50                  55                  60

Arg Val Gly Ala Gly Tyr Glu Thr Ile Ser Tyr Gly Glu Leu Trp Ala
65                  70                  75                  80

Arg Val Gly Ala Ile Ala Ala Trp Gln Ala Asp Gly Leu Ala Pro
                85                  90                  95

Gly Asp Phe Val Ala Thr Val Gly Phe Thr Ser Pro Tyr Val Ala
            100                 105                 110

Val Asp Leu Ala Ala Ala Arg Ser Gly Leu Val Ser Val Pro Leu Gln
            115                 120                 125

Ala Gly Ala Ser Leu Ala Gln Leu Val Gly Ile Leu Glu Glu Thr Glu
        130                 135                 140

Pro Lys Val Leu Ala Ala Ser Ala Ser Ser Leu Glu Gly Ala Val Ala
145                 150                 155                 160

Cys Ala Leu Ala Ala Pro Ser Val Gln Arg Leu Val Val Phe Asp Leu
                165                 170                 175

Arg Gly Pro Asp Ala Ser Glu Ser Ala Ala Asp Glu Arg Arg Gly Ala
            180                 185                 190

Leu Ala Asp Ala Glu Glu Gln Leu Ala Arg Ala Arg Ala Val Val
            195                 200                 205

Val Glu Thr Leu Ala Asp Leu Ala Ala Arg Gly Glu Ala Leu Pro Glu
        210                 215                 220

Ala Pro Leu Phe Glu Pro Ala Glu Gly Glu Asp Pro Leu Ala Leu Leu
225                 230                 235                 240
```

```
Ile Tyr Thr Ser Gly Ser Thr Gly Ala Pro Lys Gly Ala Met Tyr Ser
                245                 250                 255

Gln Arg Leu Val Ser Gln Leu Trp Gly Arg Thr Pro Val Val Pro Gly
            260                 265                 270

Met Pro Asn Ile Ser Leu His Tyr Met Pro Leu Ser His Ser Tyr Gly
        275                 280                 285

Arg Ala Val Leu Ala Gly Ala Leu Ser Ala Gly Gly Thr Ala His Phe
    290                 295                 300

Thr Ala Asn Ser Asp Leu Ser Thr Leu Phe Glu Asp Ile Ala Leu Ala
305                 310                 315                 320

Arg Pro Thr Phe Leu Ala Leu Val Pro Arg Val Cys Glu Met Leu Phe
                325                 330                 335

Gln Glu Ser Gln Arg Gly Gln Asp Val Ala Glu Leu Arg Glu Arg Val
            340                 345                 350

Leu Gly Gly Arg Leu Leu Val Ala Val Cys Gly Ser Ala Pro Leu Ser
        355                 360                 365

Pro Glu Met Arg Ala Phe Met Glu Glu Val Leu Gly Phe Pro Leu Leu
    370                 375                 380

Asp Gly Tyr Gly Ser Thr Glu Ala Leu Gly Val Met Arg Asn Gly Ile
385                 390                 395                 400

Ile Gln Arg Pro Pro Val Ile Asp Tyr Lys Leu Val Asp Val Pro Glu
                405                 410                 415

Leu Gly Tyr Arg Thr Thr Asp Lys Pro Tyr Pro Arg Gly Glu Leu Cys
            420                 425                 430

Ile Arg Ser Thr Ser Leu Ile Ser Gly Tyr Tyr Lys Arg Pro Glu Ile
        435                 440                 445

Thr Ala Glu Val Phe Asp Ala Gln Gly Tyr Tyr Lys Thr Gly Asp Val
    450                 455                 460

Met Ala Glu Ile Ala Pro Asp His Leu Val Tyr Val Asp Arg Ser Lys
465                 470                 475                 480

Asn Val Leu Lys Leu Ser Gln Gly Glu Phe Val Ala Val Ala Lys Leu
                485                 490                 495

Glu Ala Ala Tyr Gly Thr Ser Pro Tyr Val Lys Gln Ile Phe Val Tyr
            500                 505                 510

Gly Asn Ser Glu Arg Ser Phe Leu Leu Ala Val Val Pro Asn Ala
        515                 520                 525

Glu Val Leu Gly Ala Arg Asp Gln Glu Glu Ala Lys Pro Leu Ile Ala
    530                 535                 540

Ala Ser Leu Gln Lys Ile Ala Lys Glu Ala Gly Leu Gln Ser Tyr Glu
545                 550                 555                 560

Val Pro Arg Asp Phe Leu Ile Glu Thr Glu Pro Phe Thr Thr Gln Asn
                565                 570                 575

Gly Leu Leu Ser Glu Val Gly Lys Leu Leu Arg Pro Lys Leu Lys Ala
            580                 585                 590

Arg Tyr Gly Glu Ala Leu Glu Ala Arg Tyr Asp Glu Ile Ala His Gly
        595                 600                 605

Gln Ala Asp Glu Leu Arg Ala Leu Arg Asp Gly Ala Gly Gln Arg Pro
    610                 615                 620

Val Val Glu Thr Val Arg Ala Ala Val Ala Ile Ser Gly Ser Glu
625                 630                 635                 640

Gly Ala Glu Val Gly Pro Glu Ala Asn Phe Ala Asp Leu Gly Gly Asp
                645                 650                 655
```

-continued

Ser Leu Ser Ala Leu Ser Leu Ala Asn Leu Leu His Asp Val Phe Glu
            660                 665                 670

Val Glu Val Pro Val Arg Ile Ile Ile Gly Pro Thr Ala Ser Leu Ala
        675                 680                 685

Gly Ile Ala Lys His Ile Glu Ala Glu Arg Ala Gly Ala Ser Ala Pro
    690                 695                 700

Thr Ala Ala Ser Val His Gly Ala Gly Ala Thr Arg Ile Arg Ala Ser
705                 710                 715                 720

Glu Leu Thr Leu Glu Lys Phe Leu Pro Glu Asp Leu Ala Ala Ala
                725                 730                 735

Lys Gly Leu Pro Ala Ala Asp Gln Val Arg Thr Val Leu Leu Thr Gly
            740                 745                 750

Ala Asn Gly Trp Leu Gly Arg Phe Leu Ala Leu Glu Gln Leu Glu Arg
        755                 760                 765

Leu Ala Arg Ser Gly Gln Asp Gly Gly Lys Leu Ile Cys Leu Val Arg
    770                 775                 780

Gly Lys Asp Ala Ala Ala Arg Arg Ile Glu Glu Thr Leu Gly
785                 790                 795                 800

Thr Asp Pro Ala Leu Ala Arg Phe Ala Glu Leu Ala Glu Gly Arg
                805                 810                 815

Leu Glu Val Val Pro Gly Asp Val Gly Glu Pro Lys Phe Gly Leu Asp
            820                 825                 830

Asp Ala Ala Trp Asp Arg Leu Ala Glu Glu Val Asp Ile Val His
        835                 840                 845

Pro Ala Ala Leu Val Asn His Val Leu Pro Tyr His Gln Leu Phe Gly
    850                 855                 860

Pro Asn Val Val Gly Thr Ala Glu Ile Ile Arg Leu Ala Ile Thr Ala
865                 870                 875                 880

Lys Arg Lys Pro Val Thr Tyr Leu Ser Thr Val Ala Val Ala Ala Gly
                885                 890                 895

Val Glu Pro Ser Ser Phe Glu Glu Asp Gly Asp Ile Arg Ala Val Val
            900                 905                 910

Pro Glu Arg Pro Leu Gly Asp Gly Tyr Ala Asn Gly Tyr Gly Asn Ser
        915                 920                 925

Lys Trp Ala Gly Glu Val Leu Leu Arg Glu Ala His Glu Leu Val Gly
    930                 935                 940

Leu Pro Val Ala Val Phe Arg Ser Asp Met Ile Leu Ala His Thr Arg
945                 950                 955                 960

Tyr Thr Gly Gln Leu Asn Val Pro Asp Gln Phe Thr Arg Leu Val Leu
                965                 970                 975

Ser Leu Leu Ala Thr Gly Ile Ala Pro Lys Ser Phe Tyr Gln Gln Gly
            980                 985                 990

Ala Ala Gly Glu Arg Gln Arg Ala His Tyr Asp Gly Ile Pro Val Asp
        995                 1000                1005

Phe Thr Ala Glu Ala Ile Thr Thr Leu Gly Ala Glu Pro Ser Trp Phe
    1010                1015                1020

Asp Gly Gly Ala Gly Phe Arg Ser Phe Asp Val Phe Asn Pro His His
1025                1030                1035                1040

Asp Gly Val Gly Leu Asp Glu Phe Val Asp Trp Leu Ile Glu Ala Gly
                1045                1050                1055

His Pro Ile Ser Arg Ile Asp Asp His Lys Glu Trp Phe Ala Arg Phe
            1060                1065                1070

Glu Thr Ala Val Arg Gly Leu Pro Glu Ala Gln Arg Gln His Ser Leu

-continued

```
           1075                1080                1085

Leu Pro Leu Arg Ala Tyr Ser Phe Pro His Pro Val Asp Gly
        1090                1095                1100

Ser Val Tyr Pro Thr Gly Lys Phe Gln Gly Ala Val Lys Ala Ala Gln
1105                1110                1115                1120

Val Gly Ser Asp His Asp Val Pro His Leu Gly Lys Ala Leu Ile Val
                1125                1130                1135

Lys Tyr Ala Asp Asp Leu Lys Ala Leu Gly Leu Leu
            1140                1145

<210> SEQ ID NO 5
<211> LENGTH: 1185
<212> TYPE: PRT
<213> ORGANISM: Mycobacterium massiliense

<400> SEQUENCE: 5

Met Thr Asn Glu Thr Asn Pro Gln Gln Glu Gln Leu Ser Arg Arg Ile
1               5                   10                  15

Glu Ser Leu Arg Glu Ser Asp Pro Gln Phe Arg Ala Ala Gln Pro Asp
            20                  25                  30

Pro Ala Val Ala Glu Gln Val Leu Arg Pro Gly Leu His Leu Ser Glu
        35                  40                  45

Ala Ile Ala Ala Leu Met Thr Gly Tyr Ala Glu Arg Pro Ala Leu Gly
    50                  55                  60

Glu Arg Ala Arg Glu Leu Val Ile Asp Gln Asp Gly Arg Thr Thr Leu
65                  70                  75                  80

Arg Leu Leu Pro Arg Phe Asp Thr Thr Thr Tyr Gly Glu Leu Trp Ser
                85                  90                  95

Arg Thr Thr Ser Val Ala Ala Ala Trp His His Asp Ala Thr His Pro
            100                 105                 110

Val Lys Ala Gly Asp Leu Val Ala Thr Leu Gly Phe Thr Ser Ile Asp
        115                 120                 125

Tyr Thr Val Leu Asp Leu Ala Ile Met Ile Leu Gly Gly Val Ala Val
    130                 135                 140

Pro Leu Gln Thr Ser Ala Pro Ala Ser Gln Trp Thr Thr Ile Leu Ala
145                 150                 155                 160

Glu Ala Glu Pro Asn Thr Leu Ala Val Ser Ile Glu Leu Ile Gly Ala
                165                 170                 175

Ala Met Glu Ser Val Arg Ala Thr Pro Ser Ile Lys Gln Val Val Val
            180                 185                 190

Phe Asp Tyr Thr Pro Glu Val Asp Asp Gln Arg Glu Ala Phe Glu Ala
        195                 200                 205

Ala Ser Thr Gln Leu Ala Gly Thr Gly Ile Ala Leu Glu Thr Leu Asp
    210                 215                 220

Ala Val Ile Ala Arg Gly Ala Ala Leu Pro Ala Ala Pro Leu Tyr Ala
225                 230                 235                 240

Pro Ser Ala Gly Asp Asp Pro Leu Ala Leu Leu Ile Tyr Thr Ser Gly
                245                 250                 255

Ser Thr Gly Ala Pro Lys Gly Ala Met His Ser Glu Asn Ile Val Arg
            260                 265                 270

Arg Trp Trp Ile Arg Glu Asp Val Met Ala Gly Thr Glu Asn Leu Pro
        275                 280                 285

Met Ile Gly Leu Asn Phe Met Pro Met Ser His Ile Met Gly Arg Gly
    290                 295                 300
```

```
Thr Leu Thr Ser Thr Leu Ser Thr Gly Gly Thr Gly Tyr Phe Ala Ala
305                 310                 315                 320

Ser Ser Asp Met Ser Thr Leu Phe Glu Asp Met Glu Leu Ile Arg Pro
            325                 330                 335

Thr Ala Leu Ala Leu Val Pro Arg Val Cys Asp Met Val Phe Gln Arg
        340                 345                 350

Phe Gln Thr Glu Val Asp Arg Arg Leu Ala Ser Gly Asp Thr Ala Ser
    355                 360                 365

Ala Glu Ala Val Ala Ala Glu Val Lys Ala Asp Ile Arg Asp Asn Leu
370                 375                 380

Phe Gly Gly Arg Val Ser Ala Val Met Val Gly Ser Ala Pro Leu Ser
385                 390                 395                 400

Glu Glu Leu Gly Glu Phe Ile Glu Ser Cys Phe Glu Leu Asn Leu Thr
                405                 410                 415

Asp Gly Tyr Gly Ser Thr Glu Ala Gly Met Val Phe Arg Asp Gly Ile
            420                 425                 430

Val Gln Arg Pro Pro Val Ile Asp Tyr Lys Leu Val Asp Val Pro Glu
        435                 440                 445

Leu Gly Tyr Phe Ser Thr Asp Lys Pro His Pro Arg Gly Glu Leu Leu
    450                 455                 460

Leu Lys Thr Asp Gly Met Phe Leu Gly Tyr Tyr Lys Arg Pro Glu Val
465                 470                 475                 480

Thr Ala Ser Val Phe Asp Ala Asp Gly Phe Tyr Met Thr Gly Asp Ile
                485                 490                 495

Val Ala Glu Leu Ala His Asp Asn Ile Glu Ile Ile Asp Arg Arg Asn
            500                 505                 510

Asn Val Leu Lys Leu Ser Gln Gly Glu Phe Val Ala Val Ala Thr Leu
        515                 520                 525

Glu Ala Glu Tyr Ala Asn Ser Pro Val Val His Gln Ile Tyr Val Tyr
    530                 535                 540

Gly Ser Ser Glu Arg Ser Tyr Leu Leu Ala Val Val Pro Thr Pro
545                 550                 555                 560

Glu Ala Val Ala Ala Lys Gly Asp Ala Ala Leu Lys Thr Thr
                565                 570                 575

Ile Ala Asp Ser Leu Gln Asp Ile Ala Lys Glu Ile Gln Leu Gln Ser
            580                 585                 590

Tyr Glu Val Pro Arg Asp Phe Ile Ile Glu Pro Gln Pro Phe Thr Gln
        595                 600                 605

Gly Asn Gly Leu Leu Thr Gly Ile Ala Lys Leu Ala Arg Pro Asn Leu
    610                 615                 620

Lys Ala His Tyr Gly Pro Arg Leu Glu Gln Met Tyr Ala Glu Ile Ala
625                 630                 635                 640

Glu Gln Gln Ala Ala Glu Leu Arg Ala Leu His Gly Val Asp Pro Asp
                645                 650                 655

Lys Pro Ala Leu Glu Thr Val Leu Lys Ala Ala Gln Ala Leu Leu Gly
            660                 665                 670

Val Ser Ser Ala Glu Leu Ala Ala Asp Ala His Phe Thr Asp Leu Gly
        675                 680                 685

Gly Asp Ser Leu Ser Ala Leu Ser Phe Ser Asp Leu Leu Arg Asp Ile
    690                 695                 700

Phe Ala Val Glu Val Pro Val Gly Val Ile Val Ser Ala Ala Asn Asp
705                 710                 715                 720

Leu Gly Gly Val Ala Lys Phe Val Asp Glu Gln Arg His Ser Gly Gly
```

```
                725                 730                 735
Thr Arg Pro Thr Ala Glu Thr Val His Gly Ala Gly His Thr Glu Ile
            740                 745                 750
Arg Ala Ala Asp Leu Thr Leu Asp Lys Phe Ile Asp Glu Ala Thr Leu
            755                 760                 765
His Ala Ala Pro Ser Leu Pro Lys Ala Ala Gly Ile Pro His Thr Val
            770                 775                 780
Leu Leu Thr Gly Ser Asn Gly Tyr Leu Gly His Tyr Leu Ala Leu Glu
785                 790                 795                 800
Trp Leu Glu Arg Leu Asp Lys Thr Asp Gly Lys Leu Ile Val Ile Val
                805                 810                 815
Arg Gly Lys Asn Ala Glu Ala Ala Tyr Gly Arg Leu Glu Glu Ala Phe
            820                 825                 830
Asp Thr Gly Asp Thr Glu Leu Leu Ala His Phe Arg Ser Leu Ala Asp
            835                 840                 845
Lys His Leu Glu Val Leu Ala Gly Asp Ile Gly Asp Pro Asn Leu Gly
            850                 855                 860
Leu Asp Ala Asp Thr Trp Gln Arg Leu Ala Asp Thr Val Asp Val Ile
865                 870                 875                 880
Val His Pro Ala Ala Leu Val Asn His Val Leu Pro Tyr Asn Gln Leu
                885                 890                 895
Phe Gly Pro Asn Val Val Gly Thr Ala Glu Ile Ile Lys Leu Ala Ile
            900                 905                 910
Thr Thr Lys Ile Lys Pro Val Thr Tyr Leu Ser Thr Val Ala Val Ala
            915                 920                 925
Ala Tyr Val Asp Pro Thr Thr Phe Asp Glu Glu Ser Asp Ile Arg Leu
930                 935                 940
Ile Ser Ala Val Arg Pro Ile Asp Asp Gly Tyr Ala Asn Gly Tyr Gly
945                 950                 955                 960
Asn Ala Lys Trp Ala Gly Glu Val Leu Leu Arg Glu Ala His Asp Leu
                965                 970                 975
Cys Gly Leu Pro Val Ala Val Phe Arg Ser Asp Met Ile Leu Ala His
            980                 985                 990
Ser Arg Tyr Thr Gly Gln Leu Asn Val Pro Asp Gln Phe Thr Arg Leu
            995                 1000                1005
Ile Leu Ser Leu Ile Ala Thr Gly Ile Ala Pro Gly Ser Phe Tyr Gln
        1010                1015                1020
Ala Gln Thr Thr Gly Glu Arg Pro Leu Ala His Tyr Asp Gly Leu Pro
1025                1030                1035                1040
Gly Asp Phe Thr Ala Glu Ala Ile Thr Thr Leu Gly Thr Gln Val Pro
                1045                1050                1055
Glu Gly Ser Glu Gly Phe Val Thr Tyr Asp Cys Val Asn Pro His Ala
            1060                1065                1070
Asp Gly Ile Ser Leu Asp Asn Phe Val Asp Trp Leu Ile Glu Ala Gly
            1075                1080                1085
Tyr Pro Ile Ala Arg Ile Asp Asn Tyr Thr Glu Trp Phe Thr Arg Phe
        1090                1095                1100
Asp Thr Ala Ile Arg Gly Leu Ser Glu Lys Gln Lys Gln His Ser Leu
1105                1110                1115                1120
Leu Pro Leu Leu His Ala Phe Glu Gln Pro Ser Ala Ala Glu Asn His
                1125                1130                1135
Gly Val Val Pro Ala Lys Arg Phe Gln His Ala Val Gln Ala Ala Gly
            1140                1145                1150
```

```
Ile Gly Pro Val Gly Gln Asp Gly Thr Thr Asp Ile Pro His Leu Ser
        1155                1160                1165

Arg Arg Leu Ile Val Lys Tyr Ala Lys Asp Leu Glu Gln Leu Gly Leu
    1170                1175                1180

Leu
1185

<210> SEQ ID NO 6
<211> LENGTH: 1186
<212> TYPE: PRT
<213> ORGANISM: Segniliparus rotundus

<400> SEQUENCE: 6

Met Thr Gln Ser His Thr Gln Gly Pro Gln Ala Ser Ala Ala His Ser
 1               5                  10                  15

Arg Leu Ala Arg Arg Ala Ala Glu Leu Leu Ala Thr Asp Pro Gln Ala
            20                  25                  30

Ala Ala Thr Leu Pro Asp Pro Glu Val Val Arg Gln Ala Thr Arg Pro
        35                  40                  45

Gly Leu Arg Leu Ala Glu Arg Val Asp Ala Ile Leu Ser Gly Tyr Ala
    50                  55                  60

Asp Arg Pro Ala Leu Gly Gln Arg Ser Phe Gln Thr Val Lys Asp Pro
65                  70                  75                  80

Ile Thr Gly Arg Ser Ser Val Glu Leu Leu Pro Thr Phe Asp Thr Ile
                85                  90                  95

Thr Tyr Arg Glu Leu Arg Glu Arg Ala Thr Ala Ile Ala Ser Asp Leu
            100                 105                 110

Ala His Pro Gln Ala Pro Ala Lys Pro Gly Asp Phe Leu Ala Ser
        115                 120                 125

Ile Gly Phe Ile Ser Val Asp Tyr Val Ala Ile Asp Ile Ala Gly Val
    130                 135                 140

Phe Ala Gly Leu Thr Ala Val Pro Leu Gln Thr Gly Ala Thr Leu Ala
145                 150                 155                 160

Thr Leu Thr Ala Ile Thr Ala Glu Thr Ala Pro Thr Leu Phe Ala Ala
                165                 170                 175

Ser Ile Glu His Leu Pro Thr Ala Val Asp Ala Val Leu Ala Thr Pro
            180                 185                 190

Ser Val Arg Arg Leu Leu Val Phe Asp Tyr Arg Ala Gly Ser Asp Glu
        195                 200                 205

Asp Arg Glu Ala Val Glu Ala Ala Lys Arg Lys Ile Ala Asp Ala Gly
    210                 215                 220

Ser Ser Val Leu Val Asp Val Leu Asp Glu Val Ile Ala Arg Gly Lys
225                 230                 235                 240

Ser Ala Pro Lys Ala Pro Leu Pro Pro Ala Thr Asp Ala Gly Asp Asp
                245                 250                 255

Ser Leu Ser Leu Leu Ile Tyr Thr Ser Gly Ser Thr Gly Thr Pro Lys
            260                 265                 270

Gly Ala Met Tyr Pro Glu Arg Asn Val Ala His Phe Trp Gly Gly Val
        275                 280                 285

Trp Ala Ala Phe Asp Glu Asp Ala Ala Pro Val Pro Ala Ile
    290                 295                 300

Asn Ile Thr Phe Leu Pro Leu Ser His Val Ala Ser Arg Leu Ser Leu
305                 310                 315                 320

Met Pro Thr Leu Ala Arg Gly Gly Leu Met His Phe Val Ala Lys Ser
```

-continued

```
                325                 330                 335
Asp Leu Ser Thr Leu Phe Glu Asp Leu Lys Leu Ala Arg Pro Thr Asn
            340                 345                 350
Leu Phe Leu Val Pro Arg Val Glu Met Leu Tyr Gln His Tyr Gln
        355                 360                 365
Ser Glu Leu Asp Arg Arg Gly Val Gln Asp Gly Thr Arg Glu Ala Glu
    370                 375                 380
Ala Val Lys Asp Asp Leu Arg Thr Gly Leu Leu Gly Gly Arg Ile Leu
385                 390                 395                 400
Thr Ala Gly Phe Gly Ser Ala Pro Leu Ser Ala Glu Leu Ala Gly Phe
                405                 410                 415
Ile Glu Ser Leu Leu Gln Ile His Leu Val Asp Gly Tyr Gly Ser Thr
            420                 425                 430
Glu Ala Gly Pro Val Trp Arg Asp Gly Tyr Leu Val Lys Pro Pro Val
        435                 440                 445
Thr Asp Tyr Lys Leu Ile Asp Val Pro Glu Leu Gly Tyr Phe Ser Thr
    450                 455                 460
Asp Ser Pro His Pro Arg Gly Glu Leu Ala Ile Lys Thr Gln Thr Ile
465                 470                 475                 480
Leu Pro Gly Tyr Tyr Lys Arg Pro Glu Thr Thr Ala Glu Val Phe Asp
                485                 490                 495
Glu Asp Gly Phe Tyr Leu Thr Gly Asp Val Val Ala Gln Ile Gly Pro
            500                 505                 510
Glu Gln Phe Ala Tyr Val Asp Arg Arg Lys Asn Val Leu Lys Leu Ser
        515                 520                 525
Gln Gly Glu Phe Val Thr Leu Ala Lys Leu Glu Ala Ala Tyr Ser Ser
    530                 535                 540
Ser Pro Leu Val Arg Gln Leu Phe Val Tyr Gly Ser Ser Glu Arg Ser
545                 550                 555                 560
Tyr Leu Leu Ala Val Ile Val Pro Thr Pro Asp Ala Leu Lys Lys Phe
                565                 570                 575
Gly Val Gly Glu Ala Ala Lys Ala Ala Leu Gly Glu Ser Leu Gln Lys
            580                 585                 590
Ile Ala Arg Asp Glu Gly Leu Gln Ser Tyr Glu Val Pro Arg Asp Phe
        595                 600                 605
Ile Ile Glu Thr Asp Pro Phe Thr Val Glu Asn Gly Leu Leu Ser Asp
    610                 615                 620
Ala Arg Lys Ser Leu Arg Pro Lys Leu Lys Glu His Tyr Gly Glu Arg
625                 630                 635                 640
Leu Glu Ala Met Tyr Lys Glu Leu Ala Asp Gly Gln Ala Asn Glu Leu
                645                 650                 655
Arg Asp Ile Arg Arg Gly Val Gln Gln Arg Pro Thr Leu Glu Thr Val
            660                 665                 670
Arg Arg Ala Ala Ala Met Leu Gly Ala Ser Ala Ala Glu Ile Lys
        675                 680                 685
Pro Asp Ala His Phe Thr Asp Leu Gly Gly Asp Ser Leu Ser Ala Leu
    690                 695                 700
Thr Phe Ser Asn Phe Leu His Asp Leu Phe Glu Val Asp Val Pro Val
705                 710                 715                 720
Gly Val Ile Val Ser Ala Ala Asn Thr Leu Gly Ser Val Ala Glu His
                725                 730                 735
Ile Asp Ala Gln Leu Ala Gly Gly Arg Ala Arg Pro Thr Phe Ala Thr
            740                 745                 750
```

```
Val His Gly Lys Gly Ser Thr Thr Ile Lys Ala Ser Asp Leu Thr Leu
        755                 760                 765

Asp Lys Phe Ile Asp Glu Gln Thr Leu Glu Ala Ala Lys His Leu Pro
    770                 775                 780

Lys Pro Ala Asp Pro Pro Arg Thr Val Leu Leu Thr Gly Ala Asn Gly
785                 790                 795                 800

Trp Leu Gly Arg Phe Leu Ala Leu Glu Trp Leu Glu Arg Leu Ala Pro
                805                 810                 815

Ala Gly Gly Lys Leu Ile Thr Ile Val Arg Gly Lys Asp Ala Ala Gln
            820                 825                 830

Ala Lys Ala Arg Leu Asp Ala Ala Tyr Glu Ser Gly Asp Pro Lys Leu
        835                 840                 845

Ala Gly His Tyr Gln Asp Leu Ala Ala Thr Thr Leu Glu Val Leu Ala
    850                 855                 860

Gly Asp Phe Ser Glu Pro Arg Leu Gly Leu Asp Glu Ala Thr Trp Asn
865                 870                 875                 880

Arg Leu Ala Asp Glu Val Asp Phe Ile Ser His Pro Gly Ala Leu Val
                885                 890                 895

Asn His Val Leu Pro Tyr Asn Gln Leu Phe Gly Pro Asn Val Ala Gly
            900                 905                 910

Val Ala Glu Ile Ile Lys Leu Ala Ile Thr Thr Arg Ile Lys Pro Val
        915                 920                 925

Thr Tyr Leu Ser Thr Val Ala Val Ala Gly Val Glu Pro Ser Ala
    930                 935                 940

Leu Asp Glu Asp Gly Asp Ile Arg Thr Val Ser Ala Glu Arg Ser Val
945                 950                 955                 960

Asp Glu Gly Tyr Ala Asn Gly Tyr Gly Asn Ser Lys Trp Gly Gly Glu
                965                 970                 975

Val Leu Leu Arg Glu Ala His Asp Arg Thr Gly Leu Pro Val Arg Val
            980                 985                 990

Phe Arg Ser Asp Met Ile Leu Ala His Gln Lys Tyr Thr Gly Gln Val
        995                 1000                1005

Asn Ala Thr Asp Gln Phe Thr Arg Leu Val Gln Ser Leu Leu Ala Thr
    1010                1015                1020

Gly Leu Ala Pro Lys Ser Phe Tyr Glu Leu Asp Ala Gln Gly Asn Arg
1025                1030                1035                1040

Gln Arg Ala His Tyr Asp Gly Ile Pro Val Asp Phe Thr Ala Glu Ser
                1045                1050                1055

Ile Thr Thr Leu Gly Gly Asp Gly Leu Glu Gly Tyr Arg Ser Tyr Asn
            1060                1065                1070

Val Phe Asn Pro His Arg Asp Gly Val Gly Leu Asp Glu Phe Val Asp
        1075                1080                1085

Trp Leu Ile Glu Ala Gly His Pro Ile Thr Arg Ile Asp Asp Tyr Asp
    1090                1095                1100

Gln Trp Leu Ser Arg Phe Glu Thr Ser Leu Arg Gly Leu Pro Glu Ser
1105                1110                1115                1120

Lys Arg Gln Ala Ser Val Leu Pro Leu Leu His Ala Phe Ala Arg Pro
                1125                1130                1135

Gly Pro Ala Val Asp Gly Ser Pro Phe Arg Asn Thr Val Phe Arg Thr
            1140                1145                1150

Asp Val Gln Lys Ala Lys Ile Gly Ala Glu His Asp Ile Pro His Leu
        1155                1160                1165
```

Gly Lys Ala Leu Val Leu Lys Tyr Ala Asp Asp Ile Lys Gln Leu Gly
            1170                1175                1180

Leu Leu
1185

<210> SEQ ID NO 7
<211> LENGTH: 459
<212> TYPE: PRT
<213> ORGANISM: Chromobacterium violaceum

<400> SEQUENCE: 7

Met Gln Lys Gln Arg Thr Thr Ser Gln Trp Arg Glu Leu Asp Ala Ala
  1               5                  10                  15

His His Leu His Pro Phe Thr Asp Thr Ala Ser Leu Asn Gln Ala Gly
                 20                  25                  30

Ala Arg Val Met Thr Arg Gly Glu Gly Val Tyr Leu Trp Asp Ser Glu
             35                  40                  45

Gly Asn Lys Ile Ile Asp Gly Met Ala Gly Leu Trp Cys Val Asn Val
         50                  55                  60

Gly Tyr Gly Arg Lys Asp Phe Ala Glu Ala Ala Arg Arg Gln Met Glu
 65                  70                  75                  80

Glu Leu Pro Phe Tyr Asn Thr Phe Phe Lys Thr Thr His Pro Ala Val
                 85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
            115                 120                 125

Arg Met Val Arg Arg Tyr Trp Asp Val Gln Gly Lys Pro Glu Lys Lys
        130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
    210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Lys
    290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

```
Gly Pro Tyr Met Gln Lys Arg Trp Arg Glu Thr Phe Ser Arg Phe Glu
            355                 360                 365

His Val Asp Asp Val Arg Gly Val Gly Met Val Gln Ala Phe Thr Leu
    370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Arg
                405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
            435                 440                 445

Phe Glu Gln Thr Leu Lys Ala Arg Gly Leu Ala
            450                 455

<210> SEQ ID NO 8
<211> LENGTH: 468
<212> TYPE: PRT
<213> ORGANISM: Pseudomonas aeruginosa

<400> SEQUENCE: 8

Met Asn Ala Arg Leu His Ala Thr Ser Pro Leu Gly Asp Ala Asp Leu
1               5                   10                  15

Val Arg Ala Asp Gln Ala His Tyr Met His Gly Tyr His Val Phe Asp
            20                  25                  30

Asp His Arg Val Asn Gly Ser Leu Asn Ile Ala Ala Gly Asp Gly Ala
        35                  40                  45

Tyr Ile Tyr Asp Thr Ala Gly Asn Arg Tyr Leu Asp Ala Val Gly Gly
    50                  55                  60

Met Trp Cys Thr Asn Ile Gly Leu Gly Arg Glu Glu Met Ala Arg Thr
65              70                  75                  80

Val Ala Glu Gln Thr Arg Leu Leu Ala Tyr Ser Asn Pro Phe Cys Asp
            85                  90                  95

Met Ala Asn Pro Arg Ala Ile Glu Leu Cys Arg Lys Leu Ala Glu Leu
            100                 105                 110

Ala Pro Gly Asp Leu Asp His Val Phe Leu Thr Thr Gly Gly Ser Thr
        115                 120                 125

Ala Val Asp Thr Ala Ile Arg Leu Met His Tyr Tyr Gln Asn Cys Arg
    130                 135                 140

Gly Lys Arg Ala Lys Lys His Val Ile Thr Arg Ile Asn Ala Tyr His
145                 150                 155                 160

Gly Ser Thr Phe Leu Gly Met Ser Leu Gly Gly Lys Ser Ala Asp Arg
                165                 170                 175

Pro Ala Glu Phe Asp Phe Leu Asp Glu Arg Ile His His Leu Ala Cys
            180                 185                 190

Pro Tyr Tyr Tyr Arg Ala Pro Glu Gly Leu Gly Glu Ala Glu Phe Leu
        195                 200                 205

Asp Gly Leu Val Asp Glu Phe Glu Arg Lys Ile Leu Glu Leu Gly Ala
    210                 215                 220

Asp Arg Val Gly Ala Phe Ile Ser Glu Pro Val Phe Gly Ser Gly Gly
225                 230                 235                 240

Val Ile Val Pro Pro Ala Gly Tyr His Arg Arg Met Trp Glu Leu Cys
                245                 250                 255

Gln Arg Tyr Asp Val Leu Tyr Ile Ser Asp Glu Val Val Thr Ser Phe
```

-continued

```
                260                 265                 270
Gly Arg Leu Gly His Phe Phe Ala Ser Gln Ala Val Phe Gly Val Gln
            275                 280                 285
Pro Asp Ile Ile Leu Thr Ala Lys Gly Leu Thr Ser Gly Tyr Gln Pro
        290                 295                 300
Leu Gly Ala Cys Ile Phe Ser Arg Arg Ile Trp Glu Val Ile Ala Glu
305                 310                 315                 320
Pro Asp Lys Gly Arg Cys Phe Ser His Gly Phe Thr Tyr Ser Gly His
                325                 330                 335
Pro Val Ala Cys Ala Ala Leu Lys Asn Ile Glu Ile Glu Arg
            340                 345                 350
Glu Gly Leu Leu Ala His Ala Asp Glu Val Gly Arg Tyr Phe Glu Glu
            355                 360                 365
Arg Leu Gln Ser Leu Arg Asp Leu Pro Ile Val Gly Asp Val Arg Gly
        370                 375                 380
Met Arg Phe Met Ala Cys Val Glu Phe Val Ala Asp Lys Ala Ser Lys
385                 390                 395                 400
Ala Leu Phe Pro Glu Ser Leu Asn Ile Gly Glu Trp Val His Leu Arg
                405                 410                 415
Ala Gln Lys Arg Gly Leu Leu Val Arg Pro Ile Val His Leu Asn Val
            420                 425                 430
Met Ser Pro Pro Leu Ile Leu Thr Arg Glu Gln Val Asp Thr Val Val
        435                 440                 445
Arg Val Leu Arg Glu Ser Ile Glu Gly Thr Val Glu Asp Leu Val Arg
450                 455                 460
Ala Gly His Arg
465

<210> SEQ ID NO 9
<211> LENGTH: 454
<212> TYPE: PRT
<213> ORGANISM: Pseudomonas syringae

<400> SEQUENCE: 9

Met Ser Ala Asn Asn Pro Gln Thr Leu Glu Trp Gln Ala Leu Ser Ser
1               5                   10                  15
Glu His His Leu Ala Pro Phe Ser Asp Tyr Lys Gln Leu Lys Glu Lys
            20                  25                  30
Gly Pro Arg Ile Ile Thr Arg Ala Glu Gly Val Tyr Leu Trp Asp Ser
        35                  40                  45
Glu Gly Asn Lys Ile Leu Asp Gly Met Ser Gly Leu Trp Cys Val Ala
    50                  55                  60
Ile Gly Tyr Gly Arg Glu Glu Leu Ala Asp Ala Ala Ser Lys Gln Met
65                  70                  75                  80
Arg Glu Leu Pro Tyr Tyr Asn Leu Phe Phe Gln Thr Ala His Pro Pro
                85                  90                  95
Val Leu Glu Leu Ala Lys Ala Ile Ser Asp Ile Ala Pro Glu Gly Met
            100                 105                 110
Asn His Val Phe Phe Thr Gly Ser Gly Ser Glu Gly Asn Asp Thr Met
        115                 120                 125
Leu Arg Met Val Arg His Tyr Trp Ala Leu Lys Gly Gln Pro Asn Lys
    130                 135                 140
Lys Thr Ile Ile Ser Arg Val Asn Gly Tyr His Gly Ser Thr Val Ala
145                 150                 155                 160
```

-continued

```
Gly Ala Ser Leu Gly Gly Met Thr Tyr Met His Glu Gln Gly Asp Leu
            165                 170                 175
Pro Ile Pro Gly Val Val His Ile Pro Gln Pro Tyr Trp Phe Gly Glu
        180                 185                 190
Gly Gly Asp Met Thr Pro Asp Glu Phe Gly Ile Trp Ala Ala Glu Gln
    195                 200                 205
Leu Glu Lys Lys Ile Leu Glu Leu Gly Val Glu Asn Val Gly Ala Phe
210                 215                 220
Ile Ala Glu Pro Ile Gln Gly Ala Gly Gly Val Ile Val Pro Pro Asp
225                 230                 235                 240
Ser Tyr Trp Pro Lys Ile Lys Glu Ile Leu Ser Arg Tyr Asp Ile Leu
                245                 250                 255
Phe Ala Ala Asp Glu Val Ile Cys Gly Phe Gly Arg Thr Ser Glu Trp
            260                 265                 270
Phe Gly Ser Asp Phe Tyr Gly Leu Arg Pro Asp Met Met Thr Ile Ala
        275                 280                 285
Lys Gly Leu Thr Ser Gly Tyr Val Pro Met Gly Gly Leu Ile Val Arg
    290                 295                 300
Asp Glu Ile Val Ala Val Leu Asn Gly Gly Asp Phe Asn His Gly
305                 310                 315                 320
Phe Thr Tyr Ser Gly His Pro Val Ala Ala Val Ala Leu Glu Asn
                325                 330                 335
Ile Arg Ile Leu Arg Glu Lys Ile Val Glu Arg Val Arg Ser Glu
            340                 345                 350
Thr Ala Pro Tyr Leu Gln Lys Arg Leu Arg Glu Leu Ser Asp His Pro
        355                 360                 365
Leu Val Gly Glu Val Arg Gly Val Gly Leu Leu Gly Ala Ile Glu Leu
    370                 375                 380
Val Lys Asp Lys Thr Thr Arg Glu Arg Tyr Thr Asp Lys Gly Ala Gly
385                 390                 395                 400
Met Ile Cys Arg Thr Phe Cys Phe Asp Asn Gly Leu Ile Met Arg Ala
                405                 410                 415
Val Gly Asp Thr Met Ile Ile Ala Pro Pro Leu Val Ile Ser Phe Ala
            420                 425                 430
Gln Ile Asp Glu Leu Val Glu Lys Ala Arg Thr Cys Leu Asp Leu Thr
        435                 440                 445
Leu Ala Val Leu Gln Gly
    450

<210> SEQ ID NO 10
<211> LENGTH: 467
<212> TYPE: PRT
<213> ORGANISM: Rhodobacter sphaeroides

<400> SEQUENCE: 10

Met Thr Arg Asn Asp Ala Thr Asn Ala Ala Gly Ala Val Gly Ala Ala
1               5                   10                  15
Met Arg Asp His Ile Leu Leu Pro Ala Gln Glu Met Ala Lys Leu Gly
            20                  25                  30
Lys Ser Ala Gln Pro Val Leu Thr His Ala Glu Gly Ile Tyr Val His
        35                  40                  45
Thr Glu Asp Gly Arg Arg Leu Ile Asp Gly Pro Ala Gly Met Trp Cys
    50                  55                  60
Ala Gln Val Gly Tyr Gly Arg Arg Glu Ile Val Asp Ala Met Ala His
65                  70                  75                  80
```

Gln Ala Met Val Leu Pro Tyr Ala Ser Pro Trp Tyr Met Ala Thr Ser
                85                  90                  95

Pro Ala Ala Arg Leu Ala Glu Lys Ile Ala Thr Leu Thr Pro Gly Asp
            100                 105                 110

Leu Asn Arg Ile Phe Phe Thr Thr Gly Gly Ser Thr Ala Val Asp Ser
        115                 120                 125

Ala Leu Arg Phe Ser Glu Phe Tyr Asn Asn Val Leu Gly Arg Pro Gln
    130                 135                 140

Lys Lys Arg Ile Ile Val Arg Tyr Asp Gly Tyr His Gly Ser Thr Ala
145                 150                 155                 160

Leu Thr Ala Ala Cys Thr Gly Arg Thr Gly Asn Trp Pro Asn Phe Asp
                165                 170                 175

Ile Ala Gln Asp Arg Ile Ser Phe Leu Ser Ser Pro Asn Pro Arg His
            180                 185                 190

Ala Gly Asn Arg Ser Gln Glu Ala Phe Leu Asp Asp Leu Val Gln Glu
        195                 200                 205

Phe Glu Asp Arg Ile Glu Ser Leu Gly Pro Asp Thr Ile Ala Ala Phe
    210                 215                 220

Leu Ala Glu Pro Ile Leu Ala Ser Gly Gly Val Ile Ile Pro Pro Ala
225                 230                 235                 240

Gly Tyr His Ala Arg Phe Lys Ala Ile Cys Glu Lys His Asp Ile Leu
                245                 250                 255

Tyr Ile Ser Asp Glu Val Val Thr Gly Phe Gly Arg Cys Gly Glu Trp
            260                 265                 270

Phe Ala Ser Glu Lys Val Phe Gly Val Val Pro Asp Ile Ile Thr Phe
        275                 280                 285

Ala Lys Gly Val Thr Ser Gly Tyr Val Pro Leu Gly Gly Leu Ala Ile
    290                 295                 300

Ser Glu Ala Val Leu Ala Arg Ile Ser Gly Glu Asn Ala Lys Gly Ser
305                 310                 315                 320

Trp Phe Thr Asn Gly Tyr Thr Tyr Ser Asn Gln Pro Val Ala Cys Ala
                325                 330                 335

Ala Ala Leu Ala Asn Ile Glu Leu Met Glu Arg Glu Gly Ile Val Asp
            340                 345                 350

Gln Ala Arg Glu Met Ala Asp Tyr Phe Ala Ala Leu Ala Ser Leu
        355                 360                 365

Arg Asp Leu Pro Gly Val Ala Glu Thr Arg Ser Val Gly Leu Val Gly
    370                 375                 380

Cys Val Gln Cys Leu Leu Asp Pro Thr Arg Ala Asp Gly Thr Ala Glu
385                 390                 395                 400

Asp Lys Ala Phe Thr Leu Lys Ile Asp Glu Arg Cys Phe Glu Leu Gly
                405                 410                 415

Leu Ile Val Arg Pro Leu Gly Asp Leu Cys Val Ile Ser Pro Pro Leu
            420                 425                 430

Ile Ile Ser Arg Ala Gln Ile Asp Glu Met Val Ala Ile Met Arg Gln
        435                 440                 445

Ala Ile Thr Glu Val Ser Ala Ala His Gly Leu Thr Ala Lys Glu Pro
    450                 455                 460

Ala Ala Val
465

<210> SEQ ID NO 11
<211> LENGTH: 459

<212> TYPE: PRT
<213> ORGANISM: Escherichia coli

<400> SEQUENCE: 11

Met Asn Arg Leu Pro Ser Ser Ala Ser Ala Leu Ala Cys Ser Ala His
1               5                   10                  15

Ala Leu Asn Leu Ile Glu Lys Arg Thr Leu Asp His Glu Glu Met Lys
            20                  25                  30

Ala Leu Asn Arg Glu Val Ile Glu Tyr Phe Lys Glu His Val Asn Pro
        35                  40                  45

Gly Phe Leu Glu Tyr Arg Lys Ser Val Thr Ala Gly Gly Asp Tyr Gly
    50                  55                  60

Ala Val Glu Trp Gln Ala Gly Ser Leu Asn Thr Leu Val Asp Thr Gln
65                  70                  75                  80

Gly Gln Glu Phe Ile Asp Cys Leu Gly Gly Phe Gly Ile Phe Asn Val
                85                  90                  95

Gly His Arg Asn Pro Val Val Ser Ala Val Gln Asn Gln Leu Ala
                100                 105                 110

Lys Gln Pro Leu His Ser Gln Glu Leu Leu Asp Pro Leu Arg Ala Met
            115                 120                 125

Leu Ala Lys Thr Leu Ala Ala Leu Thr Pro Gly Lys Leu Lys Tyr Ser
130                 135                 140

Phe Phe Cys Asn Ser Gly Thr Glu Ser Val Glu Ala Ala Leu Lys Leu
145                 150                 155                 160

Ala Lys Ala Tyr Gln Ser Pro Arg Gly Lys Phe Thr Phe Ile Ala Thr
                165                 170                 175

Ser Gly Ala Phe His Gly Lys Ser Leu Gly Ala Leu Ser Ala Thr Ala
            180                 185                 190

Lys Ser Thr Phe Arg Lys Pro Phe Met Pro Leu Leu Pro Gly Phe Arg
        195                 200                 205

His Val Pro Phe Gly Asn Ile Glu Ala Met Arg Thr Ala Leu Asn Glu
    210                 215                 220

Cys Lys Lys Thr Gly Asp Asp Val Ala Ala Val Ile Leu Glu Pro Ile
225                 230                 235                 240

Gln Gly Glu Gly Gly Val Ile Leu Pro Pro Gly Tyr Leu Thr Ala
                245                 250                 255

Val Arg Lys Leu Cys Asp Glu Phe Gly Ala Leu Met Ile Leu Asp Glu
            260                 265                 270

Val Gln Thr Gly Met Gly Arg Thr Gly Lys Met Phe Ala Cys Glu His
        275                 280                 285

Glu Asn Val Gln Pro Asp Ile Leu Cys Leu Ala Lys Ala Leu Gly Gly
    290                 295                 300

Gly Val Met Pro Ile Gly Ala Thr Ile Ala Thr Glu Glu Val Phe Ser
305                 310                 315                 320

Val Leu Phe Asp Asn Pro Phe Leu His Thr Thr Thr Phe Gly Gly Asn
                325                 330                 335

Pro Leu Ala Cys Ala Ala Ala Leu Ala Thr Ile Asn Val Leu Leu Glu
            340                 345                 350

Gln Asn Leu Pro Ala Gln Ala Glu Gln Lys Gly Asp Met Leu Leu Asp
        355                 360                 365

Gly Phe Arg Gln Leu Ala Arg Glu Tyr Pro Asp Leu Val Gln Glu Ala
    370                 375                 380

Arg Gly Lys Gly Met Leu Met Ala Ile Glu Phe Val Asp Asn Glu Ile
385                 390                 395                 400

Gly Tyr Asn Phe Ala Ser Glu Met Phe Arg Gln Arg Val Leu Val Ala
                405                 410                 415

Gly Thr Leu Asn Asn Ala Lys Thr Ile Arg Ile Glu Pro Pro Leu Thr
            420                 425                 430

Leu Thr Ile Glu Gln Cys Glu Leu Val Ile Lys Ala Ala Arg Lys Ala
        435                 440                 445

Leu Ala Ala Met Arg Val Ser Val Glu Glu Ala
    450                 455

<210> SEQ ID NO 12
<211> LENGTH: 453
<212> TYPE: PRT
<213> ORGANISM: Vibrio Fluvialis

<400> SEQUENCE: 12

Met Asn Lys Pro Gln Ser Trp Glu Ala Arg Ala Glu Thr Tyr Ser Leu
 1               5                  10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val Asn Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Val His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Arg Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Met Gly Ala Val Ile Leu Gly Pro Glu Leu Ser
    290                 295                 300

Lys Arg Leu Glu Thr Ala Ile Glu Ala Ile Glu Glu Phe Pro His Gly

```
            305                 310                 315                 320
        Phe Thr Ala Ser Gly His Pro Val Gly Cys Ala Ile Ala Leu Lys Ala
                    325                 330                 335

Ile Asp Val Val Met Asn Glu Gly Leu Ala Glu Asn Val Arg Arg Leu
                    340                 345                 350

Ala Pro Arg Phe Glu Arg Leu Lys His Ile Ala Glu Arg Pro Asn
                    355                 360                 365

Ile Gly Glu Tyr Arg Gly Ile Gly Phe Met Trp Ala Leu Glu Ala Val
                    370                 375                 380

Lys Asp Lys Ala Ser Lys Thr Pro Phe Asp Gly Asn Leu Ser Val Ser
        385                 390                 395                 400

Glu Arg Ile Ala Asn Thr Cys Thr Asp Leu Gly Leu Ile Cys Arg Pro
                            405                 410                 415

Leu Gly Gln Ser Val Val Leu Cys Pro Pro Phe Ile Leu Thr Glu Ala
                        420                 425                 430

Gln Met Asp Glu Met Phe Asp Lys Leu Glu Lys Ala Leu Asp Lys Val
                    435                 440                 445

Phe Ala Glu Val Ala
            450

<210> SEQ ID NO 13
<211> LENGTH: 418
<212> TYPE: PRT
<213> ORGANISM: Polaromonas sp. JS666

<400> SEQUENCE: 13

Met Ser Glu Ala Ile Val Val Asn Asn Gln Asn Asp Gln Ser Arg Ala
        1               5                   10                  15

Tyr Ala Ile Pro Leu Glu Asp Ile Asp Val Ser Asn Pro Glu Leu Phe
                    20                  25                  30

Arg Asp Asn Thr Met Trp Gly Tyr Phe Glu Arg Leu Arg Arg Glu Asp
                    35                  40                  45

Pro Val His Tyr Cys Lys Asp Ser Leu Phe Gly Pro Tyr Trp Ser Val
            50                  55                  60

Thr Lys Phe Lys Asp Ile Met Gln Val Glu Thr His Pro Glu Ile Phe
        65                  70                  75                  80

Ser Ser Glu Gly Asn Ile Thr Ile Met Glu Ser Asn Ala Ala Val Thr
                        85                  90                  95

Leu Pro Met Phe Ile Ala Met Asp Pro Pro Lys His Asp Val Gln Arg
                    100                 105                 110

Met Ala Val Ser Pro Ile Val Ala Pro Glu Asn Leu Ala Lys Leu Glu
                    115                 120                 125

Gly Leu Ile Arg Glu Arg Thr Gly Arg Ala Leu Asp Gly Leu Pro Ile
                    130                 135                 140

Asn Glu Thr Phe Asp Trp Val Lys Leu Val Ser Ile Asn Leu Thr Thr
        145                 150                 155                 160

Gln Met Leu Ala Thr Leu Phe Asp Phe Pro Trp Glu Asp Arg Ala Lys
                    165                 170                 175

Leu Thr Arg Trp Ser Asp Val Ala Thr Ala Leu Val Gly Thr Gly Ile
                    180                 185                 190

Ile Asp Ser Glu Glu Gln Arg Met Glu Glu Leu Lys Gly Cys Val Gln
                    195                 200                 205

Tyr Met Thr Arg Leu Trp Asn Glu Arg Val Asn Val Pro Pro Gly Asn
                    210                 215                 220
```

-continued

```
Asp Leu Ile Ser Met Met Ala His Thr Glu Ser Met Arg Asn Met Thr
225                 230                 235                 240

Pro Glu Glu Phe Leu Gly Asn Leu Ile Leu Leu Ile Val Gly Gly Asn
            245                 250                 255

Asp Thr Thr Arg Asn Ser Met Thr Gly Gly Val Leu Ala Leu Asn Glu
        260                 265                 270

Asn Pro Asp Glu Tyr Arg Lys Leu Cys Ala Asn Pro Ala Leu Ile Ala
    275                 280                 285

Ser Met Val Pro Glu Ile Val Arg Trp Gln Thr Pro Leu Ala His Met
290                 295                 300

Arg Arg Thr Ala Leu Gln Asp Thr Glu Leu Gly Gly Lys Ser Ile Arg
305                 310                 315                 320

Lys Gly Asp Lys Val Ile Met Trp Tyr Val Ser Gly Asn Arg Asp Pro
                325                 330                 335

Glu Ala Ile Glu Asn Pro Asp Ala Phe Ile Ile Asp Arg Ala Lys Pro
            340                 345                 350

Arg His His Leu Ser Phe Gly Phe Gly Ile His Arg Cys Val Gly Asn
        355                 360                 365

Arg Leu Ala Glu Leu Gln Leu Arg Ile Val Trp Glu Glu Leu Leu Lys
    370                 375                 380

Arg Trp Pro Asn Pro Gly Gln Ile Glu Val Val Gly Ala Pro Glu Arg
385                 390                 395                 400

Val Leu Ser Pro Phe Val Lys Gly Tyr Glu Ser Leu Pro Val Arg Ile
                405                 410                 415

Asn Ala
```

<210> SEQ ID NO 14
<211> LENGTH: 420
<212> TYPE: PRT
<213> ORGANISM: Mycobacterium sp. HXN-1500

<400> SEQUENCE: 14

```
Met Thr Glu Met Thr Val Ala Ala Ser Asp Ala Thr Asn Ala Ala Tyr
1               5                   10                  15

Gly Met Ala Leu Glu Asp Ile Asp Val Ser Asn Pro Val Leu Phe Arg
            20                  25                  30

Asp Asn Thr Trp His Pro Tyr Phe Lys Arg Leu Arg Glu Glu Asp Pro
        35                  40                  45

Val His Tyr Cys Lys Ser Ser Met Phe Gly Pro Tyr Trp Ser Val Thr
    50                  55                  60

Lys Tyr Arg Asp Ile Met Ala Val Glu Thr Asn Pro Lys Val Phe Ser
65                  70                  75                  80

Ser Glu Ala Lys Ser Gly Gly Ile Thr Ile Met Asp Asp Asn Ala Ala
                85                  90                  95

Ala Ser Leu Pro Met Phe Ile Ala Met Asp Pro Pro Lys His Asp Val
            100                 105                 110

Gln Arg Lys Thr Val Ser Pro Ile Val Ala Pro Glu Asn Leu Ala Thr
        115                 120                 125

Met Glu Ser Val Ile Arg Gln Arg Thr Ala Asp Leu Leu Asp Gly Leu
    130                 135                 140

Pro Ile Asn Glu Glu Phe Asp Trp Val His Arg Val Ser Ile Glu Leu
145                 150                 155                 160

Thr Thr Lys Met Leu Ala Thr Leu Phe Asp Phe Pro Trp Asp Asp Arg
                165                 170                 175
```

-continued

Ala Lys Leu Thr Arg Trp Ser Asp Val Thr Ala Leu Pro Gly Gly
             180                 185                 190

Gly Ile Ile Asp Ser Glu Glu Gln Arg Met Ala Glu Leu Met Glu Cys
         195                 200                 205

Ala Thr Tyr Phe Thr Glu Leu Trp Asn Gln Arg Val Asn Ala Glu Pro
     210                 215                 220

Lys Asn Asp Leu Ile Ser Met Met Ala His Ser Glu Ser Thr Arg His
225                 230                 235                 240

Met Ala Pro Glu Glu Tyr Leu Gly Asn Ile Val Leu Ile Val Gly
                 245                 250                 255

Gly Asn Asp Thr Thr Arg Asn Ser Met Thr Gly Gly Val Leu Ala Leu
             260                 265                 270

Asn Glu Phe Pro Asp Glu Tyr Arg Lys Leu Ser Ala Asn Pro Ala Leu
         275                 280                 285

Ile Ser Ser Met Val Ser Glu Ile Ile Arg Trp Gln Thr Pro Leu Ser
     290                 295                 300

His Met Arg Arg Thr Ala Leu Glu Asp Ile Glu Phe Gly Gly Lys His
305                 310                 315                 320

Ile Arg Gln Gly Asp Lys Val Val Met Trp Tyr Val Ser Gly Asn Arg
                 325                 330                 335

Asp Pro Glu Ala Ile Asp Asn Pro Asp Thr Phe Ile Ile Asp Arg Ala
             340                 345                 350

Lys Pro Arg Gln His Leu Ser Phe Gly Phe Gly Ile His Arg Cys Val
         355                 360                 365

Gly Asn Arg Leu Ala Glu Leu Gln Leu Asn Ile Leu Trp Glu Glu Ile
     370                 375                 380

Leu Lys Arg Trp Pro Asp Pro Leu Gln Ile Gln Val Leu Gln Glu Pro
385                 390                 395                 400

Thr Arg Val Leu Ser Pro Phe Val Lys Gly Tyr Glu Ser Leu Pro Val
                 405                 410                 415

Arg Ile Asn Ala
             420

<210> SEQ ID NO 15
<211> LENGTH: 420
<212> TYPE: PRT
<213> ORGANISM: Mycobacterium austroafricanum

<400> SEQUENCE: 15

Met Thr Glu Met Thr Val Ala Ala Asn Asp Ala Thr Asn Ala Ala Tyr
1               5                   10                  15

Gly Met Ala Leu Glu Asp Ile Asp Val Ser Asn Pro Val Leu Phe Arg
             20                  25                  30

Asp Asn Thr Trp His Pro Tyr Phe Lys Arg Leu Arg Glu Asp Pro
         35                  40                  45

Val His Tyr Cys Lys Ser Ser Met Phe Gly Pro Tyr Trp Ser Val Thr
     50                  55                  60

Lys Tyr Arg Asp Ile Met Ala Val Glu Thr Asn Pro Lys Val Phe Ser
65                  70                  75                  80

Ser Glu Ala Lys Ser Gly Gly Ile Thr Ile Met Asp Asp Asn Ala Ala
                 85                  90                  95

Ala Ser Leu Pro Met Phe Ile Ala Met Asp Pro Pro Lys His Asp Val
             100                 105                 110

Gln Arg Lys Thr Val Ser Pro Ile Val Ala Pro Glu Asn Leu Ala Thr
         115                 120                 125

```
Met Glu Ser Val Ile Arg Gln Arg Thr Ala Asp Leu Leu Asp Gly Leu
        130                 135                 140

Pro Ile Asn Glu Glu Phe Asp Trp Val His Arg Val Ser Ile Asp Leu
145                 150                 155                 160

Thr Thr Lys Met Leu Ala Thr Leu Phe Asp Phe Pro Trp Asp Asp Arg
                165                 170                 175

Ala Lys Leu Thr Arg Trp Ser Asp Val Thr Thr Ala Leu Pro Gly Gly
            180                 185                 190

Gly Ile Ile Asp Ser Glu Gln Arg Met Ala Glu Leu Met Glu Cys
        195                 200                 205

Ala Thr Tyr Phe Thr Glu Leu Trp Asn Gln Arg Val Asn Ala Glu Pro
        210                 215                 220

Lys Asn Asp Leu Ile Ser Met Met Ala His Ser Glu Ser Thr Arg His
225                 230                 235                 240

Met Ala Pro Glu Glu Tyr Leu Gly Asn Ile Val Leu Ile Val Gly
                245                 250                 255

Gly Asn Asp Thr Thr Arg Asn Ser Met Thr Gly Val Leu Ala Leu
            260                 265                 270

Asn Glu Phe Pro Asp Glu Tyr Arg Lys Leu Ser Ala Asn Pro Ala Leu
        275                 280                 285

Ile Ser Ser Met Val Ser Glu Ile Ile Arg Trp Gln Thr Pro Leu Ser
290                 295                 300

His Met Arg Arg Thr Ala Leu Glu Asp Ile Glu Phe Gly Gly Lys His
305                 310                 315                 320

Ile Arg Gln Gly Asp Lys Val Val Met Trp Tyr Val Ser Gly Asn Arg
                325                 330                 335

Asp Pro Glu Ala Ile Asp Asn Pro Asp Thr Phe Ile Ile Asp Arg Ala
            340                 345                 350

Lys Pro Arg Gln His Leu Ser Phe Gly Phe Gly Ile His Arg Cys Val
            355                 360                 365

Gly Asn Arg Leu Ala Glu Leu Gln Leu Asn Ile Leu Trp Glu Glu Ile
370                 375                 380

Leu Lys Arg Trp Pro Asp Pro Leu Gln Ile Gln Val Leu Gln Glu Pro
385                 390                 395                 400

Thr Arg Val Leu Ser Pro Phe Val Lys Gly Tyr Glu Ser Leu Pro Val
                405                 410                 415

Arg Ile Asn Ala
            420

<210> SEQ ID NO 16
<211> LENGTH: 405
<212> TYPE: PRT
<213> ORGANISM: Polaromonas sp. JS666

<400> SEQUENCE: 16

Met Ser Glu Thr Val Ile Ile Ala Gly Ala Gly Gln Ala Ala Gly Gln
1               5                   10                  15

Ala Val Ala Ser Leu Arg Gln Glu Gly Phe Asp Gly Arg Ile Val Leu
            20                  25                  30

Val Gly Ala Glu Pro Val Leu Pro Tyr Gln Arg Pro Pro Leu Ser Lys
        35                  40                  45

Ala Phe Leu Ala Gly Thr Leu Pro Leu Glu Arg Leu Phe Leu Lys Pro
    50                  55                  60

Pro Ala Phe Tyr Glu Gln Ala Arg Val Asp Thr Leu Leu Gly Val Ala
```

```
                65                  70                  75                  80
Val Thr Glu Leu Asp Ala Ala Arg Arg Gln Val Arg Leu Asp Asp Gly
                    85                  90                  95

Arg Glu Leu Ala Phe Asp His Leu Leu Leu Ala Thr Gly Gly Arg Ala
                100                 105                 110

Arg Arg Leu Asp Cys Pro Gly Ala Asp His Pro Arg Leu His Tyr Leu
                115                 120                 125

Arg Thr Val Ala Asp Val Asp Gly Ile Arg Ala Ala Leu Arg Pro Gly
            130                 135                 140

Ala Arg Leu Val Leu Ile Gly Gly Tyr Val Gly Leu Glu Ile Ala
145                 150                 155                 160

Ala Val Ala Ala Lys Leu Gly Leu Ala Val Thr Val Leu Glu Ala Ala
                165                 170                 175

Pro Thr Val Leu Ala Arg Val Thr Cys Pro Ala Val Ala Arg Phe Phe
                180                 185                 190

Glu Ser Val His Arg Gln Ala Gly Val Thr Ile Arg Cys Ala Thr Thr
                195                 200                 205

Val Ser Gly Ile Glu Gly Asp Ala Ser Leu Ala Arg Val Val Thr Gly
            210                 215                 220

Asp Gly Glu Arg Ile Asp Ala Asp Leu Val Ile Ala Gly Ile Gly Leu
225                 230                 235                 240

Leu Pro Asn Val Glu Leu Ala Gln Ala Ala Gly Leu Val Cys Asp Asn
                245                 250                 255

Gly Ile Val Val Asp Glu Glu Cys Arg Thr Ser Val Pro Gly Ile Phe
                260                 265                 270

Ala Ala Gly Asp Cys Thr Gln His Pro Asn Ala Ile Tyr Asp Ser Arg
            275                 280                 285

Leu Arg Leu Glu Ser Val His Asn Ala Ile Glu Gln Gly Lys Thr Ala
                290                 295                 300

Ala Ala Ala Met Cys Gly Lys Ala Arg Pro Tyr Arg Gln Val Pro Trp
305                 310                 315                 320

Phe Trp Ser Asp Gln Tyr Asp Leu Lys Leu Gln Thr Ala Gly Leu Asn
                325                 330                 335

Arg Gly Tyr Asp Gln Val Val Met Arg Gly Ser Thr Asp Asn Arg Ser
                340                 345                 350

Phe Ala Ala Phe Tyr Leu Arg Asp Gly Arg Leu Leu Ala Val Asp Ala
            355                 360                 365

Val Asn Arg Pro Val Glu Phe Met Val Ala Lys Ala Leu Ile Ala Asn
370                 375                 380

Arg Thr Val Ile Ala Pro Glu Arg Leu Ala Asp Glu Arg Ile Ala Ala
385                 390                 395                 400

Lys Asp Leu Ala Gly
                405

<210> SEQ ID NO 17
<211> LENGTH: 424
<212> TYPE: PRT
<213> ORGANISM: Mycobacterium sp. HXN-1500

<400> SEQUENCE: 17

Met Ile His Thr Gly Val Thr Glu Ala Val Val Val Gly Ala Gly
1               5                   10                  15

Gln Ala Gly Ala Gln Thr Val Ser Leu Arg Gln Arg Gly Phe Glu
                20                  25                  30
```

-continued

```
Gly Gln Ile Thr Leu Leu Gly Asp Glu Pro Ala Leu Pro Tyr Gln Arg
         35                  40                  45

Pro Pro Leu Ser Lys Ala Phe Leu Ala Gly Thr Leu Pro Leu Asp Arg
 50                  55                  60

Leu Tyr Leu Arg Pro Ala Ala Phe Tyr Gln Gln Ala His Val Asp Val
 65                  70                  75                  80

Met Val Asp Thr Gly Val Ser Glu Leu Asp Thr Glu Asn Arg Arg Ile
                 85                  90                  95

Arg Leu Thr Asp Gly Arg Ala Ile Ser Phe Asp His Leu Val Leu Ala
            100                 105                 110

Thr Gly Gly Arg Pro Arg Pro Leu Ala Cys Pro Gly Ala Asp His Pro
        115                 120                 125

Arg Val His Tyr Leu Arg Thr Val Thr Asp Val Asp Arg Ile Arg Ser
    130                 135                 140

Gln Phe His Pro Gly Thr Arg Leu Val Leu Val Gly Gly Gly Tyr Ile
145                 150                 155                 160

Gly Leu Glu Ile Ala Ala Val Ala Ala Glu Leu Gly Leu Thr Val Thr
                165                 170                 175

Val Leu Glu Ala Gln Thr Thr Val Leu Ala Arg Val Thr Cys Pro Thr
            180                 185                 190

Val Ala Arg Phe Phe Glu His Thr His Arg Arg Ala Gly Val Thr Ile
        195                 200                 205

Arg Cys Ala Thr Thr Val Thr Arg Ile His Asp Ser Ser Thr Ala
    210                 215                 220

Arg Ile Glu Leu Asp Ser Gly Glu Tyr Ile Asp Ala Asp Leu Val Ile
225                 230                 235                 240

Val Gly Ile Gly Leu Leu Pro Asn Val Asp Leu Ala Ser Ala Ala Gly
                245                 250                 255

Leu Thr Cys Glu Ser Gly Ile Val Val Asp Ser Arg Cys Gln Thr Ser
            260                 265                 270

Ala Pro Gly Ile Tyr Ala Ala Gly Asp Cys Thr Gln Tyr Pro Ser Pro
        275                 280                 285

Ile Tyr Gly Arg Pro Leu His Leu Glu Ser Val His Asn Ala Ile Glu
290                 295                 300

Gln Ala Lys Thr Ala Ala Ala Ile Leu Gly Arg Asp Glu Pro Phe
305                 310                 315                 320

Arg Gln Val Pro Trp Phe Trp Ser Asp Gln Tyr Asn Ile Lys Leu Gln
                325                 330                 335

Thr Ala Gly Val Asn Glu Gly Tyr Asp Asp Val Ile Ile Arg Gly Asp
            340                 345                 350

Pro Ala Ser Ala Ser Phe Ala Ala Phe Tyr Leu Arg Ala Gly Lys Leu
        355                 360                 365

Leu Ala Val Asp Ala Ile Asn Arg Pro Arg Glu Phe Met Ala Ser Lys
370                 375                 380

Thr Leu Ile Ala Glu Arg Ala Glu Val Asp Pro Thr Gln Leu Ala Asp
385                 390                 395                 400

Glu Ser Leu Pro Pro Thr Ala Leu Ala Ala Val Asn Gly Pro Thr
                405                 410                 415

Arg Ala Thr Ser Pro Thr Ser Leu
            420

<210> SEQ ID NO 18
<211> LENGTH: 106
<212> TYPE: PRT
```

<213> ORGANISM: Polaromonas sp. JS666

<400> SEQUENCE: 18

Met Thr Lys Val Thr Phe Ile Glu His Asn Gly Thr Val Arg Asn Val
1               5                   10                  15

Asp Val Asp Asp Gly Leu Ser Val Met Glu Ala Ala Val Asn Asn Leu
            20                  25                  30

Val Pro Gly Ile Asp Gly Asp Cys Gly Gly Ala Cys Ala Cys Ala Thr
        35                  40                  45

Cys His Val His Ile Asp Ala Ala Trp Leu Asp Lys Leu Pro Pro Met
    50                  55                  60

Glu Ala Met Glu Lys Ser Met Leu Glu Phe Ala Glu Gly Arg Asn Glu
65                  70                  75                  80

Ser Ser Arg Leu Gly Cys Gln Ile Lys Leu Ser Pro Ala Leu Asp Gly
                85                  90                  95

Ile Val Val Arg Thr Pro Leu Gly Gln His
            100                 105

<210> SEQ ID NO 19
<211> LENGTH: 106
<212> TYPE: PRT
<213> ORGANISM: Mycobacterium sp. HXN-1500

<400> SEQUENCE: 19

Met Pro Lys Ile Thr Tyr Ile Asp Tyr Thr Gly Thr Ser Arg Cys Val
1               5                   10                  15

Asp Ala Glu Asn Gly Met Ser Leu Met Glu Ile Ala Ile Asn Asn Asn
            20                  25                  30

Val Pro Gly Ile Asp Gly Asp Cys Gly Gly Glu Cys Ala Cys Ala Thr
        35                  40                  45

Cys His Val His Val Asp Ala Asp Trp Leu Asp Lys Leu Pro Pro Ser
    50                  55                  60

Ser Asp Gln Glu Val Ser Met Leu Glu Phe Cys Asp Gly Val Asp His
65                  70                  75                  80

Thr Ser Arg Leu Gly Cys Gln Ile Lys Ile Cys Pro Thr Leu Asp Gly
                85                  90                  95

Ile Val Val Arg Thr Pro Ala Ala Gln His
            100                 105

<210> SEQ ID NO 20
<211> LENGTH: 224
<212> TYPE: PRT
<213> ORGANISM: Bacillus subtilis

<400> SEQUENCE: 20

Met Lys Ile Tyr Gly Ile Tyr Met Asp Arg Pro Leu Ser Gln Glu Glu
1               5                   10                  15

Asn Glu Arg Phe Met Ser Phe Ile Ser Pro Glu Lys Arg Glu Lys Cys
            20                  25                  30

Arg Arg Phe Tyr His Lys Glu Asp Ala His Arg Thr Leu Leu Gly Asp
        35                  40                  45

Val Leu Val Arg Ser Val Ile Ser Arg Gln Tyr Gln Leu Asp Lys Ser
    50                  55                  60

Asp Ile Arg Phe Ser Thr Gln Glu Tyr Gly Lys Pro Cys Ile Pro Asp
65                  70                  75                  80

Leu Pro Asp Ala His Phe Asn Ile Ser His Ser Gly Arg Trp Val Ile
                85                  90                  95

```
Cys Ala Phe Asp Ser Gln Pro Ile Gly Ile Asp Ile Glu Lys Thr Lys
            100                 105                 110

Pro Ile Ser Leu Glu Ile Ala Lys Arg Phe Phe Ser Lys Thr Glu Tyr
        115                 120                 125

Ser Asp Leu Leu Ala Lys Asp Lys Asp Glu Gln Thr Asp Tyr Phe Tyr
    130                 135                 140

His Leu Trp Ser Met Lys Glu Ser Phe Ile Lys Gln Glu Gly Lys Gly
145                 150                 155                 160

Leu Ser Leu Pro Leu Asp Ser Phe Ser Val Arg Leu His Gln Asp Gly
                165                 170                 175

Gln Val Ser Ile Glu Leu Pro Asp Ser His Ser Pro Cys Tyr Ile Lys
            180                 185                 190

Thr Tyr Glu Val Asp Pro Gly Tyr Lys Met Ala Val Cys Ala Ala His
        195                 200                 205

Pro Asp Phe Pro Glu Asp Ile Thr Met Val Ser Tyr Glu Glu Leu Leu
    210                 215                 220

<210> SEQ ID NO 21
<211> LENGTH: 222
<212> TYPE: PRT
<213> ORGANISM: Nocardia sp. NRRL 5646

<400> SEQUENCE: 21

Met Ile Glu Thr Ile Leu Pro Ala Gly Val Glu Ser Ala Glu Leu Leu
1               5                   10                  15

Glu Tyr Pro Glu Asp Leu Lys Ala His Pro Ala Glu Glu His Leu Ile
            20                  25                  30

Ala Lys Ser Val Glu Lys Arg Arg Asp Phe Ile Gly Ala Arg His
        35                  40                  45

Cys Ala Arg Leu Ala Leu Ala Glu Leu Gly Glu Pro Pro Val Ala Ile
    50                  55                  60

Gly Lys Gly Glu Arg Gly Ala Pro Ile Trp Pro Arg Gly Val Val Gly
65                  70                  75                  80

Ser Leu Thr His Cys Asp Gly Tyr Arg Ala Ala Val Ala His Lys
                85                  90                  95

Met Arg Phe Arg Ser Ile Gly Ile Asp Ala Glu Pro His Ala Thr Leu
            100                 105                 110

Pro Glu Gly Val Leu Asp Ser Val Ser Leu Pro Pro Glu Arg Glu Trp
        115                 120                 125

Leu Lys Thr Thr Asp Ser Ala Leu His Leu Asp Arg Leu Leu Phe Cys
    130                 135                 140

Ala Lys Glu Ala Thr Tyr Lys Ala Trp Trp Pro Leu Thr Ala Arg Trp
145                 150                 155                 160

Leu Gly Phe Glu Glu Ala His Ile Thr Phe Glu Ile Glu Asp Gly Ser
                165                 170                 175

Ala Asp Ser Gly Asn Gly Thr Phe His Ser Glu Leu Leu Val Pro Gly
            180                 185                 190

Gln Thr Asn Asp Gly Gly Thr Pro Leu Leu Ser Phe Asp Gly Arg Trp
        195                 200                 205

Leu Ile Ala Asp Gly Phe Ile Leu Thr Ala Ile Ala Tyr Ala
    210                 215                 220

<210> SEQ ID NO 22
<211> LENGTH: 368
<212> TYPE: PRT
```

<213> ORGANISM: Mycobacterium marinum

<400> SEQUENCE: 22

Met Pro Arg Glu Ile Arg Leu Pro Glu Ser Val Val Arg Pro
1               5                   10                  15

Ala Pro Met Glu Ser Ala Thr Tyr Ser Gln Ser Ser Arg Leu Gln Ala
            20                  25                  30

Ala Gly Leu Ser Pro Ala Ile Thr Leu Phe Glu Lys Ala Ala Gln Thr
        35                  40                  45

Val Pro Leu Pro Asp Ala Pro Gln Pro Val Val Ile Ala Asp Tyr Gly
    50                  55                  60

Val Ala Thr Gly His Asn Ser Leu Lys Pro Met Met Ala Ala Ile Asn
65                  70                  75                  80

Ala Leu Arg Arg Arg Ile Arg Glu Asp Arg Ala Ile Met Val Ala His
                85                  90                  95

Thr Asp Val Pro Asp Asn Asp Phe Thr Ala Leu Phe Arg Thr Leu Ala
            100                 105                 110

Asp Asp Pro Asp Ser Tyr Leu His His Asp Ser Ala Ser Phe Ala Ser
        115                 120                 125

Ala Val Gly Arg Ser Phe Tyr Thr Gln Ile Leu Pro Ser Asn Thr Val
    130                 135                 140

Ser Leu Gly Trp Ser Ser Trp Ala Ile Gln Trp Leu Ser Arg Ile Pro
145                 150                 155                 160

Ala Gly Ala Pro Glu Leu Thr Asp His Val Gln Val Ala Tyr Ser Lys
                165                 170                 175

Asp Glu Arg Ala Arg Ala Ala Tyr Ala His Gln Ala Ala Thr Asp Trp
            180                 185                 190

Gln Asp Phe Leu Ala Phe Arg Gly Arg Glu Leu Cys Pro Gly Gly Arg
        195                 200                 205

Leu Val Val Leu Thr Met Ala Leu Asp Glu His Gly His Phe Gly Tyr
    210                 215                 220

Arg Pro Met Asn Asp Ala Leu Val Ala Leu Asn Asp Gln Val Arg
225                 230                 235                 240

Asp Gly Leu Leu Arg Pro Glu Glu Leu Arg Arg Met Ala Ile Pro Val
                245                 250                 255

Val Ala Arg Ala Glu Lys Asp Leu Arg Ala Pro Phe Ala Pro Arg Gly
            260                 265                 270

Trp Phe Glu Gly Leu Thr Ile Glu Gln Leu Asp Val Phe Asn Ala Glu
        275                 280                 285

Asp Arg Phe Trp Ala Ala Phe Gln Ser Asp Gly Asp Ala Glu Ser Phe
    290                 295                 300

Gly Ala Gln Trp Ala Gly Phe Ala Arg Ala Ala Leu Phe Pro Thr Leu
305                 310                 315                 320

Ala Ala Ala Leu Asp Cys Gly Thr Gly Asp Pro Arg Ala Thr Ala Phe
                325                 330                 335

Ile Glu Gln Leu Glu Ala Ser Val Ala Asp Arg Leu Ala Ser Gln Pro
            340                 345                 350

Glu Pro Met Arg Ile Pro Leu Ala Ser Leu Val Leu Ala Lys Arg Ala
        355                 360                 365

<210> SEQ ID NO 23
<211> LENGTH: 360
<212> TYPE: PRT
<213> ORGANISM: Mycobacterium smegmatis

<400> SEQUENCE: 23

Met Pro Lys Phe Arg Val Ala Val Asp Pro Glu Pro Asp Asp Pro Thr
1               5                   10                  15

Pro Lys Met Arg Ala Pro Arg Pro His Ala Ala Gly Leu Asn Ser Ala
            20                  25                  30

Ile Ala Leu Leu Glu Glu Ala Ala Arg Thr Val Pro Leu Pro Glu Ala
            35                  40                  45

Pro Tyr Pro Ile Val Ile Ala Asp Tyr Gly Val Gly Thr Gly Arg Asn
        50                  55                  60

Ser Met Arg Pro Ile Ala Ala Ile Ala Ala Leu Arg Gly Arg Thr
65                  70                  75                  80

Arg Pro Glu His Ser Val Leu Val Thr His Thr Asp Asn Ala Asp Asn
                85                  90                  95

Asp Phe Thr Ala Val Phe Arg Gly Leu Ala Asp Asn Pro Asp Ser Tyr
                100                 105                 110

Leu Arg Arg Asp Thr Ser Thr Tyr Pro Ser Ala Val Gly Arg Ser Phe
            115                 120                 125

Tyr Thr Gln Ile Leu Pro Ser Lys Ser Val His Val Gly Trp Ser Ala
130                 135                 140

Trp Ala Ile Val Arg Val Gly Arg Met Pro Met Pro Val Pro Asp His
145                 150                 155                 160

Val Ala Ala Ser Phe Ser Gly Asp Pro Gln Val Val Ala Ala Tyr Ala
                165                 170                 175

Arg Gln Ala Ala Phe Asp Trp His Glu Phe Val Ala Phe Arg Gly Arg
            180                 185                 190

Glu Leu Ala Ser Gly Ala Gln Leu Val Val Leu Thr Ala Ala Leu Gly
            195                 200                 205

Asp Asp Gly Asp Phe Gly Tyr Arg Pro Leu Phe Ala Ala Val Met Asp
        210                 215                 220

Thr Leu Arg Glu Leu Thr Ala Asp Gly Val Leu Arg Gln Asp Glu Leu
225                 230                 235                 240

His Arg Met Ser Leu Pro Ile Val Gly Arg Arg Ala Asn Asp Phe Met
                245                 250                 255

Ala Pro Phe Ala Pro Ser Gly Arg Phe Glu Arg Leu Ser Ile Ser His
            260                 265                 270

Leu Glu Val Tyr Asp Ala Glu Asp Val Ile Tyr Ser Ser Tyr Gln Lys
            275                 280                 285

Asp Arg Asp Thr Asp Val Phe Gly Leu Arg Trp Ala Asp Phe Cys Arg
290                 295                 300

Phe Thr Phe Phe Ser Asp Leu Cys Thr Ala Leu Asp Asp Ala Ala
305                 310                 315                 320

Arg Cys Thr Gln Phe Gln Asp Arg Leu His Ala Gly Ile Ala Ala Arg
                325                 330                 335

Leu Ser Ala Gln Pro Glu Gln Met Arg Ile Pro Leu Ala Gln Leu Val
            340                 345                 350

Leu Glu Arg Arg Arg Arg Ser Gly
            355                 360

<210> SEQ ID NO 24
<211> LENGTH: 394
<212> TYPE: PRT
<213> ORGANISM: Pseudomonas putida

<400> SEQUENCE: 24

```
Met Leu Ala Gln Leu Pro Pro Ala Leu Gln Ser Leu His Leu Pro Leu
 1               5                  10                 15

Arg Leu Lys Leu Trp Asp Gly Asn Gln Phe Asp Leu Gly Pro Ser Pro
             20                  25                  30

Gln Val Thr Ile Leu Val Lys Glu Pro Gln Leu Ile Gly Gln Leu Thr
             35                  40                  45

His Pro Ser Met Glu Gln Leu Gly Thr Ala Phe Val Glu Gly Lys Leu
 50                  55                  60

Glu Leu Glu Gly Asp Ile Gly Glu Ala Ile Arg Val Cys Asp Glu Leu
65                   70                  75                  80

Ser Glu Ala Leu Phe Thr Asp Glu Asp Glu Gln Pro Pro Glu Arg Arg
                 85                  90                  95

Ser His Asp Lys Arg Thr Asp Ala Glu Ala Ile Ser Tyr His Tyr Asp
             100                 105                 110

Val Ser Asn Ala Phe Tyr Gln Leu Trp Leu Asp Gln Asp Met Ala Tyr
             115                 120                 125

Ser Cys Ala Tyr Phe Arg Glu Pro Asp Asn Thr Leu Asp Gln Ala Gln
     130                 135                 140

Gln Asp Lys Phe Asp His Leu Cys Arg Lys Leu Arg Leu Asn Ala Gly
145                 150                 155                 160

Asp Tyr Leu Leu Asp Val Gly Cys Gly Trp Gly Leu Ala Arg Phe
                 165                 170                 175

Ala Ala Arg Glu Tyr Asp Ala Lys Val Phe Gly Ile Thr Leu Ser Lys
             180                 185                 190

Glu Gln Leu Lys Leu Gly Arg Gln Arg Val Lys Ala Glu Gly Leu Thr
             195                 200                 205

Asp Lys Val Asp Leu Gln Ile Leu Asp Tyr Arg Asp Leu Pro Gln Asp
    210                 215                 220

Gly Arg Phe Asp Lys Val Val Ser Val Gly Met Phe Glu His Val Gly
225                 230                 235                 240

His Ala Asn Leu Ala Leu Tyr Cys Gln Lys Leu Phe Gly Ala Val Arg
                245                 250                 255

Glu Gly Gly Leu Val Met Asn His Gly Ile Thr Ala Lys His Val Asp
             260                 265                 270

Gly Arg Pro Val Gly Arg Gly Ala Gly Glu Phe Ile Asp Arg Tyr Val
     275                 280                 285

Phe Pro His Gly Glu Leu Pro His Leu Ser Met Ile Ser Ala Ser Ile
290                 295                 300

Cys Glu Ala Gly Leu Glu Val Val Asp Val Glu Ser Leu Arg Leu His
305                 310                 315                 320

Tyr Ala Lys Thr Leu His His Trp Ser Glu Asn Leu Glu Asn Gln Leu
                325                 330                 335

His Lys Ala Ala Ala Leu Val Pro Glu Lys Thr Leu Arg Ile Trp Arg
             340                 345                 350

Leu Tyr Leu Ala Gly Cys Ala Tyr Ala Phe Glu Lys Gly Trp Ile Asn
     355                 360                 365

Leu His Gln Ile Leu Ala Val Lys Pro Tyr Ala Asp Gly His His Asp
    370                 375                 380

Leu Pro Trp Thr Arg Glu Asp Met Tyr Arg
385                 390
```

<210> SEQ ID NO 25
<211> LENGTH: 451
<212> TYPE: PRT

<213> ORGANISM: Saccharomyces cerevisiae

<400> SEQUENCE: 25

```
Met Ser Glu Val Ser Lys Trp Pro Ala Ile Asn Pro Phe His Trp Gly
1               5                   10                  15
Tyr Asn Gly Thr Val Ser His Ile Val Gly Glu Asn Gly Ser Ile Lys
            20                  25                  30
Leu His Leu Lys Asp Asn Lys Glu Gln Val Asp Phe Asp Glu Phe Ala
        35                  40                  45
Asn Lys Tyr Val Pro Thr Leu Lys Asn Gly Ala Gln Phe Lys Leu Ser
    50                  55                  60
Pro Tyr Leu Phe Thr Gly Ile Leu Gln Thr Tyr Leu Gly Ala Ala
65                  70                  75                  80
Asp Phe Ser Lys Lys Phe Pro Val Phe Tyr Gly Arg Glu Ile Val Lys
                85                  90                  95
Phe Ser Asp Gly Gly Val Cys Thr Ala Asp Trp Leu Ile Asp Ser Trp
            100                 105                 110
Lys Lys Asp Tyr Glu Phe Asp Gln Ser Thr Thr Ser Phe Asp Lys Lys
        115                 120                 125
Lys Phe Asp Lys Asp Glu Lys Ala Thr His Pro Glu Gly Trp Pro Arg
    130                 135                 140
Leu Gln Pro Arg Thr Arg Tyr Leu Lys Asp Asn Glu Leu Glu Leu
145                 150                 155                 160
Arg Glu Val Asp Leu Pro Leu Val Val Ile Leu His Gly Leu Ala Gly
                165                 170                 175
Gly Ser His Glu Pro Ile Ile Arg Ser Leu Ala Glu Asn Leu Ser Arg
            180                 185                 190
Ser Gly Arg Phe Gln Val Val Leu Asn Thr Arg Gly Cys Ala Arg
        195                 200                 205
Ser Lys Ile Thr Thr Arg Asn Leu Phe Thr Ala Tyr His Thr Met Asp
    210                 215                 220
Ile Arg Glu Phe Leu Gln Arg Glu Lys Gln Arg His Pro Asp Arg Lys
225                 230                 235                 240
Leu Tyr Ala Val Gly Cys Ser Phe Gly Ala Thr Met Leu Ala Asn Tyr
                245                 250                 255
Leu Gly Glu Glu Gly Asp Lys Ser Pro Leu Ser Ala Ala Ala Thr Leu
            260                 265                 270
Cys Asn Pro Trp Asp Leu Leu Leu Ser Ala Ile Arg Met Ser Gln Asp
        275                 280                 285
Trp Trp Ser Arg Thr Leu Phe Ser Lys Asn Ile Ala Gln Phe Leu Thr
    290                 295                 300
Arg Thr Val Gln Val Asn Met Gly Glu Leu Gly Val Pro Asn Gly Ser
305                 310                 315                 320
Leu Pro Asp His Pro Thr Val Lys Asn Pro Ser Phe Tyr Met Phe
                325                 330                 335
Thr Pro Glu Asn Leu Ile Lys Ala Lys Ser Phe Lys Ser Thr Arg Glu
            340                 345                 350
Phe Asp Glu Val Tyr Thr Ala Pro Ala Leu Gly Phe Pro Asn Ala Met
        355                 360                 365
Glu Tyr Tyr Lys Ala Ala Ser Ser Ile Asn Arg Val Asp Thr Ile Arg
    370                 375                 380
Val Pro Thr Leu Val Ile Asn Ser Arg Asp Asp Pro Val Val Gly Pro
385                 390                 395                 400
```

```
Asp Gln Pro Tyr Ser Ile Val Glu Lys Asn Pro Arg Ile Leu Tyr Cys
                405                 410                 415

Arg Thr Asp Leu Gly Gly His Leu Ala Tyr Leu Asp Lys Asp Asn Asn
            420                 425                 430

Ser Trp Ala Thr Lys Ala Ile Ala Glu Phe Phe Thr Lys Phe Asp Glu
        435                 440                 445

Leu Val Val
    450

<210> SEQ ID NO 26
<211> LENGTH: 382
<212> TYPE: PRT
<213> ORGANISM: Pseudomonas fluorescens

<400> SEQUENCE: 26

Met Gln Ile Gln Gly His Tyr Glu Leu Gln Phe Glu Ala Val Arg Glu
 1               5                  10                  15

Ala Phe Ala Ala Leu Phe Asp Asp Pro Gln Glu Arg Gly Ala Gly Leu
             20                  25                  30

Cys Ile Gln Ile Gly Gly Glu Thr Val Val Asp Leu Trp Ala Gly Thr
         35                  40                  45

Ala Asp Lys Asp Gly Thr Glu Ala Trp His Ser Asp Thr Ile Val Asn
     50                  55                  60

Leu Phe Ser Cys Thr Lys Thr Phe Thr Ala Val Thr Ala Leu Gln Leu
 65                  70                  75                  80

Val Ala Glu Gly Lys Leu Gln Leu Asp Ala Pro Val Ala Asn Tyr Trp
                 85                  90                  95

Pro Glu Phe Ala Ala Ala Gly Lys Glu Ala Ile Thr Leu Arg Gln Leu
            100                 105                 110

Leu Cys His Gln Ala Gly Leu Pro Ala Ile Arg Glu Met Leu Pro Thr
        115                 120                 125

Glu Ala Leu Tyr Asp Trp Arg Leu Met Val Asp Thr Leu Ala Ala Glu
    130                 135                 140

Ala Pro Trp Trp Thr Pro Gly Gln Gly His Gly Tyr Glu Ala Ile Thr
145                 150                 155                 160

Tyr Gly Trp Leu Val Gly Glu Leu Leu Arg Arg Ala Asp Gly Arg Gly
                165                 170                 175

Pro Gly Glu Ser Ile Val Ala Arg Val Ala Arg Pro Leu Gly Leu Asp
            180                 185                 190

Phe His Val Gly Leu Ala Asp Glu Glu Phe Tyr Arg Val Ala His Ile
        195                 200                 205

Ala Arg Ser Lys Gly Asn Met Gly Asp Glu Ala Ala Gln Arg Leu Leu
    210                 215                 220

Gln Val Met Met Arg Glu Pro Thr Ala Met Thr Thr Arg Ala Phe Ala
225                 230                 235                 240

Asn Pro Pro Ser Ile Leu Thr Ser Thr Asn Lys Pro Glu Trp Arg Arg
                245                 250                 255

Met Gln Gln Pro Ala Ala Asn Gly His Gly Asn Ala Arg Ser Leu Ala
            260                 265                 270

Gly Phe Tyr Ser Gly Leu Leu Asp Gly Ser Leu Leu Glu Ala Asp Met
        275                 280                 285

Leu Glu Gln Leu Thr Arg Glu His Ser Ile Gly Pro Asp Lys Thr Leu
    290                 295                 300

Leu Thr Gln Thr Arg Phe Gly Leu Gly Cys Met Leu Asp Gln Gln Pro
305                 310                 315                 320
```

```
Gln Leu Pro Asn Ala Thr Phe Gly Leu Gly Pro Arg Ala Phe Gly His
                325                 330                 335

Pro Arg Ser Ala Pro Val Val Arg Trp Val Leu Pro Glu His Asp Val
            340                 345                 350

Ala Phe Gly Phe Val Thr Asn Thr Leu Gly Pro Tyr Val Leu Met Asp
        355                 360                 365

Pro Arg Ala Gln Lys Leu Val Gly Ile Leu Ala Gly Cys Leu
    370                 375                 380

<210> SEQ ID NO 27
<211> LENGTH: 402
<212> TYPE: PRT
<213> ORGANISM: Pseudomonas putida

<400> SEQUENCE: 27

Met Asn Gly Lys Ser Ser Val Leu Asp Ser Ala Pro Glu Tyr Val Asp
 1               5                  10                  15

Lys Lys Lys Tyr Phe Trp Ile Leu Ser Thr Phe Trp Pro Ala Thr Pro
             20                  25                  30

Met Ile Gly Ile Trp Leu Ala Asn Glu Thr Gly Trp Gly Ile Phe Tyr
         35                  40                  45

Gly Leu Val Leu Ala Val Trp Tyr Gly Val Leu Pro Leu Leu Asp Ala
     50                  55                  60

Met Phe Gly Glu Asp Phe Asn Asn Pro Pro Glu Val Val Glu Lys
 65                  70                  75                  80

Leu Glu Lys Glu Arg Tyr Tyr Arg Val Leu Thr Tyr Leu Thr Val Pro
                 85                  90                  95

Met His Tyr Ala Ala Leu Ile Val Ser Ala Trp Trp Val Gly Thr Gln
            100                 105                 110

Ser Met Ser Trp Phe Glu Ile Val Ala Leu Ala Leu Ser Leu Gly Ile
        115                 120                 125

Val Asn Gly Leu Ala Leu Asn Thr Gly His Glu Leu Gly His Lys Lys
    130                 135                 140

Glu Ala Phe Asp Arg Trp Met Ala Lys Ile Val Leu Ala Val Val Gly
145                 150                 155                 160

Tyr Gly His Phe Phe Ile Glu His Asn Lys Gly His His Arg Asp Val
                165                 170                 175

Ala Thr Pro Met Asp Pro Ala Thr Ser Arg Met Gly Glu Asn Ile Tyr
            180                 185                 190

Lys Phe Ser Thr Arg Glu Ile Pro Gly Ala Phe Arg Arg Ala Trp Gly
        195                 200                 205

Leu Glu Glu Gln Arg Leu Ser Arg Arg Gly Gln Ser Val Trp Ser Phe
    210                 215                 220

Asp Asn Glu Ile Leu Gln Pro Met Val Ile Thr Val Val Leu Tyr Thr
225                 230                 235                 240

Leu Leu Leu Ala Phe Gly Pro Lys Met Leu Val Phe Leu Pro Ile
                245                 250                 255

Gln Met Ala Phe Gly Trp Trp Gln Leu Thr Ser Ala Asn Tyr Ile Glu
            260                 265                 270

His Tyr Gly Leu Leu Arg Glu Lys Met Ala Asp Gly Arg Tyr Glu His
        275                 280                 285

Gln Lys Pro His His Ser Trp Asn Ser Asn His Ile Val Ser Asn Leu
    290                 295                 300

Val Leu Phe His Leu Gln Arg His Ser Asp His His Ala His Pro Thr
```

```
            305                 310                 315                 320
Arg Ser Tyr Gln Ser Leu Arg Asp Phe Pro Gly Leu Pro Ala Leu Pro
                325                 330                 335

Thr Gly Tyr Pro Gly Ala Phe Leu Met Ala Met Ile Pro Gln Trp Phe
                340                 345                 350

Arg Ser Val Met Asp Pro Lys Val Val Asn Trp Ala Asn Gly Asp Leu
                355                 360                 365

Ser Lys Ile Gln Ile Glu Asp Ser Met Arg Ala Glu Tyr Ile Lys Lys
                370                 375                 380

Phe Thr His Asn Val Gly Ala Asp Asp Lys Arg Gly Ala Thr Ala Val
385                 390                 395                 400

Ala Ser

<210> SEQ ID NO 28
<211> LENGTH: 523
<212> TYPE: PRT
<213> ORGANISM: Candida maltose

<400> SEQUENCE: 28

Met Ala Ile Glu Gln Ile Ile Glu Glu Val Leu Pro Tyr Leu Thr Lys
1               5                   10                  15

Trp Tyr Thr Ile Leu Phe Gly Ala Ala Val Thr Tyr Phe Leu Ser Ile
                20                  25                  30

Ala Leu Arg Asn Lys Phe Tyr Glu Tyr Lys Leu Lys Cys Glu Asn Pro
                35                  40                  45

Val Tyr Phe Glu Asp Ala Gly Leu Phe Gly Ile Pro Ala Leu Ile Asp
        50                  55                  60

Ile Ile Lys Val Arg Lys Ala Gly Gln Leu Ala Asp Tyr Thr Asp Thr
65                  70                  75                  80

Thr Phe Asp Lys Tyr Pro Asn Leu Ser Ser Tyr Met Thr Val Ala Gly
                85                  90                  95

Val Leu Lys Ile Val Phe Thr Val Asp Pro Glu Asn Ile Lys Ala Val
                100                 105                 110

Leu Ala Thr Gln Phe Asn Asp Phe Ala Leu Gly Ala Arg His Ala His
                115                 120                 125

Phe Asp Pro Leu Leu Gly Asp Gly Ile Phe Thr Leu Asp Gly Glu Gly
        130                 135                 140

Trp Lys Leu Ser Arg Ala Met Leu Arg Pro Gln Phe Ala Arg Glu Gln
145                 150                 155                 160

Ile Ala His Val Lys Ala Leu Glu Pro His Val Gln Ile Leu Ala Lys
                165                 170                 175

Gln Ile Lys Leu Asn Lys Gly Lys Thr Phe Asp Leu Gln Glu Leu Phe
                180                 185                 190

Phe Arg Phe Thr Val Asp Thr Ala Thr Glu Phe Leu Phe Gly Glu Ser
                195                 200                 205

Val His Ser Leu Tyr Asp Glu Lys Leu Gly Ile Pro Ala Pro Asn Asp
        210                 215                 220

Ile Pro Gly Arg Glu Asn Phe Ala Glu Ala Phe Asn Thr Ser Gln His
225                 230                 235                 240

Tyr Leu Ala Thr Arg Thr Tyr Ser Gln Ile Phe Tyr Trp Leu Thr Asn
                245                 250                 255

Pro Lys Glu Phe Arg Asp Cys Asn Ala Lys Val His Lys Leu Ala Gln
                260                 265                 270

Tyr Phe Val Asn Thr Ala Leu Asn Ala Thr Glu Lys Glu Val Glu Glu
```

```
            275                 280                 285
Lys Ser Lys Gly Gly Tyr Val Phe Leu Tyr Glu Leu Val Lys Gln Thr
290                 295                 300

Arg Asp Pro Lys Val Leu Gln Asp Gln Leu Leu Asn Ile Met Val Ala
305                 310                 315                 320

Gly Arg Asp Thr Thr Ala Gly Leu Leu Ser Phe Ala Met Phe Glu Leu
                    325                 330                 335

Ala Arg Asn Pro Lys Ile Trp Asn Lys Leu Arg Glu Glu Val Glu Val
                340                 345                 350

Asn Phe Gly Leu Gly Asp Glu Ala Arg Val Asp Glu Ile Ser Phe Glu
            355                 360                 365

Thr Leu Lys Lys Cys Glu Tyr Leu Lys Ala Val Leu Asn Glu Thr Leu
370                 375                 380

Arg Met Tyr Pro Ser Val Pro Ile Asn Phe Arg Thr Ala Thr Arg Asp
385                 390                 395                 400

Thr Thr Leu Pro Arg Gly Gly Lys Asp Gly Asn Ser Pro Ile Phe
                    405                 410                 415

Val Pro Lys Gly Ser Ser Val Val Tyr Ser Val Tyr Lys Thr His Arg
                420                 425                 430

Leu Lys Gln Phe Tyr Gly Glu Asp Ala Tyr Glu Phe Arg Pro Glu Arg
            435                 440                 445

Trp Phe Glu Pro Ser Thr Arg Lys Leu Gly Trp Ala Tyr Leu Pro Phe
450                 455                 460

Asn Gly Gly Pro Arg Ile Cys Leu Gly Gln Gln Phe Ala Leu Thr Glu
465                 470                 475                 480

Ala Ser Tyr Val Ile Ala Arg Leu Ala Gln Met Glu His Leu Glu
                    485                 490                 495

Ser Lys Asp Glu Thr Tyr Pro Pro Asn Lys Cys Ile His Leu Thr Met
                500                 505                 510

Asn His Asn Glu Gly Val Phe Ile Ser Ala Lys
            515                 520

<210> SEQ ID NO 29
<211> LENGTH: 464
<212> TYPE: PRT
<213> ORGANISM: Salmonella enterica subsp. enterica serovar Typhimurium

<400> SEQUENCE: 29

Met Asn Thr Ser Glu Leu Glu Thr Leu Ile Arg Thr Ile Leu Ser Glu
1               5                   10                  15

Gln Leu Thr Thr Pro Ala Gln Thr Pro Val Gln Pro Gly Lys Gly
                20                  25                  30

Ile Phe Gln Ser Val Ser Glu Ala Ile Asp Ala Ala His Gln Ala Phe
            35                  40                  45

Leu Arg Tyr Gln Gln Cys Pro Leu Lys Thr Arg Ser Ala Ile Ile Ser
        50                  55                  60

Ala Met Arg Gln Glu Leu Thr Pro Leu Leu Ala Pro Leu Ala Glu Glu
65                  70                  75                  80

Ser Ala Asn Glu Thr Gly Met Gly Asn Lys Glu Asp Lys Phe Leu Lys
                85                  90                  95

Asn Lys Ala Ala Leu Asp Asn Thr Pro Gly Val Glu Asp Leu Thr Thr
            100                 105                 110

Thr Ala Leu Thr Gly Asp Gly Gly Met Val Leu Phe Glu Tyr Ser Pro
        115                 120                 125
```

```
Phe Gly Val Ile Gly Ser Val Ala Pro Ser Thr Asn Pro Thr Glu Thr
    130                 135                 140
Ile Ile Asn Asn Ser Ile Ser Met Leu Ala Ala Gly Asn Ser Ile Tyr
145                 150                 155                 160
Phe Ser Pro His Pro Gly Ala Lys Lys Val Ser Leu Lys Leu Ile Ser
                165                 170                 175
Leu Ile Glu Glu Ile Ala Phe Arg Cys Cys Gly Ile Arg Asn Leu Val
            180                 185                 190
Val Thr Val Ala Glu Pro Thr Phe Glu Ala Thr Gln Gln Met Met Ala
        195                 200                 205
His Pro Arg Ile Ala Val Leu Ala Ile Thr Gly Gly Pro Gly Ile Val
    210                 215                 220
Ala Met Gly Met Lys Ser Gly Lys Lys Val Ile Gly Ala Gly Ala Gly
225                 230                 235                 240
Asn Pro Pro Cys Ile Val Asp Glu Thr Ala Asp Leu Val Lys Ala Ala
                245                 250                 255
Glu Asp Ile Ile Asn Gly Ala Ser Phe Asp Tyr Asn Leu Pro Cys Ile
            260                 265                 270
Ala Glu Lys Ser Leu Ile Val Val Glu Ser Val Ala Glu Arg Leu Val
        275                 280                 285
Gln Gln Met Gln Thr Phe Gly Ala Leu Leu Leu Ser Pro Ala Asp Thr
    290                 295                 300
Asp Lys Leu Arg Ala Val Cys Leu Pro Glu Gly Gln Ala Asn Lys Lys
305                 310                 315                 320
Leu Val Gly Lys Ser Pro Ser Ala Met Leu Glu Ala Ala Gly Ile Ala
                325                 330                 335
Val Pro Ala Lys Ala Pro Arg Leu Leu Ile Ala Leu Val Asn Ala Asp
            340                 345                 350
Asp Pro Trp Val Thr Ser Glu Gln Leu Met Pro Met Leu Pro Val Val
        355                 360                 365
Lys Val Ser Asp Phe Asp Ser Ala Leu Ala Leu Ala Leu Lys Val Glu
    370                 375                 380
Glu Gly Leu His His Thr Ala Ile Met His Ser Gln Asn Val Ser Arg
385                 390                 395                 400
Leu Asn Leu Ala Ala Arg Thr Leu Gln Thr Ser Ile Phe Val Lys Asn
                405                 410                 415
Gly Pro Ser Tyr Ala Gly Ile Gly Val Gly Gly Glu Gly Phe Thr Thr
            420                 425                 430
Phe Thr Ile Ala Thr Pro Thr Gly Glu Gly Thr Thr Ser Ala Arg Thr
        435                 440                 445
Phe Ala Arg Ser Arg Arg Cys Val Leu Thr Asn Gly Phe Ser Ile Arg
    450                 455                 460

<210> SEQ ID NO 30
<211> LENGTH: 471
<212> TYPE: PRT
<213> ORGANISM: Sphingomonas paucimobilis

<400> SEQUENCE: 30

Met Ser Thr Pro Thr Asn Leu Glu Gln Val Leu Ala Ala Gly Gly Asn
1               5                   10                  15

Thr Val Glu Met Leu Arg Asn Ser Gln Ile Gly Ala Tyr Val Tyr Pro
            20                  25                  30

Val Val Ala Pro Glu Phe Ser Asn Trp Arg Thr Glu Gln Trp Ala Trp
        35                  40                  45
```

```
Arg Asn Ser Ala Val Leu Phe Asp Gln Thr His His Met Val Asp Leu
    50                  55                  60

Tyr Ile Arg Gly Lys Asp Ala Leu Lys Leu Leu Ser Asp Thr Met Ile
65                  70                  75                  80

Asn Ser Pro Lys Gly Trp Glu Pro Asn Lys Ala Lys Gln Tyr Val Pro
                85                  90                  95

Val Thr Pro Tyr Gly His Val Ile Gly Asp Gly Ile Ile Phe Tyr Leu
               100                 105                 110

Ala Glu Glu Glu Phe Val Tyr Val Gly Arg Ala Pro Ala Ala Asn Trp
            115                 120                 125

Leu Met Tyr His Ala Gln Thr Gly Gly Tyr Asn Val Asp Ile Val His
        130                 135                 140

Asp Asp Arg Ser Pro Ser Arg Pro Met Gly Lys Pro Val Gln Arg Ile
145                 150                 155                 160

Ser Trp Arg Phe Gln Ile Gln Gly Pro Lys Ala Trp Asp Val Ile Glu
                165                 170                 175

Lys Leu His Gly Gly Thr Leu Glu Lys Leu Lys Phe Phe Asn Met Ala
                180                 185                 190

Glu Met Asn Ile Ala Gly Met Lys Ile Arg Thr Leu Arg His Gly Met
            195                 200                 205

Ala Gly Ala Pro Gly Leu Glu Ile Trp Gly Pro Tyr Glu Thr Gln Glu
        210                 215                 220

Lys Ala Arg Asn Ala Ile Leu Glu Ala Gly Lys Glu Phe Gly Leu Ile
225                 230                 235                 240

Pro Val Gly Ser Arg Ala Tyr Pro Ser Asn Thr Leu Glu Ser Gly Trp
                245                 250                 255

Ile Pro Ser Pro Leu Pro Ala Ile Tyr Thr Gly Asp Lys Leu Lys Ala
            260                 265                 270

Tyr Arg Glu Trp Leu Pro Ala Asn Ser Tyr Glu Ala Ser Gly Ala Ile
        275                 280                 285

Gly Gly Ser Phe Val Ser Ser Asn Ile Glu Asp Tyr Tyr Val Asn Pro
    290                 295                 300

Tyr Glu Ile Gly Tyr Gly Pro Phe Val Lys Phe Asp His Asp Phe Ile
305                 310                 315                 320

Gly Arg Asp Ala Leu Glu Ala Ile Asp Pro Ala Thr Gln Arg Lys Lys
                325                 330                 335

Val Thr Leu Ala Trp Asn Gly Asp Asp Met Ala Lys Ile Tyr Ala Ser
            340                 345                 350

Leu Phe Asp Thr Glu Ala Asp Ala His Tyr Lys Phe Phe Asp Leu Pro
        355                 360                 365

Leu Ala Asn Tyr Ala Asn Thr Asn Ala Asp Ala Val Leu Asp Ala Ala
    370                 375                 380

Gly Asn Val Val Gly Met Ser Met Phe Thr Gly Tyr Ser Tyr Asn Glu
385                 390                 395                 400

Lys Arg Ala Leu Ser Leu Ala Thr Ile Asp His Glu Ile Pro Val Gly
                405                 410                 415

Thr Glu Leu Thr Val Leu Trp Gly Glu Asn Gly Gly Thr Arg Lys
            420                 425                 430

Thr Thr Val Glu Pro His Lys Gln Met Ala Val Arg Ala Val Val Ser
        435                 440                 445

Pro Val Pro Tyr Ser Val Thr Ala Arg Glu Thr Tyr Glu Gly Gly Trp
    450                 455                 460
```

Arg Lys Ala Ala Val Thr Ala
465                 470

<210> SEQ ID NO 31
<211> LENGTH: 462
<212> TYPE: PRT
<213> ORGANISM: Sphingomonas paucimobilis

<400> SEQUENCE: 31

Met Ala Lys Ser Leu Gln Asp Val Leu Asp Asn Ala Gly Asn Ala Val
1               5                   10                  15

Asp Phe Leu Arg Asn Gln Gln Thr Gly Pro Asn Val Tyr Pro Gly Val
                20                  25                  30

Pro Ala Glu Tyr Ser Asn Trp Arg Asn Glu Gln Arg Ala Trp Ala Lys
            35                  40                  45

Thr Ala Val Leu Phe Asn Gln Ser Tyr His Met Val Glu Leu Met Val
    50                  55                  60

Glu Gly Pro Asp Ala Phe Ala Phe Leu Asn Tyr Leu Gly Ile Asn Ser
65                  70                  75                  80

Phe Lys Asn Phe Ala Pro Gly Lys Ala Lys Gln Trp Val Pro Val Thr
                85                  90                  95

Ala Glu Gly Tyr Val Ile Gly Asp Val Ile Leu Phe Tyr Leu Ala Glu
            100                 105                 110

Asn Gln Phe Asn Leu Val Gly Arg Ala Pro Ala Ile Glu Trp Ala Glu
        115                 120                 125

Phe His Ala Ala Thr Gly Lys Trp Asn Val Thr Leu Thr Arg Asp Glu
    130                 135                 140

Arg Thr Ala Leu Arg Thr Asp Gly Val Arg Arg His Tyr Arg Phe Gln
145                 150                 155                 160

Leu Gln Gly Pro Asn Ala Met Ala Ile Leu Thr Asp Ala Met Gly Gln
                165                 170                 175

Thr Pro Pro Asp Leu Lys Phe Phe Asn Met Ala Asp Ile Gln Ile Ala
            180                 185                 190

Gly Lys Thr Val Gly Ala Leu Arg His Gly Met Ala Gly Gln Pro Gly
        195                 200                 205

Tyr Glu Leu Tyr Gly Pro Trp Ala Asp Tyr Glu Ala Val His Ser Ala
    210                 215                 220

Leu Val Ala Ala Gly Lys Asn His Gly Leu Ala Leu Val Gly Gly Arg
225                 230                 235                 240

Ala Tyr Ser Ser Asn Thr Leu Glu Ser Gly Trp Val Pro Ser Pro Phe
                245                 250                 255

Pro Gly Tyr Leu Phe Gly Glu Gly Ser Ala Asp Phe Arg Lys Trp Ala
            260                 265                 270

Gly Glu Asn Ser Tyr Gly Ala Lys Cys Ser Ile Gly Ser Tyr Val
        275                 280                 285

Pro Glu Ser Leu Glu Gly Tyr Gly Leu Thr Pro Trp Asp Ile Gly Tyr
    290                 295                 300

Gly Ile Ile Val Lys Phe Asp His Asp Phe Ile Gly Lys Glu Ala Leu
305                 310                 315                 320

Glu Lys Met Ala Asn Glu Pro His Leu Glu Lys Val Thr Leu Ala Leu
                325                 330                 335

Asp Asp Glu Asp Met Leu Arg Val Met Ser Ser Tyr Phe Ser Asp Ser
            340                 345                 350

Gly Arg Ala Lys Tyr Phe Glu Phe Pro Ser Ala Val Tyr Ser Met His
        355                 360                 365

```
Pro Tyr Asp Ser Val Leu Val Asp Gly Lys His Val Gly Val Ser Thr
    370                 375                 380

Trp Val Gly Tyr Ser Ser Asn Glu Gly Lys Met Leu Thr Leu Ala Met
385                 390                 395                 400

Ile Asp Pro Lys Tyr Ala Lys Pro Gly Thr Glu Val Ser Leu Leu Trp
                405                 410                 415

Gly Glu Pro Asn Gly Gly Thr Ser Lys Pro Thr Val Glu Pro His Glu
                420                 425                 430

Gln Thr Glu Ile Lys Ala Val Val Ala Pro Val Pro Tyr Ser Ala Val
            435                 440                 445

Ala Arg Thr Gly Tyr Ala Asp Ser Trp Arg Thr Lys Lys Ala
    450                 455                 460
```

<210> SEQ ID NO 32
<211> LENGTH: 246
<212> TYPE: PRT
<213> ORGANISM: Lactobacillus brevis

<400> SEQUENCE: 32

```
Met Ala Ala Asn Glu Phe Ser Glu Thr His Arg Val Val Tyr Tyr Glu
1               5                   10                  15

Ala Asp Asp Thr Gly Gln Leu Thr Leu Ala Met Leu Ile Asn Leu Phe
            20                  25                  30

Val Leu Val Ser Glu Asp Gln Asn Asp Ala Leu Gly Leu Ser Thr Ala
        35                  40                  45

Phe Val Gln Ser His Gly Val Gly Trp Val Val Thr Gln Tyr His Leu
    50                  55                  60

His Ile Asp Glu Leu Pro Arg Thr Gly Ala Gln Val Thr Ile Lys Thr
65                  70                  75                  80

Arg Ala Thr Ala Tyr Asn Arg Tyr Phe Ala Tyr Arg Glu Tyr Trp Leu
                85                  90                  95

Leu Asp Asp Ala Gly Gln Val Leu Ala Tyr Gly Glu Gly Ile Trp Val
            100                 105                 110

Thr Met Ser Tyr Ala Thr Arg Lys Ile Thr Thr Ile Pro Ala Glu Val
        115                 120                 125

Met Ala Pro Tyr His Ser Glu Glu Gln Thr Arg Leu Pro Arg Leu Pro
    130                 135                 140

Arg Pro Asp His Phe Asp Glu Ala Val Asn Gln Thr Leu Lys Pro Tyr
145                 150                 155                 160

Thr Val Arg Tyr Phe Asp Ile Asp Gly Asn Gly His Val Asn Asn Ala
                165                 170                 175

His Tyr Phe Asp Trp Met Leu Asp Val Leu Pro Ala Thr Phe Leu Arg
            180                 185                 190

Ala His His Pro Thr Asp Val Lys Ile Arg Phe Glu Asn Glu Val Gln
        195                 200                 205

Tyr Gly His Gln Val Thr Ser Glu Leu Ser Gln Ala Ala Ala Leu Thr
    210                 215                 220

Thr Gln His Met Ile Lys Val Gly Asp Leu Thr Ala Val Lys Ala Thr
225                 230                 235                 240

Ile Gln Trp Asp Asn Arg
                245
```

<210> SEQ ID NO 33
<211> LENGTH: 261
<212> TYPE: PRT

<213> ORGANISM: Lactobacillus plantarum

<400> SEQUENCE: 33

```
Met Ala Thr Leu Gly Ala Asn Ala Ser Leu Tyr Ser Glu Gln His Arg
1               5                   10                  15

Ile Thr Tyr Tyr Glu Cys Asp Arg Thr Gly Arg Ala Thr Leu Thr Thr
            20                  25                  30

Leu Ile Asp Ile Ala Val Leu Ala Ser Glu Asp Gln Ser Asp Ala Leu
        35                  40                  45

Gly Leu Thr Thr Glu Met Val Gln Ser His Gly Val Gly Trp Val Val
    50                  55                  60

Thr Gln Tyr Ala Ile Asp Ile Thr Arg Met Pro Arg Gln Asp Glu Val
65                  70                  75                  80

Val Thr Ile Ala Val Arg Gly Ser Ala Tyr Asn Pro Tyr Phe Ala Tyr
                85                  90                  95

Arg Glu Phe Trp Ile Arg Asp Ala Asp Gly Gln Gln Leu Ala Tyr Ile
            100                 105                 110

Thr Ser Ile Trp Val Met Met Ser Gln Thr Thr Arg Arg Ile Val Lys
        115                 120                 125

Ile Leu Pro Glu Leu Val Ala Pro Tyr Gln Ser Glu Val Val Lys Arg
    130                 135                 140

Ile Pro Arg Leu Pro Arg Pro Ile Ser Phe Glu Ala Thr Asp Thr Thr
145                 150                 155                 160

Ile Thr Lys Pro Tyr His Val Arg Phe Phe Asp Ile Asp Pro Asn Arg
                165                 170                 175

His Val Asn Asn Ala His Tyr Phe Asp Trp Leu Val Asp Thr Leu Pro
            180                 185                 190

Ala Thr Phe Leu Leu Gln His Asp Leu Val His Val Asp Val Arg Tyr
        195                 200                 205

Glu Asn Glu Val Lys Tyr Gly Gln Thr Val Thr Ala His Ala Asn Ile
    210                 215                 220

Leu Pro Ser Glu Val Ala Asp Gln Val Thr Thr Ser His Leu Ile Glu
225                 230                 235                 240

Val Asp Asp Glu Lys Cys Cys Val Thr Ile Gln Trp Arg Thr Leu
                245                 250                 255

Pro Glu Pro Ile Gln
            260
```